United States Patent
Yang et al.

(10) Patent No.: US 11,611,043 B1
(45) Date of Patent: Mar. 21, 2023

(54) NITROGEN-CONTAINING COMPOUND, ELECTRONIC COMPONENT AND ELECTRONIC DEVICE

(71) Applicant: Shaanxi Lighte Optoelectronics Material Co., Ltd., Xi'an (CN)

(72) Inventors: Min Yang, Xi'an (CN); Peng Nan, Xi'an (CN); Lingang Li, Xi'an (CN); Tiantian Ma, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/613,416

(22) PCT Filed: Jun. 8, 2020

(86) PCT No.: PCT/CN2020/094957
§ 371 (c)(1),
(2) Date: Nov. 22, 2021

(87) PCT Pub. No.: WO2020/248943
PCT Pub. Date: Dec. 17, 2020

(30) Foreign Application Priority Data

Jun. 14, 2019 (CN) .......................... 201910515733.1
Mar. 18, 2020 (CN) .......................... 202010192954.2
May 20, 2020 (CN) .......................... 202010432540.2

(51) Int. Cl.
*H01L 51/00* (2006.01)
*C07C 211/61* (2006.01)
*H01L 51/50* (2006.01)

(52) U.S. Cl.
CPC .......... *H01L 51/006* (2013.01); *C07C 211/61* (2013.01); *H01L 51/0058* (2013.01); *C07C 2603/18* (2017.05); *C07C 2603/74* (2017.05); *C07C 2603/97* (2017.05); *C07C 2603/98* (2017.05); *H01L 51/0056* (2013.01); *H01L 51/5056* (2013.01); *H01L 51/5064* (2013.01); *H01L 51/5096* (2013.01)

(58) Field of Classification Search
CPC . C07B 2200/05; C07B 59/001; C07C 211/54; C07C 211/56; C07C 211/58; C07C 211/61; C07C 255/58; C07C 2603/18; C07C 2603/26; C07C 2603/94; C07D 209/82; C07D 209/86; C07D 209/88; C07D 213/36; C07D 215/12; C07D 265/38; C07D 307/91; C07D 311/80; C07D 319/24; C07D 333/76; C07D 339/08; C07D 403/12; C07D 405/12; C07D 407/12; C07D 409/12; C07D 471/04; C07F 7/081; C07F 7/0812; C07F 7/0816; H01L 51/0052; H01L 51/0058; H01L 51/0059; H01L 51/006; H01L 51/0061; H01L 51/0067; H01L 51/0072; H01L 51/0073; H01L 51/0074; H01L 51/5064; Y02E 10/549
See application file for complete search history.

(56) References Cited

U.S. PATENT DOCUMENTS

| | | | |
|---|---|---|---|
| 7,507,485 B2* | 3/2009 | Oh | .......................... C09B 15/00 |
| | | | 313/506 |
| 9,312,495 B2* | 4/2016 | Pflumm | .................. C09K 11/06 |
| 2004/0124766 A1* | 7/2004 | Nakagawa | .......... H01L 51/0064 |
| | | | 313/506 |
| 2021/0130295 A1* | 5/2021 | Kim | ...................... H01L 51/006 |
| 2021/0206741 A1* | 7/2021 | Nie | ..................... H01L 51/0052 |

FOREIGN PATENT DOCUMENTS

| | | |
|---|---|---|
| CN | 103108859 A | 5/2013 |
| CN | 104583176 A | 4/2015 |
| CN | 106008424 A | 10/2016 |

(Continued)

OTHER PUBLICATIONS

Synthetic Metals, vol. 143, (2004), pp. 215-220. (Year: 2004).*

(Continued)

*Primary Examiner* — Dawn L Garrett
(74) *Attorney, Agent, or Firm* — Tucker Ellis LLP

(57) ABSTRACT

The present application, which pertains to the technical field of organic materials, provides a nitrogen-containing compound, an electronic component, and an electronic device. The structure of the nitrogen-containing compound is shown in Formula 1, in which A is the group represented by Formula 2. The nitrogen-containing compound can improve the performance of electronic component.

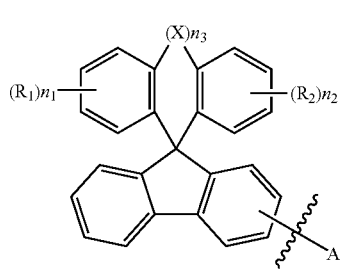

Formula 1

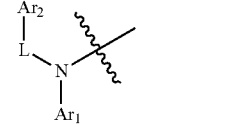

Formula 2

13 Claims, 2 Drawing Sheets

(56) References Cited

FOREIGN PATENT DOCUMENTS

| | | | | |
|---|---|---|---|---|
| CN | 107459466 A | | 12/2017 | |
| CN | 109574925 A | | 4/2019 | |
| CN | 110128279 A | | 8/2019 | |
| CN | 110467536 A | | 11/2019 | |
| CN | 111995533 A | * | 11/2020 | ........... C07C 211/54 |
| KR | 20190041938 A | | 4/2019 | |
| KR | 1020190035567 A | | 4/2019 | |
| KR | 1020190041938 A | | 4/2019 | |
| KR | 1020190118515 A | | 10/2019 | |
| KR | 1020200037732 A | | 4/2020 | |
| WO | 2018164265 A | | 9/2018 | |
| WO | 2018164265 A1 | | 9/2018 | |
| WO | 2020050623 A1 | | 3/2020 | |
| WO | 2020060271 A1 | | 3/2020 | |
| WO | WO-2020050623 A1 | * | 3/2020 | ........... C07C 211/61 |
| WO | 2020080849 A1 | | 4/2020 | |

OTHER PUBLICATIONS

International Search Report from corresponding International Application No. PCT/CN2020/094957, dated Aug. 14, 2020, 4 pages.
Partial European Search Report dated Aug. 13, 2020 for Application Serial No. EP20174234 (4 pages).
Chen, et al. "Synthesis and Characterization of spiro(adamantane-2,9'-fluorene)-based triaryldiamines: Thermally Stable Hole-Transporting Materials," Department of Applied Chemistry, National Chiao Tung University, Hsin-Chu 30035, Taiwan, Synthetic Metials, vol. 143 pp. 215-220 (2004) (6 pages).

* cited by examiner

NITROGEN-CONTAINING COMPOUND, ELECTRONIC COMPONENT AND ELECTRONIC DEVICE

CROSS-REFERENCE

The present application claims the priority of the Chinese Invention Application CN201910515733.1 filed on Jun. 14, 2019, the Chinese Invention Application CN202010192954.2 filed on Mar. 18, 2020, and the Chinese Invention Application CN202010432540.2 filed on May 20, 2020, the entirety of which are incorporated herein by reference.

TECHNICAL FIELD

The present application relates to the technical field of organic material, in particular to a nitrogen-containing compound, an electronic component comprising the nitrogen-containing compound, and an electronic device comprising such electronic component.

BACKGROUND

With the development of electronic technology and the progress of material science, the application scope of electronic components used to realize electroluminescent or photoelectric conversion becomes wider. These electronic components usually comprise a cathode and an anode arranged oppositely, and a functional layer arranged therebetween. This functional layer consists of multiple layers of organic or inorganic films, and generally comprises an energy conversion layer, a hole transport layer between the energy conversion layer and the anode, and an electron transport layer between the energy conversion layer and the cathode.

For example, when the electronic component is an organic electroluminescent device, it generally comprises an anode, a hole transport layer, an electroluminescent layer as the energy conversion layer, an electron transport layer, and a cathode that are stacked in turn. When the cathode and anode are applied with a voltage, the two electrodes generate an electric field. Under the effect of the electric field, the electrons on the cathode side move towards the electroluminescent layer, the holes on the anode side also move towards the luminescent layer, so that the electrons and the holes combine in the electroluminescent layer to form excitons, which in the excited state release energy outside to make the electroluminescent layer emit light.

As the molecular weight of the organic hole transport materials reported at present is comparatively small, such as those disclosed in CN109574925A, CN103108859A, KR1020190041938A, and WO2018164265A1, the glass-transition temperature of these materials is relatively low. During the use of the materials, due to repeated charging and discharging, the material is easy to crystallize and the uniformity of the film is destroyed, which affects the service life of the materials. Therefore, it is of important practical application value to develop stable and efficient organic hole transport materials to reduce the driving voltage, improve the luminous efficiency of the device, and extend the life of the device.

The foresaid information disclosed in background section is only intended to strengthen the understanding of the background of the application, and therefore it may include information that does not constitute the prior art known to those of ordinary skill in the art.

CONTENTS OF INVENTION

The object of the present application to provide a nitrogen-containing compound, an electronic component, and an electronic device, in which the nitrogen-containing compound can improve the performance of the electronic component and the electronic device.

In order to achieve the above-mentioned object of the invention, the present application adopts the following technical solutions.

According to the first aspect of the present application, there is provided a nitrogen-containing compound represented by the Formula 1:

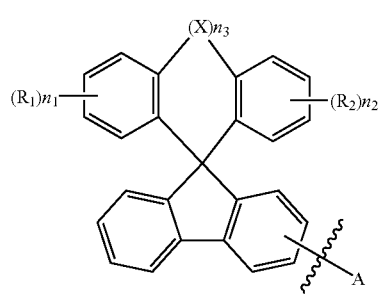

Formula 1

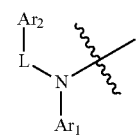

Formula 2

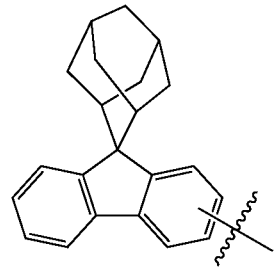

Formula 3 wherein ⁂ represents a chemical bond:

A is a group represented by the Formula 2:

X is $C(R_3R_4)$, and $R_3$ and $R_4$ are each independently selected from hydrogen, alkyl with 1-10 carbon atoms;

$R_1$ and $R_2$ are identical or different, and are each independently selected from hydrogen, alkyl with 1-10 carbon atoms, aryl with 6-20 carbon atoms, and heteroaryl with 3-20 carbon atoms;

$n_1$ is selected from 1, 2, 3, or 4, and when $n_1$ is greater than or equal to 2, any two $R_1$ are identical or different;

$n_2$ is selected from 1, 2, 3, or 4, and when $n_2$ is greater than or equal to 2, any two $R_2$ are identical or different;

$n_3$ is selected from 0, 1, or 2, and when $n_3$ is greater than or equal to 2, any two $R_3$ are identical or different and any two $R_4$ are identical or different;

L is selected from single-bond, substituted or unsubstituted arylidene with 6-20 carbon atoms, and substituted or unsubstituted heteroarylidene with 3-30 carbon atoms;

$Ar_1$ is selected from substituted or unsubstituted aryl with 6-30 carbon atoms, and substituted or unsubstituted heteroaryl with 3-30 carbon atoms;

$Ar_2$ is a group represented by the Formula 3; and wherein the substituents in the L and $Ar_1$ are each independently selected from deuterium, halogen, cyano, heteroaryl with 3-18 carbon atoms, aryl with 6-18 carbon atoms, halogenated aryl with 6-20 carbon atoms, trialkylsilyl with 3-12 carbon atoms, aryl silicyl with 8-12 carbon atoms, alkyl with 1-10 carbon atoms, halogenated alkyl with 1-10 carbon atoms, alkenyl with 2-6 carbon atoms, alkynyl with 2-6 carbon atoms, cycloalkyl with 3-10 carbon atoms, heterocycloalkyl with 2-10 carbon atoms, cycloalkenyl with 5-10 carbon atoms, heterocycloalkenyl with 4-10 carbon atoms, alkoxy with 1-10 carbon atoms, alkylthio with 1-10 carbon atoms, aryloxy with 6-18 carbon atoms, arylthio with 6-18 carbon atoms, and phosphonoxy with 6-18 carbon atoms.

The nitrogen-containing compound provided in the present application is a Spiro compound. By introducing the arylamine group with a strong electron donating ability to the Spiro system with a large conjugated structure with good luminescence properties, the Spiro structure is endowed with rigid plane structure and high luminous quantum efficiency, which can improve the heat stability, film stability, carrier mobility stability, and intersolubility of the material. One of the substituents of arylamine must be adamantane fluorene group which has a proper molecular weight and steric-hinerance effect to effectively improve the glass-transition temperature of the material, the adamantyl in the fluorenyl has a great space volume and a comparatively strong rigidness.

The nitrogen-containing compound provided in the present application can reduce the interaction force between the large planar conjugated structures, decrease the π-π stacking between molecules, and adjust the stacking degree between molecules, so as to avoid the nitrogen-containing compound from crystallization or aggregation during film formation. In this way, the material can have more and more stable amorphous state, so that the material has the advantages of low voltage, high efficiency, and long life in the device.

According to the second aspect of the present application, there is provided an electronic component comprising an anode and a cathode arranged oppositely and a functional layer arranged therebetween, the functional layer comprising foresaid nitrogen-containing compound. According to an embodiment of the present application, the electronic component is an organic electroluminescent device. According to another embodiment of the present application, the electronic component is a solar cell.

According to the third aspect of the present application, there is provided an electronic device comprising foresaid electronic component.

DESCRIPTION OF FIGURES

The above and other features and advantages of the present invention will become more apparent to those of ordinary skill in the art by describing exemplary embodiments thereof in detail with reference to the accompanying drawings, in which.

Figure 1:
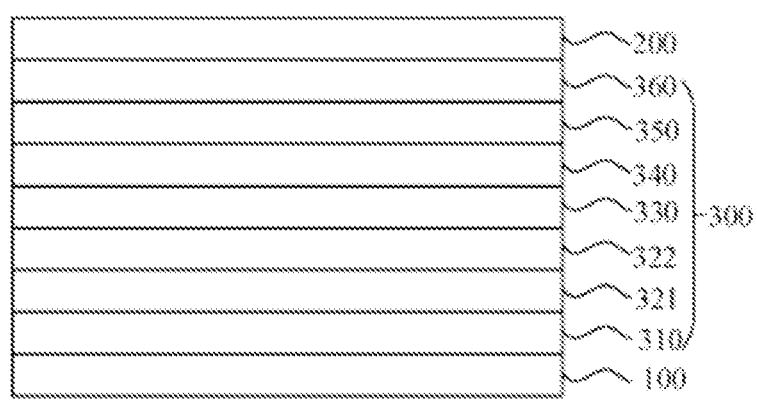
FIG. 1 is a schematic structural diagram of an organic electroluminescent device according to an embodiment of the present application.

The marks of the attached figure of major components are described as follows:

100 anode; 200 cathode; 300 functional layer; 310 hole injection layer; 321 hole transport layer; 322 hole adjustment layer; 330 organic electroluminescent layer; 340 hole blocking layer; 350 electron transport layer; 360 electron injection layer; 370 photoelectric conversion layer; 400 the first electronic device; 500 the second electronic device.

DETAILED DESCRIPTION OF THE DISCLOSURE

The sample examples are hereby described more comprehensively by reference to the attached figures. However, the sample examples can be implemented in various forms, and should not be understood to be limited to the examples stated here; on the contrary, these examples provided make the present application more comprehensive and complete, and pass on the conception of the sample examples to the technicians in this field in a more comprehensive way. The described features, structures or properties described can be combined in one or more examples in any proper way. In the description below, many specific details are provided for the full understanding of the examples of the present application.

In the figures, the thickness of area and layer may be exaggerated for clarity. The same marks in the figure mean identical or similar structures so that the detailed description is omitted.

The described features, structures or properties described can be combined in an or more examples in any proper way. In the description below, many specific details are provided for the full understanding of the examples of the present application. However, the technicians in this field will realize that they can practice the technical solution of the present application without one or more of the specific details, or adopt other methods, components, materials, etc. In other cases, no detailed presentation or description of known structure, material, or operation is provided to avoid blurring the main technical idea of the present application.

The present application provides a nitrogen-containing compound represented by the Formula 1:

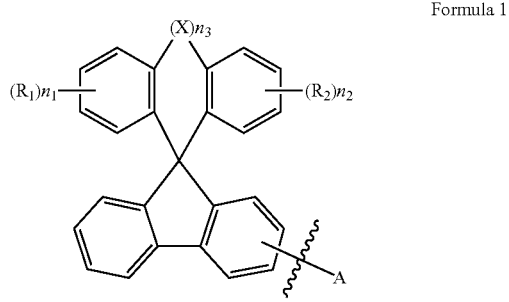

Formula 1

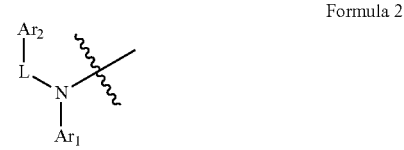

Formula 2

-continued

Formula 3

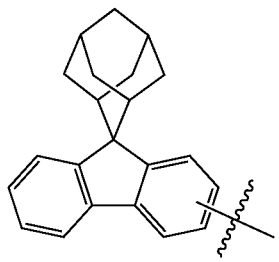

wherein ⸸ represents a chemical bond:

A is a group represented by the Formula 2:

X is C(R$_3$R$_4$), and R$_3$ and R$_4$ are each independently selected from hydrogen, alkyl with 1-10 carbon atoms;

R$_1$ and R$_2$ are identical or different, and are each independently selected from hydrogen, alkyl with 1-10 carbon atoms, the aryl with 6-20 carbon atoms, and heteroaryl with 3-20 carbon atoms;

n$_1$ is selected from 1, 2, 3, or 4, and when n$_1$ is greater than or equal to 2, any two R$_1$ are identical or different;

n$_2$ is selected from 1, 2, 3, or 4, and when n$_2$ is greater than or equal to 2, any two R$_2$ are identical or different;

n$_3$ is selected from 0, 1, or 2, and when n$_3$ is greater than or equal to 2, any two R$_3$ are identical or different and any two R$_4$ are identical or different;

L is selected from single-bond, substituted or unsubstituted arylidene with 6-20 carbon atoms, and substituted or unsubstituted heteroarylidene with 3-30 carbon atoms;

Ar$_1$ is selected from substituted or unsubstituted aryl with 6-30 carbon atoms, and substituted or unsubstituted heteroaryl with 3-30 carbon atoms;

Ar$_2$ is a group represented by the Formula 3; and wherein the substituents in the L and Ar$_1$ are each independently from deuterium, halogen, cyano, heteroaryl with 3-18 carbon atoms, aryl with 6-18 carbon atoms, halogenated aryl with 6-20 carbon atoms, trialkylsilyl with 3-12 carbon atoms, arylsilyl with 8-12 carbon atoms, alkyl with 1-10 carbon atoms, halogenated alkyl with 1-10 carbon atoms, alkenyl with 2-6 carbon atoms, alkynyl with 2-6 carbon atoms, cycloalkyl with 3-10 carbon atoms, heterocycloalkyl with 2-10 carbon atoms, cycloalkenyl with 5-10 carbon atoms, heterocycloalkenyl with 4-10 carbon atoms, alkoxy with 1-10 carbon atoms, alkylthio with 1-10 carbon atoms, aryloxy with 6-18 carbon atoms, arylthio with 6-18 carbon atoms, and phosphonoxy with 6-18 carbon atoms.

In the present application, as for the

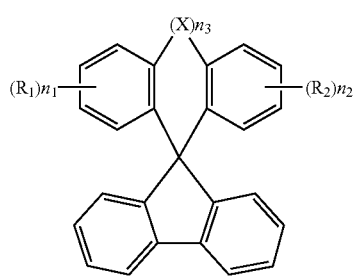

in the Formula 1 ("Structure a" for short), when n$_3$ is equal to 0, it means that X does not exist, i.e., the Structure a is

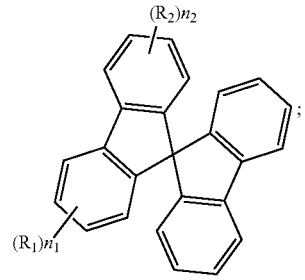

when n$_3$ is equal to 1, the Structure a is

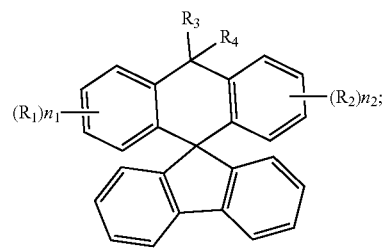

when n$_3$ is equal to 2, and both R$_3$ and R$_4$ are H, the Structure a is

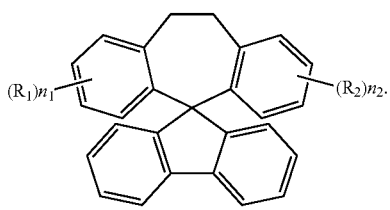

In the present application, as the adamantane is of a stereochemical structure, in the structure diagram of the compound, different plane shapes will be presented because of different drawing angles. The ring structures formed on 9, 9-dimethyl fluorene are all adamantane, and the connection positions are identical. For example, the following structures are of the same:

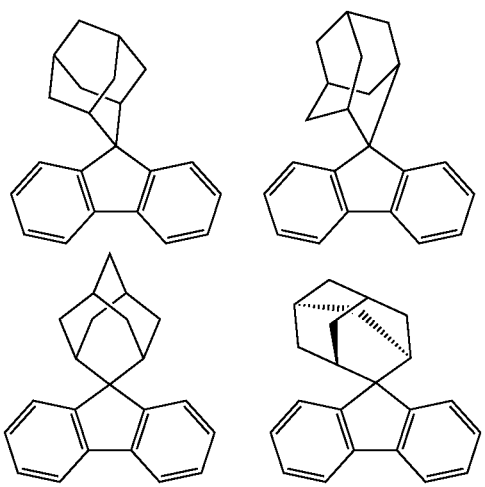

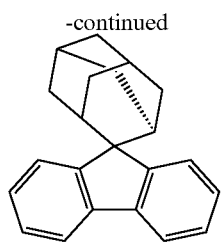

The nitrogen-containing compound provided in the present application is a spiro compound. By introducing the arylamine group with a strong electron donating ability to the Spiro system with a large conjugated structure with good luminescence properties, the Spiro structure is endowed with rigid planar structure and high luminous quantum efficiency, which can improve the heat stability, film stability, carrier mobility stability, and intersolubility of the material. One of the substituents of arylamine must be adamantane fluorene group which has a proper molecular weight and steric-hinerance effect to effectively improve the glass-transition temperature of the material, the adamantyl in the fluorenyl has a great space volume and a comparatively strong rigidity.

The nitrogen-containing compound provided in the present application can reduce the interaction force between the large planner conjugated structures, decrease the π-π stacking between molecules, and adjust the stacking degree between molecules, so as to avoid the nitrogen-containing compound from crystallization or aggregation during film formation. In this way, the material can have more and more stable amorphous state, so that the material has the advantages of low voltage, high efficiency, and long life in the device.

In the present application, the terms " . . . is independently" and " . . . is are each independently" and " . . . is independently selected from" may be used interchangeably and should be interpreted broadly. It can mean that in different groups, the specific options expressed by the same symbol do not affect each other, or that in the same group, the specific options expressed by the same symbol do not affect each other. For example, formula Q-1 formula Q-2

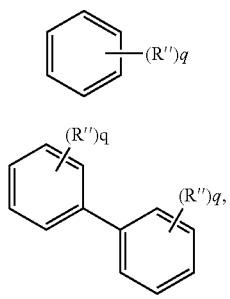

wherein each q is independently 0, 1, 2, or 3, and each R" is independently selected from hydrogen, deuterium, fluorine, or chlorine". Formula Q-1 means that there are q substituent(s) R" on the benzene ring, each R" can be identical or different, and the options of each R" do not affect each other; Formula Q-2 means that there are q substituent(s) R" on every benzene ring of biphenyl, the number q of the R" substituents on two benzene rings can be identical or different, each R" can be identical or different, and the options of each R" do not affect each other.

In the present application, the number of carbon atoms in L, $Ar_1$, and $R_1$ to $R_4$ refers to the number of all carbon atoms. For example, if L is selected from the substituted arylidene with 12 carbon atoms, the number of all the carbon atoms of arylidene and its substituent is 12. For example, $Ar_1$ is

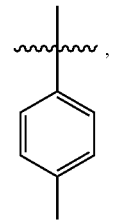

and its number of carbon atoms is 7; L is

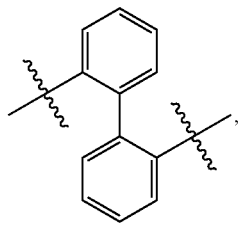 [SMILES: *c1ccccc1-c1ccccc1*]

and its number of carbon atoms is 12.

In the present application, the substituted L and $Ar_1$ consist of basic groups and the substituents connected thereto. The substituents of L and $Ar_1$ refer to those that are connected to the basic groups. For example, in $Ar_1$, the heteroaryl substituted aryl is

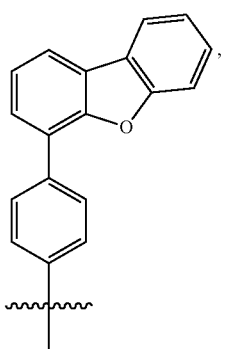 [SMILES: *c1ccc(-c2cccc3c2oc2ccccc23)cc1]

in which phenyl is the basic group of aryl, and dibenzofuran is the substituent. The number of carbon atoms of $Ar_1$ is 18.

In the present application, when $R_1$, $R_2$, $R_3$, or $R_4$ is not H, all the groups shown are unsubstituted.

In the present application, when no specific definition is provided otherwise, "hetero" means that a functional group at least comprises one heteroatom such as B, N, O, S, or P, with remaining atoms being carbon and hydrogen. The unsubstituted alkyl may be a saturated alkyl without any double bond or triple bond.

In the present application, "alkyl" may comprise linear alkyl or branched alkyl. The alkyl may have 1 to 10 carbon atoms. In the present application, the numerical range from "1 to 10" refers to every integer within the given range. For example, "1 to 10 carbon atoms" may refer to the alkyl comprising 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. The alkyl may also be a low-level alkyl with 1 to 6 carbon atoms. Besides, the alkyl may be substituted or unsubstituted.

Optionally, the alkyl is selected from alkyl with 1-6 carbon atoms, and the specific examples may include but are not limited to methyl, ethyl, n-propyl, isopropyl, n-butyl, isobutyl, sec-butyl, tert-butyl, pentyl, and hexyl.

In the present application, the aryl refers to any functional group or substituent derived from arene ring. The aryl may be monocyclic aryl or polycyclic aryl. In other words, the aryl may be monocyclic aryl, fused-ring aryl, two or more monocyclic aryl conjugated by carbon-carbon bonds, monocyclic aryl and fused-ring aryl conjugated by carbon-carbon bonds, and two or more fused-ring aryl conjugated by carbon-carbon bonds. That is, two or more aromatic groups conjugated by carbon-carbon bonds may also be regarded as aryl in the present application. Among them, the aryl does not comprise the heteroatoms such as B, N, O, S, or P. For example, in the present application, phenyl, biphenyl, terphenyl, and the like are aryl. The examples of aryl may comprise, but not limited to, phenyl, naphthyl, fluorenyl, anthryl, phenanthryl, biphenyl, terphenyl, quaterphenyl, quinquephenyl, benzo[9, 10]phenanthryl, pyrenyl, benzofluoranthrene group, chrysene group, etc. The "aryl" in the present application may comprise 6 to 30 carbon atoms. In some examples, the number of carbon atoms in the aryl may vary from 6 to 25, the number of carbon atoms in the aryl in some other examples may vary from 6 to 18, and the number of carbon atoms in the aryl in some other examples may vary from 6 to 13. For example, the number of carbon atoms in the aryl may be 6, 12, 13, 18, 20, 25, or 30. Of course, the number of carbon atoms may be other numbers, which will not be listed here.

In the present application, the substituted aryl means that one or more hydrogen atoms in the aryl are substituted by other groups. For example, at least one hydrogen atom is substituted by deuterium atom, halogen, cyan, hydroxy, branched alkyl, linear alkyl, cycloalkyl, heterocycloalkyl, aryl, heteroaryl, alkoxy, alkylthio, aryloxy, arylthio, phosphooxy, other groups. It should be understood that the substituted aryl with 18 carbon atoms means that the total number of carbon atoms of aryl and the substituents on the aryl is 18. For example, the number of carbon atoms of 2,3-dimethyl-6-phenyl is 18, and the number of carbon atoms of both 9,9-diphenyl fluorenyl and spiro-2-fluorenyl is 25. Among them, the biphenyl may be interpreted as aryl or substituted phenyl.

In the present application, the heteroaryl may be the heteroaryl comprising at least one of B, O, N, P, Si, and S as the heteroatom. The heteroaryl may be monocyclic heteroaryl or polycyclic heteroaryl. In other words, the heteroaryl may be can be a single aromatic ring system or polycyclic aromatic ring systems conjugated through carbon-carbon bonds, and any aromatic ring system is an aromatic monocyclic ring or an aromatic fused ring. For example, the heteroaryl may comprise, but not limited to, thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, dibenzofuranyl substituted phenyl, etc. Among them, thienyl, furanyl, phenanthrolinyl, etc. are the heteroaryl of one single aromatic ring system, and N-arylcarbazolyl, N-heteroarylcarbazolyl, and the like are the heteroaryl of multiple aromatic ring systems connected by carbon-carbon bond.

In the present application, the substituted heteroaryl means that one or more hydrogen atoms in the heteroaryl are substituted by other groups. For example, at least one hydrogen atom is substituted by deuterium atom, halogen, cyano, alkyl, haloalkyl, cycloalkyl, heterocycloalkyl, aryl, alkoxy, alkylthio, aryloxy, arylthio, silylation, triarylmethane, phosphono, or other groups.

In the present application, the interpretation of aryl may be applied to arylidene, and the interpretation of heteroaryl may also be applied to heteroarylidene.

In the present application, the halogen may be F, Cl, Br, and I.

These characteristics of nitrogen-containing compound in the present application allow it to be used in the preparation of organic electroluminescent device and photoelectric conversion device, especially suitable for preparing the hole transport layer or hole adjustment layer (also called hole auxiliary layer, or second hole transport layer, etc.) of the organic electroluminescent device and photoelectric conversion device, so as to improve the efficiency and life of the organic electroluminescent device and photoelectric conversion device, reduce the working voltage of the organic electroluminescent device, increase the open-circuit voltage of the photoelectric conversion device, and improve the volume production stability of the photoelectric conversion device and organic electroluminescent device.

According to one embodiment, the nitrogen-containing compound is selected from a group consisting of the following formulas:

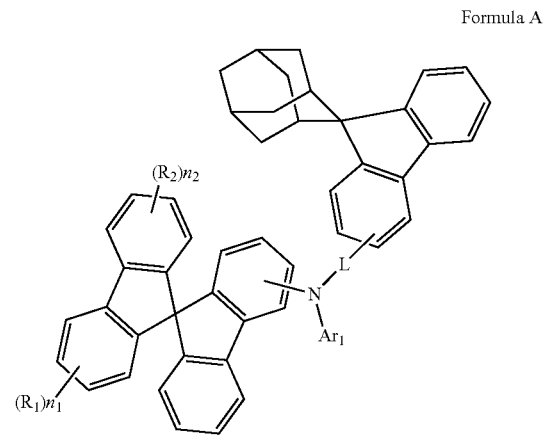

Formula A

Formula B

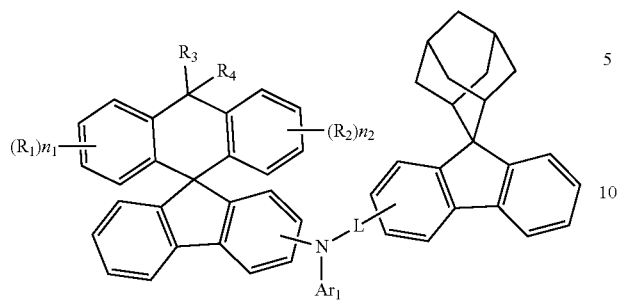

Formula C

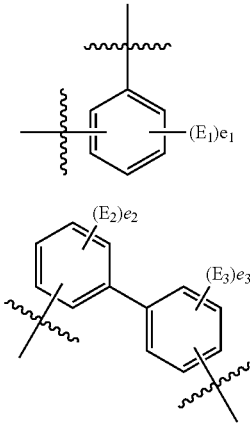

Optionally, $R_1$ and $R_2$ are identical or different, and are each independently selected from hydrogen, alkyl with 1-6 carbon atoms, and the aryl with 6-12 carbon atoms.

Optionally, $R_1$ and $R_2$ are identical or different, and are each independently selected from hydrogen, methyl, ethyl, n-propyl, tert-butyl, phenyl, biphenyl, naphthyl, and isopropyl.

Optionally, L is selected from single bond, substituted or unsubstituted arylidene with 6-18 carbon atoms. Further optionally, L is selected from single bond, substituted or unsubstituted arylidene with 6-15 carbon atoms. More optionally, L is selected from single bond, substituted or unsubstituted arylidene with 6-12 carbon atoms.

Optionally, L is selected from single-bond substituted or unsubstituted phenylene, substituted or unsubstituted biphenylene, substituted or unsubstituted naphthylene, and substituted or unsubstituted 9,9 dimethyl fluorenylene.

Optionally, the substituent in L is selected from deuterium, halogen, cyano, alkyl with 1-4 carbon atoms, cycloalkyl with 3-10 carbon atoms, and aryl with 6-12 carbon atoms. Specifically, the substituent in L is selected from deuterium, fluorine, cyano, methyl, ethyl, n-propyl, tert-butyl, phenyl, naphthyl, biphenyl, cyclohexane, cyclopentyl, adamantyl, and isopropyl.

In some embodiments, L is selected from the group consisting of single bonds or groups represented by formula j-1 to j-6:

Formula j-1

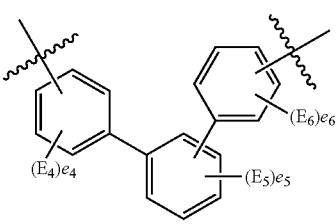

Formula j-2

Formula j-3

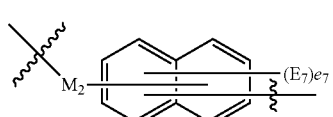

Formula j-4

Formula j-5

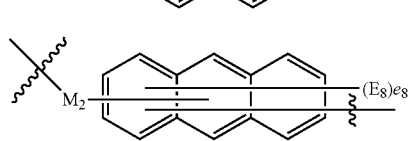

Formula j-6

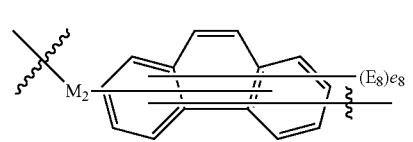

wherein $M_2$ is selected from single bond or

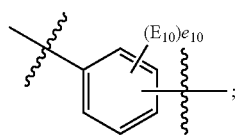

$E_1$~$E_{10}$ are each independently selected from deuterium, halogen, cyano, trialkylsilyl with 3-12 carbon atoms, arylsilyl with 8-12 carbon atoms, alkyl 1-10 carbon atoms, halogenated alkyl with 1-10 carbon atoms, alkenyl with 2-6 carbon atoms, alkynyl with 2-6 carbon atoms, cycloalkyl with 3-10 carbon atoms, heterocycloalkyl with 2-10 carbon atoms, cycloalkenyl with 5-10 carbon atoms, heterocycloalkenyl with 4-10 carbon atoms, alkoxy with 1-10 carbon atoms, the alkylthio with 1-10 carbon atoms, aryloxy with 6-18 carbon atoms, arylthio with 6-18 carbon atoms, phosphonoxy with 6-18 carbon atoms, heteroaryl with 3-18 carbon atoms, and aryl with 6-18 carbon atoms;

$e_r$ is the number of the substituent $E_r$, and r is any integer from 1 to 10; when r is selected from 1, 2, 3, 4, 5, and 6, $e_r$ is selected from 0, 1, 2, 3, or 4; when r is 7, e$_r$ is selected from 0, 1, 2, 3, 4, 5, or 6; when r is 10, e$_r$ is selected from 0, 1, 2, 3, or 4; when r is selected from 8 or 9, e$_r$ is selected from 0, 1, 2, 3, 4, 5, 6, 7, or 8; when e$_r$ is greater than 1, any two E$_r$ are identical or different.

Optionally, L is selected from a group consisting of single bonds or groups represented by the following groups:

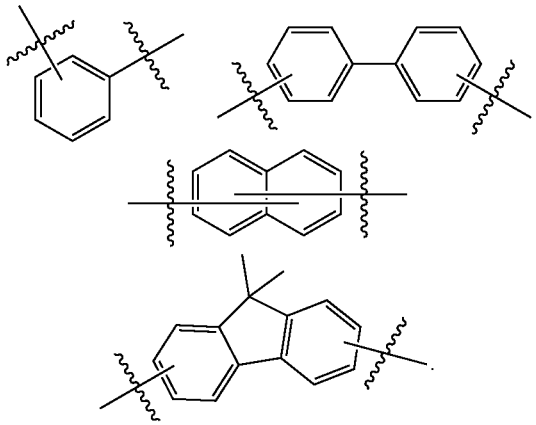

Preferably, L is selected from single bond or

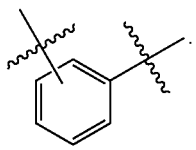

Optionally, L is

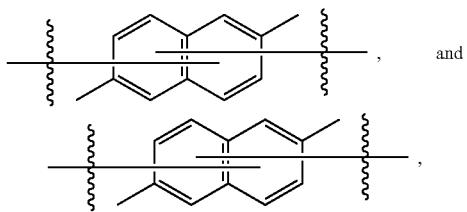, and for example L can be

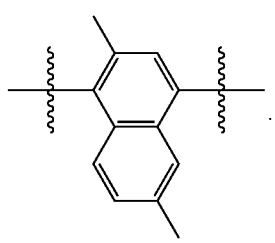 [SMILES: *c1cc(C)c(*)c2ccc(C)cc12]

Optionally, Ar$_1$ is selected from substituted or unsubstituted aryl with 6-20 carbon atoms.

Optionally, the substituent in Ar$_1$ is selected from deuterium, halogen, cyano, alkyl with 1-4 carbon atoms, cycloalkyl with 3-15 carbon atoms, and aryl with 6-12 carbon atoms.

Optionally, the substituent in Ar$_1$ is selected from deuterium, fluorine, cyano, methyl, ethyl, n-propyl, tert-butyl, phenyl, naphthyl, biphenyl, cyclohexane, cyclopentyl, adamantyl, and isopropyl.

In some embodiments, Ar$_1$ is selected from the groups represented by the following chemical formula i-1 to chemical formula i-4;

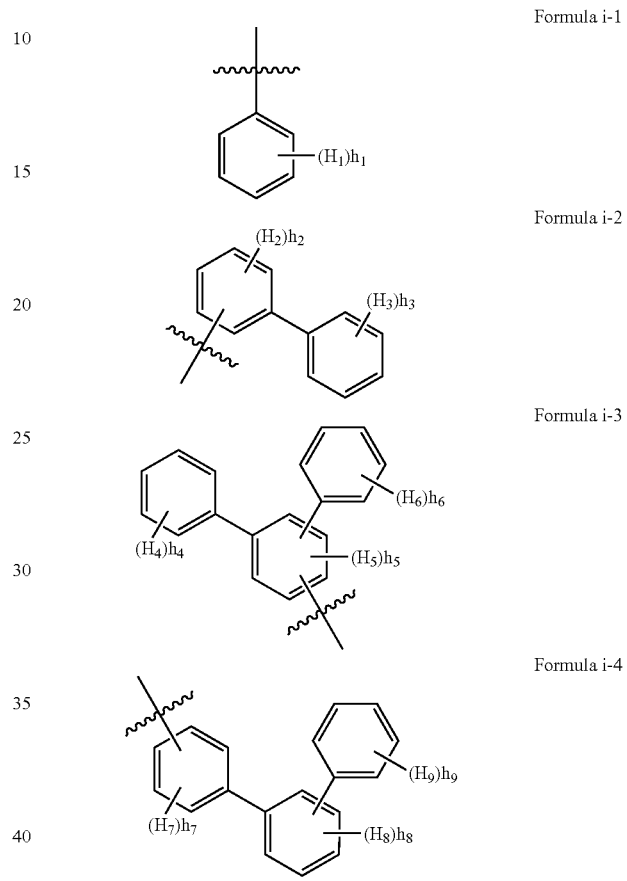

wherein H$_1$~H$_6$ are independently selected from deuterium, halogen, heteroaryl with 3-18 carbon atoms, trialkylsilyl with 3-12 carbon atoms, arylsilyl with 8-12 carbon atoms, alkyl with 1-10 carbon atoms, halogenated alkyl with 1-10 carbon atoms, alkenyl with 2-6 carbon atoms, alkynyl with 2-6 carbon atoms, cycloalkyl with 3-10 carbon atoms, heterocycloalkyl with 2-10 carbon atoms, cycloalkenyl with 5-10 carbon atoms, heterocycloalkenyl with 4-10 carbon atoms, alkoxy with 1-10 carbon atoms, alkylthio with 1-10 carbon atoms, aryloxy with 6-18 carbon atoms, arylthio with 6-18 carbon atoms, and phosphonoxy with 6-18 carbon atoms;

H$_7$~H$_9$ are independently selected from deuterium, halogen, heteroaryl with 3-18 carbon atoms, trialkylsilyl with 3-12 carbon atoms, arylsilyl with 8-12 carbon atoms, alkyl with 1-10 carbon atoms, halogenated alkyl with 1-10 carbon atoms, alkenyl with 2-6 carbon atoms, alkynyl with 2-6 carbon atoms, cycloalkyl with 3-10 carbon atoms, heterocycloalkyl with 2-10 carbon atoms, cycloalkenyl with 5-10 carbon atoms, heterocycloalkenyl with 4-10 carbon atoms, alkoxy with 1-10 carbon atoms, alkylthio with 1-10 carbon atoms, aryloxy with 6-18 carbon atoms, arylthio with 6-18 carbon atoms, phosphonoxy with 6-18 carbon atoms, and the aryl with 6-12 carbon atoms;

h$_k$ is the number of the substituent H$_k$, and k is any integer from 1 to 9; when k is 5, h$_k$ is selected from 0, 1, 2, or 3;

when k is selected from 2, 7, or 8, $h_k$ is selected from 0, 1, 2, 3, or 4; when k is selected from 1, 3, 4, 6, or 9, $h_k$ is selected from 0, 1, 2, 3, 4, or 5; when $h_k$ is greater than 1, any two $H_k$ are identical or different.

In a special embodiment, $Ar_1$ is selected from the following group

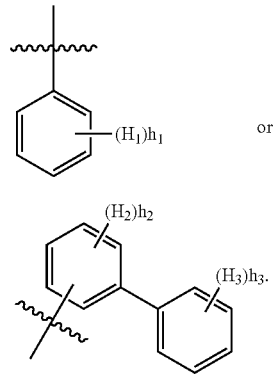

Optionally, $Ar_1$ is selected from a group consisting of the following groups:

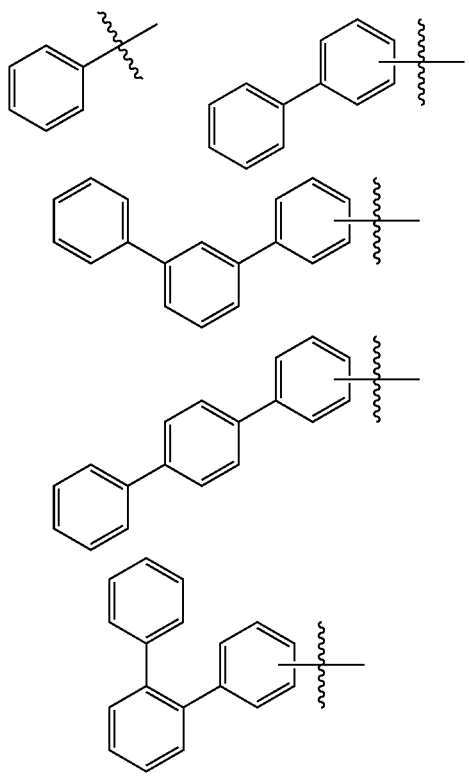

-continued

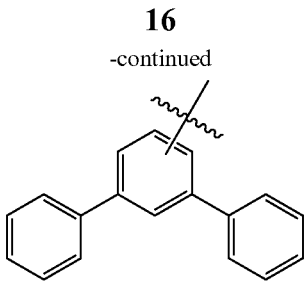

In an embodiment, $Ar_1$ is

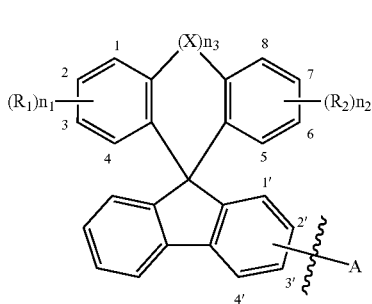

Optionally, the nitrogen-containing compound is selected from a group consisting of the following compounds:

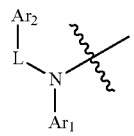

Formula 1

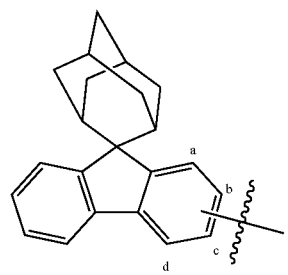

Formula 2

Formula 3

| Compound No. | $n_3$ | Connection position between Formula 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| A-1 | 0 | 2' | b | 4 | H | — | 4 | H | — | I-D | Single bond |

-continued

| Compound No. | $n_3$ | Connection position between Formula 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| A-2  | 0 | 2' | c | 4 | H | — | 4 | H | — | I-D | Single bond |
| A-3  | 0 | 2' | b | 4 | H | — | 4 | H | — | I-D | L-A |
| A-4  | 0 | 2' | b | 4 | H | — | 4 | H | — | I-B | Single bond |
| A-5  | 0 | 2' | b | 4 | H | — | 4 | H | — | I-K | Single bond |
| A-39 | 0 | 1' | b | 4 | H | — | 4 | H | — | I-D | L-G |
| A-40 | 0 | 1' | b | 4 | H | — | 4 | H | — | I-D | Single bond |
| A-41 | 0 | 1' | c | 4 | H | — | 4 | H | — | I-E | Single bond |
| A-48 | 0 | 4' | b | 4 | H | — | 4 | H | — | I-D | Single bond |
| A-49 | 0 | 4' | c | 4 | H | — | 4 | H | — | I-D | Single bond |
| B-3  | 1 | 2' | c | 4 | H | — | 4 | H | — | I-D | Single bond |
| B-4  | 1 | 2' | b | 4 | H | — | 4 | H | — | I-D | Single bond |
| B-5  | 1 | 2' | b | 4 | H | — | 4 | H | — | I-K | Single bond |
| B-26 | 1 | 1' | d | 4 | H | — | 4 | H | — | I-J | Single bond |
| B-27 | 1 | 1' | b | 4 | H | — | 4 | H | — | I-D | Single bond |
| B-28 | 1 | 3' | d | 4 | H | — | 4 | H | — | I-D | Single bond |
| B-29 | 1 | 3' | a | 4 | H | — | 4 | H | — | I-L | Single bond |
| B-34 | 1 | 4' | a | 4 | H | — | 4 | H | — | I-G | Single bond |
| B-35 | 1 | 4' | c | 4 | H | — | 4 | H | — | I-B | Single bond |
| B-36 | 1 | 4' | a | 4 | H | — | 4 | H | — | I-H | L-C |
| C-1  | 2 | 2' | c | 4 | H | — | 4 | H | — | I-D | Single bond |
| C-2  | 2 | 2' | b | 4 | H | — | 4 | H | — | I-D | Single bond |
| C-3  | 2 | 2' | b | 4 | H | — | 4 | H | — | I-D | L-C |
| C-4  | 2 | 2' | b | 4 | H | — | 4 | H | — | I-M | Single bond |
| C-18 | 2 | 1' | d | 4 | H | — | 4 | H | — | I-F | Single bond |
| C-19 | 2 | 3' | c | 4 | H | — | 4 | H | — | I-G | Single bond |
| C-28 | 2 | 4' | a | 4 | H | — | 4 | H | — | I-A | Single bond |
| A-50 | 0 | 3' | b | 4 | H | — | 4 | H | — | I-D | Single bond |
| A-51 | 0 | 3' | c | 4 | H | — | 4 | H | — | I-D | Single bond |
| A-53 | 0 | 2' | b | 4 | H | — | 4 | H | — | I-B | Single bond |
| A-52 | 0 | 2' | b | 1 | tert-butyl | 3 | 1 | tert-butyl | 6 | I-B | Single bond |
| A-6  | 0 | 2' | b | 1 | tert-butyl | 3 | 1 | tert-butyl | 6 | I-D | Single bond |
| A-7  | 0 | 2' | c | 1 | tert-butyl | 3 | 1 | tert-butyl | 6 | I-D | Single bond |
| A-8  | 0 | 2' | c | 1 | tert-butyl | 3 | 1 | tert-butyl | 6 | I-A | Single bond |
| A-9  | 0 | 2' | b | 1 | tert-butyl | 3 | 1 | tert-butyl | 6 | I-D | L-C |
| A-10 | 0 | 2' | c | 1 | tert-butyl | 3 | 1 | tert-butyl | 6 | I-B | Single bond |
| A-11 | 0 | 2' | c | 1 | R-E | 2 | 1 | R-E | 7 | I-A | Single bond |
| A-12 | 0 | 2' | c | 1 | R-E | 2 | 1 | R-E | 7 | I-I | Single bond |
| A-13 | 0 | 2' | d | 1 | R-A | 4 | 1 | tert-butyl | 6 | I-A | Single bond |

-continued

| Compound No. | n₃ | Connection position between Formula 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| A-14 | 0 | 2' | d | 1 | R-A | 4 | 1 | tert-butyl | 6 | I-C | Single bond |
| A-15 | 0 | 2' | c | 1 | R-B | 3 | 1 | R-B | 6 | I-A | Single bond |
| A-16 | 0 | 2' | c | 1 | R-B | 3 | 1 | R-B | 6 | I-B | Single bond |
| A-17 | 0 | 2' | b | 1 | R-B | 3 | 1 | R-B | 6 | I-E | Single bond |
| A-18 | 0 | 2' | a | 1 | R-C | 3 | 1 | Ethyl | 6 | I-A | Single bond |
| A-19 | 0 | 2' | c | 1 | R-C | 3 | 1 | Ethyl | 6 | I-B | Single bond |
| A-20 | 0 | 1' | d | 1 | tert-butyl | 4 | 1 | Ethyl | 6 | I-C | Single bond |
| A-21 | 0 | 1' | d | 1 | tert-butyl | 4 | 1 | Ethyl | 6 | I-J | Single bond |
| A-22 | 0 | 3' | d | 1 | tert-butyl | 4 | 1 | Ethyl | 6 | I-D | Single bond |
| A-23 | 0 | 3' | a | 1 | tert-butyl | 4 | 1 | Ethyl | 6 | I-K | Single bond |
| A-24 | 0 | 1' | c | 1 | R-A | 1 | 1 | R-A | 8 | I-F | Single bond |
| A-25 | 0 | 1' | b | 1 | R-A | 1 | 1 | R-A | 8 | I-D | L-I |
| A-26 | 0 | 3' | b | 1 | R-A | 1 | 1 | R-A | 8 | I-M | Single bond |
| A-27 | 0 | 3' | d | 1 | R-A | 1 | 1 | R-A | 8 | I-K | Single bond |
| A-28 | 0 | 4' | a | 1 | Methyl | 2 | 1 | Methyl | 6 | I-H | Single bond |
| A-29 | 0 | 4' | b | 1 | Methyl | 2 | 1 | Methyl | 6 | I-D | Single bond |
| A-30 | 0 | 4' | d | 1 | Methyl | 2 | 1 | Methyl | 6 | I-C | Single bond |
| A-31 | 0 | 4' | a | 1 | R-D | 4 | 1 | R-D | 5 | I-A | Single bond |
| A-32 | 0 | 4' | d | 1 | R-D | 4 | 1 | R-D | 5 | I-J | Single bond |
| A-44 | 0 | 4' | a | 1 | R-A | 3 | 1 | R-A | 6 | I-G | Single bond |
| A-45 | 0 | 4' | b | 1 | R-A | 3 | 1 | R-A | 6 | I-L | Single bond |
| B-8 | 1 | 2' | b | 1 | tert-butyl | 3 | 1 | tert-butyl | 6 | I-H | Single bond |
| B-9 | 1 | 2' | c | 1 | tert-butyl | 3 | 1 | tert-butyl | 6 | I-K | L-B |
| B-10 | 1 | 2' | b | 1 | Methyl | 2 | 1 | Methyl | 7 | I-C | Single bond |
| B-11 | 1 | 2' | b | 1 | Methyl | 2 | 1 | Methyl | 7 | I-E | Single bond |
| B-12 | 1 | 2' | b | 1 | R-C | 3 | 1 | R-C | 7 | I-F | Single bond |
| B-13 | 1 | 2' | b | 1 | R-C | 3 | 1 | R-C | 7 | I-G | Single bond |
| B-14 | 1 | 2' | d | 1 | R-F | 4 | 1 | R-F | 5 | I-K | Single bond |
| B-15 | 1 | 2' | d | 1 | R-F | 4 | 1 | R-F | 5 | I-M | Single bond |
| B-16 | 1 | 2' | c | 1 | R-B | 2 | 1 | R-B | 7 | I-F | L-E |
| B-17 | 1 | 2' | b | 1 | R-B | 2 | 1 | R-B | 7 | I-G | Single bond |
| B-18 | 1 | 1' | a | 1 | R-A | 2 | 1 | R-A | 7 | I-K | Single bond |
| B-19 | 1 | 1' | b | 1 | R-A | 2 | 1 | R-A | 7 | I-F | Single bond |
| B-20 | 1 | 3' | d | 1 | R-A | 2 | 1 | R-A | 7 | I-F | Single bond |
| B-21 | 1 | 3' | d | 1 | R-A | 2 | 1 | R-A | 7 | I-E | Single bond |
| B-22 | 1 | 1' | b | 1 | tert-butyl | 3 | 1 | tert-butyl | 6 | I-J | Single bond |
| B-23 | 1 | 1' | a | 1 | tert-butyl | 3 | 1 | tert-butyl | 6 | I-L | Single bond |

-continued

| Compound No. | n₃ | Connection position between Formula 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| B-24 | 1 | 3' | c | 1 | tert-butyl | 3 | 1 | tert-butyl | 6 | I-H | Single bond |
| B-25 | 1 | 3' | a | 1 | tert-butyl | 3 | 1 | tert-butyl | 6 | I-K | Single bond |
| B-30 | 1 | 4' | d | 1 | Methyl | 2 | 1 | Methyl | 7 | I-L | Single bond |
| B-31 | 1 | 4' | d | 1 | Methyl | 2 | 1 | Methyl | 7 | I-A | Single bond |
| C-9 | 2 | 2' | d | 1 | tert-butyl | 2 | 1 | tert-butyl | 7 | I-H | Single bond |
| C-10 | 2 | 2' | a | 1 | tert-butyl | 2 | 1 | tert-butyl | 7 | I-J | Single bond |
| C-11 | 2 | 3' | a | 1 | R-A | 3 | 1 | R-A | 6 | I-B | L-G |
| C-12 | 2 | 2' | b | 1 | R-A | 3 | 1 | R-A | 6 | I-H | Single bond |
| C-13 | 2 | 2' | a | 1 | R-C | 1 | 1 | R-C | 8 | I-H | Single bond |
| C-14 | 2 | 2' | b | 1 | R-C | 1 | 1 | R-C | 8 | I-E | Single bond |
| C-16 | 2 | 2' | b | 1 | Methyl | 2 | 1 | Methyl | 7 | I-K | Single bond |
| C-22 | 2 | 1' | a | 1 | Methyl | 2 | 1 | Isopropyl | 7 | I-K | Single bond |
| C-23 | 2 | 3' | a | 1 | Methyl | 2 | 1 | Isopropyl | 7 | I-I | Single bond |
| C-24 | 2 | 4' | c | 1 | Methyl | 3 | 1 | Methyl | 6 | I-F | Single bond |
| C-25 | 2 | 4' | b | 1 | R-E | 3 | 1 | R-E | 6 | I-J | Single bond |
| C-26 | 2 | 4' | d | 1 | R-B | 3 | 1 | R-B | 8 | I-D | Single bond |
| C-29 | 2 | 2' | d | 1 | Methyl | 2 | 1 | Methyl | 7 | I-C | L-A |
| C-30 | 2 | 2' | d | 1 | tert-butyl | 2 | 1 | tert-butyl | 7 | I-G | L-F |
| A-42 | 0 | 4' | d | 4 | H | — | 1 | R-C | 6 | I-K | Single bond |
| A-43 | 0 | 4' | b | 4 | H | — | 1 | R-C | 6 | I-F | Single bond |
| B-1 | 1 | 2' | a | 4 | H | — | 1 | R-A | 7 | I-I | Single bond |
| B-32 | 1 | 4' | d | 4 | H | — | 1 | R-A | 7 | I-C | Single bond |
| B-33 | 1 | 4' | b | 4 | H | — | 1 | R-A | 7 | I-H | Single bond |
| C-5 | 2 | 2' | b | 4 | H | — | 1 | R-D | 7 | I-M | Single bond |
| C-6 | 2 | 2' | a | 4 | H | — | 1 | R-D | 7 | I-D | Single bond |
| C-7 | 2 | 2' | c | 4 | H | — | 1 | R-E | 6 | I-E | Single bond |
| C-8 | 2 | 2' | b | 4 | H | — | 1 | R-E | 6 | I-G | Single bond |
| C-15 | 2 | 2' | a | 4 | H | — | 1 | R-A | 7 | I-K | Single bond |
| C-17 | 2 | 2' | b | 4 | H | — | 1 | Methyl | 7 | I-I | Single bond |
| C-20 | 2 | 2' | b | 4 | H | — | 1 | tert-butyl | 6 | I-F | Single bond |
| C-21 | 2 | 3' | a | 4 | H | — | 1 | tert-butyl | 6 | I-H | Single bond |
| C-27 | 2 | 4' | c | 4 | H | — | 1 | Ethyl | 7 | I-D | Single bond |
| A-33 | 0 | 4' | a | 1 | R-E | 1 | 4 | H | — | I-D | Single bond |
| A-34 | 0 | 4' | d | 1 | R-E | 1 | 4 | H | — | I-E | Single bond |
| A-35 | 0 | 4' | c | 1 | R-F | 3 | 4 | H | — | I-D | Single bond |
| A-36 | 0 | 4' | b | 1 | R-F | 3 | 4 | H | — | I-J | Single bond |
| A-37 | 0 | 1' | c | 1 | R-A | 3 | 4 | H | — | I-D | Single bond |

-continued

| Compound No. | $n_3$ | Connection position between Formula 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| A-38 | 0 | 1' | b | 1 | R-A | 2 | 4 | H | — | I-I | Single bond |
| A-46 | 0 | 3' | d | 1 | R-A | 2 | 4 | H | — | I-K | Single bond |
| A-47 | 0 | 3' | d | 1 | R-A | 2 | 4 | H | — | I-C | Single bond |
| B-2 | 1 | 2' | b | 1 | R-A | 2 | 4 | H | — | I-A | L-D |
| B-6 | 1 | 2' | c | 1 | R-E | 3 | 4 | H | — | I-K | Single bond |
| B-7 | 1 | 2' | d | 1 | R-E | 3 | 4 | H | — | I-L | Single bond |
| A-54 | 0 | 2' | b | 4 | H | — | 4 | H | — | I-C | Single bond |
| A-55 | 0 | 1' | b | 4 | H | — | 4 | H | — | I-C | Single bond |
| A-56 | 0 | 1' | b | 4 | H | — | 4 | H | — | I-K | Single bond |
| A-57 | 0 | 1' | b | 4 | H | — | 4 | H | — | I-B | Single bond |
| A-58 | 0 | 1' | a | 4 | H | — | 4 | H | — | I-C | Single bond |
| A-59 | 0 | 1' | a | 4 | H | — | 4 | H | — | I-D | Single bond |
| A-60 | 0 | 1' | a | 4 | H | — | 4 | H | — | I-B | Single bond |
| A-61 | 0 | 1' | c | 4 | H | — | 4 | H | — | I-C | Single bond |
| A-62 | 0 | 1' | c | 4 | H | — | 4 | H | — | I-D | Single bond |
| A-63 | 0 | 1' | c | 4 | H | — | 4 | H | — | I-B | Single bond |
| A-64 | 0 | 1' | d | 4 | H | — | 4 | H | — | I-C | Single bond |
| A-65 | 0 | 1' | d | 4 | H | — | 4 | H | — | I-D | Single bond |
| A-66 | 0 | 1' | d | 4 | H | — | 4 | H | — | I-B | Single bond |
| A-67 | 0 | 2' | c | 4 | H | — | 4 | H | — | I-B | Single bond |
| A-68 | 0 | 2' | c | 4 | H | — | 4 | H | — | I-C | Single bond |
| A-69 | 0 | 3' | b | 4 | H | — | 4 | H | — | I-B | Single bond |
| A-70 | 0 | 3' | b | 4 | H | — | 4 | H | — | I-C | Single bond |
| A-71 | 0 | 3' | c | 4 | H | — | 4 | H | — | I-B | Single bond |
| A-72 | 0 | 3' | c | 4 | H | — | 4 | H | — | I-C | Single bond |
| A-73 | 0 | 3' | d | 4 | H | — | 4 | H | — | I-C | Single bond |
| A-74 | 0 | 3' | d | 4 | H | — | 4 | H | — | I-D | Single bond |
| A-75 | 0 | 3' | d | 4 | H | — | 4 | H | — | I-B | Single bond |
| A-76 | 0 | 3' | a | 4 | H | — | 4 | H | — | I-C | Single bond |
| A-77 | 0 | 3' | a | 4 | H | — | 4 | H | — | I-D | Single bond |
| A-78 | 0 | 3' | a | 4 | H | — | 4 | H | — | I-B | Single bond |
| A-79 | 0 | 4' | a | 4 | H | — | 4 | H | — | I-C | Single bond |
| A-80 | 0 | 4' | a | 4 | H | — | 4 | H | — | I-D | Single bond |
| A-81 | 0 | 4' | a | 4 | H | — | 4 | H | — | I-B | Single bond |
| A-82 | 0 | 4' | b | 4 | H | — | 4 | H | — | I-B | Single bond |
| A-83 | 0 | 4' | b | 4 | H | — | 4 | H | — | I-C | Single bond |
| A-84 | 0 | 4' | c | 4 | H | — | 4 | H | — | I-B | Single bond |

-continued

| Compound No. | n₃ | Connection position between Formula 1 and 2 | Connection position of Ar₂ | n₁ | R₁ | Position of R₁ | n₂ | R₂ | Position of R₂ | Ar₁ | L |
| --- | --- | --- | --- | --- | --- | --- | --- | --- | --- | --- | --- |
| A-85 | 0 | 4' | c | 4 | H | — | 4 | H | — | I-C | Single bond |
| A-86 | 0 | 4' | d | 4 | H | — | 4 | H | — | I-C | Single bond |
| A-87 | 0 | 4' | d | 4 | H | — | 4 | H | — | I-D | Single bond |
| A-88 | 0 | 4' | d | 4 | H | — | 4 | H | — | I-B | Single bond |
| A-89 | 0 | 2' | b | 1 | tert-butyl | 3 | 1 | tert-butyl | 6 | I-C | Single bond |
| A-90 | 0 | 1' | b | 1 | tert-butyl | 3 | 1 | tert-butyl | 6 | I-C | Single bond |
| A-91 | 0 | 1' | b | 1 | tert-butyl | 3 | 1 | tert-butyl | 6 | I-E | Single bond |
| A-92 | 0 | 1' | b | 1 | tert-butyl | 3 | 1 | tert-butyl | 6 | I-B | Single bond |
| A-93 | 0 | 1' | a | 1 | tert-butyl | 3 | 1 | tert-butyl | 6 | I-C | Single bond |
| A-94 | 0 | 1' | a | 1 | tert-butyl | 3 | 1 | tert-butyl | 6 | I-D | Single bond |
| A-95 | 0 | 1' | a | 1 | tert-butyl | 3 | 1 | tert-butyl | 6 | I-B | Single bond |
| A-96 | 0 | 1' | c | 1 | tert-butyl | 3 | 1 | tert-butyl | 6 | I-C | Single bond |
| A-97 | 0 | 1' | c | 1 | tert-butyl | 3 | 1 | tert-butyl | 6 | I-D | Single bond |
| A-98 | 0 | 1' | e | 1 | tert-butyl | 3 | 1 | tert-butyl | 6 | I-B | Single bond |
| A-99 | 0 | 1' | d | 1 | tert-butyl | 3 | 1 | tert-butyl | 6 | I-C | Single bond |
| A-100 | 0 | 1' | d | 1 | tert-butyl | 3 | 1 | tert-butyl | 6 | I-D | Single bond |
| A-101 | 0 | 1' | d | 1 | tert-butyl | 3 | 1 | tert-butyl | 6 | I-B | Single bond |
| A-102 | 0 | 2' | c | 1 | tert-butyl | 3 | 1 | tert-butyl | 6 | I-C | Single bond |
| A-103 | 0 | 3' | b | 1 | tert-butyl | 3 | 1 | tert-butyl | 6 | I-B | Single bond |
| A-104 | 0 | 3' | b | 1 | tert-butyl | 3 | 1 | tert-butyl | 6 | I-C | Single bond |
| A-105 | 0 | 3' | c | 1 | tert-butyl | 3 | 1 | tert-butyl | 6 | I-B | Single bond |
| A-106 | 0 | 3' | c | 1 | tert-butyl | 3 | 1 | tert-butyl | 6 | I-C | Single bond |
| A-107 | 0 | 3' | d | 1 | tert-butyl | 3 | 1 | tert-butyl | 6 | I-C | Single bond |
| A-108 | 0 | 3' | d | 1 | tert-butyl | 3 | 1 | tert-butyl | 6 | I-D | Single bond |
| A-109 | 0 | 3' | d | 1 | tert-butyl | 3 | 1 | tert-butyl | 6 | I-B | Single bond |
| A-110 | 0 | 3' | a | 1 | tert-butyl | 3 | 1 | tert-butyl | 6 | I-C | Single bond |
| A-111 | 0 | 3' | a | 1 | tert-butyl | 3 | 1 | tert-butyl | 6 | I-D | Single bond |
| A-112 | 0 | 3' | a | 1 | tert-butyl | 3 | 1 | tert-butyl | 6 | I-B | Single bond |
| A-113 | 0 | 4' | a | 1 | tert-butyl | 3 | 1 | tert-butyl | 6 | I-C | Single bond |
| A-114 | 0 | 4' | a | 1 | tert-butyl | 3 | 1 | tert-butyl | 6 | I-D | Single bond |
| A-115 | 0 | 4' | a | 1 | tert-butyl | 3 | 1 | tert-butyl | 6 | I-B | Single bond |
| A-116 | 0 | 4' | b | 1 | tert-butyl | 3 | 1 | tert-butyl | 6 | I-C | Single bond |
| A-117 | 0 | 4' | b | 1 | tert-butyl | 3 | 1 | tert-butyl | 6 | I-D | Single bond |
| A-118 | 0 | 4' | b | 1 | tert-butyl | 3 | 1 | tert-butyl | 6 | I-B | Single bond |
| A-119 | 0 | 4' | c | 1 | tert-butyl | 3 | 1 | tert-butyl | 6 | I-C | Single bond |
| A-120 | 0 | 4' | c | 1 | tert-butyl | 3 | 1 | tert-butyl | 6 | I-D | Single bond |

-continued

| Compound No. | n₃ | Connection position between Formula 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| A-121 | 0 | 4' | c | 1 | tert-butyl | 3 | 1 | tert-butyl | 6 | I-B | Single bond |
| A-122 | 0 | 4' | d | 1 | tert-butyl | 3 | 1 | tert-butyl | 6 | I-C | Single bond |
| A-123 | 0 | 4' | d | 1 | tert-butyl | 3 | 1 | tert-butyl | 6 | I-D | Single bond |
| A-124 | 0 | 4' | d | 1 | tert-butyl | 3 | 1 | tert-butyl | 6 | I-B | Single bond |
| A-125 | 0 | 3' | b | 1 | tert-butyl | 3 | 1 | tert-butyl | 6 | I-D | Single bond |
| A-126 | 0 | 3' | c | 1 | tert-butyl | 3 | 1 | tert-butyl | 6 | I-D | Single bond |
| B-37 | 1 | 2' | b | 4 | H | — | 4 | H | — | I-C | Single bond |
| B-38 | 1 | 1' | b | 4 | H | — | 4 | H | — | I-C | Single bond |
| B-39 | 1 | 1' | b | 4 | H | — | 4 | H | — | I-K | Single bond |
| B-40 | 1 | 1' | b | 4 | H | — | 4 | H | — | I-B | Single bond |
| B-41 | 1 | 1' | a | 4 | H | — | 4 | H | — | I-C | Single bond |
| B-42 | 1 | 1' | a | 4 | H | — | 4 | H | — | I-D | Single bond |
| B-43 | 1 | 1' | a | 4 | H | — | 4 | H | — | I-B | Single bond |
| B-44 | 1 | 1' | c | 4 | H | — | 4 | H | — | I-C | Single bond |
| B-45 | 1 | 1' | c | 4 | H | — | 4 | H | — | I-D | Single bond |
| B-46 | 1 | 1' | c | 4 | H | — | 4 | H | — | I-B | Single bond |
| B-47 | 1 | 1' | d | 4 | H | — | 4 | H | — | I-C | Single bond |
| B-48 | 1 | 1' | d | 4 | H | — | 4 | H | — | I-D | Single bond |
| B-49 | 1 | 1' | d | 4 | H | — | 4 | H | — | I-B | Single bond |
| B-50 | 1 | 2' | c | 4 | H | — | 4 | H | — | I-B | Single bond |
| B-51 | 1 | 2' | c | 4 | H | — | 4 | H | — | I-C | Single bond |
| B-52 | 1 | 3' | b | 4 | H | — | 4 | H | — | I-B | Single bond |
| B-53 | 1 | 3' | b | 4 | H | — | 4 | H | — | I-C | Single bond |
| B-54 | 1 | 3' | c | 4 | H | — | 4 | H | — | I-B | Single bond |
| B-55 | 1 | 3' | c | 4 | H | — | 4 | H | — | I-C | Single bond |
| B-56 | 1 | 3' | d | 4 | H | — | 4 | H | — | I-C | Single bond |
| B-57 | 1 | 3' | d | 4 | H | — | 4 | H | — | I-D | Single bond |
| B-58 | 1 | 3' | d | 4 | H | — | 4 | H | — | I-B | Single bond |
| B-59 | 1 | 3' | a | 4 | H | — | 4 | H | — | I-C | Single bond |
| B-60 | 1 | 3' | a | 4 | H | — | 4 | H | — | I-D | Single bond |
| B-61 | 1 | 3' | a | 4 | H | — | 4 | H | — | I-B | Single bond |
| B-62 | 1 | 4' | a | 4 | H | — | 4 | H | — | I-C | Single bond |
| B-63 | 1 | 4' | a | 4 | H | — | 4 | H | — | I-D | Single bond |
| B-64 | 1 | 4' | a | 4 | H | — | 4 | H | — | I-B | Single bond |
| B-65 | 1 | 4' | b | 4 | H | — | 4 | H | — | I-B | Single bond |
| B-66 | 1 | 4' | b | 4 | H | — | 4 | H | — | I-C | Single bond |

-continued

| Compound No. | $n_3$ | Connection position between Formula 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| B-67 | 1 | 4' | c | 4 | H | — | 4 | H | — | I-B | Single bond |
| B-68 | 1 | 4' | c | 4 | H | — | 4 | H | — | I-C | Single bond |
| B-69 | 1 | 4' | d | 4 | H | — | 4 | H | — | I-C | Single bond |
| B-70 | 1 | 4' | d | 4 | H | — | 4 | H | — | I-D | Single bond |
| B-71 | 1 | 4' | d | 4 | H | — | 4 | H | — | I-B | Single bond |
| B-72 | 1 | 2' | b | 1 | tert-butyl | 3 | 1 | tert-butyl | 6 | I-C | Single bond |
| B-73 | 1 | 1' | b | 1 | tert-butyl | 3 | 1 | tert-butyl | 6 | I-C | Single bond |
| B-74 | 1 | 1' | b | 1 | tert-butyl | 3 | 1 | tert-butyl | 6 | I-E | Single bond |
| B-75 | 1 | 1' | b | 1 | tert-butyl | 3 | 1 | tert-butyl | 6 | I-B | Single bond |
| B-76 | 1 | 1' | a | 1 | tert-butyl | 3 | 1 | tert-butyl | 6 | I-C | Single bond |
| B-77 | 1 | 1' | a | 1 | tert-butyl | 3 | 1 | tert-butyl | 6 | I-D | Single bond |
| B-78 | 1 | 1' | a | 1 | tert-butyl | 3 | 1 | tert-butyl | 6 | I-B | Single bond |
| B-79 | 1 | 1' | c | 1 | tert-butyl | 3 | 1 | tert-butyl | 6 | I-C | Single bond |
| B-80 | 1 | 1' | c | 1 | tert-butyl | 3 | 1 | tert-butyl | 6 | I-D | Single bond |
| B-81 | 1 | 1' | c | 1 | tert-butyl | 3 | 1 | tert-butyl | 6 | I-B | Single bond |
| B-82 | 1 | 1' | d | 1 | tert-butyl | 3 | 1 | tert-butyl | 6 | I-C | Single bond |
| B-83 | 1 | 1' | d | 1 | tert-butyl | 3 | 1 | tert-butyl | 6 | I-D | Single bond |
| B-84 | 1 | 1' | d | 1 | tert-butyl | 3 | 1 | tert-butyl | 6 | I-B | Single bond |
| B-85 | 1 | 2' | c | 1 | tert-butyl | 3 | 1 | tert-butyl | 6 | I-C | Single bond |
| B-86 | 1 | 3' | b | 1 | tert-butyl | 3 | 1 | tert-butyl | 6 | I-B | Single bond |
| B-87 | 1 | 3' | b | 1 | tert-butyl | 3 | 1 | tert-butyl | 6 | I-C | Single bond |
| B-88 | 1 | 3' | c | 1 | tert-butyl | 3 | 1 | tert-butyl | 6 | I-B | Single bond |
| B-89 | 1 | 3' | c | 1 | tert-butyl | 3 | 1 | tert-butyl | 6 | I-C | Single bond |
| B-90 | 1 | 3' | d | 1 | tert-butyl | 3 | 1 | tert-butyl | 6 | I-C | Single bond |
| B-91 | 1 | 3' | d | 1 | tert-butyl | 3 | 1 | tert-butyl | 6 | I-D | Single bond |
| B-92 | 1 | 3' | d | 1 | tert-butyl | 3 | 1 | tert-butyl | 6 | I-B | Single bond |
| B-93 | 1 | 3' | a | 1 | tert-butyl | 3 | 1 | tert-butyl | 6 | I-C | Single bond |
| B-94 | 1 | 3' | a | 1 | tert-butyl | 3 | 1 | tert-butyl | 6 | I-D | Single bond |
| B-95 | 1 | 3' | a | 1 | tert-butyl | 3 | 1 | tert-butyl | 6 | I-B | Single bond |
| B-96 | 1 | 4' | a | 1 | tert-butyl | 3 | 1 | tert-butyl | 6 | I-C | Single bond |
| B-97 | 1 | 4' | a | 1 | tert-butyl | 3 | 1 | tert-butyl | 6 | I-D | Single bond |
| B-98 | 1 | 4' | a | 1 | tert-butyl | 3 | 1 | tert-butyl | 6 | I-B | Single bond |
| B-99 | 1 | 4' | b | 1 | tert-butyl | 3 | 1 | tert-butyl | 6 | I-C | Single bond |
| B-101 | 1 | 4' | b | 1 | tert-butyl | 3 | 1 | tert-butyl | 6 | I-D | Single bond |
| B-102 | 1 | 4' | b | 1 | tert-butyl | 3 | 1 | tert-butyl | 6 | I-B | Single bond |
| B-103 | 1 | 4' | c | 1 | tert-butyl | 3 | 1 | tert-butyl | 6 | I-C | Single bond |

-continued

| Compound No. | n₃ | Connection position between Formula 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| B-104 | 1 | 4' | c | 1 | tert-butyl | 3 | 1 | tert-butyl | 6 | I-D | Single bond |
| B-105 | 1 | 4' | c | 1 | tert-butyl | 3 | 1 | tert-butyl | 6 | I-B | Single bond |
| B-106 | 1 | 4' | d | 1 | tert-butyl | 3 | 1 | tert-butyl | 6 | I-C | Single bond |
| B-107 | 1 | 4' | d | 1 | tert-butyl | 3 | 1 | tert-butyl | 6 | I-D | Single bond |
| B-108 | 1 | 4' | d | 1 | tert-butyl | 3 | 1 | tert-butyl | 6 | I-B | Single bond |
| B-109 | 1 | 3' | b | 1 | tert-butyl | 3 | 1 | tert-butyl | 6 | I-D | Single bond |
| B-110 | 1 | 3' | c | 1 | tert-butyl | 3 | 1 | tert-butyl | 6 | I-D | Single bond |
| C-31 | 2 | 2' | b | 4 | H | — | 4 | H | — | I-C | Single bond |
| C-32 | 2 | 1' | b | 4 | H | — | 4 | H | — | I-C | Single bond |
| C-33 | 2 | 1' | b | 4 | H | — | 4 | H | — | I-K | Single bond |
| C-34 | 2 | 1' | b | 4 | H | — | 4 | H | — | I-B | Single bond |
| C-35 | 2 | 1' | a | 4 | H | — | 4 | H | — | I-C | Single bond |
| C-36 | 2 | 1' | a | 4 | H | — | 4 | H | — | I-D | Single bond |
| C-37 | 2 | 1' | a | 4 | H | — | 4 | H | — | I-B | Single bond |
| C-38 | 2 | 1' | c | 4 | H | — | 4 | H | — | I-C | Single bond |
| C-39 | 2 | 1' | c | 4 | H | — | 4 | H | — | I-D | Single bond |
| C-40 | 2 | 1' | c | 4 | H | — | 4 | H | — | I-B | Single bond |
| C-41 | 2 | 1' | d | 4 | H | — | 4 | H | — | I-C | Single bond |
| C-42 | 2 | 1' | d | 4 | H | — | 4 | H | — | I-D | Single bond |
| C-43 | 2 | 1' | d | 4 | H | — | 4 | H | — | I-B | Single bond |
| C-44 | 2 | 2' | c | 4 | H | — | 4 | H | — | I-B | Single bond |
| C-45 | 2 | 2' | c | 4 | H | — | 4 | H | — | I-C | Single bond |
| C-46 | 2 | 3' | b | 4 | H | — | 4 | H | — | I-B | Single bond |
| C-47 | 2 | 3' | b | 4 | H | — | 4 | H | — | I-C | Single bond |
| C-48 | 2 | 3' | c | 4 | H | — | 4 | H | — | I-B | Single bond |
| C-49 | 2 | 3' | c | 4 | H | — | 4 | H | — | I-C | Single bond |
| C-50 | 2 | 3' | d | 4 | H | — | 4 | H | — | I-C | Single bond |
| C-51 | 2 | 3' | d | 4 | H | — | 4 | H | — | I-D | Single bond |
| C-52 | 2 | 3' | d | 4 | H | — | 4 | H | — | I-B | Single bond |
| C-53 | 2 | 3' | a | 4 | H | — | 4 | H | — | I-C | Single bond |
| C-54 | 2 | 3' | a | 4 | H | — | 4 | H | — | I-D | Single bond |
| C-55 | 2 | 3' | a | 4 | H | — | 4 | H | — | I-B | Single bond |
| C-56 | 2 | 4' | a | 4 | H | — | 4 | H | — | I-C | Single bond |
| C-57 | 2 | 4' | a | 4 | H | — | 4 | H | — | I-D | Single bond |
| C-58 | 2 | 4' | a | 4 | H | — | 4 | H | — | I-B | Single bond |
| C-59 | 2 | 4' | b | 4 | H | — | 4 | H | — | I-B | Single bond |

-continued

| Compound No. | n₃ | Connection position between Formula 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| C-60 | 2 | 4' | b | 4 | H | — | 4 | H | — | I-C | Single bond |
| C-61 | 2 | 4' | c | 4 | H | — | 4 | H | — | I-B | Single bond |
| C-62 | 2 | 4' | c | 4 | H | — | 4 | H | — | I-C | Single bond |
| C-63 | 2 | 4' | d | 4 | H | — | 4 | H | — | I-C | Single bond |
| C-64 | 2 | 4' | d | 4 | H | — | 4 | H | — | I-D | Single bond |
| C-65 | 2 | 4' | d | 4 | H | — | 4 | H | — | I-B | Single bond |
| C-66 | 2 | 2' | b | 1 | tert-butyl | 3 | 1 | tert-butyl | 6 | I-C | Single bond |
| C-67 | 2 | 1' | b | 1 | tert-butyl | 3 | 1 | tert-butyl | 6 | I-C | Single bond |
| C-68 | 2 | 1' | b | 1 | tert-butyl | 3 | 1 | tert-butyl | 6 | I-E | Single bond |
| C-69 | 2 | 1' | b | 1 | tert-butyl | 3 | 1 | tert-butyl | 6 | I-B | Single bond |
| C-70 | 2 | 1' | a | 1 | tert-butyl | 3 | 1 | tert-butyl | 6 | I-C | Single bond |
| C-71 | 2 | 1' | a | 1 | tert-butyl | 3 | 1 | tert-butyl | 6 | I-D | Single bond |
| C-72 | 2 | 1' | a | 1 | tert-butyl | 3 | 1 | tert-butyl | 6 | I-B | Single bond |
| C-73 | 2 | 1' | c | 1 | tert-butyl | 3 | 1 | tert-butyl | 6 | I-C | Single bond |
| C-74 | 2 | 1' | c | 1 | tert-butyl | 3 | 1 | tert-butyl | 6 | I-D | Single bond |
| C-75 | 2 | 1' | c | 1 | tert-butyl | 3 | 1 | tert-butyl | 6 | I-B | Single bond |
| C-76 | 2 | 1' | d | 1 | tert-butyl | 3 | 1 | tert-butyl | 6 | I-C | Single bond |
| C-77 | 2 | 1' | d | 1 | tert-butyl | 3 | 1 | tert-butyl | 6 | I-D | Single bond |
| C-78 | 2 | 1' | d | 1 | tert-butyl | 3 | 1 | tert-butyl | 6 | I-B | Single bond |
| C-79 | 2 | 2' | c | 1 | tert-butyl | 3 | 1 | tert-butyl | 6 | I-C | Single bond |
| C-80 | 2 | 3' | b | 1 | tert-butyl | 3 | 1 | tert-butyl | 6 | I-B | Single bond |
| C-81 | 2 | 3' | b | 1 | tert-butyl | 3 | 1 | tert-butyl | 6 | I-C | Single bond |
| C-82 | 2 | 3' | c | 1 | tert-butyl | 3 | 1 | tert-butyl | 6 | I-B | Single bond |
| C-83 | 2 | 3' | c | 1 | tert-butyl | 3 | 1 | tert-butyl | 6 | I-C | Single bond |
| C-84 | 2 | 3' | d | 1 | tert-butyl | 3 | 1 | tert-butyl | 6 | I-C | Single bond |
| C-85 | 2 | 3' | d | 1 | tert-butyl | 3 | 1 | tert-butyl | 6 | I-D | Single bond |
| C-86 | 2 | 3' | d | 1 | tert-butyl | 3 | 1 | tert-butyl | 6 | I-B | Single bond |
| C-87 | 2 | 3' | a | 1 | tert-butyl | 3 | 1 | tert-butyl | 6 | I-C | Single bond |
| C-88 | 2 | 3' | a | 1 | tert-butyl | 3 | 1 | tert-butyl | 6 | I-D | Single bond |
| C-89 | 2 | 3' | a | 1 | tert-butyl | 3 | 1 | tert-butyl | 6 | I-B | Single bond |
| C-90 | 2 | 4' | a | 1 | tert-butyl | 3 | 1 | tert-butyl | 6 | I-C | Single bond |
| C-91 | 2 | 4' | a | 1 | tert-butyl | 3 | 1 | tert-butyl | 6 | I-D | Single bond |
| C-92 | 2 | 4' | a | 1 | tert-butyl | 3 | 1 | tert-butyl | 6 | I-B | Single bond |
| C-93 | 2 | 4' | b | 1 | tert-butyl | 3 | 1 | tert-butyl | 6 | I-C | Single bond |
| C-94 | 2 | 4' | b | 1 | tert-butyl | 3 | 1 | tert-butyl | 6 | I-D | Single bond |
| C-95 | 2 | 4' | b | 1 | tert-butyl | 3 | 1 | tert-butyl | 6 | I-B | Single bond |

-continued

| Compound No. | $n_3$ | Connection position between Formula 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| C-96 | 2 | 4' | c | 1 | tert-butyl | 3 | 1 | tert-butyl | 6 | I-C | Single bond |
| C-97 | 2 | 4' | c | 1 | tert-butyl | 3 | 1 | tert-butyl | 6 | I-D | Single bond |
| C-98 | 2 | 4' | c | 1 | tert-butyl | 3 | 1 | tert-butyl | 6 | I-B | Single bond |
| C-99 | 2 | 4' | d | 1 | tert-butyl | 3 | 1 | tert-butyl | 6 | I-C | Single bond |
| C-100 | 2 | 4' | d | 1 | tert-butyl | 3 | 1 | tert-butyl | 6 | I-D | Single bond |
| C-101 | 2 | 4' | d | 1 | tert-butyl | 3 | 1 | tert-butyl | 6 | I-B | Single bond |
| C-102 | 2 | 3' | b | 1 | tert-butyl | 3 | 1 | tert-butyl | 6 | I-D | Single bond |
| C-103 | 2 | 3' | c | 1 | tert-butyl | 3 | 1 | tert-butyl | 6 | I-D | Single bond |

In particular, when $n_3$=0, the structural formula of Formula 1 is

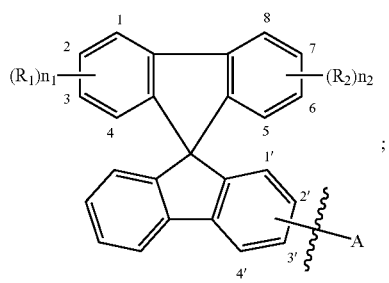

;

when $n_3$=1, both $R_3$ and $R_4$ are methyl, and the structural formula of Formula 1 is

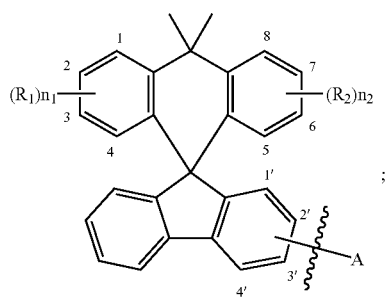

;

when $n_3$=2, both $R_3$ and $R_4$ are H, and the structural formula of Formula 1 is

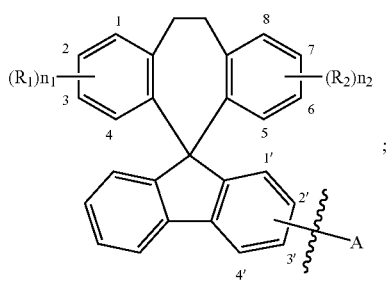

;

"-" means that $R_1$ is connected at the 1, 2, 3, or 4 position of the Formula 1, and "--" means that $R_2$ is connected at the 5, 6, 7, or 8 position of the Formula 1;

R-A, R-B, R-C, R-D, R-E, and R-f refer to $R_1$ or $R_2$ with different structures and respectively correspond to the groups shown below:

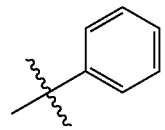

R-A

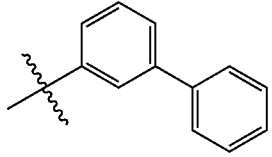

R-B

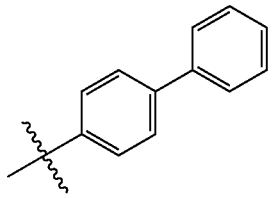

R-C

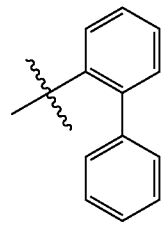

R-D

R-E
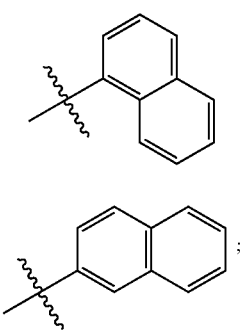
R-F
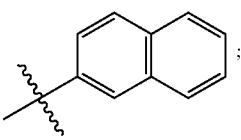
;
L-A, L-B, L-C, L-D, L-E, L-F, L-G, L-H, and L-I refer to L with different structures and respectively correspond to the groups shown below:
L-A
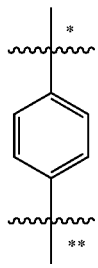
L-B
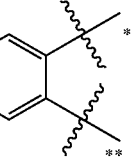
L-C
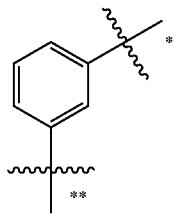
L-D
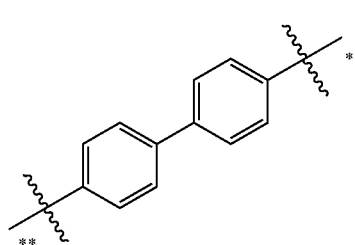
L-E
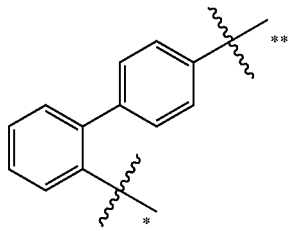
L-F
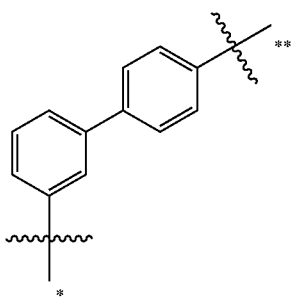
L-G
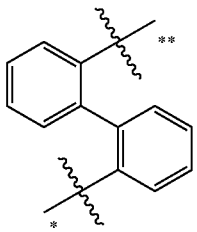
L-H
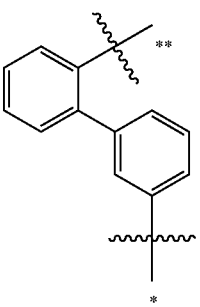
L-I
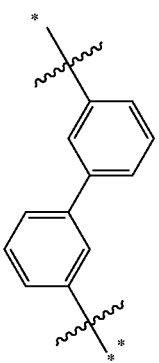

** means to connect with
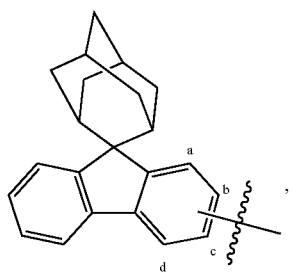
and means to connect with
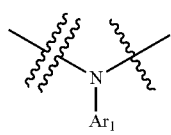
in -ξ-ξ-;
I-A, I-B, I-C, I-D, I-E, I-F, I-G, I-H, I-I, I-J, I-K, I-L, and I-M mean Ar₁ with different structures and respectively correspond to the groups shown below:
I-A
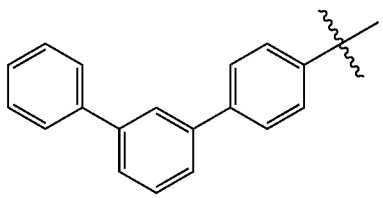
I-B
I-C
I-D
-continued
I-E
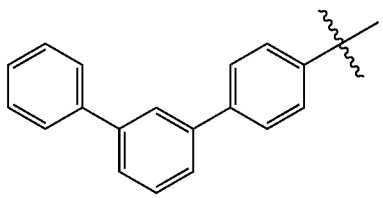
I-F
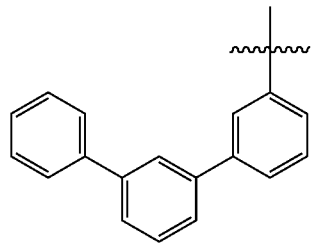
I-G
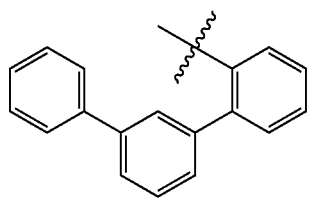
I-H
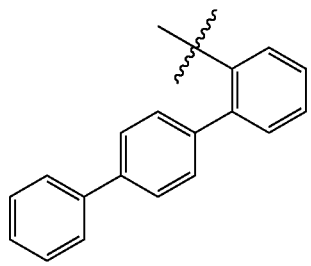
I-I
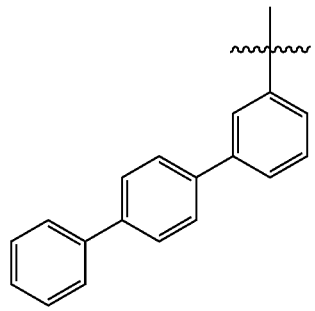
I-J
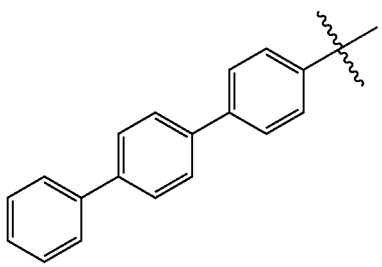

I-K

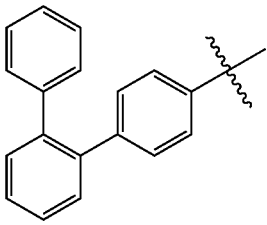

I-L

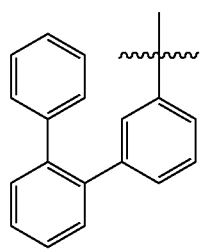

I-M

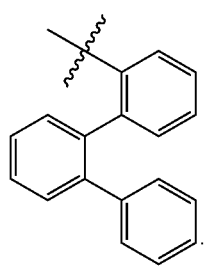

Or the nitrogen-containing compound is selected from the following compounds:

compound 127

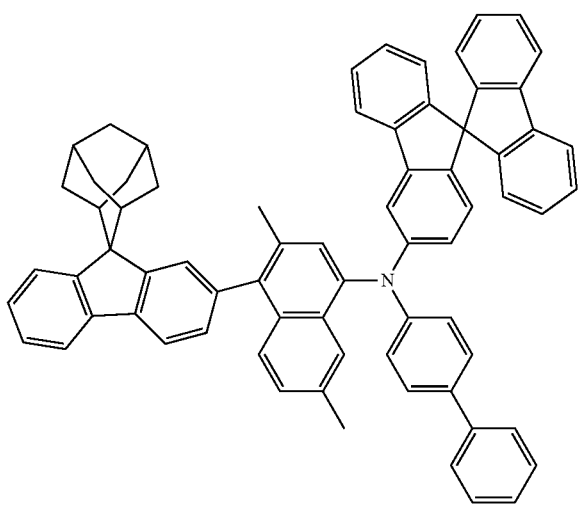

compound 128

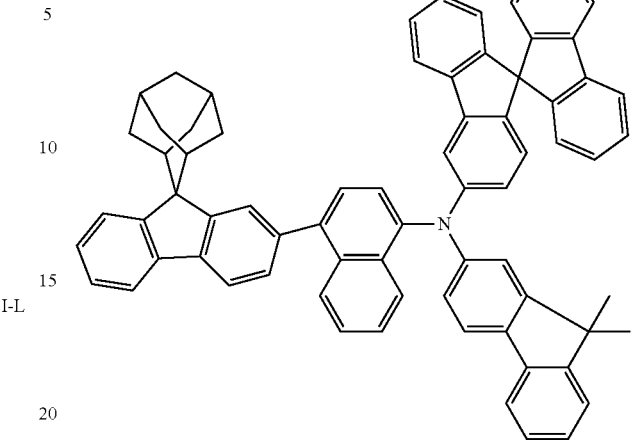

The present application also provides an electronic component, which comprising an anode and a cathode arranged oppositely, and a functional layer provided between the anode and the cathode, the functional layer comprising the nitrogen-containing compound of the present application. The electronic component can be used to realize photoelectric conversion or electro-optical conversion.

The electronic component of the present application may be an organic electroluminescent device or photoelectric conversion device for example.

According to an embodiment, the electronic component is an organic electroluminescent device. For example, the organic electroluminescent device may be a red organic electroluminescence device, a green organic electroluminescence device, or a blue organic electroluminescence device.

As shown in FIG. 1, the organic electroluminescent device comprises an anode 100 and a cathode 200 arranged oppositely, and a functional layer 300 arranged between the anode 100 and the cathode 200, wherein the functional layer 300 comprising the nitrogen-containing compound provided in the present application.

Optionally, the functional layer 300 comprises a hole adjustment layer 322.

Optionally, the functional layer 300 comprises a hole transport layer 321.

In a special embodiment, the hole adjustment layer 322 comprises the nitrogen-containing compound provided in the present application. Wherein, the hole adjustment layer 322 may consist of the nitrogen-containing compound provided in the present application or consist of the nitrogen-containing compound provided in the present application and other materials. Optionally, the organic electroluminescent device may be a red organic electroluminescent device or a green organic electroluminescent device.

In another special embodiment, the hole transport layer 321 comprises the nitrogen-containing compound provided in the present application to improve the transmittability of holes in the electronic component. Optionally, the organic electroluminescent device may be a blue organic electroluminescent device.

In a special embodiment of the present application, the organic electroluminescent device may comprise an anode 100, a hole transport layer 321, a hole adjustment layer 322, an organic electroluminescent layer 330 as an energy conversion layer, an electron transport layer 350, and a cathode 200 that are stacked in turn. The nitrogen-containing compound provided in the present application may be applied in the hole adjustment layer 322 or the hole transport layer 321 of the organic electroluminescent device, which can effectively improve the emitting efficiency and life of the organic electroluminescent device and reduce the driving voltage of the organic electroluminescent device.

Optionally, the anode 100 comprises the following anode material, which is preferably a material with a large work function that facilitates the hole injection to the functional layer. Special examples of the anode material include a metal, such as nickel, platinum, vanadium, chrome, copper, zinc, and gold, or an alloy thereof; a metallic oxide, such as zinc oxide, indium oxide, indium tin oxid (ITO), and indium zinc oxide (IZO); composition of metal and metal oxygen compound, such as ZnO:Al or $SnO_2$:Sb; or a conductive polymer, such as, but not limited to, poly (3-methylthiophene), poly [3,4-(ethylene-1, 2-dioxy) thiophene] (PEDT), polypyrrole (PPY), and polyaniline (PANI). Preferably, it comprises a transparent electrode containing indium tin oxide (ITO) as the anode.

Optionally, the hole transport layer 321 may comprise one or more hole transport materials, which can selected from carbazole polymers, carbazole-linked triarylamine compounds or other types of compounds, which are not specifically limited here. In an embodiment of the present application, the hole transport layer 321 consists of the compound NPB.

Optionally, the hole adjustment layer 322 may be selected from carbazole-linked triarylamine compounds, TCTA and other types of compounds, which are not specifically limited here. For example, the hole adjustment layer may comprise the compound EB-01.

Optionally, the organic electroluminescent layer 330 may consist of a single emitting material or may consist of a host material and a guest material. Optionally, the organic electroluminescent layer 330 consists of a host material and a guest material. The holes injected into the organic emitting layer 330 and the electrons injected into the organic emitting layer 330 can be compounded in the organic emitting layer 330 to form excitons. The excitons transfer energy to the host material, and the host material transfer energy to the guest material, which in turn makes the guest material can emit light.

The host material of the organic electroluminescent layer 330 can be a metal chelating compound, a bis-styryl derivative, an aromatic amine derivative, a dibenzofuran derivative or other types of materials, which are not specifically limited here. In an embodiment of the present application, the host material of the organic electroluminescent layer 330 may be CBP or BH-01. The guest material of the organic electroluminescent layer 330 may be a compound having a condensed aryl ring or its derivatives, a compound having a heteroaryl ring or its derivatives, an aromatic amine derivative or other materials, which are not specifically limited here. In an embodiment of the present application, the guest material of the organic electroluminescent layer 330 may be $Ir(piq)_2(acac)$, $Ir(ppy)_3$, or BD-01.

The electron transport layer 350 may be of a single-layer structure or a multi-layer structure, which can comprise one or more electron transport materials may be selected from benzimidazole derivatives, oxadiazole derivatives, quinoxaline derivatives or other electron transport materials, which are not specifically limited here. For example, in an embodiment of the present application, the electron transport layer 340 may comprise ET-06 and LiQ.

In the present application, the specific structures of the compounds EB-01, BH-01, BD-01 and ET-06 are shown in the following examples and will not be repeated here.

Optionally, the cathode 200 comprises the following cathode materials, which are the materials with a small work function that facilitate the injection of electrons into the functional layer. Specific examples of cathode materials include, but no limited to, a metal, such as magnesium, calcium, sodium, potassium, titanium, indium, yttrium, lithium, gadolinium, aluminum, silver, tin, and lead, or an alloy thereof; or a multilayer material, such as LiF/Al, Liq/Al, $LiO_2$/Al, LiF/Ca, LiF/Al, and $BaF_2$/Ca. Preferably, it comprises a metal electrode comprising magnesium (Mg) and silver (Ag) as the cathode.

Optionally, as shown in FIG. 1, a hole injection layer 310 may also be provided between the anode 100 and the hole transport layer 321 to enhance the ability to inject hole into the hole transport layer 321. The hole injection layer 310 may be selected from benzidine derivatives, starburst aryl amines, phthalocyanine derivatives or other materials, which are not specifically limited here. For example, the hole injection layer 310 may consist of F4-TCNQ.

Optionally, as shown in FIG. 1, an electron injection layer 360 may also be provided between the cathode 200 and the electron transport layer 340 to enhance the ability to inject electrons into the electron transport layer 350. The electron injection layer 360 may comprise an inorganic material, such as alkali metal sulfides and alkali metal halides, or may comprise complexes of alkali metals with organics. For example, the electron injection layer 360 may comprise Yb.

Optionally, a hole blocking layer 340 may also be provided between the organic electroluminescent layer 330 and the electron transport layer 350.

Figure 2:
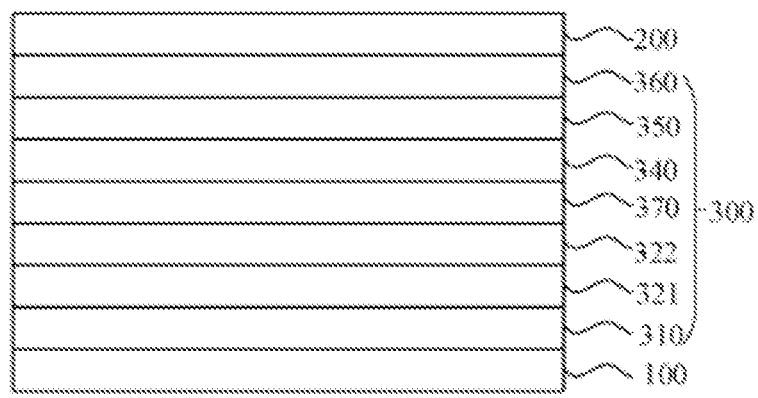
FIG. 2 is a schematic structural diagram of a photoelectric conversion device according to an embodiment of the present application.

According to another embodiment, the electronic component is a photoelectric conversion device. As shown in FIG. 2, the photoelectric conversion device may comprise an anode 100 and a cathode 200 arranged oppositely, and a functional layer 300 arranged between the anode 100 and the cathode 200, the functional layer 300 comprising the nitrogen-containing compound provided in the present application.

Optionally, the functional layer 300 comprises a hole adjustment layer 322. The nitrogen-containing compound provided in the present application can be applied to the hole adjustment layer 322 of the photoelectric conversion device, which can effectively improve the luminescence efficiency and life of the photoelectric conversion device. Specifically, the hole adjustment layer 322 comprises the nitrogen-containing compound provided in the present application. It may be consist of the nitrogen-containing compound provided in the present application, or it may be consist of the nitrogen-containing compound provided in the present application and other materials.

Optionally, as shown in FIG. 2, the photoelectric conversion device may comprise an anode 100, a hole transport layer 321, a hole adjustment layer 322, an electro-optical conversion layer 370 as the energy conversion layer, an electron transport layer 350, and a cathode 200 that are stacked in turn. Optionally, a hole injection layer 310 may also be provided between the anode 100 and the hole transport layer 321.

Optionally, an electron injection layer 360 may also be provided between the cathode 200 and the electron transport layer 350.

Optionally, a hole blocking layer 340 may also be provided between the electro-optical conversion layer 370 and the electron transport layer 350.

Optionally, the photoelectric conversion device may be a solar cell, particularly an organic thin-film solar cell. For example, as shown in FIG. 2, in an embodiment of the present application, the solar cell pack may comprise an anode 100, a hole transport layer 321, a hole adjustment layer 322, an electro-optical conversion layer 370, an electron transport layer 350, and a cathode 200 that are stacked in turn. Wherein, the hole adjustment layer 322 comprises the nitrogen-containing Intermediate in the present application.

The present application also provides an electronic device comprising the electronic component.

Figure 3:
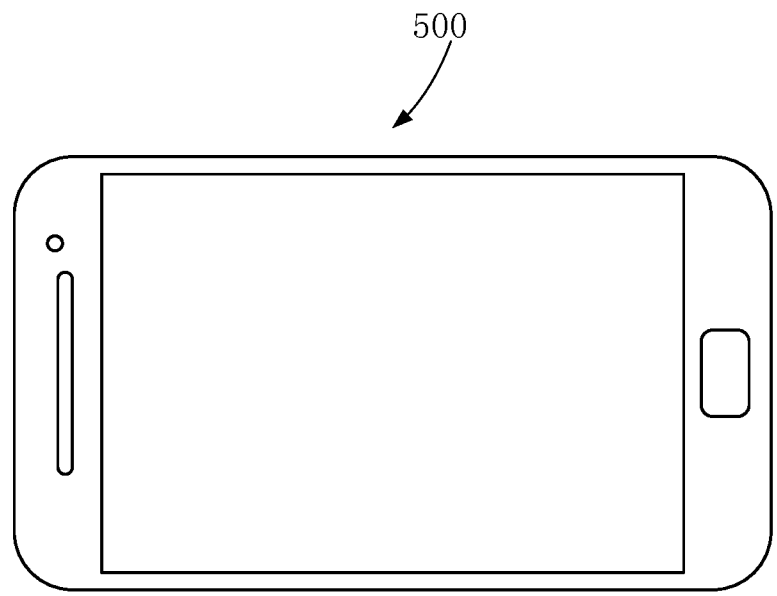
FIG. 3 is a schematic structural diagram of an electronic device according to an embodiment of the present application.

According to one embodiment, as shown in FIG. 3, the electronic device provided in the present application is a first electronic device 400 that comprises the organic electroluminescent device. The electronic device may be, for example, a display device, lighting device, optical communication device or other types of electronic devices, such as but not limited to computer screens, cell phone screens, televisions, electronic paper, emergency lighting, optical modules, etc. Because the electronic device has the organic electroluminescent device, it has identical beneficial effects, which will not be repeated here.

Figure 4:
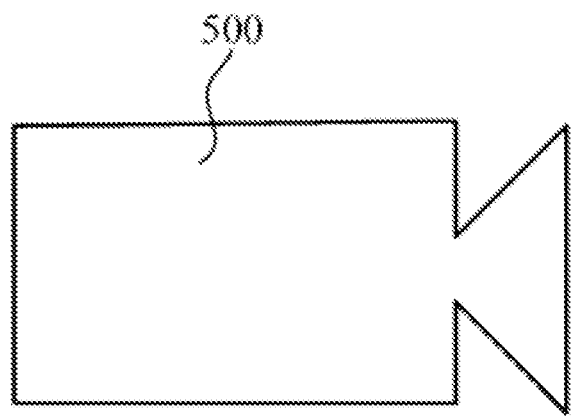
FIG. 4 is a schematic structural diagram of an electronic device according to another embodiment of the present application.

According to another embodiment, as shown in FIG. 4, the electronic device provided in the present application is a second electronic device 500 that comprises the photoelectric conversion device. The electronic device may be, for example, a solar power device, a light detector, a fingerprint recognition device, an optical module, a CCD camera, or other types of electronic devices. Because the electronic device has the photoelectric conversion device, it has identical beneficial effects, which will not be repeated here.

In the following, the present application is described in further detail by examples. However, the following examples are only examples of the present application, other than restricting the present application.

Synthesis of Compound

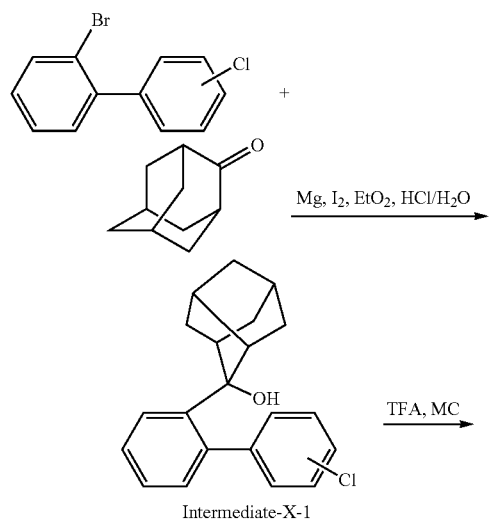

Intermediate-X-1

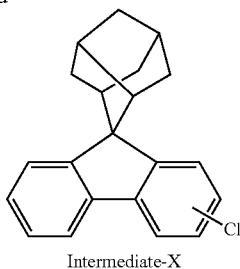

Intermediate-X

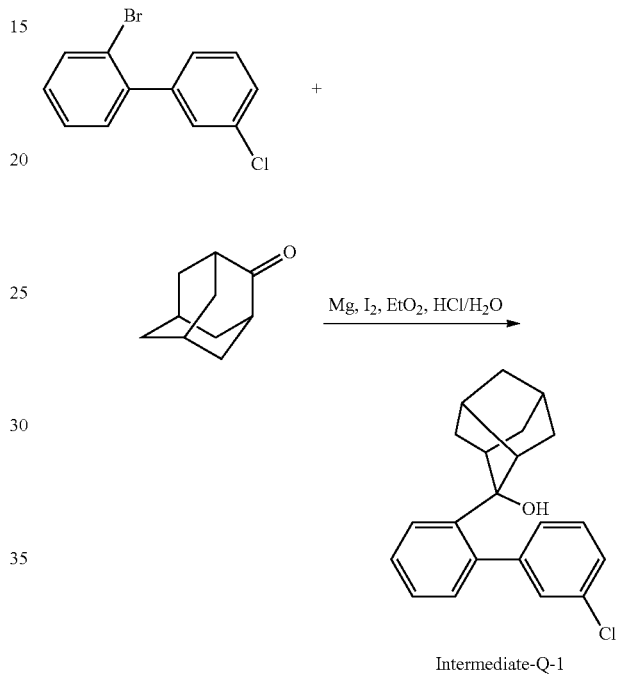

Intermediate-Q-1

Magnesium strips (67.5 g, 2812 mmol) and diethyl ether (500 mL) were placed in a dry round-bottom flask under the protection of nitrogen gas, and iodine (500 mg) was added. Then, the 2-bromo-3'-chloro-1,1'-biphenyl (240 g, 900 mmol) dissolved into diethyl ether (1000 mL) was dropped into the flask, the temperature was raised to 35° C. after dropping, and the stirring was carried out for 3 hours. The reaction solution was coiled to 0° C., the solution of adamantanone (112.5 g, 745 mmol) dissolved in diethyl ether (1000 mL) into the flask, the temperature was raised to 35° C. after dropping, and stirring was carried out for 6 hours. The reaction solution was cooled to room temperature, 5% hydrochloric acid was added into the reaction until the pH<7, and the stirring was carried out for 1 hour. Diethyl ether (1000 mL) was added into the reaction solution for extraction, the combined organic phases were dried by using anhydrous magnesium sulfate, the mixture was filtered, and the solvent was removed under reduced pressure. The crude product was purified by silica column chromatography using n-heptane as the mobile phase to obtain the solid Intermediate Q-1 (210 g, 84% yield).

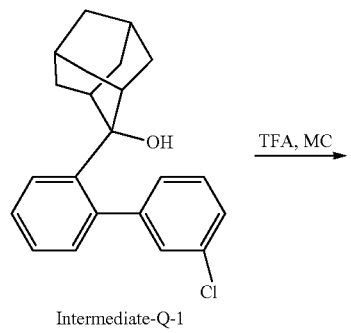

Intermediate-Q-1

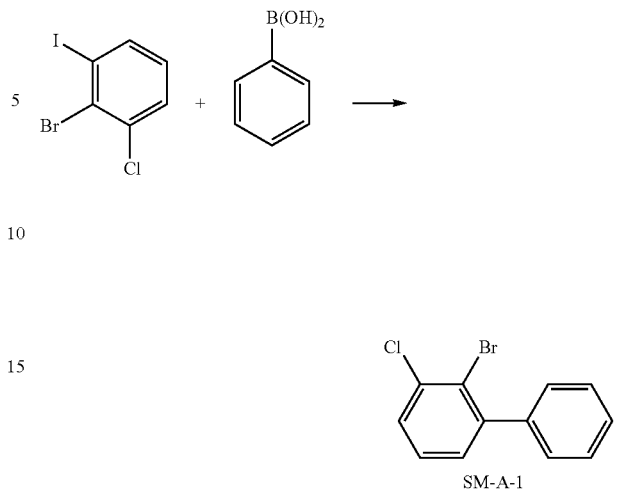

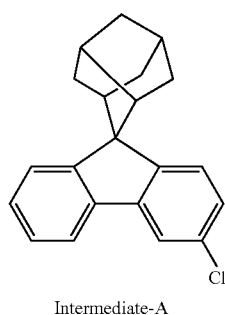

Intermediate-A

Intermediate-Q-1 (210 g, 619.5 mmol), trifluoroacetic acid (211.5 g, 1855 mmol) and dichloromethane (MC, 2500 mL) were added into a round-bottom flask, and the stirring was carried out under the protection of nitrogen gas for 2 hours. Then, an aqueous solution of sodium hydroxide was added into the reaction solution until pH=8, followed by liquid separation, the organic phase was dried with anhydrous magnesium sulfate, the mixture was filtered, and the solvent was removed under reduced pressure. The crude product was separated by silica column chromatography using dichloromethane/n-heptane (1:2) to obtain Intermediate-A as a white solid (112.1 g, 56% yield).

2-bromo-1-chloro-3-iodobenzene (CAS. NO.: 1369793-66-7) (200 g, 630.2 mmol), phenylboronic acid (76.8 g, 630.2 mmol), tetrakis(triphenylphosphine)palladium (36.4 g, 31.5 mmol), potassium carbonate (260.9 g, 1890 mmol), tetrabutylammonium chloride (8.72 g, 31.5 mmol), 1.6 L toluene, 0.8 L ethanol and 0.4 L deionized water were added into a three-necked flask, the temperature was raised to 78° C. under the protection of nitrogen gas, and the stirring was carried out for 6 hours. Then the above reaction solution was cooled to room temperature, 500 mL toluene was added for extraction. The organic phase were combined, the organic phase was dried with anhydrous magnesium sulfate, the mixture was filtered, and the crude product obtained by concentrating the filtrate under reduced pressure. The crude product was purified by silica column chromatography using n-heptane as the mobile phase, and then purified by recrystallization using dichloromethane/n-heptane system (1:3) to obtain SM-A-1 (134.9 g, 80% yield).

Referring to the synthetic method of Intermediate-A to synthesize Intermediate-X shown in Table 1, wherein the difference was that SM-A-G was used instead of 2'-bromo-3-chlorobiphenyl. X may be B, C, or D, and G may be 1, 2, or 3.

TABLE 1

| SM-A-G | Intermediate-X-G | Intermediate-X | Mass (g) | Yield (%) |
|---|---|---|---|---|
| 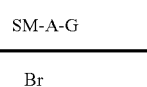<br>SM-A-1 | 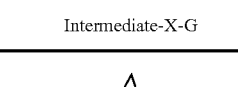<br>Intermediate-B-1 | 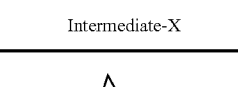<br>Intermediate-B | 99.1 | 77 |

TABLE 1-continued

| SM-A-G | Intermediate-X-G | Intermediate-X | Mass (g) | Yield (%) |
|---|---|---|---|---|
| SM-A-2 | Intermediate-C-1 | Intermediate-C | 150 | 74 |
| SM-A-3 | Intermediate-D-1 | Intermediate-D | 162.5 | 80 |

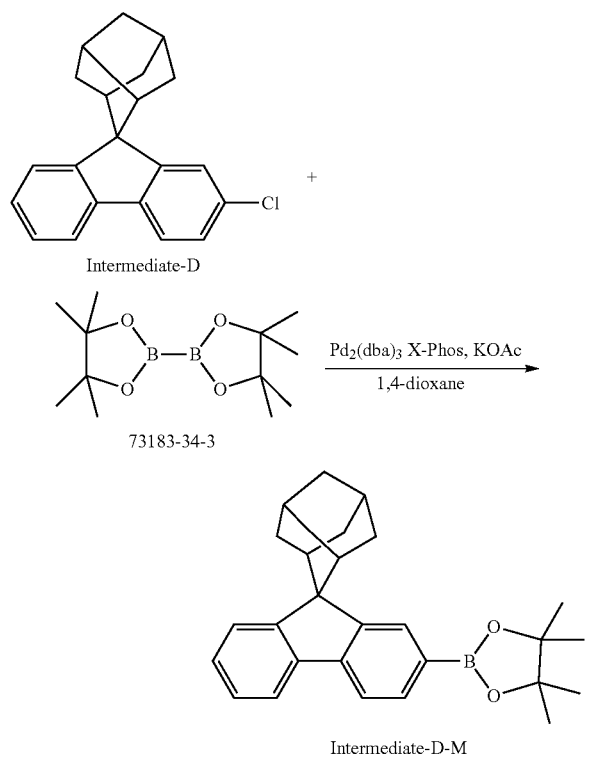

Intermediate-D (30 g, 93.4 mmol), biboronic acid pinacol ester (23.7 g, 93.4 mmol), tris (dibenzylideneacetone) dipalladium (0.9 g, 0.9 mmol), 2-dicyclohexylphosphino-2,4,6-triisopropylbiphenyl (0.8 g, 1.8 mmol), potassium acetate (18.3 g, 186.9 mmol) and 1,4-dioxane (300 mL) were added into the reaction flask, the temperature was raised to 110° C. under the protection of nitrogen gas, the reaction solution was heated and stirred at reflux for 5 hours. After the reaction solution was cooled to room temperature, the reaction solution was extracted with dichloromethane and water, the organic layer was dried over anhydrous magnesium sulfate and filtered, after filtration, the filtrate was passed through a short silica gel column, the solvent was removed from the filteate under reduced pressure, the crude product was purified by recrystallization using a dichloromethane/n-heptane (1:3) system to obtain Compound D-M (27.3 g, 71% yield).

In some embodiment, the Intermediate-X-M shown in Table 2 was synthesized with reference to the synthetic method of Intermediate-D-M, with the difference was that Intermediate-X was used instead of Intermediate-D for the preparation of Intermediate-D-M, and Intermediate-X-M produced was shown in Table 2 below.

TABLE 2
| Intermediate-X | Intermediate-X-M | Mass (g) | Yield (%) |
|---|---|---|---|
| 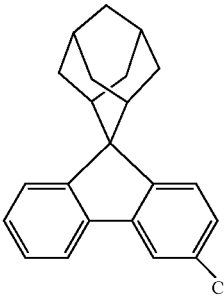<br>Intermediate-A | 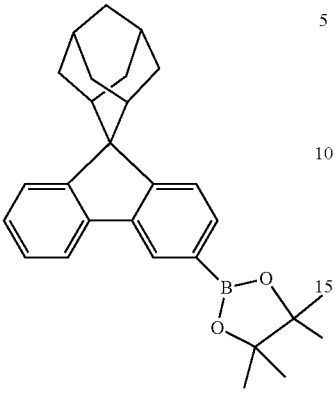<br>Intermediate-A-M | 27.3 | 71 |
| 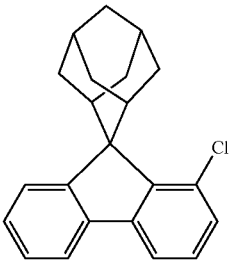 [SMILES: Clc1cccc2c1C1(c3ccccc3-2)C2CC3CC(C2)CC1C3]<br>Intermediate-B | 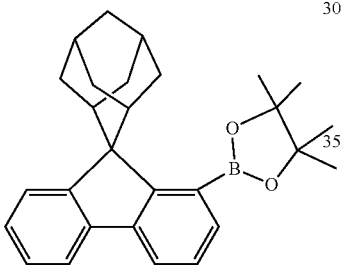<br>Intermediate-B-M | 26.8 | 70 |
| 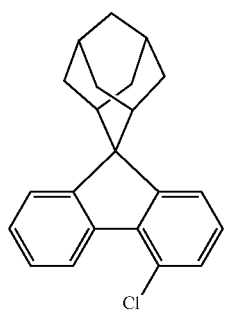 [SMILES: Clc1cccc2c1-c1ccccc1C21C2CC3CC(C2)CC1C3]<br>Intermediate-C | 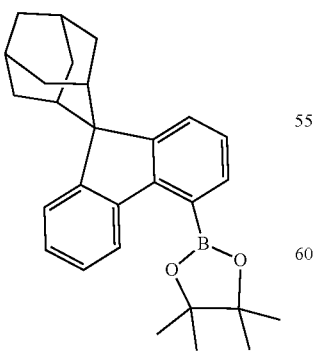<br>Intermediate-C-M | 26.8 | 70 |

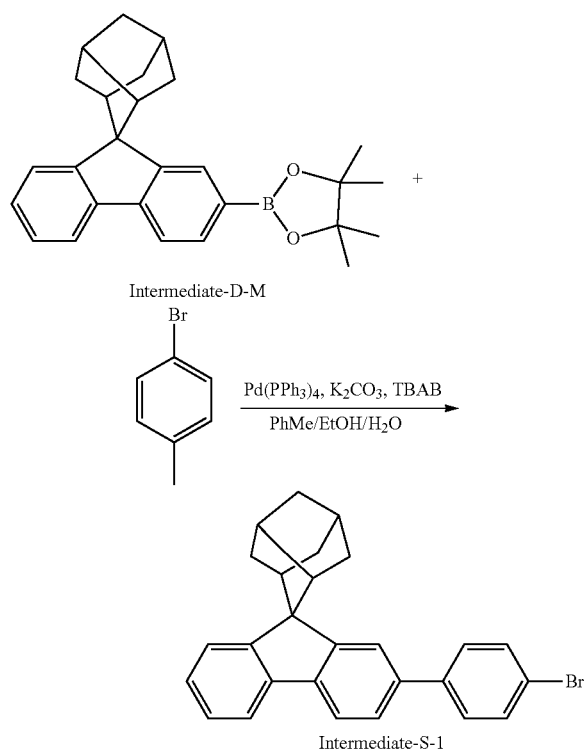

Intermediate-D-M (20 g, 48.5 mmol), p-bromoiodobenzene (13.7 g, 48.5 mmol), tetrakis (triphenylphosphine) palladium (2.8 g, 2.4 mmol), potassium carbonate (13.4 g, 96.9 mmol), tetrabutylammonium bromide (0.3 g, 0.9 mmol), toluene (160 mL), ethanol (80 mL) and deionized water (40 mL) were added into a round-bottom flask, the temperature was raised to 80° C. under the protection of nitrogen gas, and stirred for 12 hours. The reaction solution was cooled to the room temperature, toluene (100 mL) was added for extraction, the organic phase were combined, the combined organic phase was dried by using anhydrous magnesium sulfate, the mixture was filtered, and the solvent was removed under reduced pressure. The crude product is purified by silica column chromatography using n-heptane as mobile phase and then purified by recrystallization using dichloromethane/ethyl acetate system (1:5) to obtain Intermediate-S-1 (14.9 g, 70% yield).

In some embodiment, the Intermediate-S-1 shown in Table 3 was synthesized with reference to the synthesis method of Intermediate S-1, with the difference was that the Compound SMS-X was used instead of p-bromoiodobenzene for the preparation of Intermediate S-1, and Intermediate X-M was used instead of Intermediate-D-M for the preparation of Intermediate-S-1, and each combination of Compound SMS-X and Intermediate-X-M can prepare the unique counterpart Intermediate-S-X. Intermediate-S-X produced was shown in Table 3 below.

TABLE 3

| Intermediate-X-M | SMS-X | Intermediate-S-X | Mass (g) | Yield (%) |
|---|---|---|---|---|
| Intermediate-D-M | 591-48-4 | Intermediate-S-2 | 14.9 | 70 |
| | 187275-76-9 | Intermediate-S-3 | 17.6 | 70 |

TABLE 3-continued
| Intermediate-X-M | SMS-X | Intermediate-S-X | Mass (g) | Yield (%) |
|---|---|---|---|---|
| | 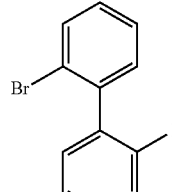 39655-12-4 | 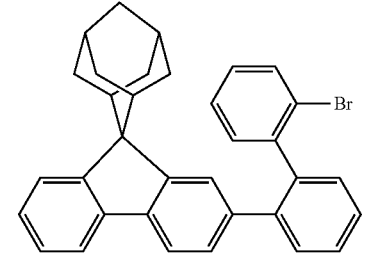 [SMILES: Brc1ccccc1-c1ccccc1-c1ccc2c(c1)C1(c3ccccc3-2)C2CC3CC(C2)CC1C3] Intermediate-S-4 | 17.8 | 71 |
| | 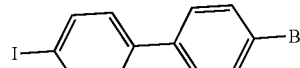 105946-82-5 | 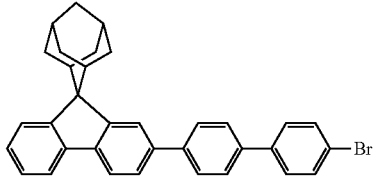 [SMILES: Brc1ccc(-c2ccc(-c3ccc4c(c3)C3(c5ccccc5-4)C4CC5CC(C4)CC3C5)cc2)cc1] Intermediate-S-5 | 17.6 | 70 |
| | 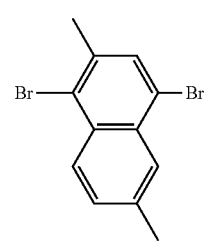 2209102-13-4 | 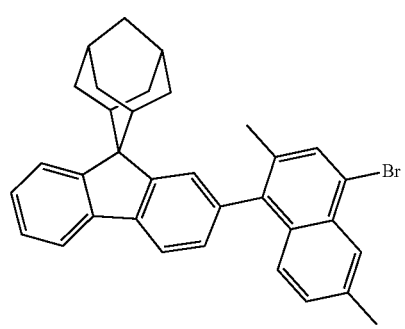 [SMILES: Cc1ccc2c(-c3ccc4c(c3)C3(c5ccccc5-4)C4CC5CC(C4)CC3C5)c(C)cc(Br)c2c1] Intermediate-S-12 | 18.2 | 70 |
| 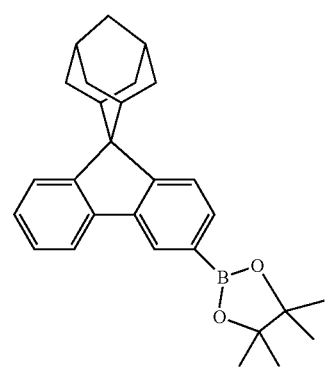 [SMILES: CC1(C)OB(c2ccc3c(c2)-c2ccccc2C32C3CC4CC(C3)CC2C4)OC1(C)C] Intermediate-A-M | 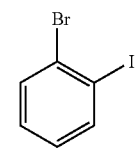 583-55-1 | 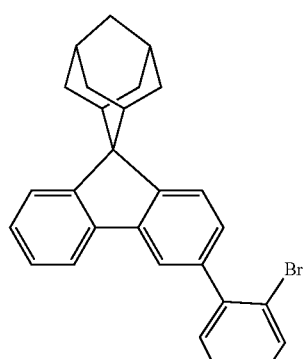 Intermediate-S-6 | 14.9 | 70 |

TABLE 3-continued
| Intermediate-X-M | SMS-X | Intermediate-S-X | Mass (g) | Yield (%) |
|---|---|---|---|---|
| | 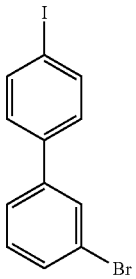 187275-73-6 | 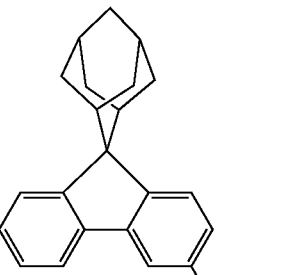 Intermediate-S-7 | 17.8 | 71 |
| 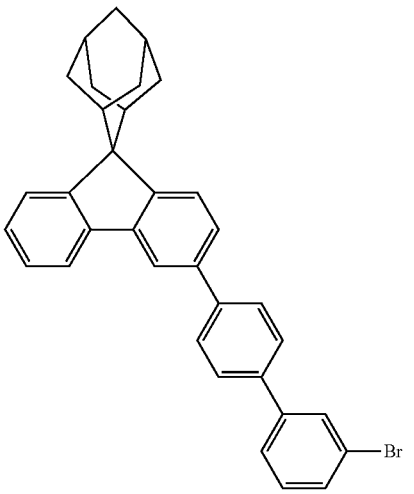 [SMILES: Brc1cccc(-c2ccc(-c3ccc4c(c3)-c3ccccc3C43C4CC5CC(C4)CC3C5)cc2)c1] Intermediate-B-M | 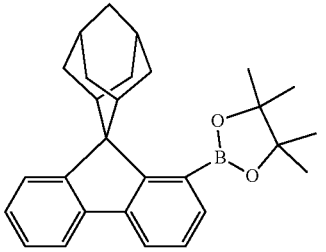 591-48-4 | 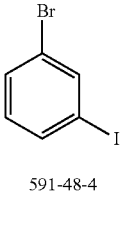 Intermediate-S-8 | 14.9 | 70 |
| | 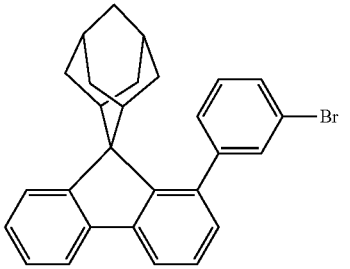 39655-12-4 | 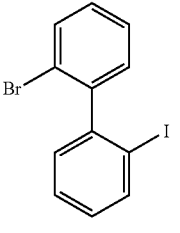 [SMILES: Brc1ccccc1-c1ccccc1I] Intermediate-S-9 | 17.8 | 71 |

TABLE 3-continued

| Intermediate-X-M | SMS-X | Intermediate-S-X | Mass (g) | Yield (%) |
|---|---|---|---|---|
| Intermediate-C-M | 589-87-7 | Intermediate-S-10 | 14.9 | 70 |
| | 187275-73-6 | Intermediate-S-11 | 17.6 | 70 |

SM-Z-1 + Intermediate-D $\xrightarrow{\text{Pd}_2(\text{dba})_3, \text{Xphos}}_{\text{tBuONa, PhMe}}$ Intermediate-Z-1

Intermediate-D (15 g, 46.7 mmol), SM-Z-1 (4.35 g, 46.7 mmol), tris (dibenzylideneacetone) dipalladium (0.8 g, 0.93 mmol), 2-dicyclohexylphosphino-2,4,6-triisopropylbiphenyl (0.20, 0.5 mmol), sodium tert-butoxide (6.7 g, 70.1 mmol) and toluene solvent (150 mL) were added into the reaction flask, the temperature was raised to 110° C. under the protection of nitrogen gas, the reaction solution was heated and stirred at reflux for 3 hours. After the reaction solution is cooled to room temperature, the reaction solution was extracted with dichloromethane and water, the organic layer was dried over anhydrous magnesium sulfate and filtered, after filtration, the filtrate was passed through a short silica column, the solvent was removed under reduced pressure, and the crude product was purified by recrystallization using a dichloromethane/n-heptane system (1:3) to obtain Intermediate-Z-1 (12.4 g, 70% yield).

In some embodiment, Intermediate-Z-1 shown in Table 4 was synthesized with reference to the synthesis method of Intermediate S-1, with the difference that was the Compound SM-Z-X was used instead of SM-Z-1 for the preparation of Intermediate-Z-1, and Intermediate-X was used instead of Intermediate-D for the preparation of Intermediate-Z-1, and each combination of Compound SMS-Z-X and Intermediate-X can be combined to produce the only corresponding Intermediate-Z-X. Intermediate-Z-X produced was shown in Table 4

TABLE 4
| SM-Z-X | Intermediate-X | Intermediate-Z-X | Mass (g) | Yield (%) |
|---|---|---|---|---|
| 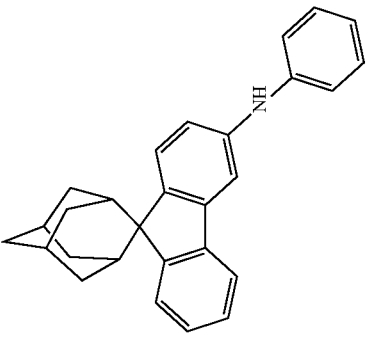 | 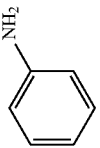 Intermediate-A | 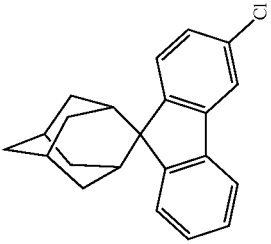 Intermediate-Z-2 | 12.5 | 71 |
|  | 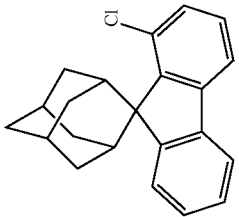 Intermediate-B | 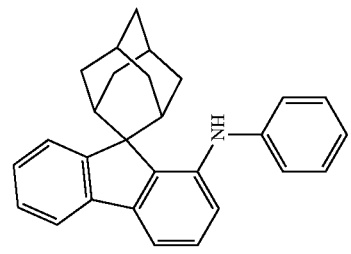 Intermediate-Z-3 | 12.0 | 68 |

TABLE 4-continued

| SM-Z-X | Intermediate-X | Intermediate-Z-X | Mass (g) | Yield (%) |
|---|---|---|---|---|
| 92-67-1 (4-aminobiphenyl) | Intermediate-C | Intermediate-Z-4 | 12.1 | 69 |
| | Intermediate-A | Intermediate-Z-5 | 13.9 | 66 |

TABLE 4-continued

| SM-Z-X | Intermediate-X | Intermediate-Z-X | Mass (g) | Yield (%) |
|---|---|---|---|---|
| | Intermediate-B | Intermediate-Z-6 | 13.7 | 65 |
| | Intermediate-D | Intermediate-Z-7 | 13.6 | 64 |

TABLE 4-continued

| SM-Z-X | Intermediate-X | Intermediate-Z-X | Mass (g) | Yield (%) |
|---|---|---|---|---|
| | Intermediate-S-12 | Intermediate-Z-52 | 11.05 | 63 |
| 2243-47-2 | Intermediate-C | Intermediate-Z-8 | 13.9 | 66 |

TABLE 4-continued

| SM-Z-X | Intermediate-X | Intermediate-Z-X | Mass (g) | Yield (%) |
|---|---|---|---|---|
| | Intermediate-D | Intermediate-Z-9 | 14.4 | 68 |
| 90-41-5 | Intermediate-A | Intermediate-Z-10 | 13.7 | 65 |

TABLE 4-continued
| SM-Z-X | Intermediate-X | Intermediate-Z-X | Mass (g) | Yield (%) |
|---|---|---|---|---|
| | 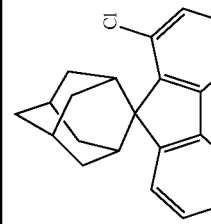  Intermediate-B | 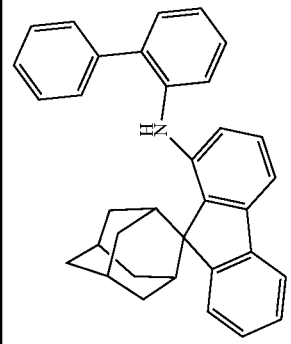  Intermediate-Z-11 | 13.6 | 64 |
| | 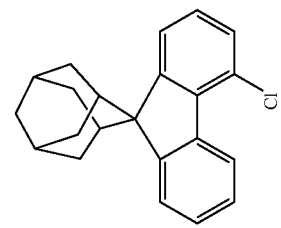  Intermediate-C | 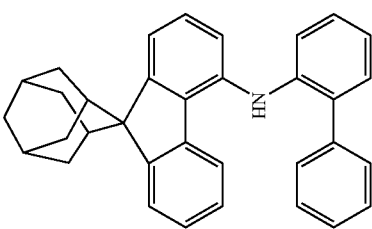  Intermediate-Z-12 | 13.9 | 66 |

TABLE 4-continued

| SM-Z-X | Intermediate-X | Intermediate-Z-X | Mass (g) | Yield (%) |
|---|---|---|---|---|
| | Intermediate-D | Intermediate-Z-13 | 13.7 | 65 |
| 7293-45-0 | Intermediate-B | Intermediate-Z-14 | 16.1 | 65 |

TABLE 4-continued
| SM-Z-X | Intermediate-X | Intermediate-Z-X | Mass (g) | Yield (%) |
|---|---|---|---|---|
| | Intermediate-C 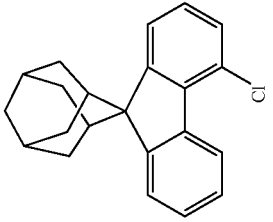 | Intermediate-Z-15 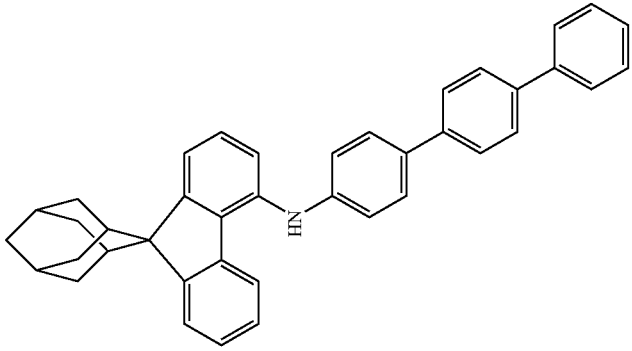 | 15.8 | 64 |

TABLE 4-continued
| SM-Z-X | Intermediate-X | Intermediate-Z-X | Mass (g) | Yield (%) |
|---|---|---|---|---|
| 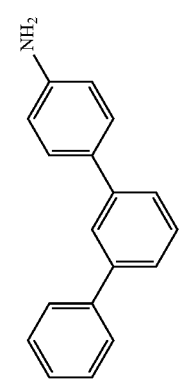 | 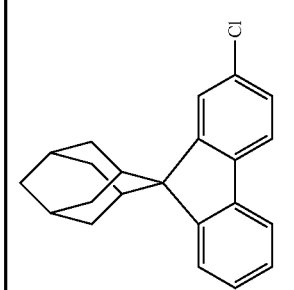 Intermediate-D | 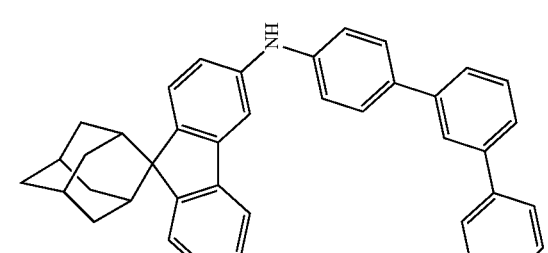 Intermediate-Z-16 | 15.6 | 63 |
| | 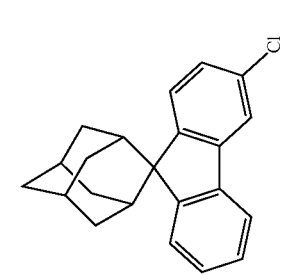 Intermediate-A |  Intermediate-Z-17 | 15.1 | 61 |
5728-67-6

TABLE 4-continued

| SM-Z-X | Intermediate-X | Intermediate-Z-X | Mass (g) | Yield (%) |
|---|---|---|---|---|
|  | Intermediate-C | Intermediate-Z-18 | 14.9 | 60 |
|  | Intermediate-D | Intermediate-Z-19 | 15.1 | 61 |

TABLE 4-continued
| SM-Z-X | Intermediate-X | Intermediate-Z-X | Mass (g) | Yield (%) |
|---|---|---|---|---|
| 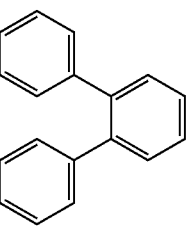 5728-65-4 | 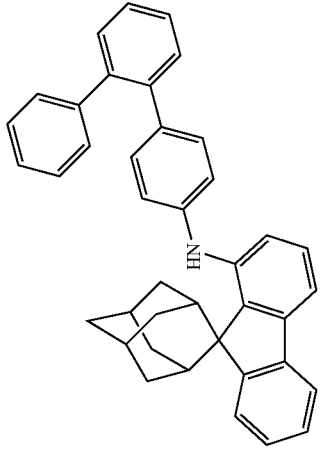 Intermediate-B | 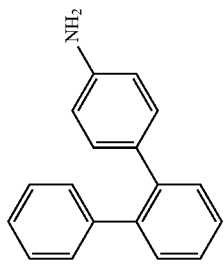 Intermediate-Z-20 | 14.9 | 60 |
| | 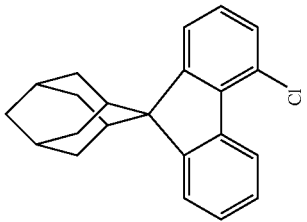 Intermediate-C | 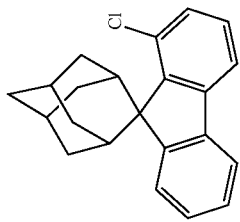 Intermediate-Z-21 | 15.1 | 61 |

TABLE 4-continued
| SM-Z-X | Intermediate-X | Intermediate-Z-X | Mass (g) | Yield (%) |
|---|---|---|---|---|
| 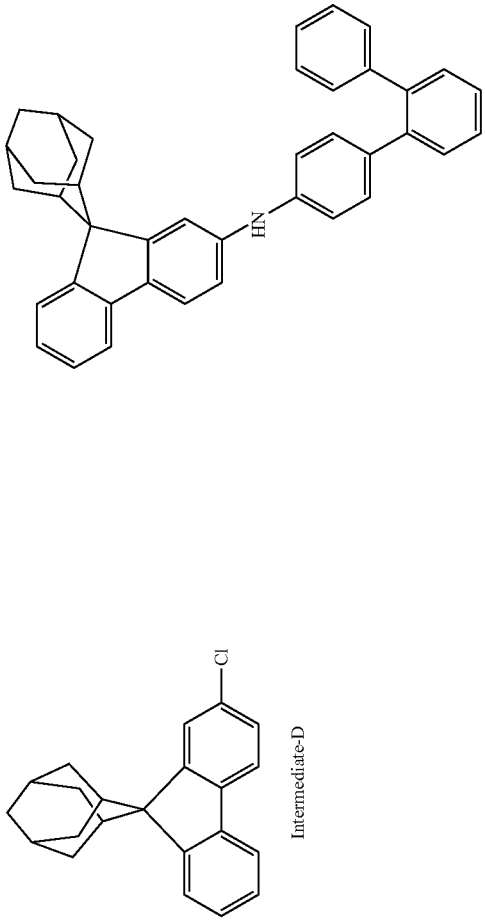 | 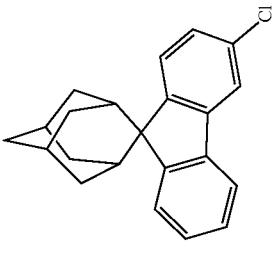Intermediate-D | 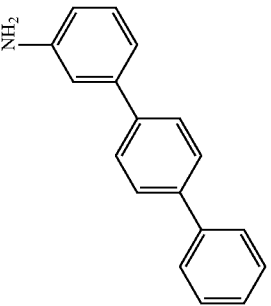Intermediate-Z-22 | 15.3 | 62 |
| 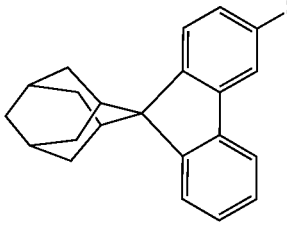98343-26-1 | 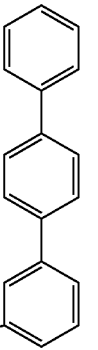Intermediate-A | 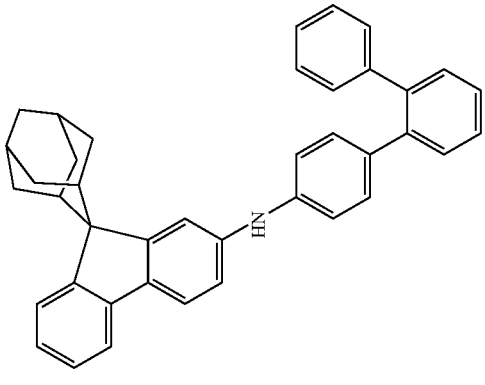Intermediate-Z-23 | 14.8 | 60 |

TABLE 4-continued
| SM-Z-X | Intermediate-X | Intermediate-Z-X | Mass (g) | Yield (%) |
|---|---|---|---|---|
| | Intermediate-B 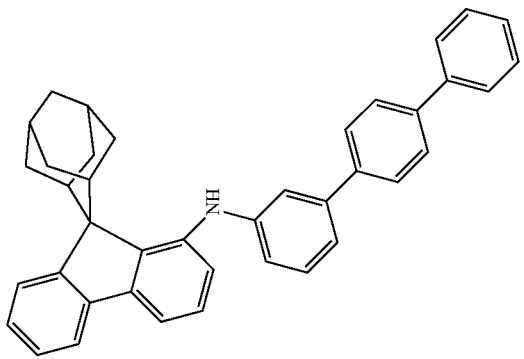 | Intermediate-Z-24 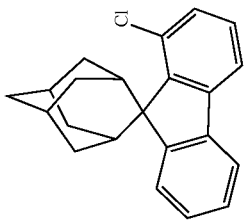 | 14.6 | 59 |

TABLE 4-continued
| SM-Z-X | Intermediate-X | Intermediate-Z-X | Mass (g) | Yield (%) |
|---|---|---|---|---|
| | Intermediate-D | Intermediate-Z-25 | 15.1 | 61 |
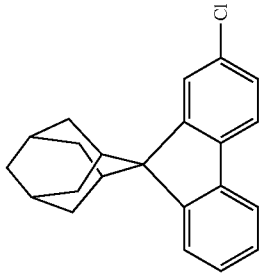
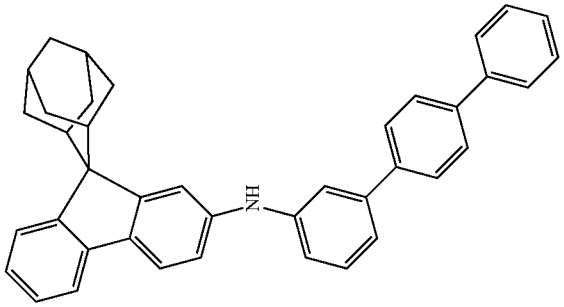

TABLE 4-continued

| SM-Z-X | Intermediate-X | Intermediate-Z-X | Mass (g) | Yield (%) |
|---|---|---|---|---|
| 78626-54-7 | Intermediate-A | Intermediate-Z-26 | 15.3 | 62 |

TABLE 4-continued
| SM-Z-X | Intermediate-X | Intermediate-Z-X | Mass (g) | Yield (%) |
|---|---|---|---|---|
| | 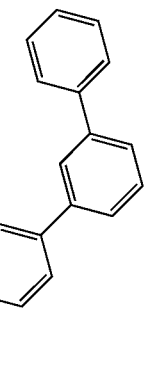<br>Intermediate-C | 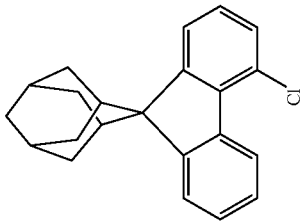<br>Intermediate-Z-27 | 15.1 | 61 |

TABLE 4-continued
| SM-Z-X | Intermediate-X | Intermediate-Z-X | Mass (g) | Yield (%) |
|---|---|---|---|---|
| | 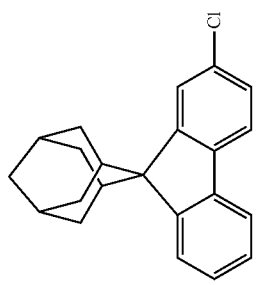 Intermediate-D | 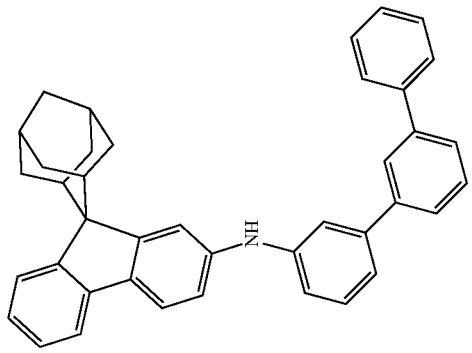 Intermediate-Z-28 | 14.6 | 59 |
| 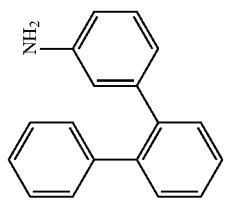 7138-08-1 | 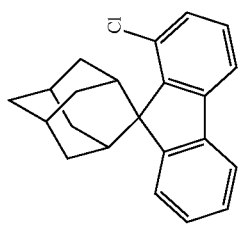 Intermediate-B | Intermediate-Z-29 | 14.8 | 60 |

TABLE 4-continued
| SM-Z-X | Intermediate-X | Intermediate-Z-X | Mass (g) | Yield (%) |
|---|---|---|---|---|
| | Intermediate-C | Intermediate-Z-30 | 15.1 | 61 |
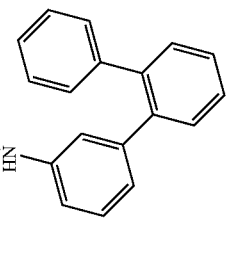

TABLE 4-continued
| SM-Z-X | Intermediate-X | Intermediate-Z-X | Mass (g) | Yield (%) |
|---|---|---|---|---|
| 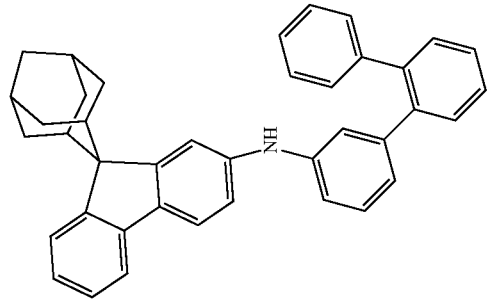 76129-23-2 | 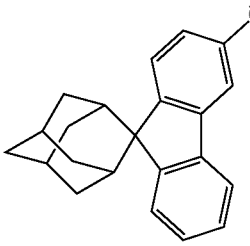 Intermediate-D | 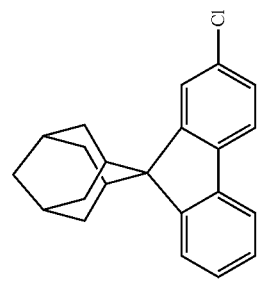 Intermediate-Z-31 | 14.6 | 59 |
| | 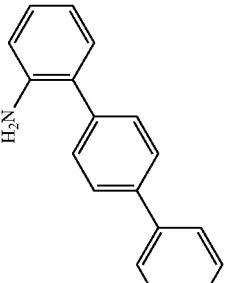 Intermediate-A | 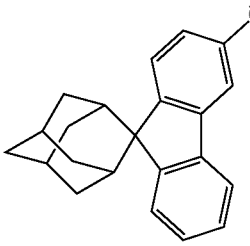 Intermediate-Z-32 | 15.3 | 62 |

TABLE 4-continued
| SM-Z-X | Intermediate-X | Intermediate-Z-X | Mass (g) | Yield (%) |
|---|---|---|---|---|
| 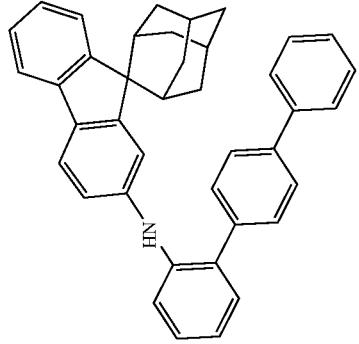 Intermediate-B | | 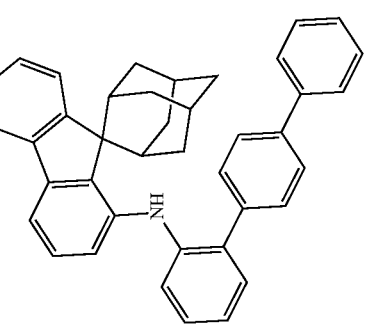 Intermediate-Z-33 | 15.6 | 63 |
| 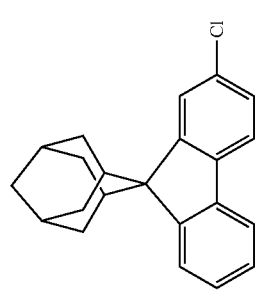 Intermediate-D | | 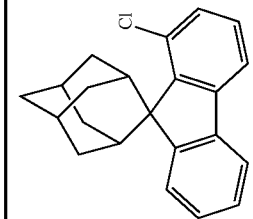 Intermediate-Z-34 | 15.1 | 61 |

TABLE 4-continued
| SM-Z-X | Intermediate-X | Intermediate-Z-X | Mass (g) | Yield (%) |
|---|---|---|---|---|
| 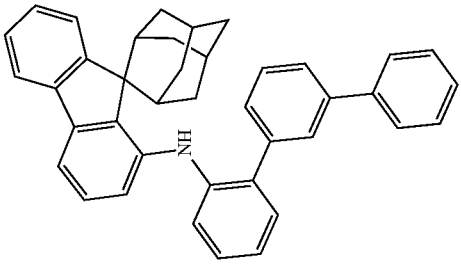<br>76129-25-4 | 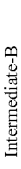<br>Intermediate-B | 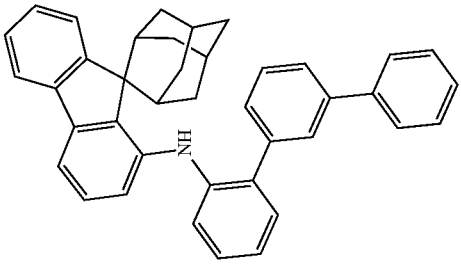<br>Intermediate-Z-35 | 14.8 | 60 |

TABLE 4-continued
| SM-Z-X | Intermediate-X | Intermediate-Z-X | Mass (g) | Yield (%) |
|---|---|---|---|---|
| | Intermediate-C | Intermediate-Z-36 | 14.6 | 59 |
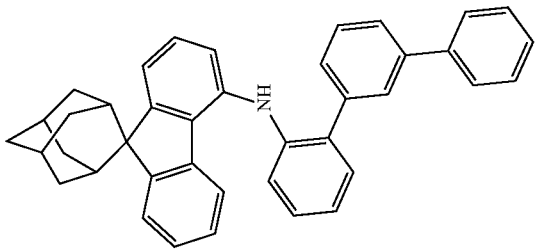
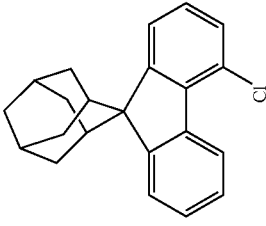

TABLE 4-continued
| SM-Z-X | Intermediate-X | Intermediate-Z-X | Mass (g) | Yield (%) |
|---|---|---|---|---|
| | Intermediate-D 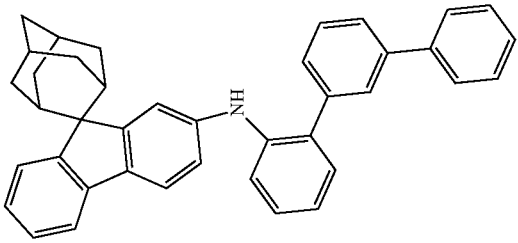 | Intermediate-Z-37 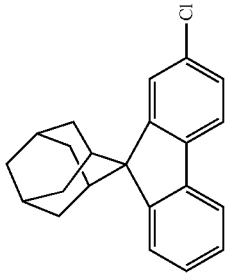 | 15.3 | 62 |

TABLE 4-continued
| SM-Z-X | Intermediate-X | Intermediate-Z-X | Mass (g) | Yield (%) |
|---|---|---|---|---|
| 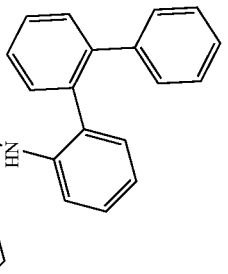<br>56970-23-1 | 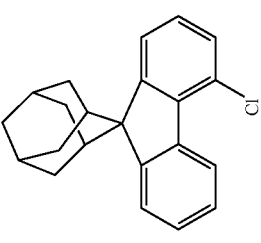<br>Intermediate-A | 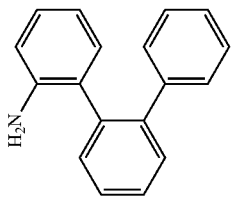<br>Intermediate-Z-38 | 14.8 | 60 |
| | 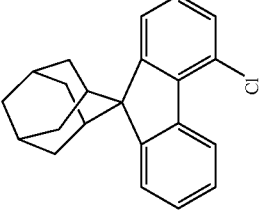<br>Intermediate-C | 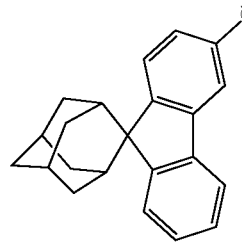<br>Intermediate-Z-39 | 15.3 | 62 |

TABLE 4-continued
| SM-Z-X | Intermediate-X | Intermediate-Z-X | Mass (g) | Yield (%) |
|---|---|---|---|---|
| 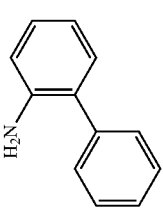 90-41-5 | 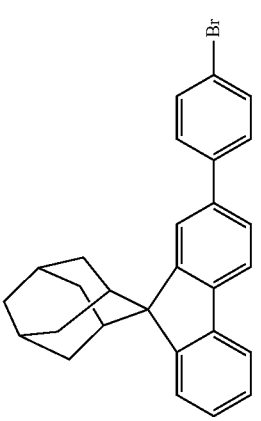 Intermediate-D | 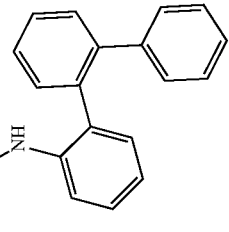 Intermediate-Z-40 | 14.6 | 59 |
| 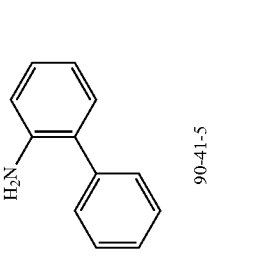 Intermediate-S-1 | | 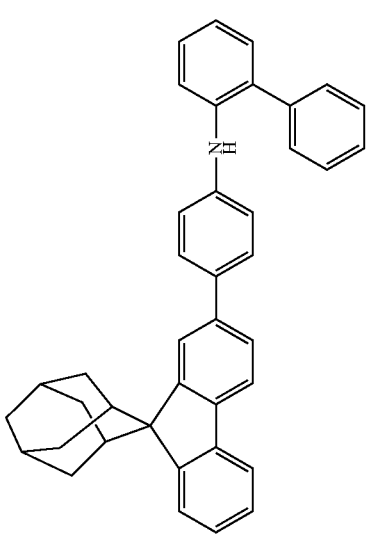 Intermediate-Z-41 | 12.6 | 70 |

TABLE 4-continued

| SM-Z-X | Intermediate-X | Intermediate-Z-X | Mass (g) | Yield (%) |
|---|---|---|---|---|
| Intermediate-S-2 | | Intermediate-Z-42 | 12.7 | 71 |
| Intermediate-S-3 | | Intermediate-Z-43 | 14.4 | 70 |
| Intermediate-S-4 | | Intermediate-Z-44 | 14.6 | 71 |

TABLE 4-continued
| SM-Z-X | Intermediate-X | Intermediate-Z-X | Mass (g) | Yield (%) |
|---|---|---|---|---|
| 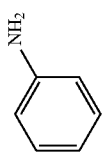 | 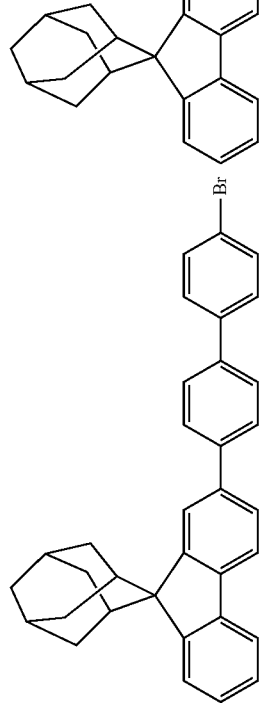 Intermediate-S-5 | 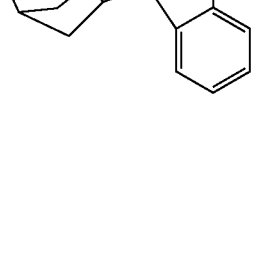 Intermediate-Z-45 | 10.7 | 70 |
| 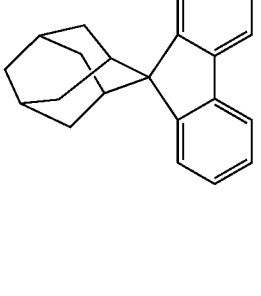 5728-65-4 | 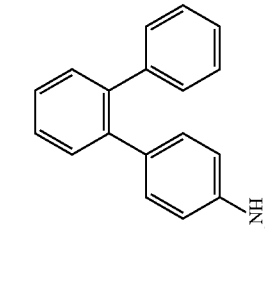 Intermediate-S-6 | 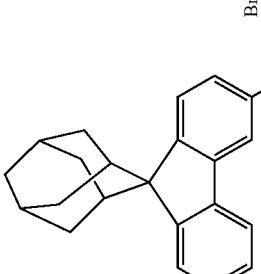 Intermediate-Z-46 | 14.4 | 70 |

TABLE 4-continued

| SM-Z-X | Intermediate-X | Intermediate-Z-X | Mass (g) | Yield (%) |
|---|---|---|---|---|
| 78626-54-7 | Intermediate-S-7 | Intermediate-Z-47 | 13.8 | 70 |
| 76129-23-2 | Intermediate-S-8 | Intermediate-Z-48 | 14.6 | 71 |

TABLE 4-continued
| SM-Z-X | Intermediate-X | Intermediate-Z-X | Mass (g) | Yield (%) |
|---|---|---|---|---|
| 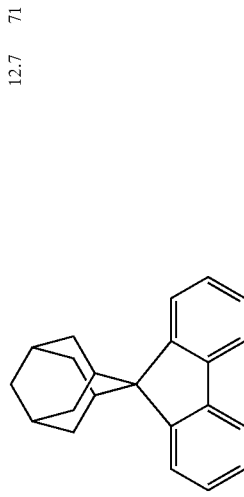 92-67-1 | 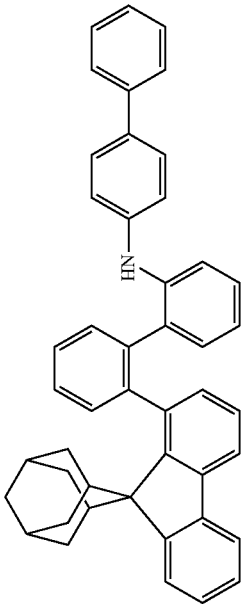 Intermediate-S-9 | 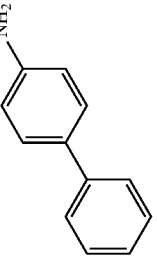 Intermediate-Z-49 | 12.3 | 70 |
|  2243-47-2 | 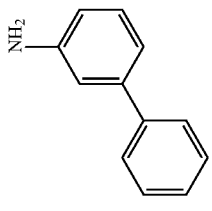 Intermediate-S-10 | 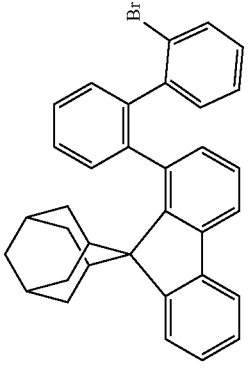 Intermediate-Z-50 | 12.7 | 71 |

TABLE 4-continued

| SM-Z-X | Intermediate-X | Intermediate-Z-X | Mass (g) | Yield (%) |
|---|---|---|---|---|
| 76129-25-4 | Intermediate-S-11 | Intermediate-Z-51 | 13.8 | 70 |

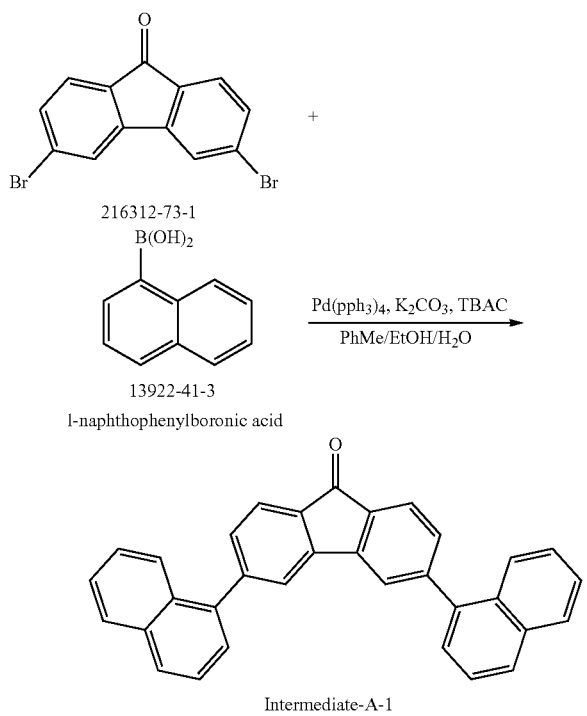

3,6-dibromofluorenone (100 g, 295.8 mmol), 1-naphthophenylboronic acid (101.7 g, 591.7 mmol), tetrakis (triphenylphosphine) palladium (34.2 g, 29.6 mmol), potassium carbonate (244.9 g, 1775.1 mmol), tetrabutylammonium chloride (8.2 g, 29.6 mmol), toluene (800 mL), ethyl alcohol (400 mL), and deionized water (200 mL) were added into the three-neck flask, the temperature was raised to 78° C. under the protection of nitrogen gas, and stirred for 8 hours. The reaction solution was cooled to the room temperature, methylbenzene (500 mL) was added for extraction, the organic phase were combined, the organic phase was dried over anhydrous magnesium sulfate and filtered, after filtration, the filtrate was concentrated under reduced pressure to obtain the crude product. The crude product was purified by silica column chromatography using n-heptane as the mobile phase, and then purified by recrystallization with dichloromethane/ethyl acetate (1:3) system to obtain Intermediate-A-1 (102.3 g, 80% yield).

In some embodiment, Intermediate-A-X shown in Table 5 was synthesized with reference to the synthetic method of Intermediate-A-1, with the difference was that Compound SM-A-X was used instead of 3,6-dibromofluorenone for the preparation of Intermediate-A-1, and SM-A-Y was used instead of 1-naphthaleneboronic acid for the preparation of Intermediate-A-1, and each combination of Compound SM-A-X and SM-A-Y can prepare the unique counterpart Intermediate-A-X. The resulting Intermediate-A-X is shown in Table 5 below.

TABLE 5
| SM-A-X | SM-A-Y | Intermediate-A-X | Mass (g) | Yield (%) |
|---|---|---|---|---|
| 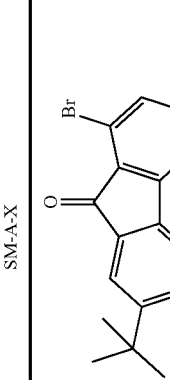 2082789-21-5 | 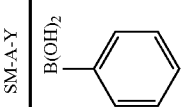 B(OH)₂ | 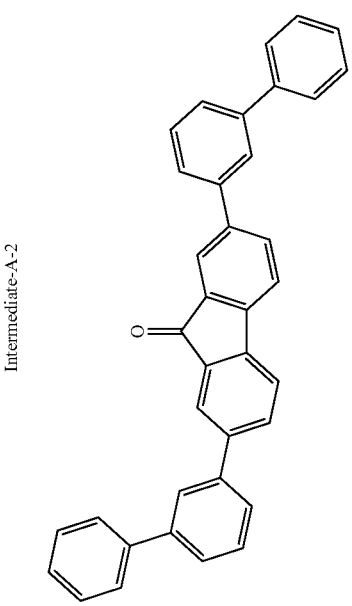 Intermediate-A-2 | 73.8 | 80 |
| 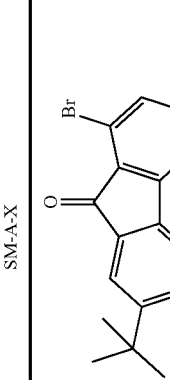 14348-75-5 | 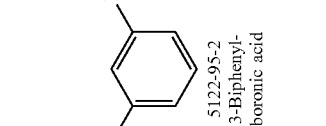 5122-95-2 3-Biphenyl-boronic acid | 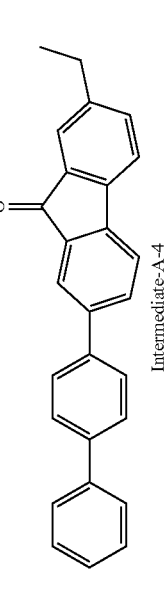 Intermediate-A-3 | 107.4 | 75 |
| 1586003-45-3 | 5122-94-1 4-Biphenyl-boronic acid | Intermediate-A-4 | 83.1 | 78 |

TABLE 5-continued
| SM-A-X | SM-A-Y | Intermediate-A-X | Mass (g) | Yield (%) |
|---|---|---|---|---|
| 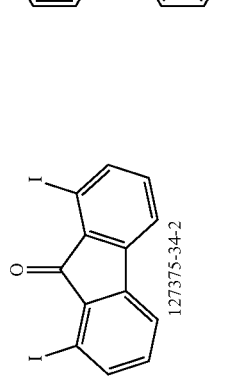 127375-34-2 | 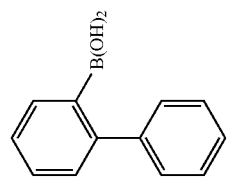 4688-76-0 2-Biphenyl-boronic acid | 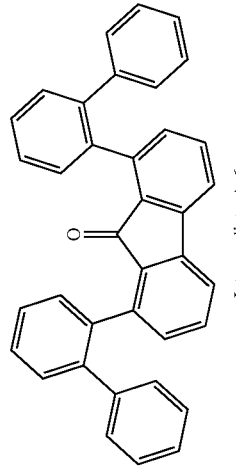 Intermediate-A-6 | 107.4 | 75 |
|  69414-97-7 | 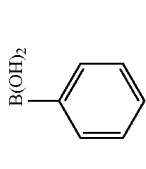 | 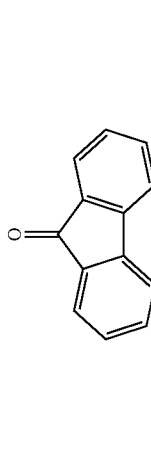 Intermediate-A-8 | 74.6 | 76 |

In some embodiment, Intermediate-B-X shown in Table 6 was synthesized with reference to the synthetic method of Intermediate-A-1, with the difference was that Compound SM-B-X was used instead of 3,6-dibromofluorenone for the preparation of Intermediate-A-1, and SM-B-Y was used instead of 1-naphthaleneboronic acid for the preparation of Intermediate-A-1, and each combination of Compound SM-B-X and SM-B-Y can prepare the unique counterpart Intermediate-B-X. The resulting Intermediate-B-X was shown in Table 6 below.

TABLE 6
| SM-B-X | SM-B-Y | Intermediate-B-X | Mass (g) | Yield (%) |
|---|---|---|---|---|
| 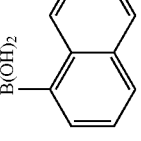 2088671-15-0 | 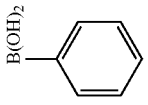 B(OH)₂ phenylboronic acid | 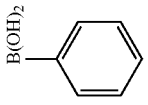 Intermediate-B-1 | 75.6 | 76 |
| 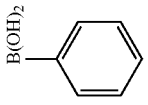 1346010-10-3 | 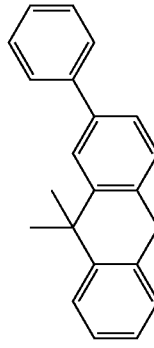 1-naphthylbenzeneboronic acid 13922-41-3 | 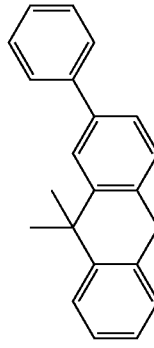 Intermediate-B-2 | 89.4 | 77 |
| 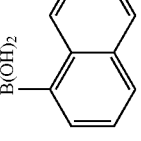 2378634-27-4 | 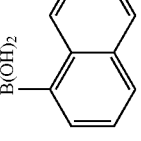 4-Biphenylboronic acid 5122-94-1 | 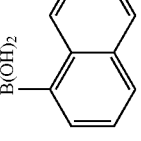 Intermediate-B-5 | 109.8 | 70 |

TABLE 6-continued
| SM-B-X | SM-B-Y | Intermediate-B-X | Mass (g) | Yield (%) |
|---|---|---|---|---|
| 20888-15-7  | 2-naphthylbenzeneboronic acid 32316-92-0 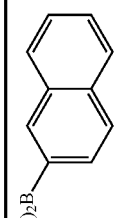 | Intermediate-B-6 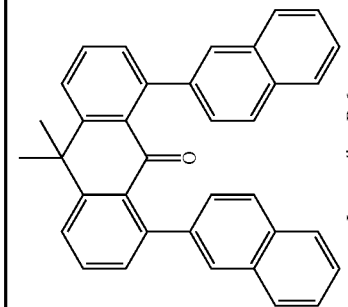 | 118.7 | 73 |

In some embodiment, Intermediate-C-X shown in Table 7 was synthesized with reference to the synthetic method of Intermediate-A-1, with the difference was that Compound SM-C-X was used instead of 3,6-dibromofluorenone for the preparation of Intermediate-A-1, and SM-C-Y was used instead of 1-naphthaleneboronic acid for the preparation of Intermediate-A-1, and each combination of Compound SM-C-X and SM-C-Y can prepare the unique counterpart Intermediate-C-X. The resulting Intermediate-C-X is shown in Table 7 below.

TABLE 7
| SM-C-X | SM-C-Y | Intermediate-C-X | Mass (g) | Yield (%) |
|---|---|---|---|---|
| 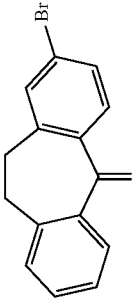 198707-82-3 | 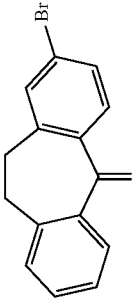 4-Biphenyl-boronic acid 4688-76-0 | 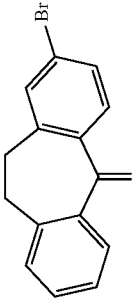 Intermediate-C-1 | 87.8 | 70 |
| 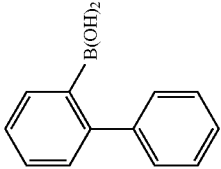 3973-53-3 | 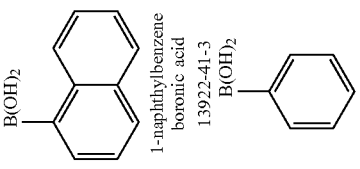 1-naphthylbenzene boronic acid 13922-41-3 | 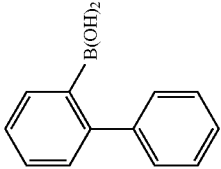 Intermediate-C-2 | 85.0 | 73 |
| 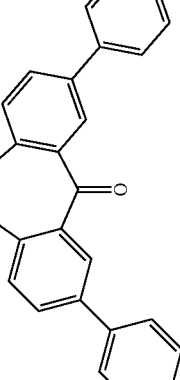 226946-20-9 | 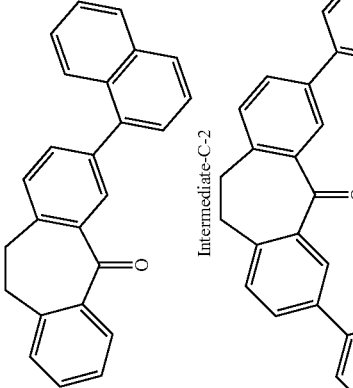 | 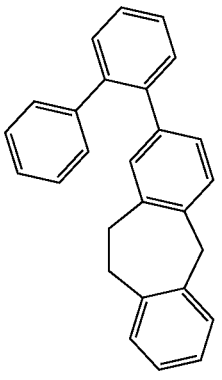 Intermediate-C-4 | 72.8 | 74 |

TABLE 7-continued
| SM-C-X | SM-C-Y | Intermediate-C-X | Mass (g) | Yield (%) |
|---|---|---|---|---|
|  226946-20-9 | 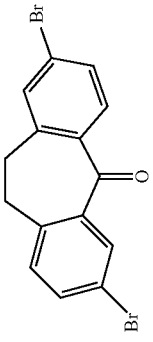 4-Biphenyl-boronic acid 5122-94-1 | 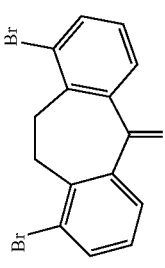 Intermediate-C-5 | 103.6 | 71 |
| 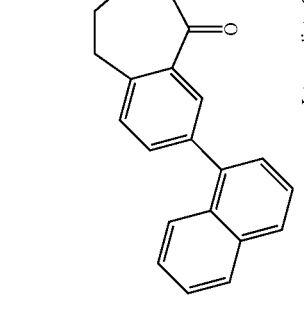 93944-85-5 | 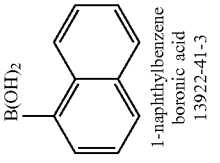 1-naphthylbenzene boronic acid 13922-41-3 | 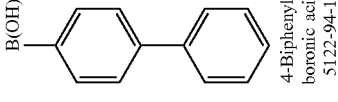 Intermediate-C-6 | 91.8 | 73 |

TABLE 7-continued
| SM-C-X | SM-C-Y | Intermediate-C-X | Mass (g) | Yield (%) |
|---|---|---|---|---|
| 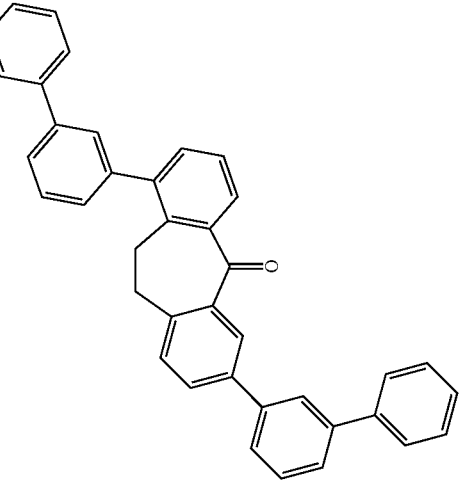<br>226946-22-1 | 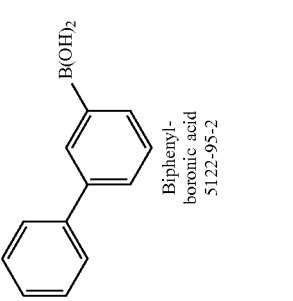<br>Biphenyl-boronic acid<br>5122-95-2 | 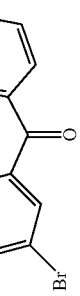<br>Intermediate-C-7 | 98.0 | 70 |

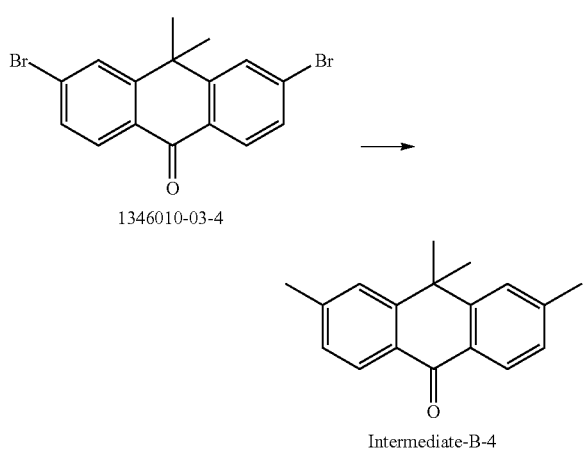

The above compound (1346010-03-4) (100 g, 263.1 mmol) was dissolved completely in tetrahydrofuran (1000 mL), n-BuLi (18.5 g, 289.4 mmol) was dropped slowly at −78° C., and stirred the mixture for 1 hour while maintaining the temperature. Iodomethane (56.0 g, 394.5 mmol) was dropped into the mixture at identical temperature, the temperature was raised to the room temperature slowly, after 15 hours of mixing, the reaction was stopped with the saturated aqueous ammonium chloride solution. The reaction solution was dried by using anhydrous magnesium sulfate, the organic layer collected by the extraction reaction was performed three times with ethyl acetate, and distilled under reduced pressure, and the product was purified by silica column chromatography to obtain Intermediate-B-4 (39.5 g, 60%).

In some embodiment, Intermediate-M-X shown in Table 8 was synthesized with reference to the synthetic method of Intermediate-B-4, with the difference was that Compound SM-M-X was used instead of the Compound (1346010-03-4) to prepare Intermediate-B-4 and SMY was used instead of iodomethane to prepare Intermediate-B-4. And each combination of Compound SM-M-X and SMY can be prepared the unique corresponding Intermediate-M-X, and Intermediate-M-X produced was shown in Table 8 below.

TABLE 8

| SM-M-X | SMY | Intermediate-M-X | Mass (g) | Yield (%) |
|---|---|---|---|---|
| 2082789-20-4 | tert-butyl boric acid 86253-12-5 | Intermediate-A-5 | 50.6 | 55 |
| 858799-69-6 | Methyl boric acid 13061-96-6 | Intermediate-A-7 | 34.5 | 56 |
| 1346009-94-6 | tert-butyl boric acid 86253-12-5 | Intermediate-B-3 | 57.3 | 58 |
| 216658-16-1 | tert-butyl boric acid 86253-12-5 | Intermediate-C-S | 46.4 | 53 |

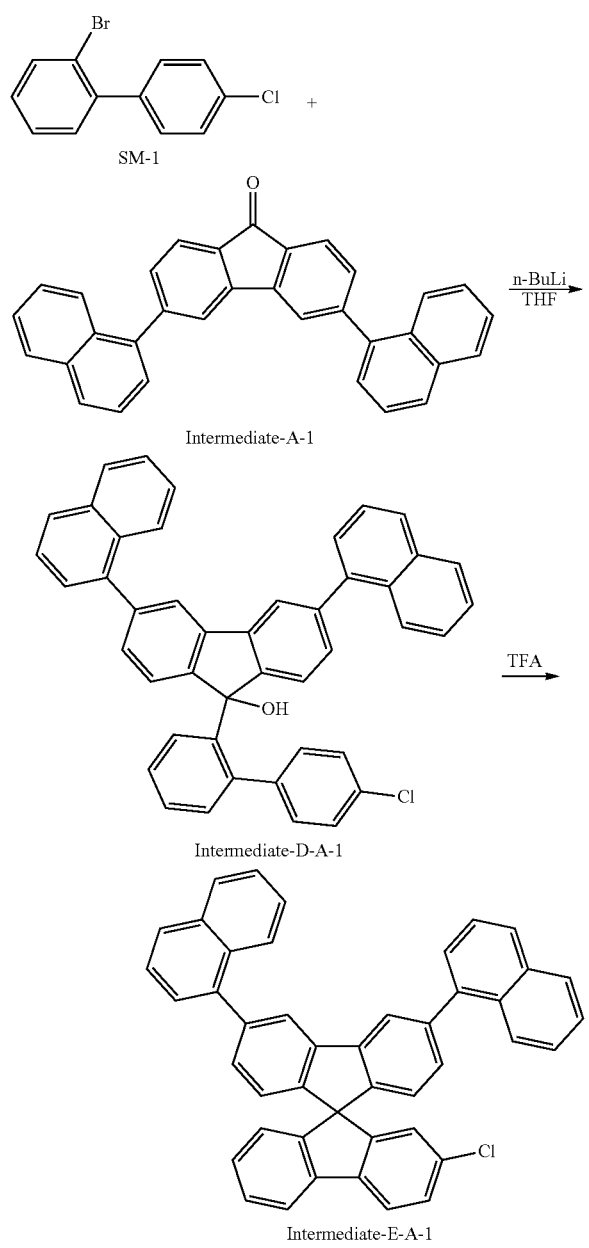

SM-1 (10.0 g, 37.4 mmol) and tetrahydrofuran (100 mL) were added into the three-necked reaction flask under the protection of nitrogen gas, started to stir, and the system was cooled to −78° C. After the temperature stabilizes, n-butyl-lithium (2.9 g, 44.9 mmol) was dropped, and the temperature was kept at −78° C. for 1 hour. Then, drop in Intermediate-A-1 (17.7 g, 41.1 mmol) diluted with tetrahydrofuran (40 mL) to the system, maintain the temperature at −78° C. for 1 hour, naturally raise the temperature to 25° C., and stir for 12 hours. After the reaction is complete, the reaction solution was poured into water (200 mL) and stirred for 10 min. Then, dichloromethane (200 mL) was added to perform extraction operation 2 times, the organic phases were combined, dried with anhydrous magnesium sulfate, and passed through a silica gel funnel, the filtrate was concentrated and dried to obtain Intermediate-D-A-1 (13.9 g, yield: 60%).

Intermediate-D-A-1 (10.0 g, 16.1 mmol) and trifluoro-acetic acid (500 mL) were added into a single-mouth flask, started to stir, and the temperature was gradually raised to 80° C. for 11 hours and refluxed reaction. After the above reaction was completed, the reaction solution was pour into water (1:20), stirred for 30 min and filtered, washed with water (1:2), and washed with ethanol (1:2) to obtain the crude product, and recrystallize the crude product with dichloromethane: n-heptane=1:2, to obtain Intermediate-E-A-1 (7.8 g, 80% yield).

In some embodiment, Intermediate-D-M-X shown in Table 9 was synthesized and E-M-X shown in Table 10 was synthesized with reference to the synthetic method of Intermediate D-A-1, with the difference was that Intermediate-M-X was used instead of Intermediate-A-1 for the preparation of Intermediate D-A-1, SM-X was used instead of SM-1 for the preparation of Intermediate D-A-1, and each combination of Compound Intermediate-M-X and SM-X can be combined to the corresponding Intermediate-D-M-X and Intermediate-E-M-X. The produced Intermediate-D-M-X and Intermediate-E-M-X were shown in Tables 9 and 10

TABLE 9
| SM-X | Intermediate-M-X | Intermediate-D-M-X | Mass (g) | Yield (%) |
|---|---|---|---|---|
| 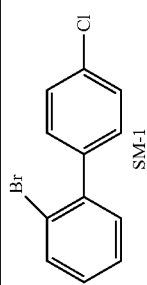 SM-1 | 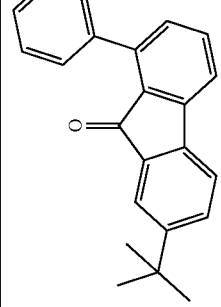 Intermediate-A-2 | 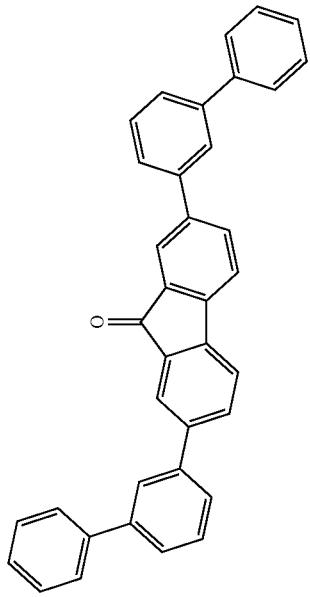 Intermediate-D-A-2 | 9.8 | 61 |
| | 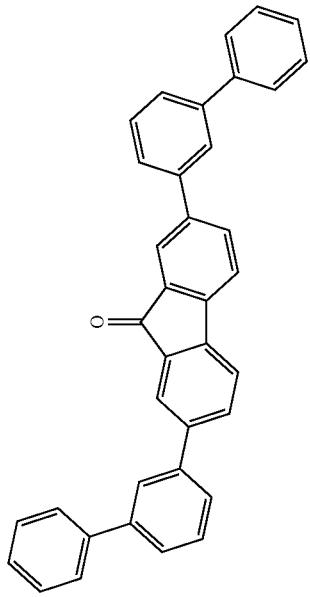 Intermediate-A-3 | 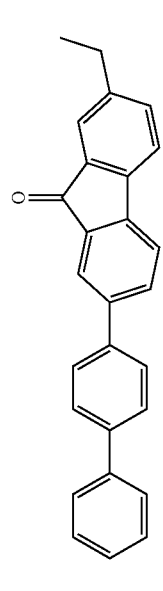 Intermediate-D-A-3 | 8.3 | 60 |
| | 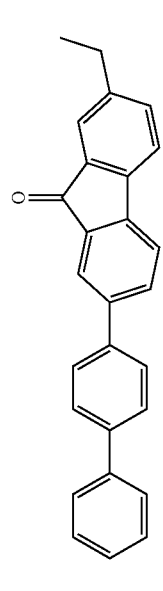 Intermediate-A-4 | 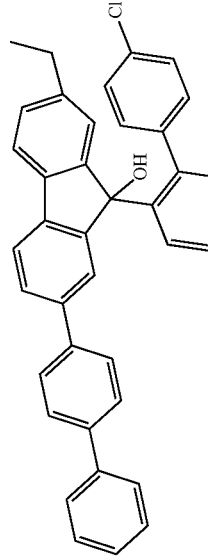 Intermediate-D-A-4 | 9.3 | 61 |

TABLE 9-continued
| SM-X | Intermediate-M-X | Intermediate-D-M-X | Mass (g) | Yield (%) |
|---|---|---|---|---|
| 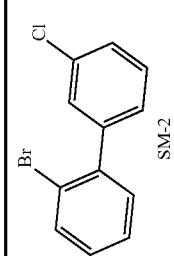 SM-2 | 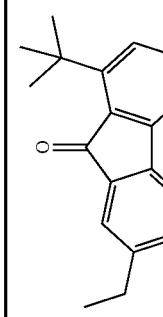 Intermediate-A-5 | 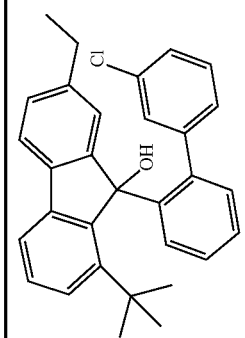 Intermediate-D-A-5 | 10.4 | 61 |
| | 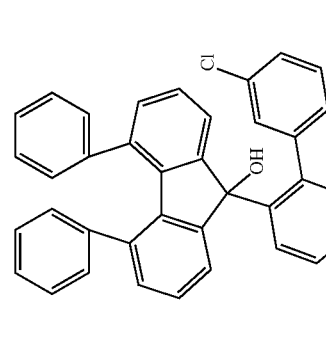 Intermediate-A-8 | 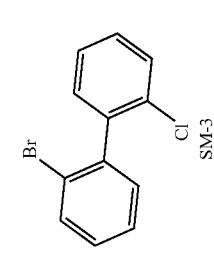 Intermediate-D-A-6 | 9.4 | 60 |
| 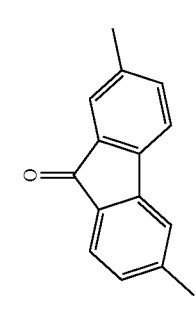 SM-3 | 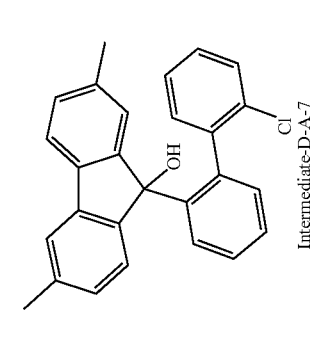 Intermediate-A-7 | Intermediate-D-A-7 | 11.4 | 60 |

TABLE 9-continued

| SM-X | Intermediate-M-X | Intermediate-D-M-X | Mass (g) | Yield (%) |
|---|---|---|---|---|
| | Intermediate-A-6 | Intermediate-D-A-8 | 8.3 | 60 |
| | Intermediate-B-1 | Intermediate-D-B-1 | 9.7 | 60 |
| | Intermediate-B-2 | Intermediate-D-B-2 | 9.3 | 60 |
| SM-1 | | | | |

TABLE 9-continued

| SM-X | Intermediate-M-X | Intermediate-D-M-X | Mass (g) | Yield (%) |
|---|---|---|---|---|
| | Intermediate-B-3 | Intermediate-D-B-3 | 9.5 | 61 |
| | Intermediate-B-4 | Intermediate-D-B-4 | 10.5 | 60 |
| | Intermediate-B-5 | Intermediate-D-B-5 | 8.1 | 60 |

TABLE 9-continued

| SM-X | Intermediate-M-X | Intermediate-D-M-X | Mass (g) | Yield (%) |
|---|---|---|---|---|
| Intermediate-B-6 | | Intermediate-D-B-6 | 8.3 | 60 |
| 5447-86-9 | | Intermediate-D-B-7 | 11.1 | 60 |
| 1346009-96-8 | | Intermediate-D-B-8 | 8.2 | 60 |

TABLE 9-continued
| SM-X | Intermediate-M-X | Intermediate-D-M-X | Mass (g) | Yield (%) |
|---|---|---|---|---|
| 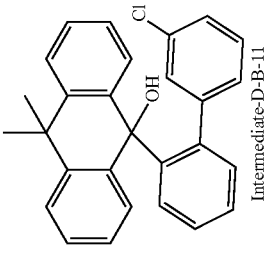 SM-2 | 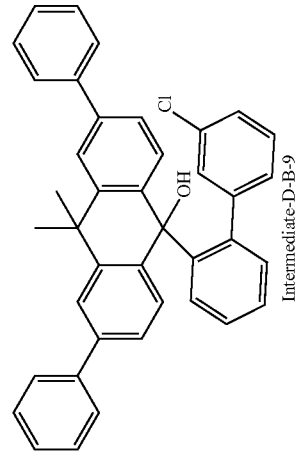 1346009-95-7 | 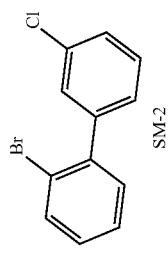 Intermediate-D-B-9 | 9.4 | 60 |
| | 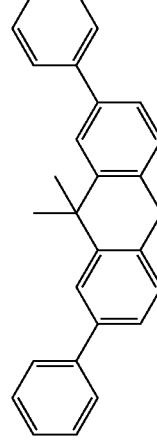 Intermediate-B-3 | 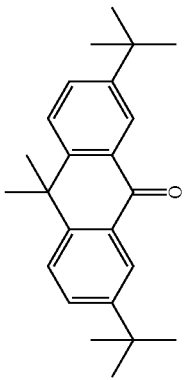 Intermediate-D-B-10 | 11.0 | 60 |
| | 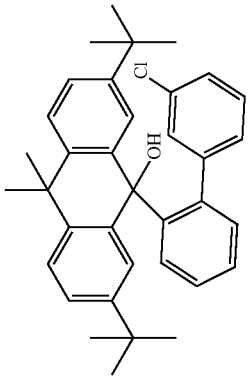 5447-86-9 | 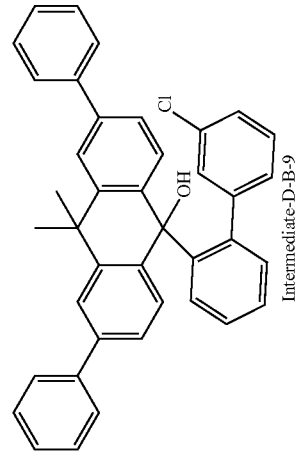 Intermediate-D-B-11 | | |

TABLE 9-continued
| SM-X | Intermediate-M-X | Intermediate-D-M-X | Mass (g) | Yield (%) |
|---|---|---|---|---|
| 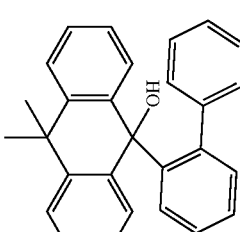 SM-3 | 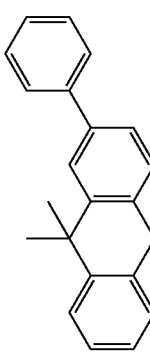 Intermediate-B-4 | 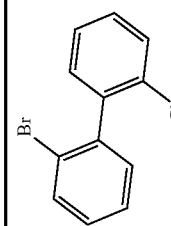 Intermediate-D-B-12 | 10.5 | 60 |
| | 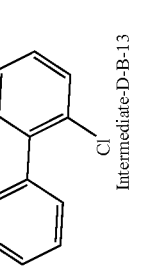 Intermediate-B-1 | 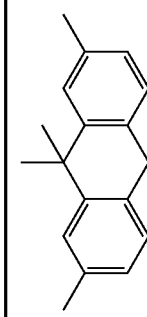 Intermediate-D-B-13 | 8.9 | 61 |
| | 5447-86-9 | 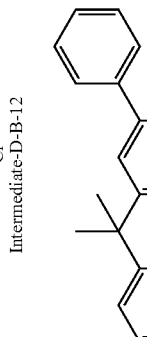 Intermediate-D-B-14 | 11.0 | 60 |

TABLE 9-continued
| SM-X | Intermediate-M-X | Intermediate-D-M-X | Mass (g) | Yield (%) |
|---|---|---|---|---|
| 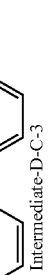 SM-1 | 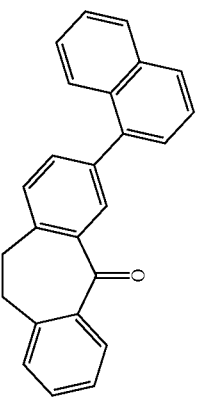 Intermediate-C-1 | 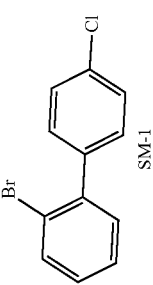 Intermediate-D-C-1 | 9.1 | 60 |
| | 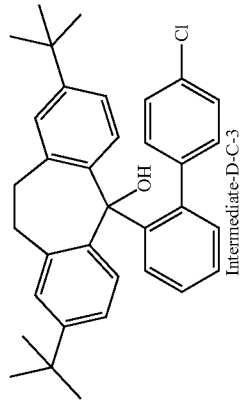 Intermediate-C-2 | 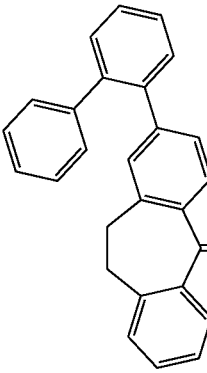 Intermediate-D-C-2 | 9.5 | 61 |
| | 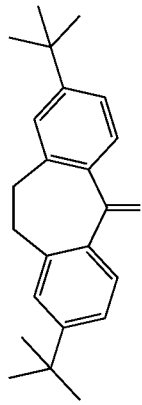 Intermediate-C-3 | 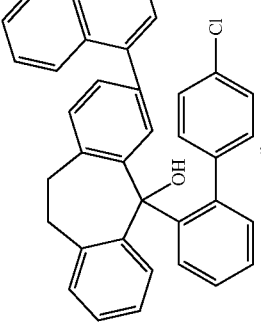 Intermediate-D-C-3 | 9.5 | 60 |

TABLE 9-continued
| SM-X | Intermediate-M-X | Intermediate-D-M-X | Mass (g) | Yield (%) |
|---|---|---|---|---|
| | 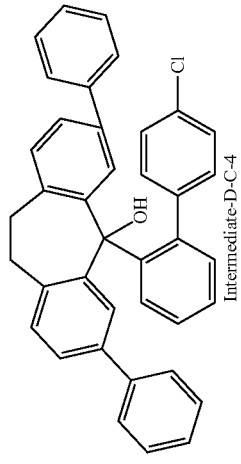 Intermediate-M-4 | 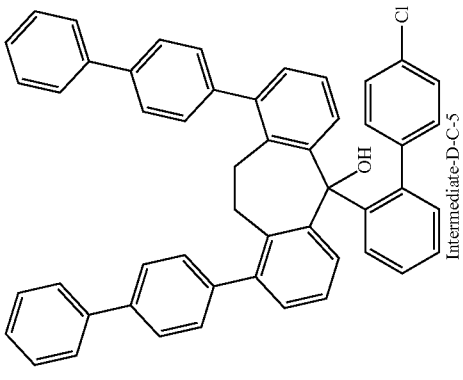 Intermediate-D-C-4 | 9.3 | 61 |
| | 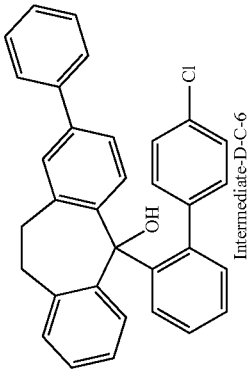 Intermediate-C-5 | 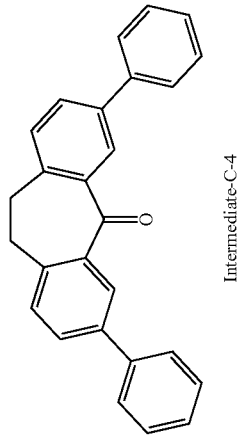 Intermediate-D-C-5 | 8.2 | 60 |
| 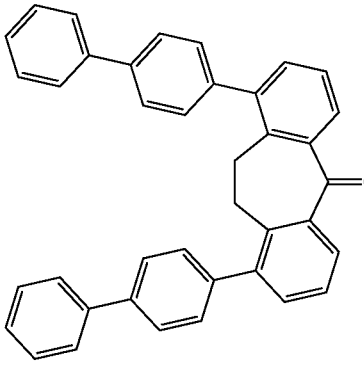 869070-31-5 | | Intermediate-D-C-6 | 9.9 | 60 |

TABLE 9-continued

| SM-X | Intermediate-M-X | Intermediate-D-M-X | Mass (g) | Yield (%) |
|---|---|---|---|---|
| | 156086-77-0 | Intermediate-D-C-7 | 10.7 | 60 |
| | 61565-77-3 | Intermediate-D-C-8 | 11.1 | 60 |
| | 1210-35-1 | Intermediate-D-C-9 | 11.4 | 60 |
| SM-2 | 1210-35-1 | Intermediate-D-C-10 | 11.2 | 59 |

TABLE 9-continued

| SM-X | Intermediate-M-X | Intermediate-D-M-X | Mass (g) | Yield (%) |
|---|---|---|---|---|
| | 33586-85-5 | Intermediate-D-C-11 | 10.3 | 60 |
| | 216658-81-0 | Intermediate-D-C-12 | 10.5 | 61 |
| | 172216-13-6 | Intermediate-D-C-13 | 10.8 | 60 |
| SM-3 | | | | |

TABLE 9-continued
| SM-X | Intermediate-M-X | Intermediate-D-M-X | Mass (g) | Yield (%) |
|---|---|---|---|---|
| | Intermediate-C-6 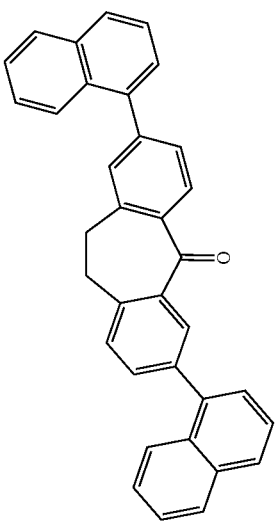 | Intermediate-D-C-14 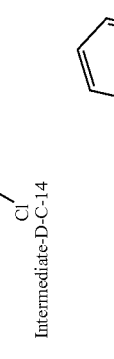 | 8.6 | 61 |
| | Intermediate-C-7 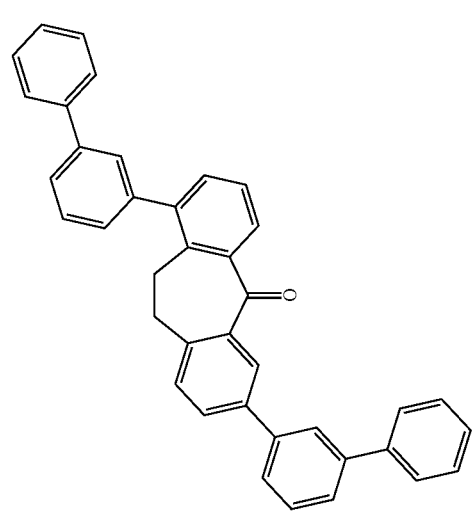 | Intermediate-D-C-15 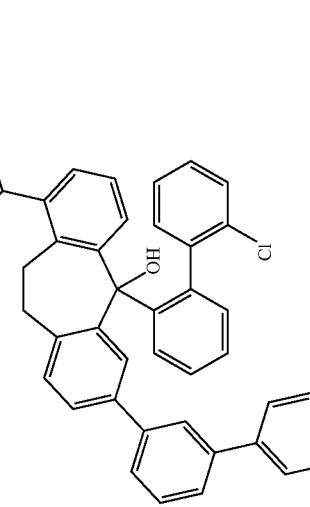 | 8.2 | 60 |

TABLE 9-continued

| SM-X | Intermediate-M-X | Intermediate-D-M-X | Mass (g) | Yield (%) |
|---|---|---|---|---|
| | 61565-91-1 (ethyl-dibenzosuberone) | Intermediate-D-C-16 | 10.9 | 61 |
| | 1210-35-1 (dibenzosuberone) | Intermediate-D-C-17 | 11.4 | 60 |

TABLE 10

| Intermediate-D-M-X | Intermediate-E-M-X | Mass (g) | Yield (%) |
|---|---|---|---|
| Intermediate-D-A-2 | Intermediate-E-A-2 | 5.0 | 80 |
| Intermediate-D-A-3 | Intermediate-E-A-3 | 5.2 | 81 |
| Intermediate-D-A-4 | Intermediate-E-A-4 | 5.1 | 80 |

TABLE 10-continued
| Intermediate-D-M-X | Intermediate-E-M-X | Mass (g) | Yield (%) |
|---|---|---|---|
| 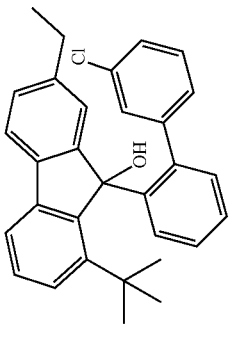 Intermediate-D-A-5 | 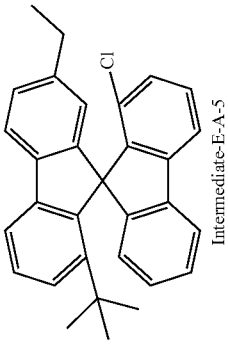 Intermediate-E-A-5 | 2.7 | 40 |
|  | 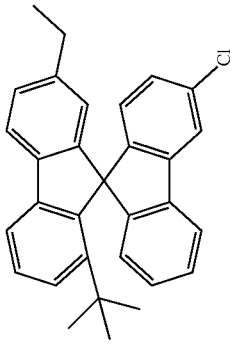 Intermediate-E-A-5-0 | 2.7 | 40 |
| 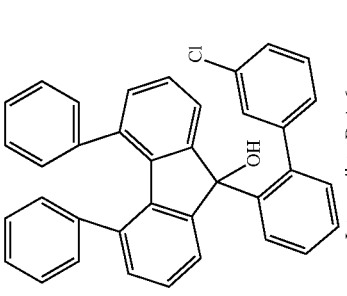 Intermediate-D-A-6 | 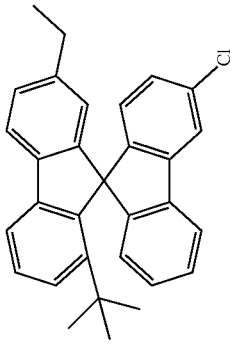 Intermediate-E-A-6 | | |

TABLE 10-continued
| Intermediate-D-M-X | Intermediate-E-M-X | Mass (g) | Yield (%) |
|---|---|---|---|
| | 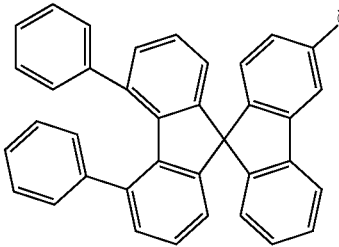<br>Intermediate-E-A-6-0 | | |
| 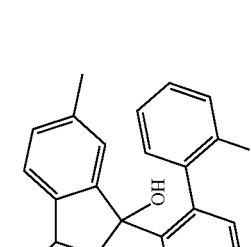<br>Intermediate-D-A-7 | 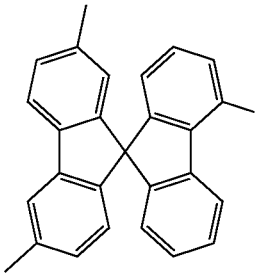<br>Intermediate-E-A-7 | 5.3 | 80 |
| 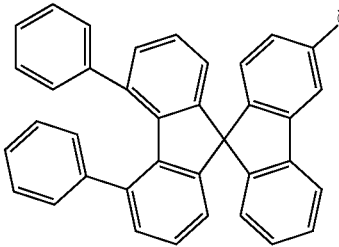<br>Intermediate-D-A-8 | <br>Intermediate-E-A-8 | 5.5 | 80 |

TABLE 10-continued

| Intermediate-D-M-X | Intermediate-E-M-X | Mass (g) | Yield (%) |
|---|---|---|---|
| Intermediate-D-B-1 | Intermediate-E-B-1 | 5.4 | 80 |
| Intermediate-D-B-2 | Intermediate-E-B-1 | 5.5 | 81 |
| Intermediate-D-B-3 | Intermediate-E-B-3 | 5.4 | 80 |

TABLE 10-continued

| Intermediate-D-M-X | Intermediate-E-M-X | Mass (g) | Yield (%) |
|---|---|---|---|
| Intermediate-D-B-4 | Intermediate-E-B-4 | 5.4 | 81 |
| Intermediate-D-B-5 | Intermediate-E-B-5 | 5.4 | 81 |
| | | 5.4 | 80 |
| Intermediate-D-B-6 | Intermediate-E-B-6 | 5.5 | 81 |

TABLE 10-continued

| Intermediate-D-M-X | Intermediate-E-M-X | Mass (g) | Yield (%) |
|---|---|---|---|
| Intermediate-D-B-7 | Intermediate-E-B-7 | 5.3 | 80 |
| Intermediate-D-B-8 | Intermediate-E-B-8 | 5.5 | 81 |
| Intermediate-D-B-9 | Intermediate-E-B-9 | 2.7 | 40 |

TABLE 10-continued

| Intermediate-D-M-X | Intermediate-E-M-X | Mass (g) | Yield (%) |
|---|---|---|---|
| Intermediate-D-B-10 | Intermediate-E-B-9-0 | 2.7 | 40 |
| | Intermediate-E-B-10 | 2.7 | 40 |
| | Intermediate-E-B-10-0 | 2.8 | 41 |

TABLE 10-continued

| Intermediate-D-M-X | Intermediate-E-M-X | Mass (g) | Yield (%) |
|---|---|---|---|
| Intermediate-D-B-11 | Intermediate-E-B-11 | 2.7 | 40 |
|  | Intermediate-E-B-11-0 | 2.7 | 40 |
| Intermediate-D-B-12 | Intermediate-E-B-12 | 5.4 | 80 |

TABLE 10-continued

| Intermediate-D-M-X | Intermediate-E-M-X | Mass (g) | Yield (%) |
|---|---|---|---|
| Intermediate-D-B-13 | Intermediate-E-B-13 | 5.5 | 81 |
| Intermediate-D-B-14 | Intermediate-E-B-14 | 5.4 | 80 |
| Intermediate-D-C-1 | Intermediate-E-C-1 | 5.5 | 81 |

TABLE 10-continued
| Intermediate-D-M-X | Intermediate-E-M-X | Mass (g) | Yield (%) |
|---|---|---|---|
| 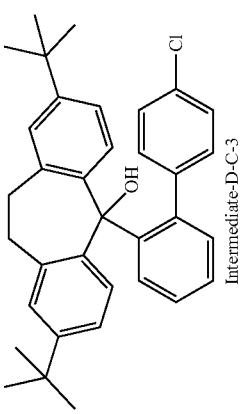 Intermediate-D-C-2 | 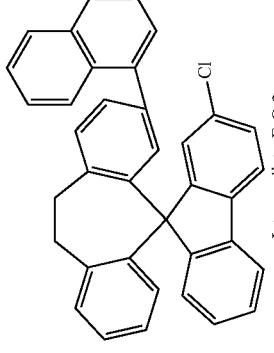 Intermediate-E-C-2 | 5.4 | 80 |
| 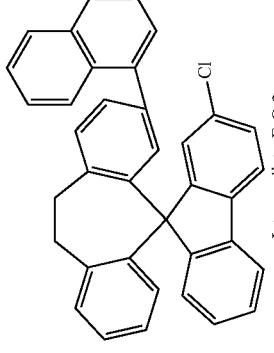 Intermediate-D-C-3 | 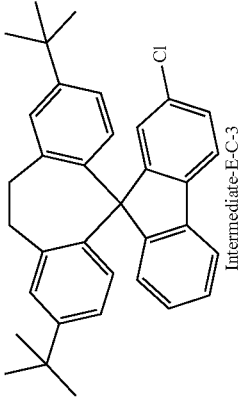 Intermediate-E-C-3 | 5.5 | 81 |
| 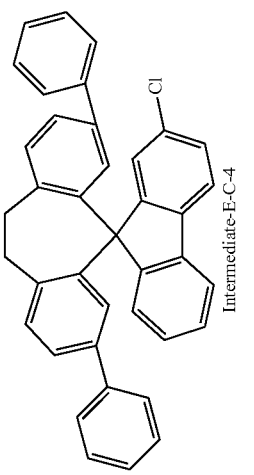 Intermediate-D-C-4 | 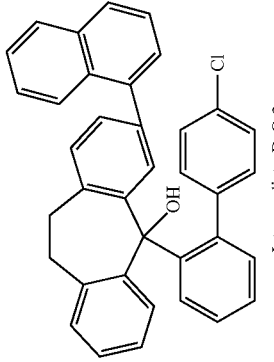 Intermediate-E-C-4 | 5.4 | 80 |

TABLE 10-continued
| Intermediate-D-M-X | Intermediate-E-M-X | Mass (g) | Yield (%) |
|---|---|---|---|
| 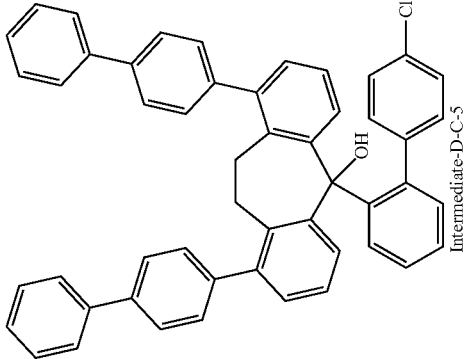 Intermediate-D-C-5 | 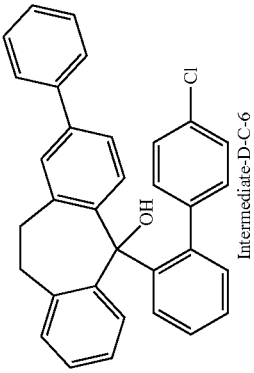 Intermediate-E-C-5 | 5.5 | 81 |
| 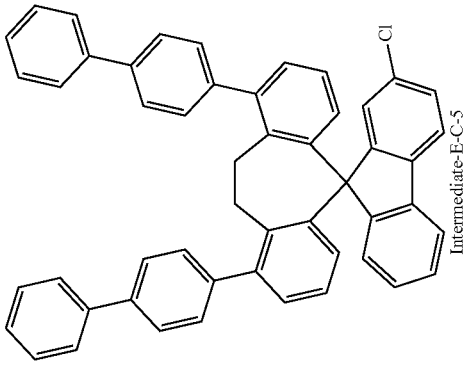 Intermediate-D-C-6 | Intermediate-E-C-6 | 5.4 | 80 |
| 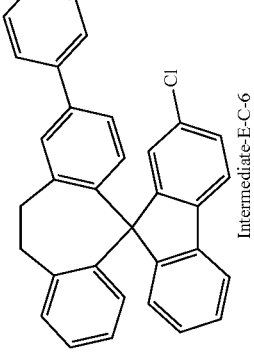 Intermediate-D-C-7 | Intermediate-E-C-7 | 5.1 | 81 |

TABLE 10-continued
| Intermediate-D-M-X | Intermediate-E-M-X | Mass (g) | Yield (%) |
|---|---|---|---|
| Intermediate-D-C-8 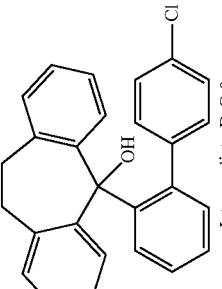 | Intermediate-E-C-8 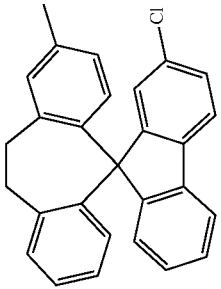 | 5.3 | 80 |
| Intermediate-D-C-9 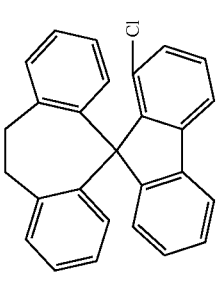 | Intermediate-E-C-9 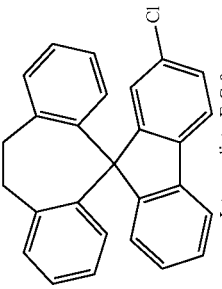 | 5.4 | 81 |
| 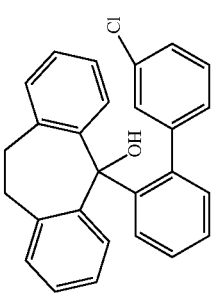 | 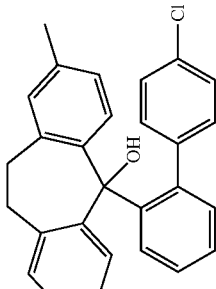 | 2.6 | 40 |

TABLE 10-continued
| Intermediate-E-M-X | Mass (g) | Yield (%) |
|---|---|---|
| 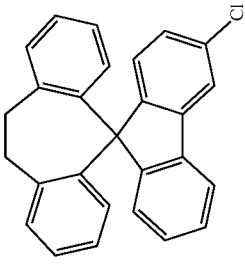 Intermediate-E-C-10-0 | 2.7 | 41 |
| 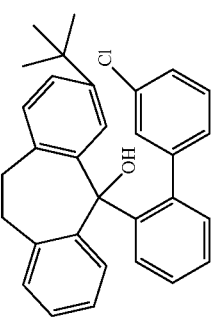 Intermediate-E-C-11 | 2.8 | 41 |
| 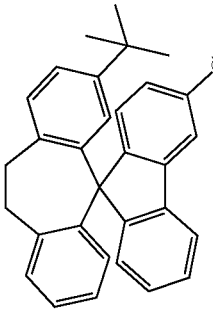 Intermediate-E-C-11-0 | 2.7 | 40 |
Intermediate-D-M-X
Intermediate-D-C-11

TABLE 10-continued
| Intermediate-D-M-X | Intermediate-E-M-X | Mass (g) | Yield (%) |
|---|---|---|---|
| 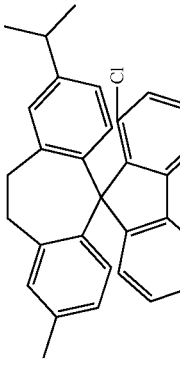 Intermediate-D-C-12 | 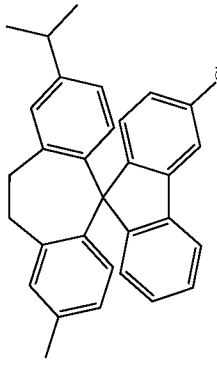 Intermediate-E-C-12 | 2.7 | 40 |
|  | 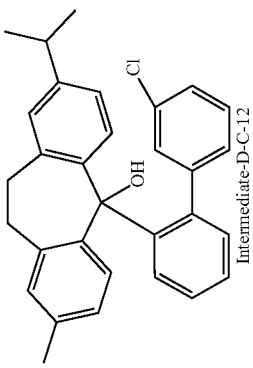 Intermediate-E-C-12-0 | 2.7 | 40 |
| 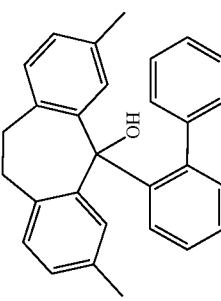 Intermediate-D-C-13 | 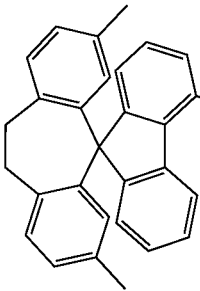 Intermediate-E-C-13 | 5.3 | 80 |

TABLE 10-continued
| Intermediate-D-M-X | Intermediate-E-M-X | Mass (g) | Yield (%) |
|---|---|---|---|
| 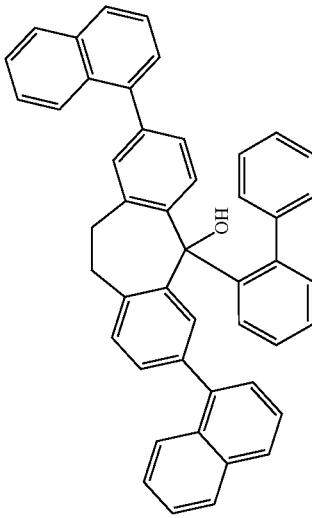 Intermediate-D-C-14 | 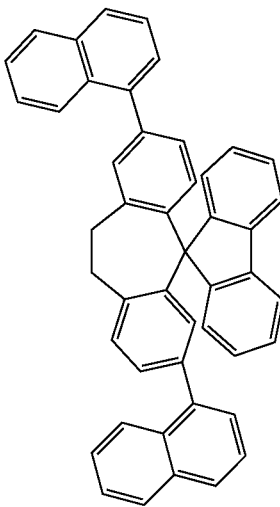 Intermediate-E-C-14 | 5.4 | 81 |
| 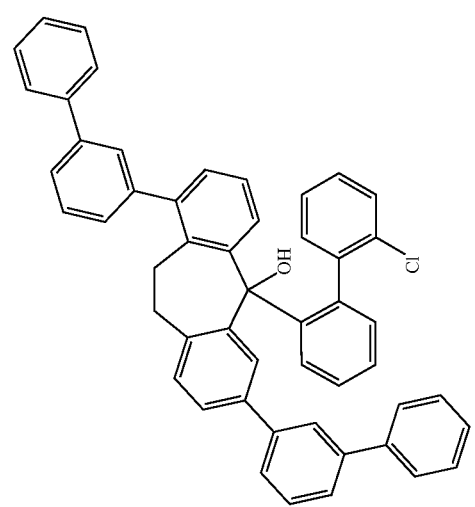 Intermediate-D-C-15 | 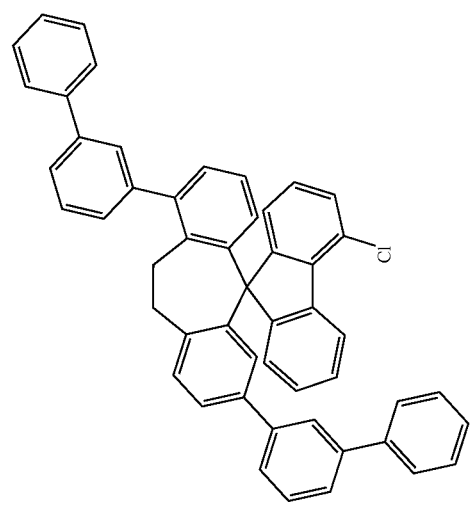 Intermediate-E-C-15 | 5.4 | 80 |

TABLE 10-continued
| Intermediate-D-M-X | Intermediate-E-M-X | Mass (g) | Yield (%) |
|---|---|---|---|
| 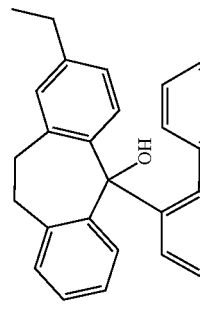 Intermediate-D-C-16 | 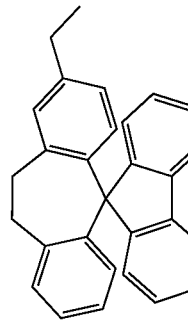 Intermediate-E-C-16 | 5.4 | 80 |
| 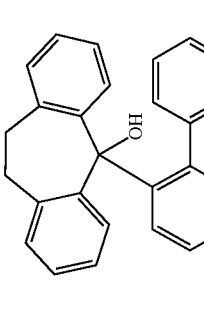 Intermediate-D-C-17 | 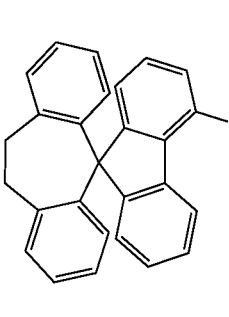 Intermediate-E-C-17 | 5.4 | 80 |

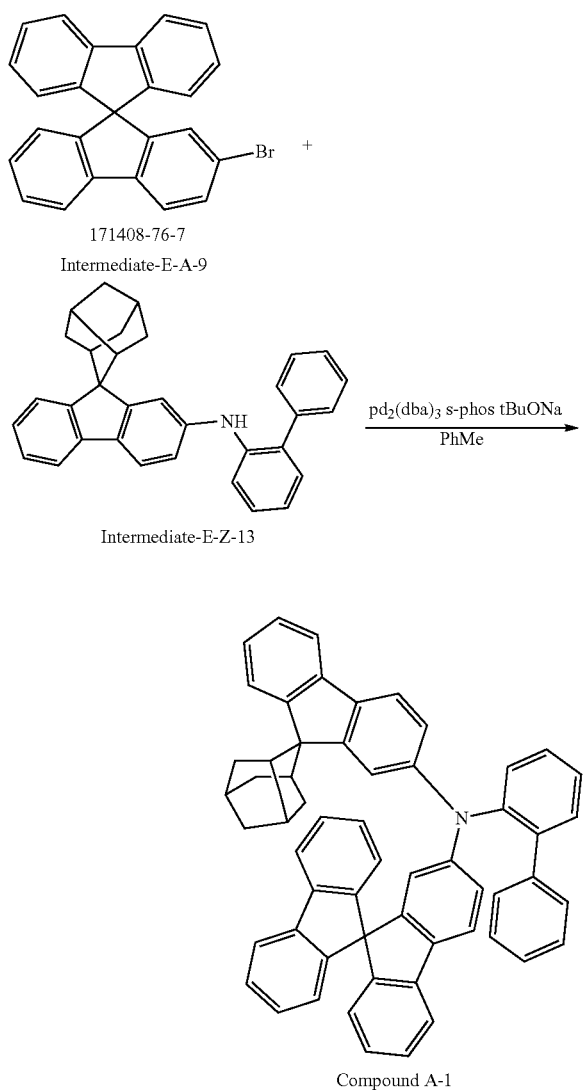

Intermediate-E-A-9 (2.0 g, 5.1 mmol), Intermediate-Z-13 (2.3 g, 5.1 mmol), tris (dibenzylideneacetone) dipalladium (0.04 g, 0.05 mmol), 2-dicyclohexylphosphino-2',6'-dimethoxy-biphenyl (0.04 g, 0.1 mmol), sodium tert-butoxide (0.73 g, 7.6 mmol) and toluene solvent (20 mL) were added into a 100 mL reaction flask, the temperature was raised to 110° C. under the protection of nitrogen gas, and the reaction solution was heated and stirred at reflux for 3 hours. After the reaction solution was cooled to room temperature, the reaction solution was extracted using dichloromethane and water, the organic layer was dried over anhydrous magnesium sulfate and filtered. After filtration, the filtrate was passed through a short silica gel column, the solvent was removed under reduced pressure, and the crude product was pruified by recrystallization using a dichloromethane/n-heptane system to obtain Compound A-1 (2.9 g, 75% yield). Mass spectrum: m/z=768.4 (M+H)$^+$.

In some embodiment, the Compound M-X shown in Table 11 was synthesized with reference to the synthetic method of Compound-A-1, with the difference was that Intermediate-E-M-X was used to replace Intermediate-E-A-9 to prepare Compound-A-1, Intermediate-Z-X is used to replace Intermediate-Z-13 to prepare Compound-A-1, and every combination of Compound E-M-X and Intermediate-Z-X can prepare the unique corresponding Compound M-X. The produced Compound M-X was shown in Table 11 below.

TABLE 11

| Intermediate-E-M-X | Intermediate-Z-X |
|---|---|
| 171408-76-7<br>Intermediate-E-A-9 | Intermediate-Z-10 |

TABLE 11-continued
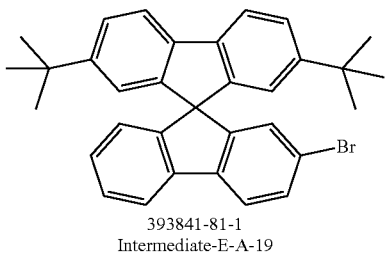
393841-81-1
Intermediate-E-A-19
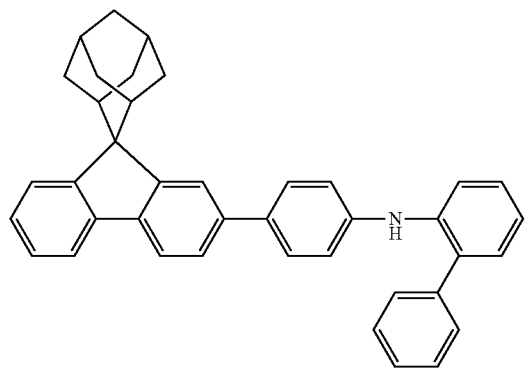 [SMILES: c1ccc(-c2ccccc2Nc2ccc(-c3ccc4c(c3)C3(c5ccccc5-4)C4CC5CC(C4)CC3C5)cc2)cc1]
Intermediate-Z-41
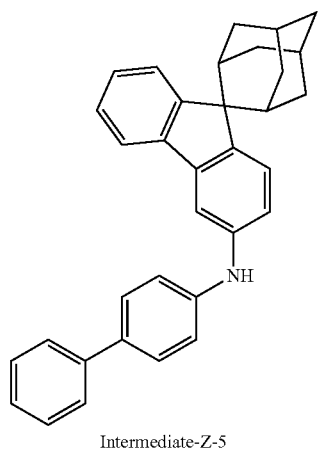
Intermediate-Z-5
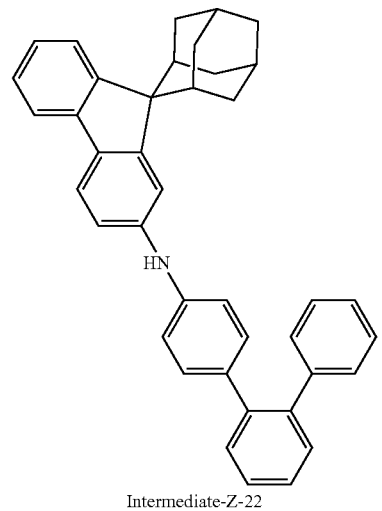
Intermediate-Z-22
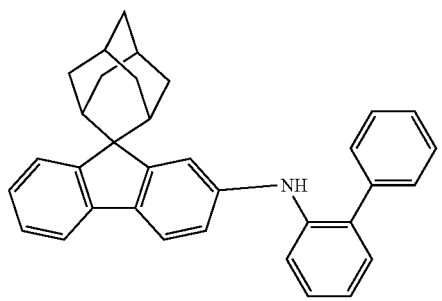 [SMILES: c1ccc(-c2ccccc2Nc2ccc3c(c2)C2(c4ccccc4-3)C3CC4CC(C3)CC2C4)cc1]

TABLE 11-continued
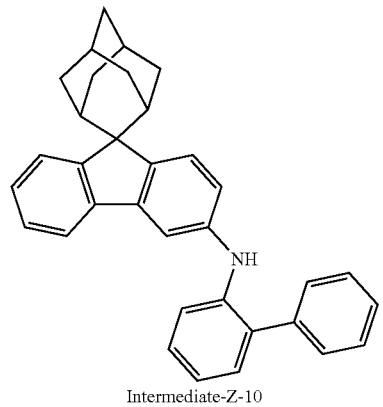
Intermediate-Z-10
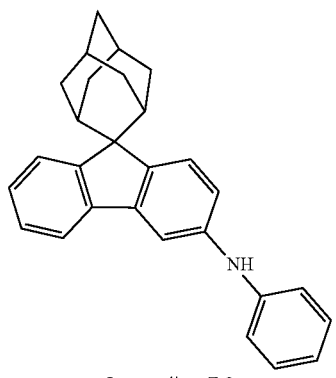
Intermediate-Z-2
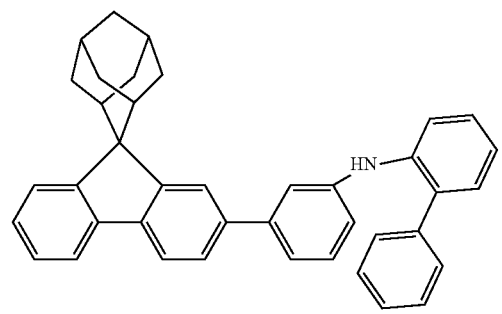 [SMILES: c1ccc(-c2ccccc2Nc2cccc(-c3ccc4c(c3)C3(c5ccccc5-4)C4CC5CC(C4)CC3C5)c2)cc1]
Intermediate-Z-42
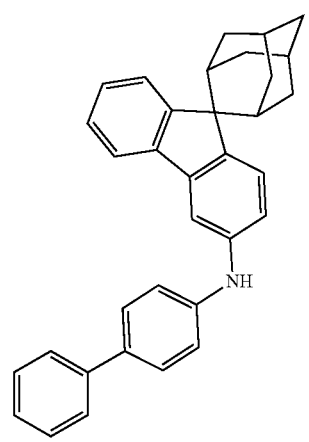 [SMILES: c1ccc(-c2ccc(Nc3ccc4c(c3)-c3ccccc3C43C4CC5CC(C4)CC3C5)cc2)cc1]
Intermediate-Z-5

TABLE 11-continued
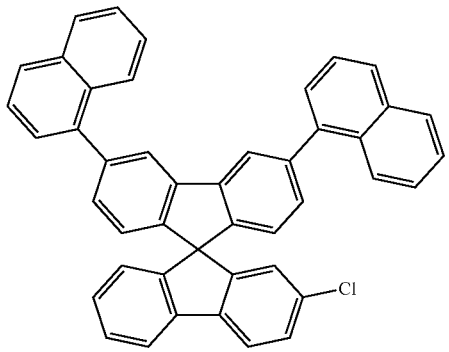 [SMILES: Clc1ccc2c(c1)C1(c3ccccc3-2)c2ccc(-c3cccc4ccccc34)cc2-c2cc(-c3cccc4ccccc34)ccc21]
Intermediate-E-A-1
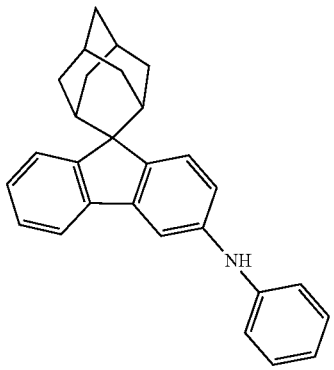 [SMILES: c1ccc(Nc2ccc3c(c2)-c2ccccc2C32C3CC4CC(C3)CC2C4)cc1]
Intermediate-Z-2
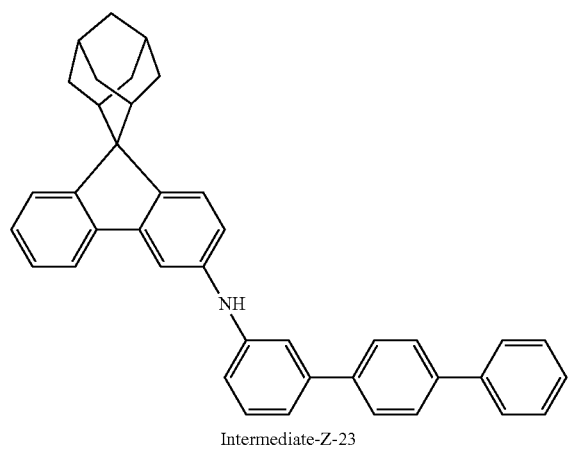
Intermediate-Z-23
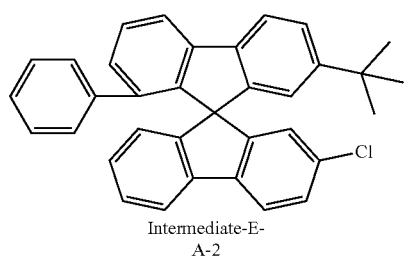
Intermediate-E-A-2
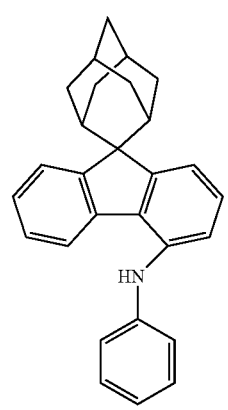 [SMILES: c1ccc(Nc2cccc3c2-c2ccccc2C32C3CC4CC(C3)CC2C4)cc1]
Intermediate-Z-4

TABLE 11-continued
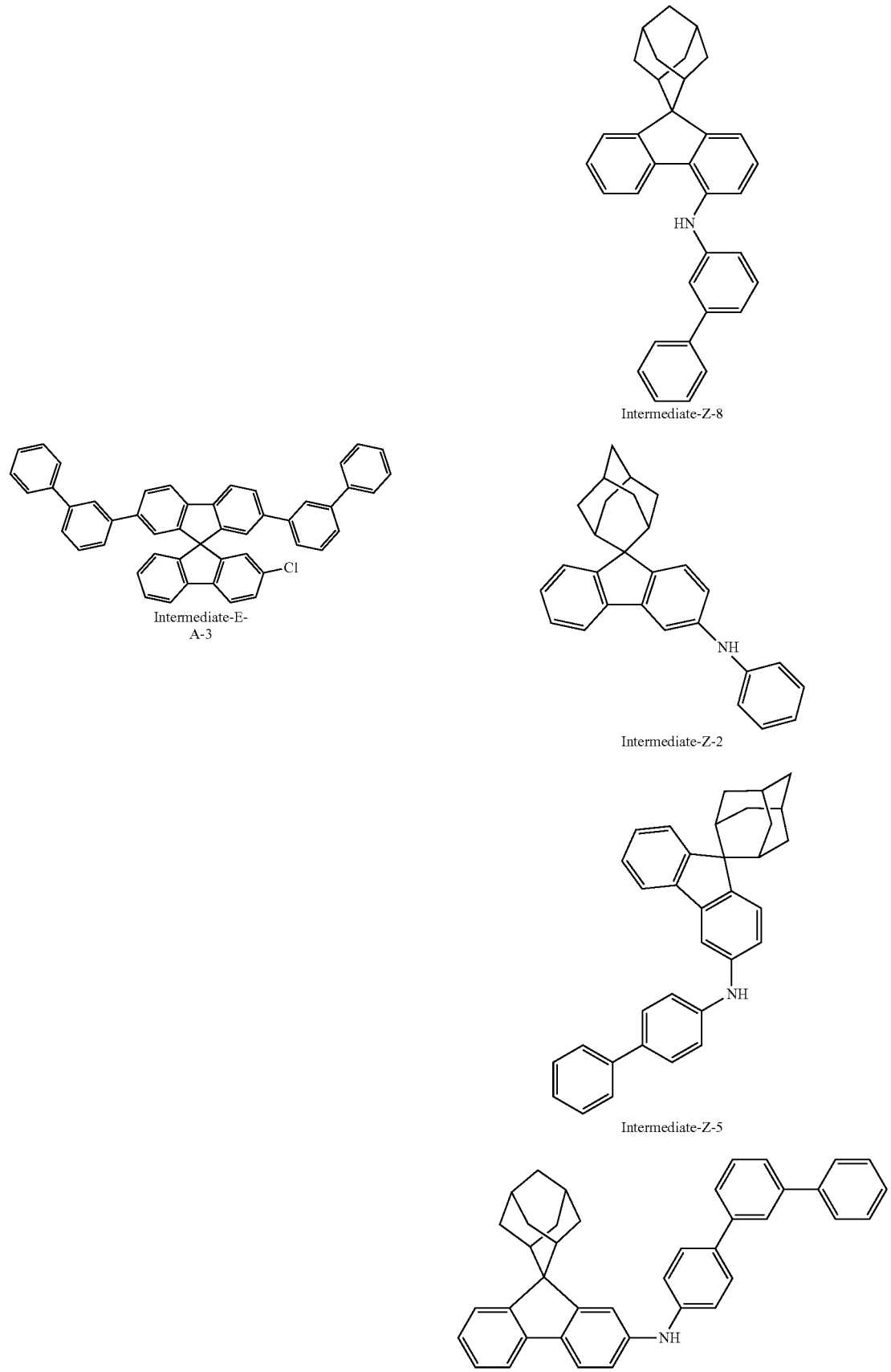

TABLE 11-continued
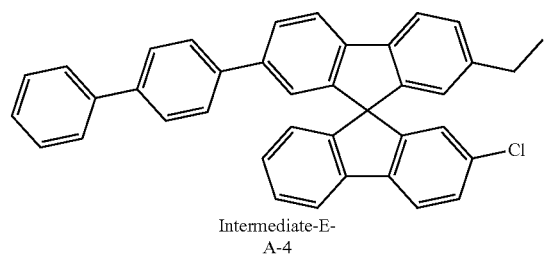
Intermediate-E-A-4
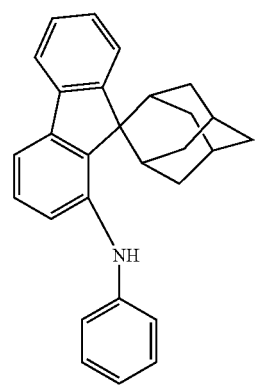 [SMILES: c1ccc(Nc2cccc3c2C2(c4ccccc4-3)C3CC4CC(C3)CC2C4)cc1]
Intermediate-Z-3
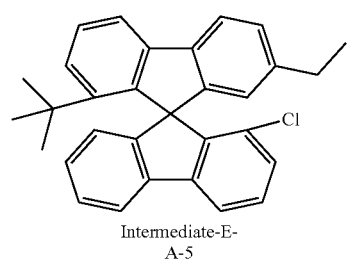
Intermediate-E-A-5
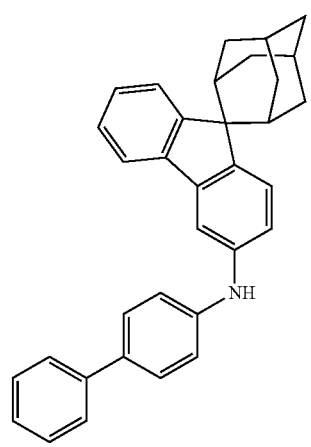 [SMILES: c1ccc(-c2ccc(Nc3ccc4c(c3)-c3ccccc3C43C4CC5CC(C4)CC3C5)cc2)cc1]
Intermediate-Z-5
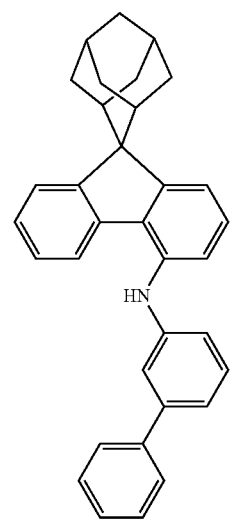 [SMILES: c1ccc(-c2cccc(Nc3cccc4c3-c3ccccc3C43C4CC5CC(C4)CC3C5)c2)cc1]
Intermediate-Z-8

TABLE 11-continued
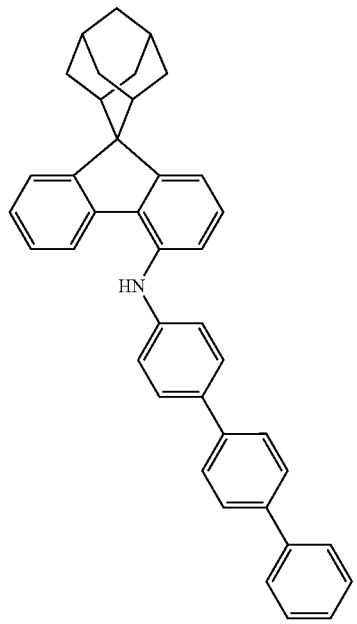 [SMILES: c1ccc(-c2ccc(-c3ccc(Nc4cccc5c4-c4ccccc4C54C5CC6CC(C5)CC4C6)cc3)cc2)cc1]
Intermediate-Z-15
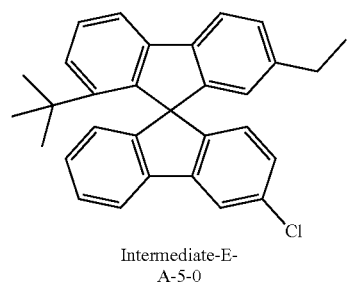
Intermediate-E-A-5-0
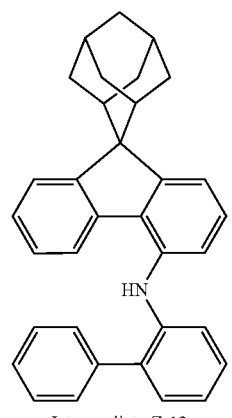
Intermediate-Z-12
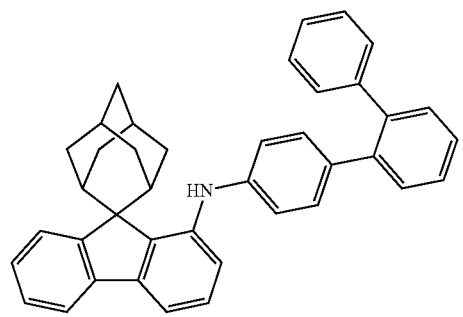 [SMILES: c1ccc(-c2ccccc2-c2ccc(Nc3cccc4c3C3(c5ccccc5-4)C4CC5CC(C4)CC3C5)cc2)cc1]
Intermediate-Z-20

TABLE 11-continued
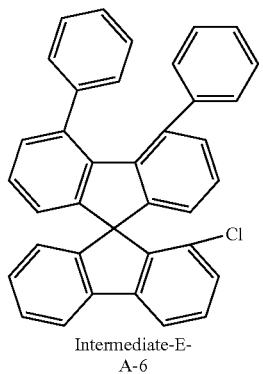
Intermediate-E-A-6
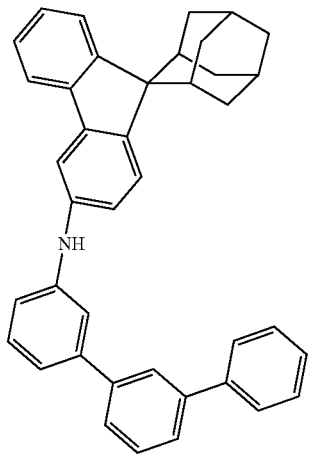 [SMILES: c1ccc(-c2cccc(-c3cccc(Nc4ccc5c(c4)-c4ccccc4C54C5CC6CC(C5)CC4C6)c3)c2)cc1]
Intermediate-Z-26
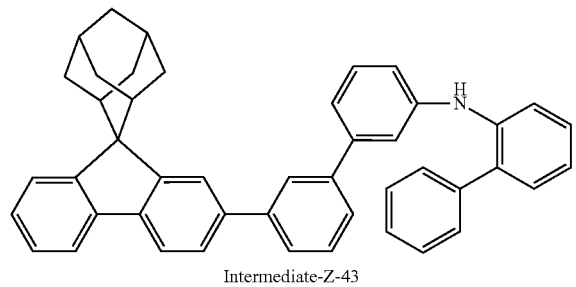
Intermediate-Z-43
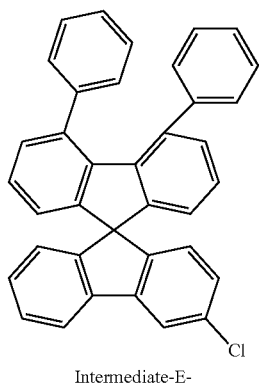
Intermediate-E-A-6-0
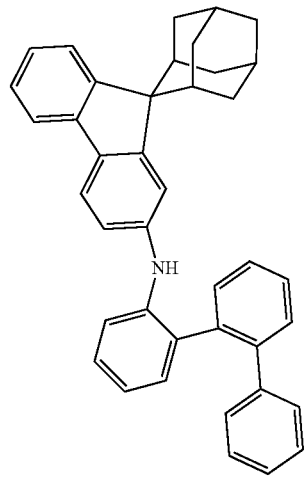 [SMILES: c1ccc(-c2ccccc2-c2ccccc2Nc2ccc3c(c2)C2(c4ccccc4-3)C3CC4CC(C3)CC2C4)cc1]
Intermediate-Z-40

TABLE 11-continued
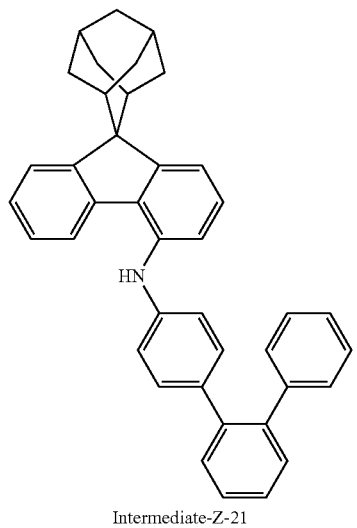
Intermediate-Z-21
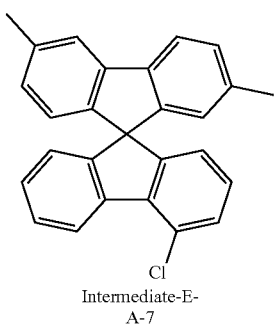
Intermediate-E-A-7
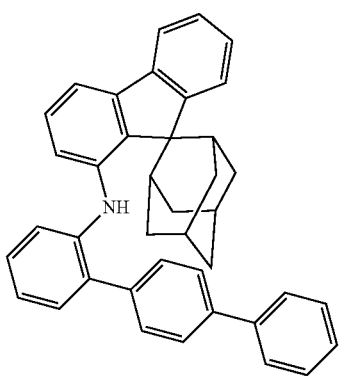 [SMILES: c1ccc(-c2ccc(-c3ccccc3Nc3cccc4c3C3(c5ccccc5-4)C4CC5CC(C4)CC3C5)cc2)cc1]
Intermediate-Z-33
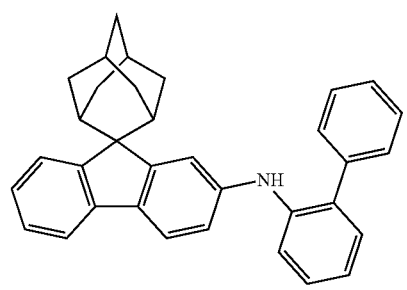 [SMILES: c1ccc(-c2ccccc2Nc2ccc3c(c2)C2(c4ccccc4-3)C3CC4CC(C3)CC2C4)cc1]
Intermediate-Z-13

TABLE 11-continued
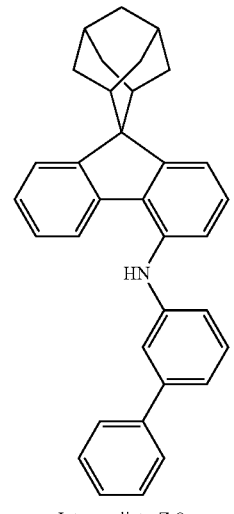
Intermediate-Z-8
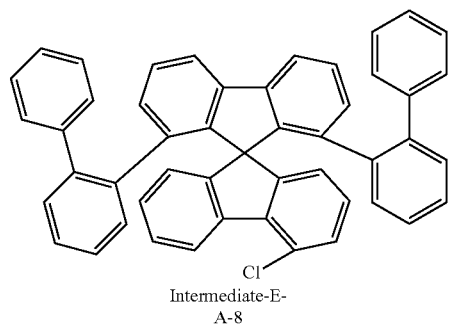
Intermediate-E-A-8
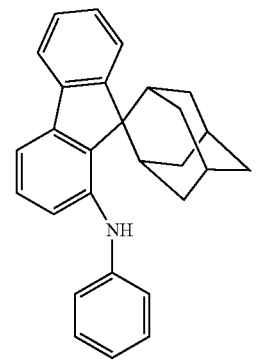 [SMILES: c1ccc(Nc2cccc3c2C2(c4ccccc4-3)C3CC4CC(C3)CC2C4)cc1]
Intermediate-Z-3
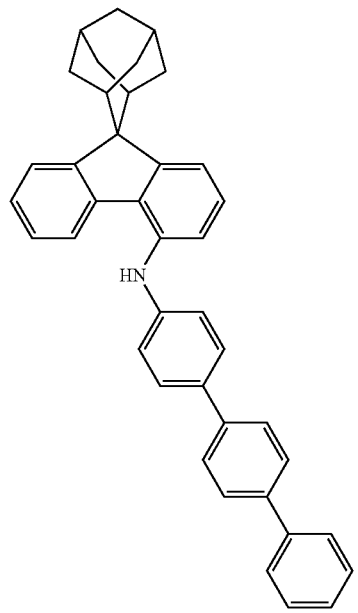 [SMILES: c1ccc(-c2ccc(-c3ccc(Nc4cccc5c4-c4ccccc4C54C5CC6CC(C5)CC4C6)cc3)cc2)cc1]
Intermediate-Z-15

TABLE 11-continued
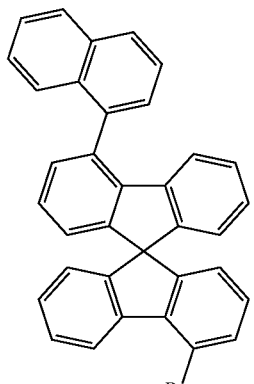
2102016-88-4
Intermediate-E-A-10
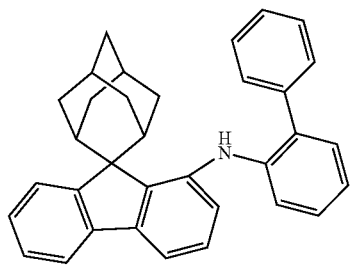 [SMILES: c1ccc(-c2ccccc2Nc2cccc3c2C2(c4ccccc4-3)C3CC4CC(C3)CC2C4)cc1]
Intermediate-Z-11
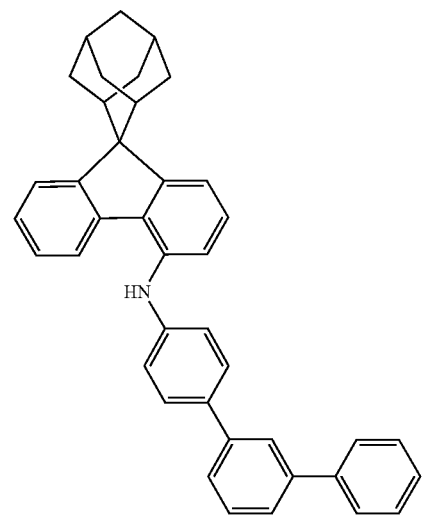 [SMILES: c1ccc(-c2cccc(-c3ccc(Nc4cccc5c4-c4ccccc4C54C5CC6CC(C5)CC4C6)cc3)c2)cc1]
Intermediate-Z-18
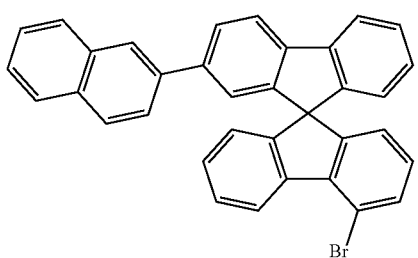 [SMILES: Brc1cccc2c1-c1ccccc1C21c2ccccc2-c2ccc(-c3ccc4ccccc4c3)cc21]
2102016-98-6
Intermediate-E-A-11
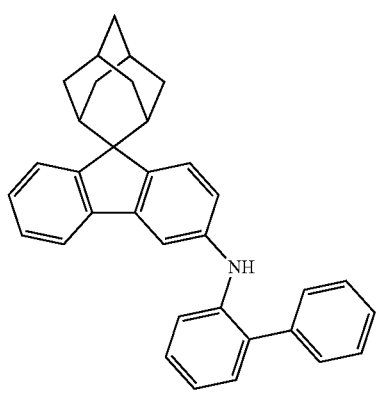 [SMILES: c1ccc(-c2ccccc2Nc2ccc3c(c2)-c2ccccc2C32C3CC4CC(C3)CC2C4)cc1]
Intermediate-Z-10

TABLE 11-continued
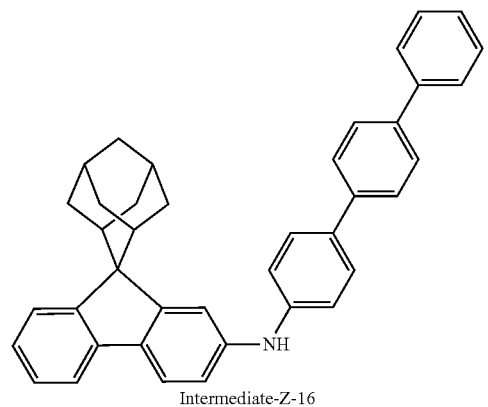
Intermediate-Z-16
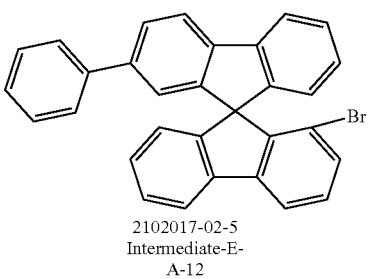
2102017-02-5
Intermediate-E-A-12
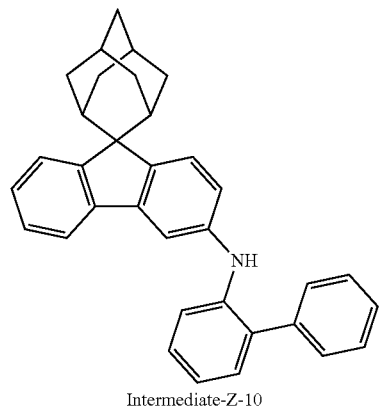
Intermediate-Z-10
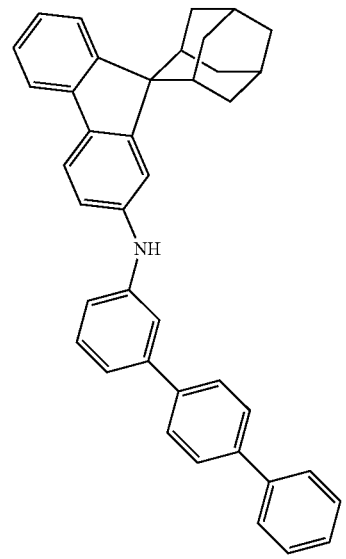 [SMILES: c1ccc(-c2ccc(-c3cccc(Nc4ccc5c(c4)C4(c6ccccc6-5)C5CC6CC(C5)CC4C6)c3)cc2)cc1]
Intermediate-Z-25
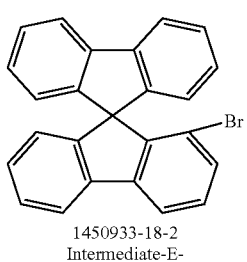
1450933-18-2
Intermediate-E-
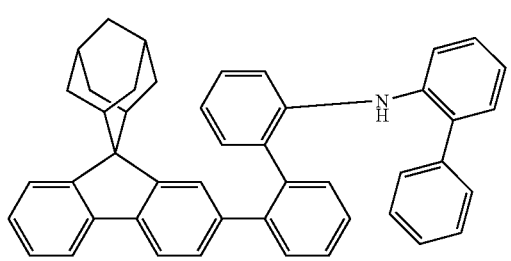 [SMILES: c1ccc(-c2ccccc2Nc2ccccc2-c2ccccc2-c2ccc3c(c2)C2(c4ccccc4-3)C3CC4CC(C3)CC2C4)cc1]

TABLE 11-continued
| A-13 | Intermediate-Z-44 |
|---|---|
| | 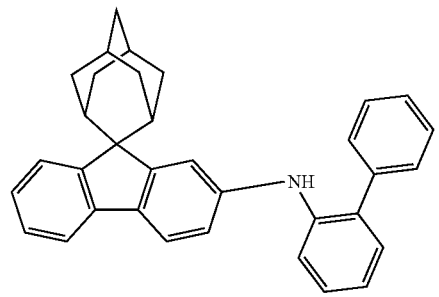 [SMILES: c1ccc(-c2ccccc2Nc2ccc3c(c2)C2(c4ccccc4-3)C3CC4CC(C3)CC2C4)cc1]
Intermediate-Z-13 |
| | 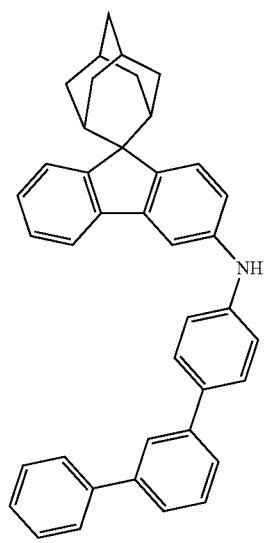 [SMILES: c1ccc(-c2cccc(-c3ccc(Nc4ccc5c(c4)-c4ccccc4C54C5CC6CC(C5)CC4C6)cc3)c2)cc1]
Intermediate-Z-17 |
| 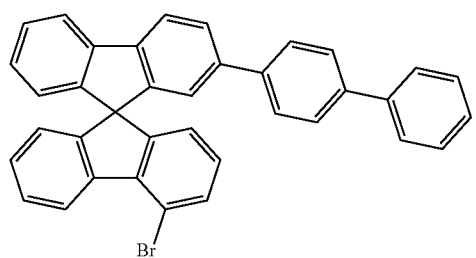 [SMILES: Brc1cccc2c1-c1ccccc1C21c2ccccc2-c2ccc(-c3ccc(-c4ccccc4)cc3)cc21]
2102016-96-4
Intermediate-E-A-14 | 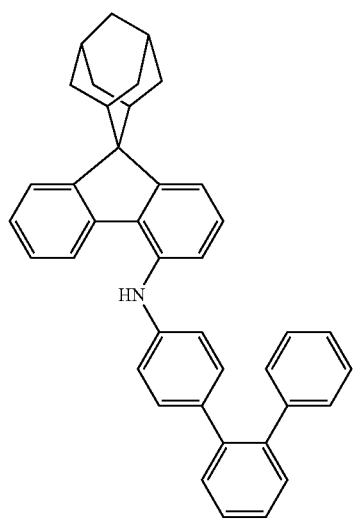 [SMILES: c1ccc(-c2ccccc2-c2ccc(Nc3cccc4c3-c3ccccc3C43C4CC5CC(C4)CC3C5)cc2)cc1]
Intermediate-Z-21 |

TABLE 11-continued
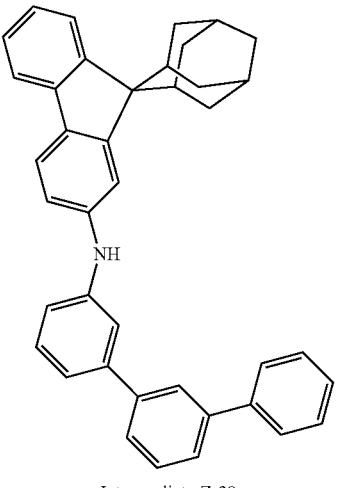
Intermediate-Z-28
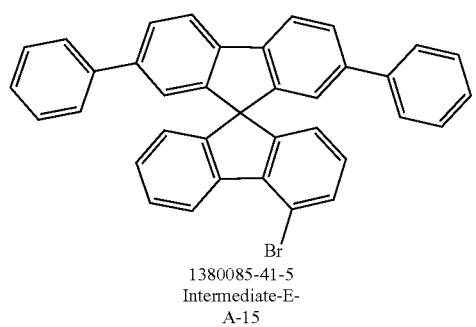
1380085-41-5
Intermediate-E-A-15
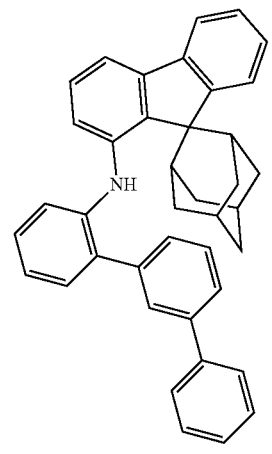 [SMILES: c1ccc(-c2cccc(-c3ccccc3Nc3cccc4c3C3(c5ccccc5-4)C4CC5CC(C4)CC3C5)c2)cc1]
Intermediate-Z-35
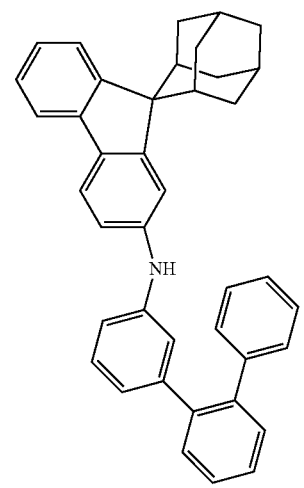 [SMILES: c1ccc(-c2ccccc2-c2cccc(Nc3ccc4c(c3)C3(c5ccccc5-4)C4CC5CC(C4)CC3C5)c2)cc1]
Intermediate-Z-31

TABLE 11-continued
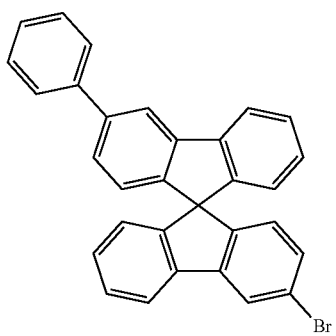 [SMILES: Brc1ccc2c(c1)-c1ccccc1C21c2ccccc2-c2cc(-c3ccccc3)ccc21]
1911626-28-2
Intermediate-E-A-16
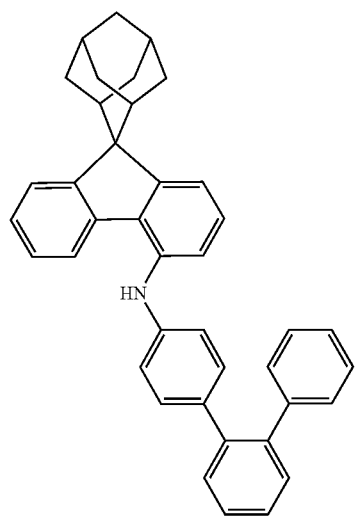 [SMILES: c1ccc(-c2ccccc2-c2ccc(Nc3cccc4c3-c3ccccc3C43C4CC5CC(C4)CC3C5)cc2)cc1]
Intermediate-Z-21
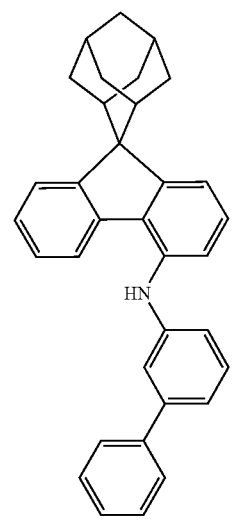 [SMILES: c1ccc(-c2cccc(Nc3cccc4c3-c3ccccc3C43C4CC5CC(C4)CC3C5)c2)cc1]
Intermediate-Z-8
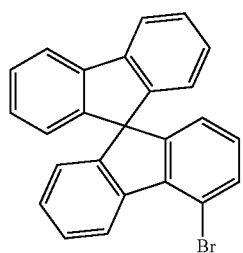 [SMILES: Brc1cccc2c1-c1ccccc1C21c2ccccc2-c2ccccc21]
1161009-88-6
Intermediate-E-A-17
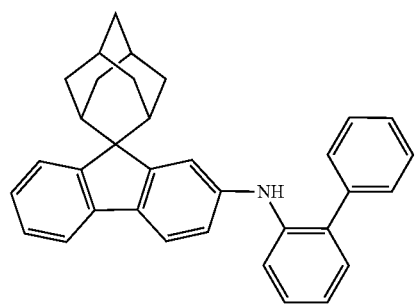 [SMILES: c1ccc(-c2ccccc2Nc2ccc3c(c2)C2(c4ccccc4-3)C3CC4CC(C3)CC2C4)cc1]
Intermediate-Z-13

TABLE 11-continued
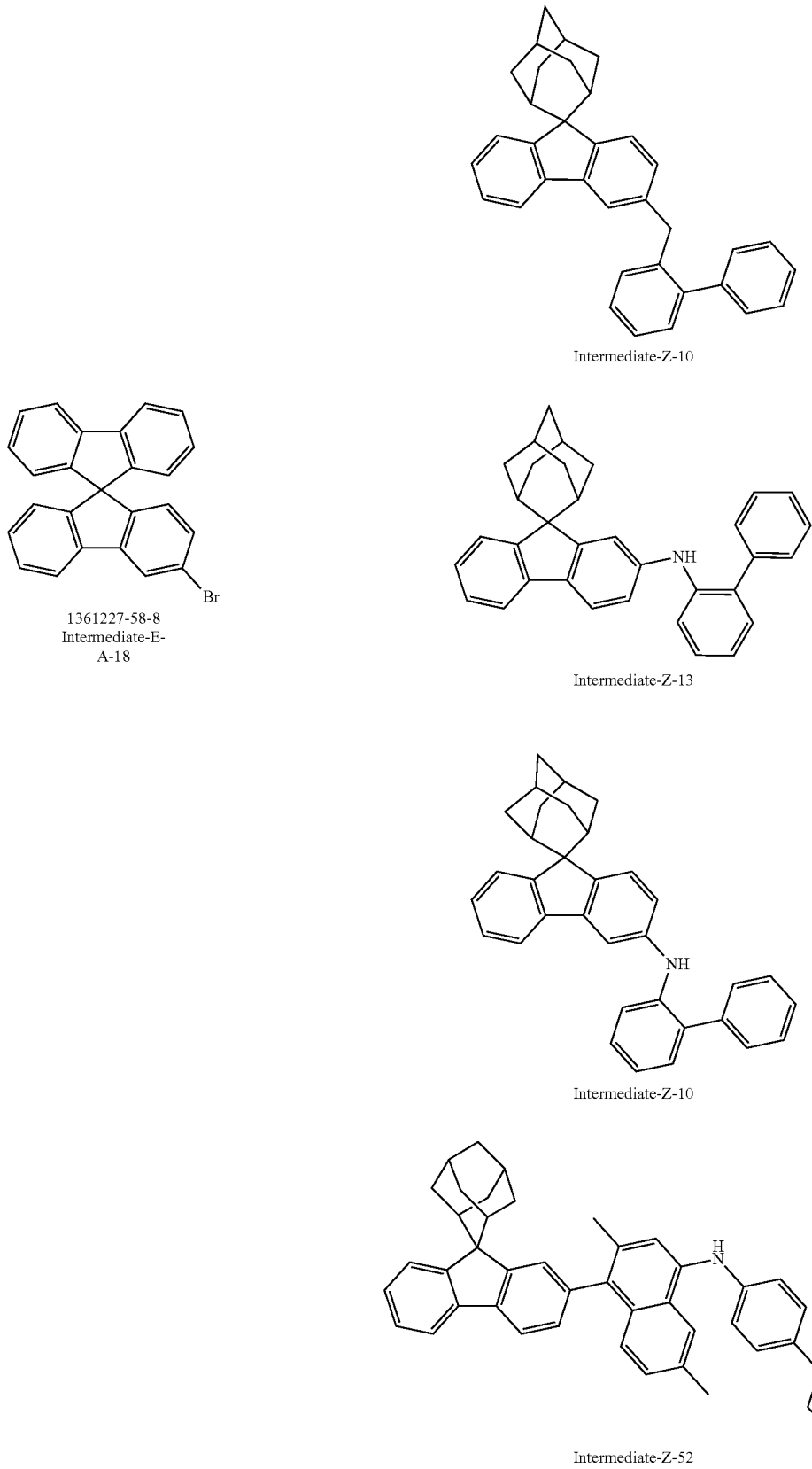

TABLE 11-continued
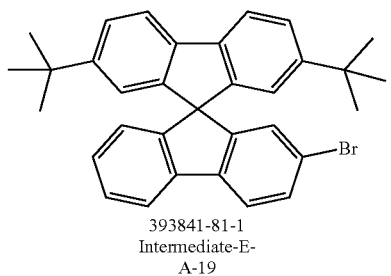
393841-81-1
Intermediate-E-A-19
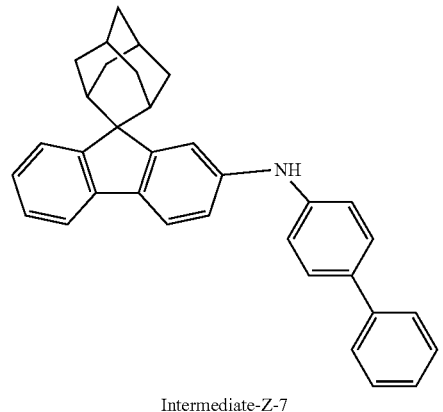
Intermediate-Z-7
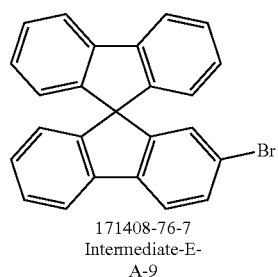
171408-76-7
Intermediate-E-A-9
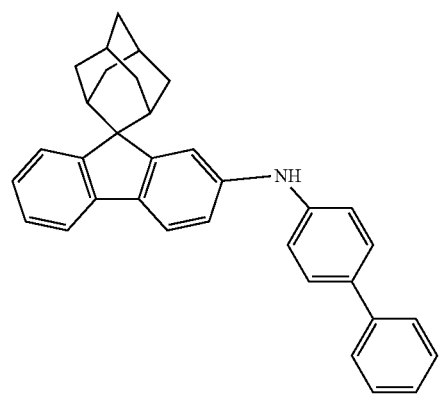 [SMILES: c1ccc(-c2ccc(Nc3ccc4c(c3)C3(c5ccccc5-4)C4CC5CC(C4)CC3C5)cc2)cc1]
Intermediate-Z-7
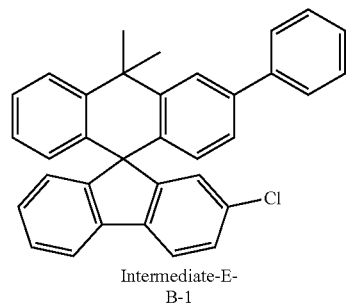
Intermediate-E-B-1
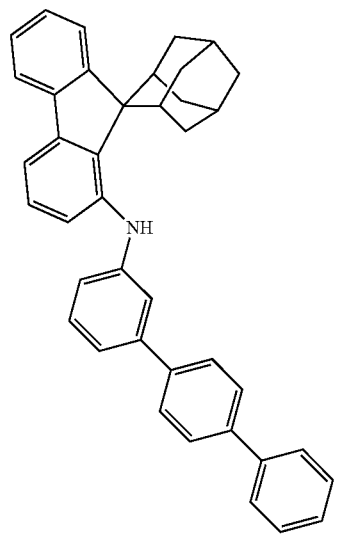 [SMILES: c1ccc(-c2ccc(-c3cccc(Nc4cccc5c4C4(c6ccccc6-5)C5CC6CC(C5)CC4C6)c3)cc2)cc1]
Intermediate-Z-24
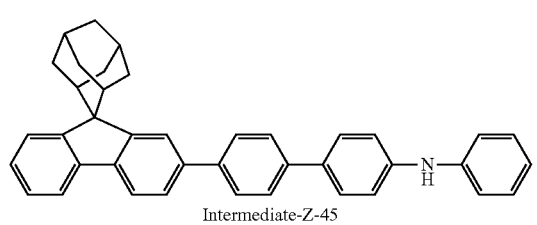
Intermediate-Z-45

TABLE 11-continued
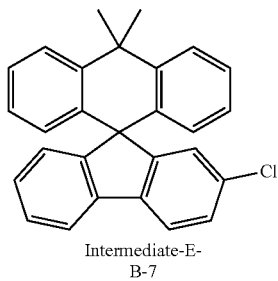
Intermediate-E-B-7
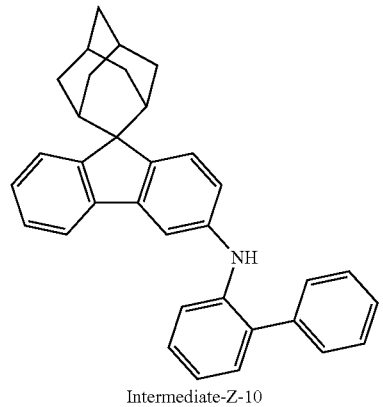
Intermediate-Z-10
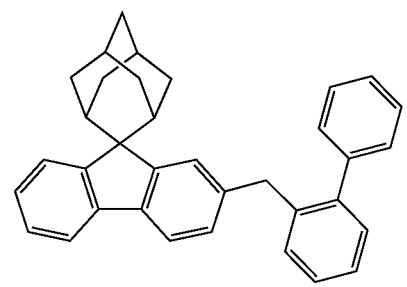 [SMILES: c1ccc(-c2ccccc2Cc2ccc3c(c2)C2(c4ccccc4-3)C3CC4CC(C3)CC2C4)cc1]
Intermediate-Z-13
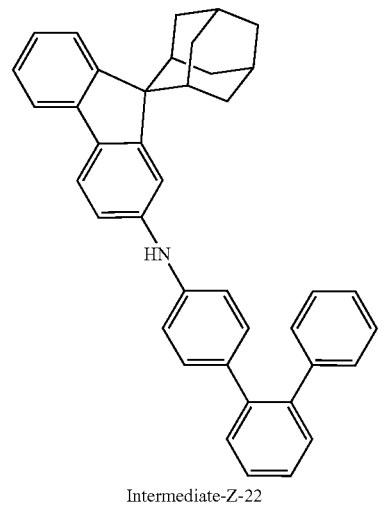
Intermediate-Z-22

TABLE 11-continued
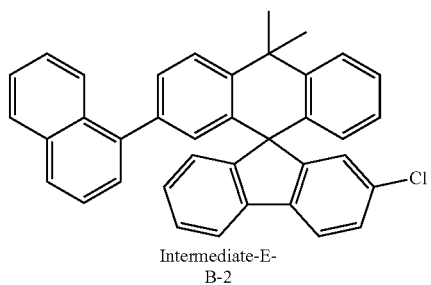
Intermediate-E-B-2
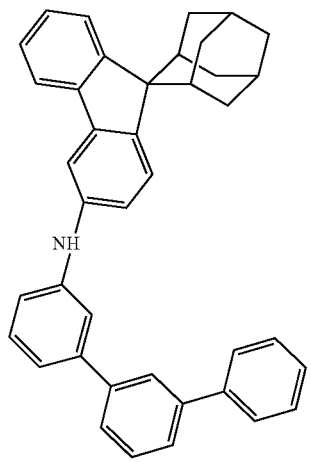 [SMILES: c1ccc(-c2cccc(-c3cccc(Nc4ccc5c(c4)-c4ccccc4C54C5CC6CC(C5)CC4C6)c3)c2)cc1]
Intermediate-Z-26
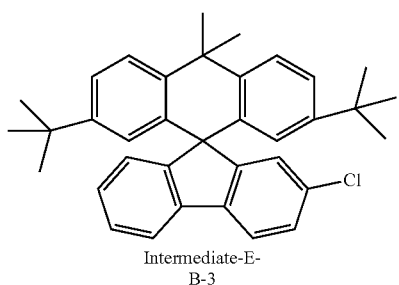
Intermediate-E-B-3
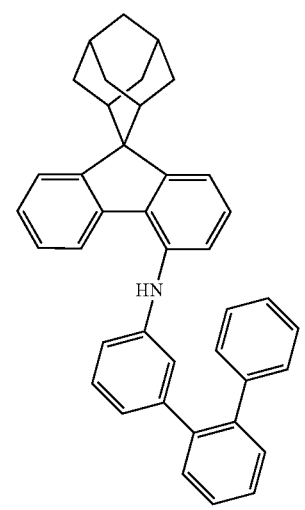 [SMILES: c1ccc(-c2ccccc2-c2cccc(Nc3cccc4c3-c3ccccc3C43C4CC5CC(C4)CC3C5)c2)cc1]
Intermediate-Z-30
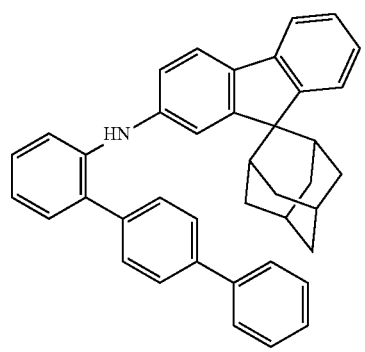 [SMILES: c1ccc(-c2ccc(-c3ccccc3Nc3ccc4c(c3)C3(c5ccccc5-4)C4CC5CC(C4)CC3C5)cc2)cc1]
Intermediate-Z-34

TABLE 11-continued
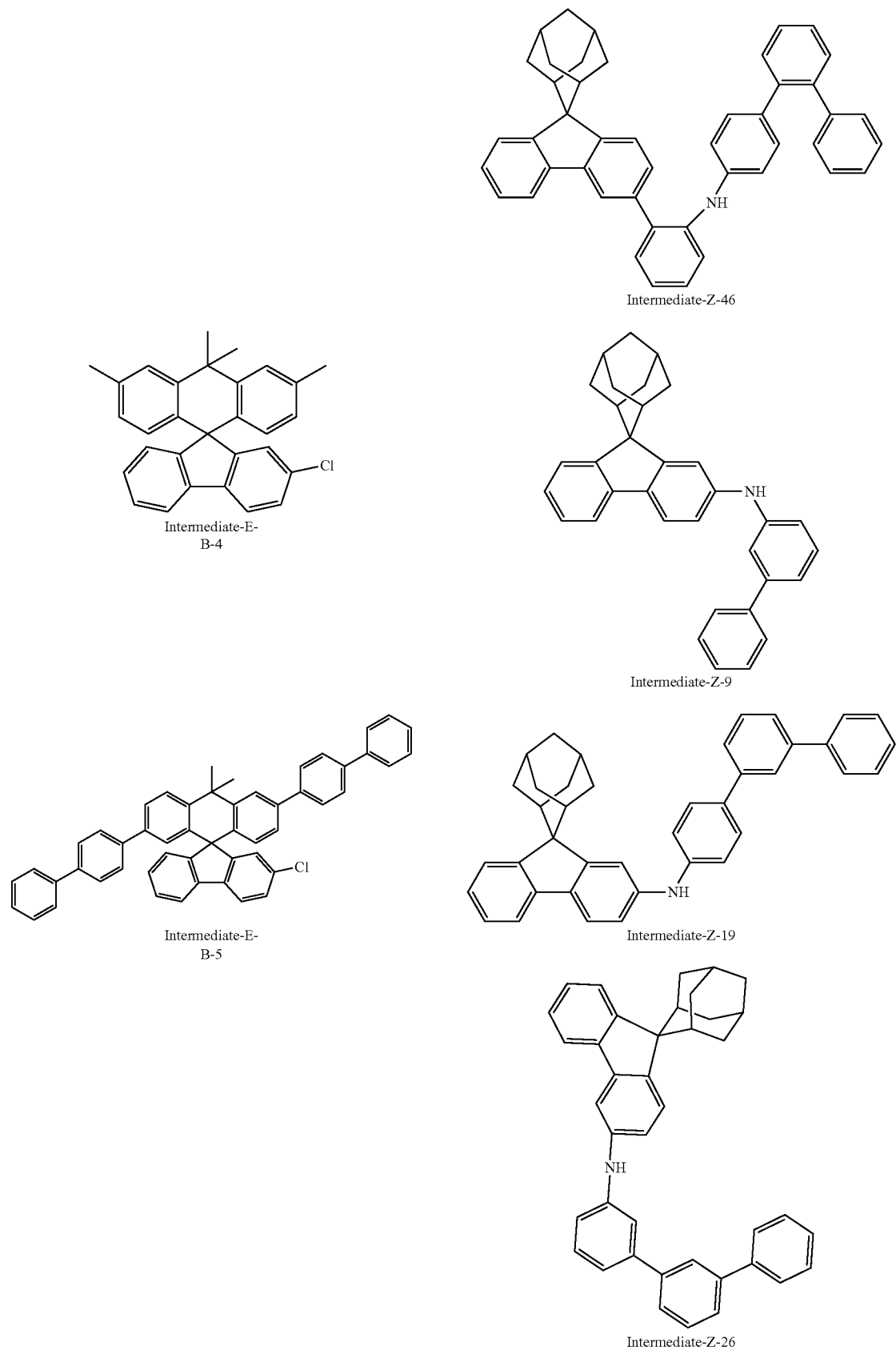

TABLE 11-continued
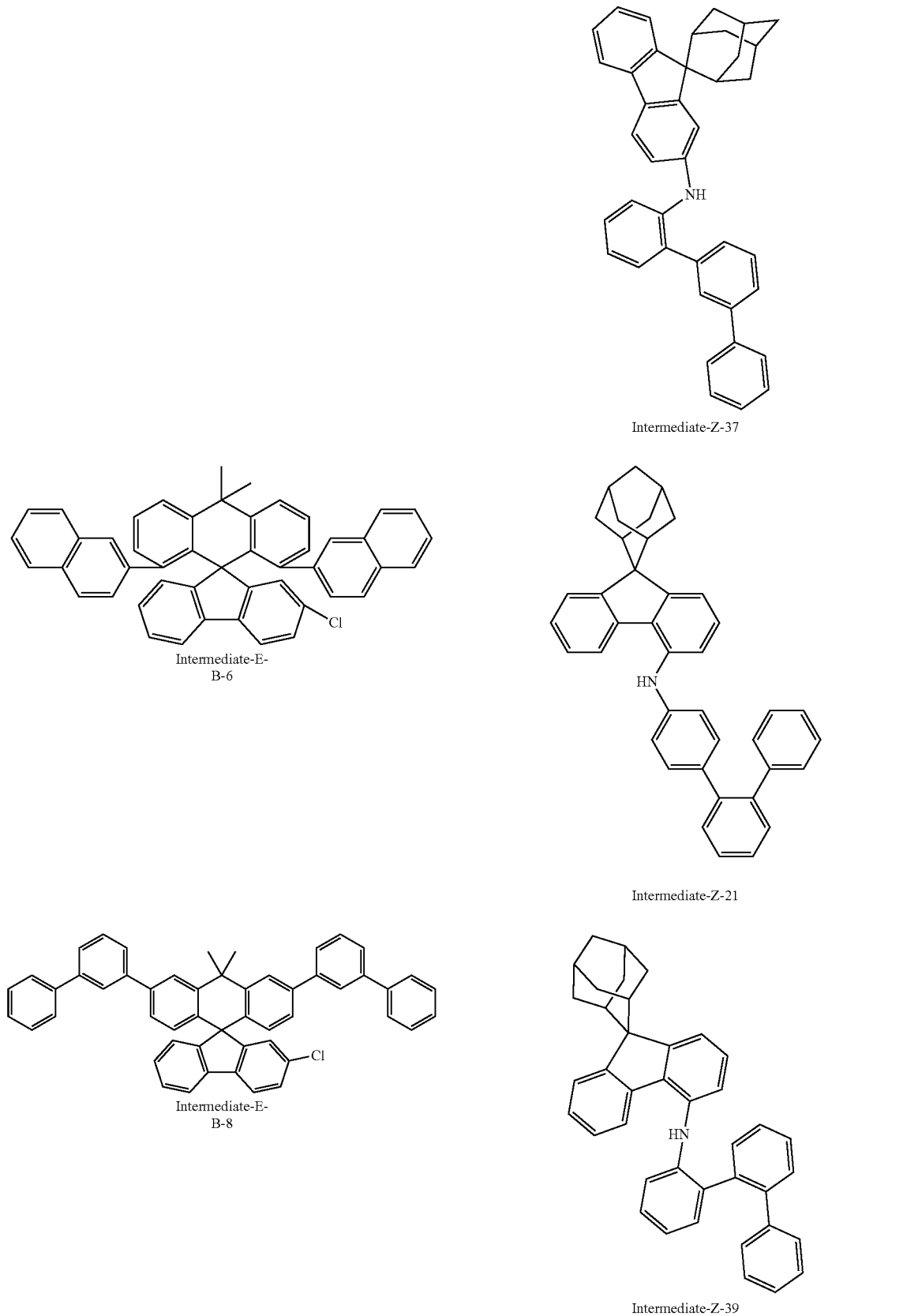

TABLE 11-continued
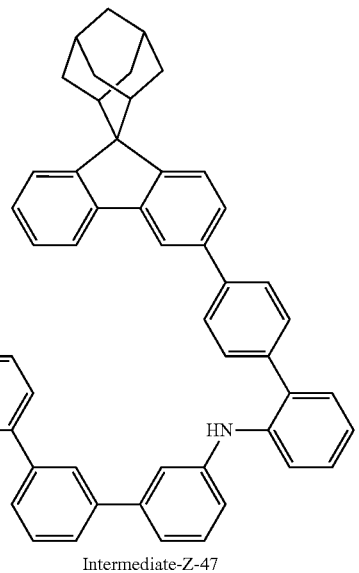
Intermediate-Z-47
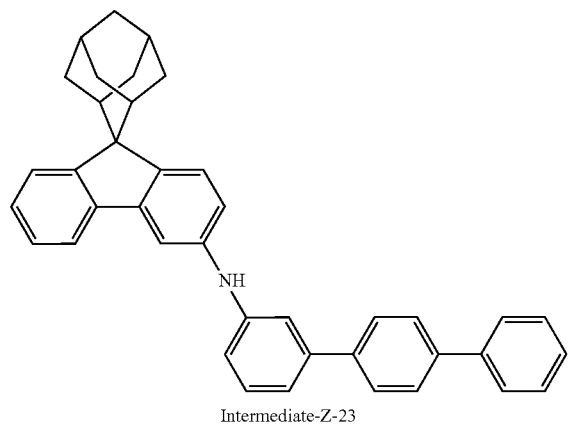
Intermediate-Z-23
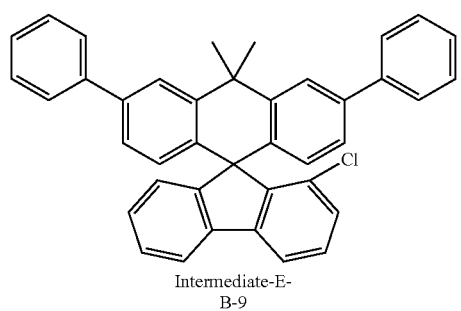
Intermediate-E-B-9
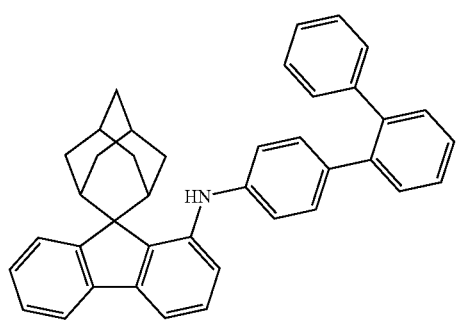
Intermediate-Z-20

TABLE 11-continued
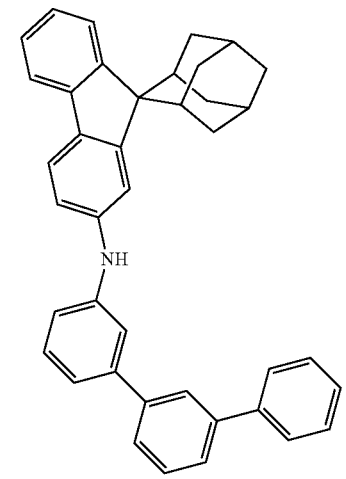 [SMILES: c1ccc(-c2cccc(-c3cccc(Nc4ccc5c(c4)C4(c6ccccc6-5)C5CC6CC(C5)CC4C6)c3)c2)cc1]
Intermediate-Z-28
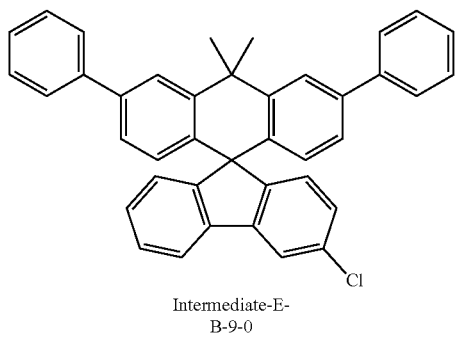
Intermediate-E-B-9-0
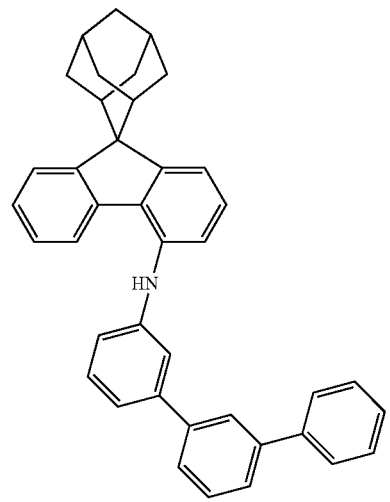 [SMILES: c1ccc(-c2cccc(-c3cccc(Nc4cccc5c4-c4ccccc4C54C5CC6CC(C5)CC4C6)c3)c2)cc1]
Intermediate-Z-27
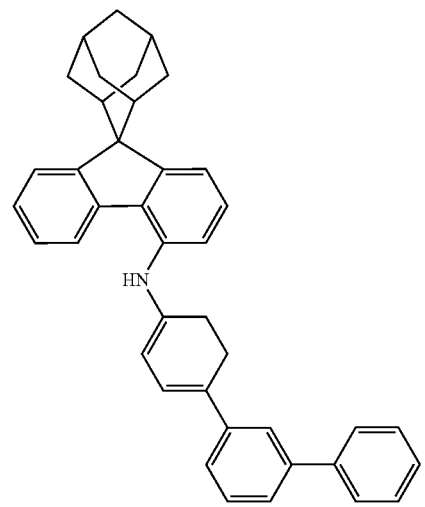 [SMILES: C1=C(Nc2cccc3c2-c2ccccc2C32C3CC4CC(C3)CC2C4)CCC(c2cccc(-c3ccccc3)c2)=C1]
Intermediate-Z-18

TABLE 11-continued
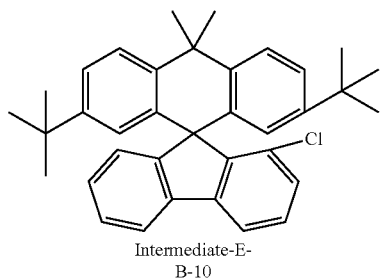
Intermediate-E-B-10
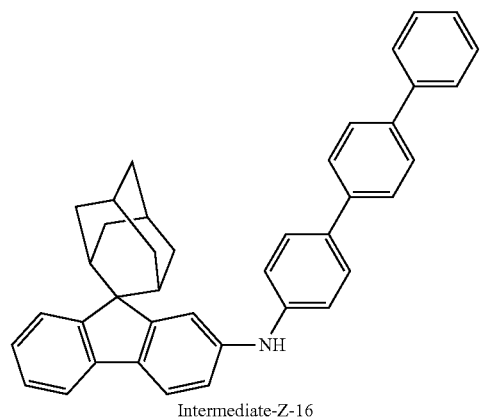
Intermediate-Z-16
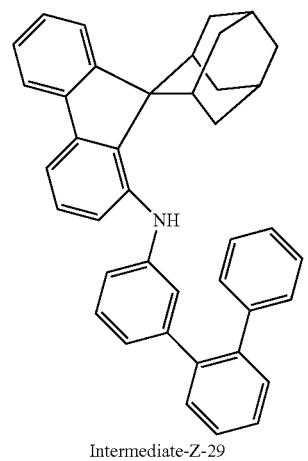
Intermediate-Z-29
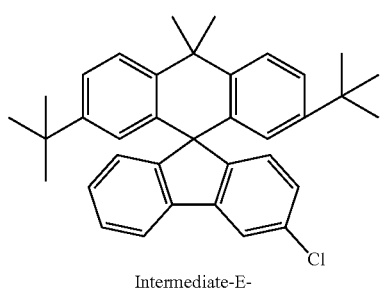
Intermediate-E-B-10-0
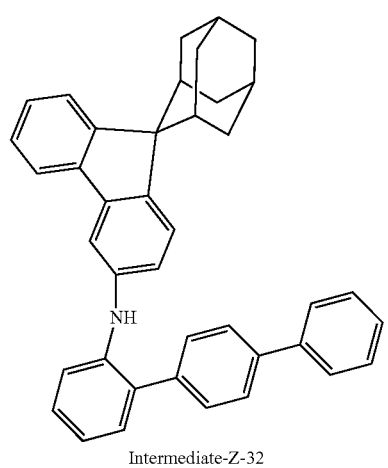
Intermediate-Z-32
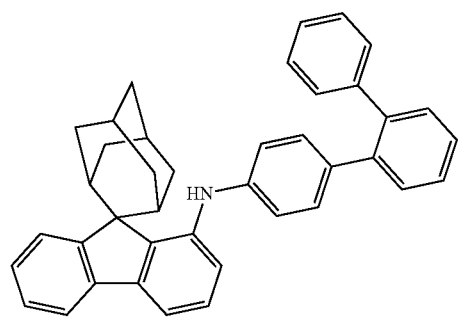 [SMILES: c1ccc(-c2ccccc2-c2ccc(Nc3cccc4c3C3(c5ccccc5-4)C4CC5CC(C4)CC3C5)cc2)cc1]

TABLE 11-continued
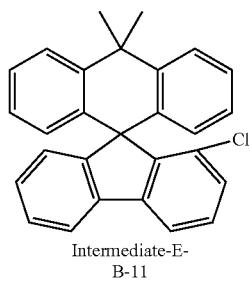
Intermediate-E-B-11
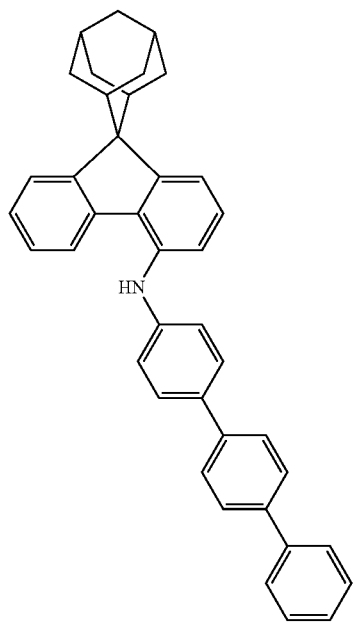 [SMILES: c1ccc(-c2ccc(-c3ccc(Nc4cccc5c4-c4ccccc4C54C5CC6CC(C5)CC4C6)cc3)cc2)cc1]
Intermediate-Z-20
Intermediate-Z-15
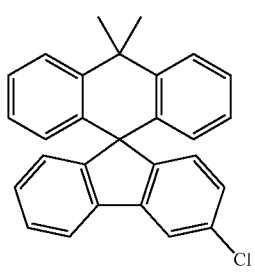 [SMILES: CC1(C)c2ccccc2C2(c3ccccc3-c3cc(Cl)ccc32)c2ccccc21]
Intermediate-E-B-11-0
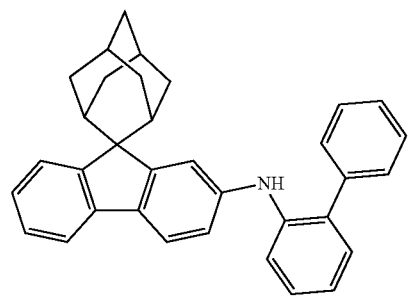 [SMILES: c1ccc(-c2ccccc2Nc2ccc3c(c2)C2(c4ccccc4-3)C3CC4CC(C3)CC2C4)cc1]
Intermediate-Z-13
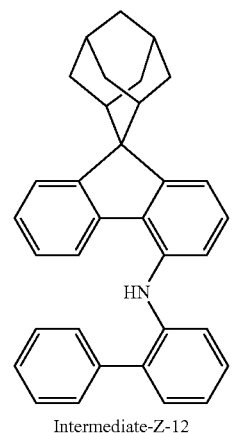
Intermediate-Z-12

TABLE 11-continued
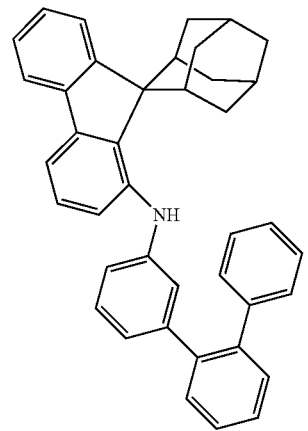 [SMILES: c1ccc(-c2ccccc2-c2cccc(Nc3cccc4c3C3(c5ccccc5-4)C4CC5CC(C4)CC3C5)c2)cc1]
Intermediate-Z-29
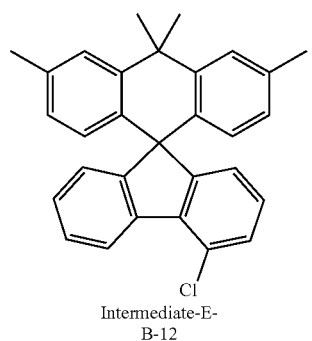
Intermediate-E-B-12
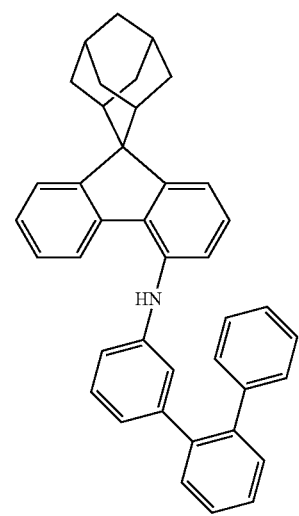
Intermediate-Z-30
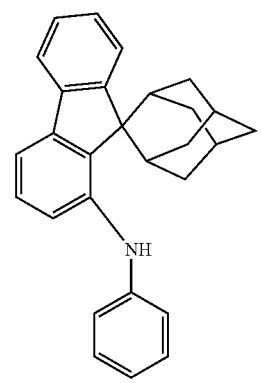 [SMILES: c1ccc(Nc2cccc3c2C2(c4ccccc4-3)C3CC4CC(C3)CC2C4)cc1]
Intermediate-Z-3

TABLE 11-continued
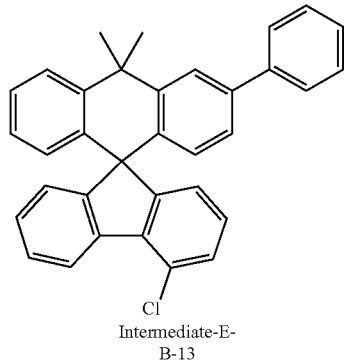
Intermediate-E-B-13
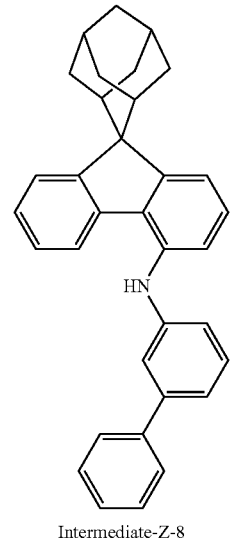
Intermediate-Z-8
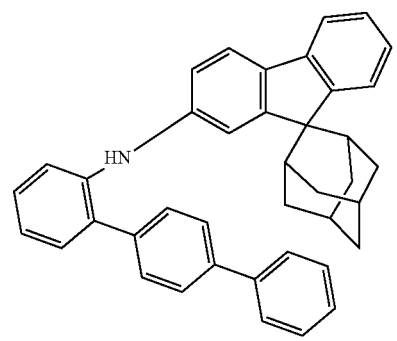 [SMILES: c1ccc(-c2ccc(-c3ccccc3Nc3ccc4c(c3)C3(c5ccccc5-4)C4CC5CC(C4)CC3C5)cc2)cc1]
Intermediate-Z-34
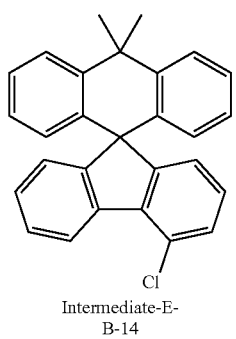
Intermediate-E-B-14
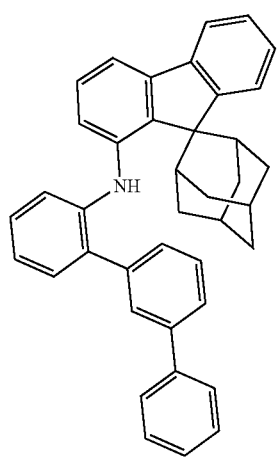 [SMILES: c1ccc(-c2cccc(-c3ccccc3Nc3cccc4c3C3(c5ccccc5-4)C4CC5CC(C4)CC3C5)c2)cc1]
Intermediate-Z-35

TABLE 11-continued
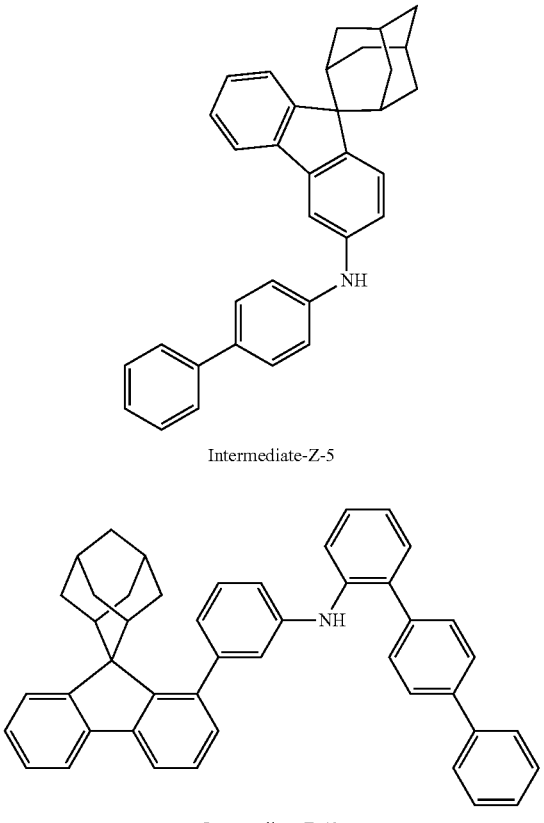
Intermediate-Z-5
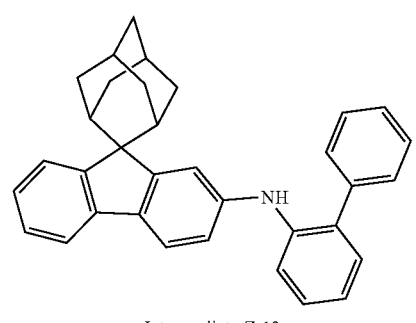
Intermediate-Z-48
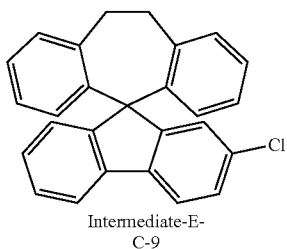
Intermediate-E-C-9
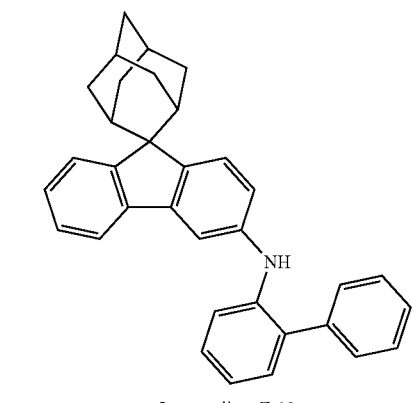
Intermediate-Z-10
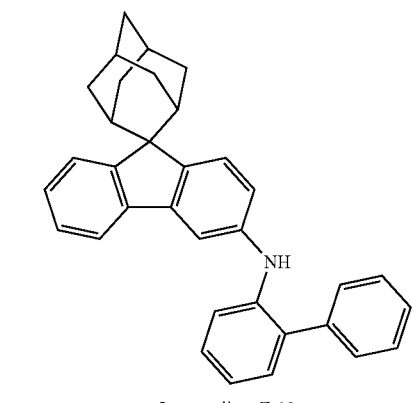
Intermediate-Z-13

TABLE 11-continued
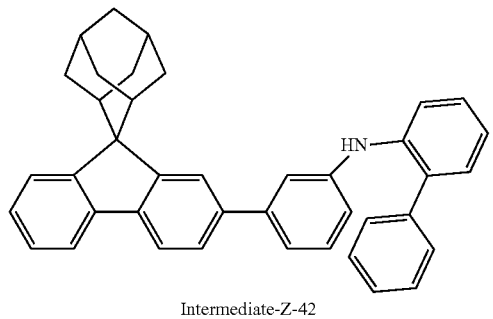
Intermediate-Z-42
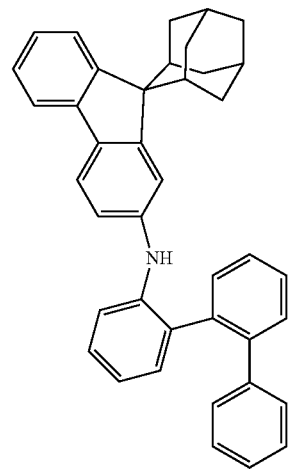 [SMILES: c1ccc(-c2ccccc2-c2ccccc2Nc2ccc3c(c2)C2(c4ccccc4-3)C3CC4CC(C3)CC2C4)cc1]
Intermediate-Z-40
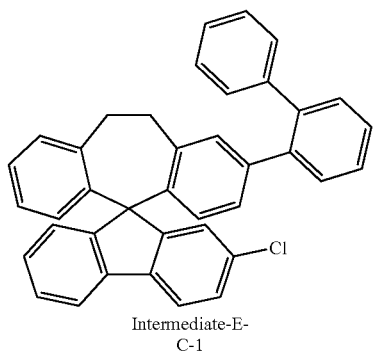
Intermediate-E-C-1
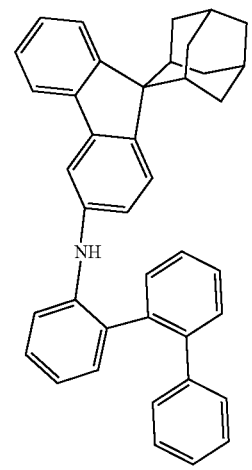 [SMILES: c1ccc(-c2ccccc2-c2ccccc2Nc2ccc3c(c2)-c2ccccc2C32C3CC4CC(C3)CC2C4)cc1]
Intermediate-Z-38
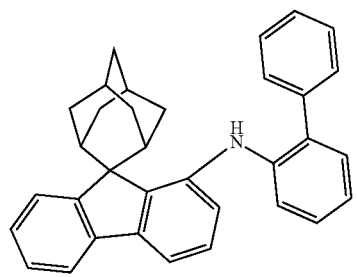 [SMILES: c1ccc(-c2ccccc2Nc2cccc3c2C2(c4ccccc4-3)C3CC4CC(C3)CC2C4)cc1]
Intermediate-Z-11

TABLE 11-continued
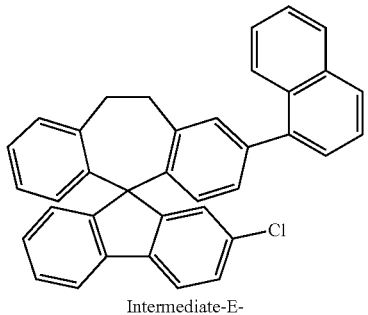
Intermediate-E-C-2
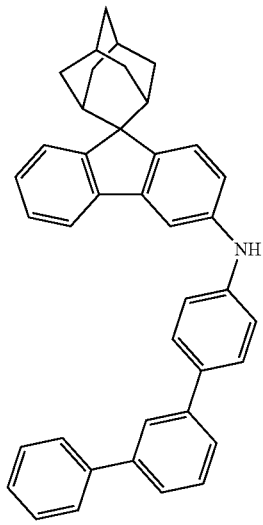 [SMILES: c1ccc(-c2cccc(-c3ccc(Nc4ccc5c(c4)-c4ccccc4C54C5CC6CC(C5)CC4C6)cc3)c2)cc1]
Intermediate-Z-17
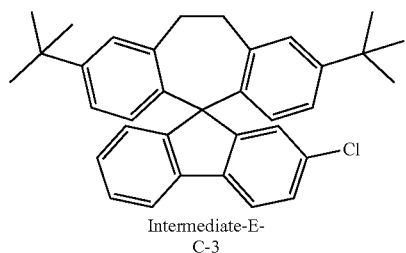
Intermediate-E-C-3
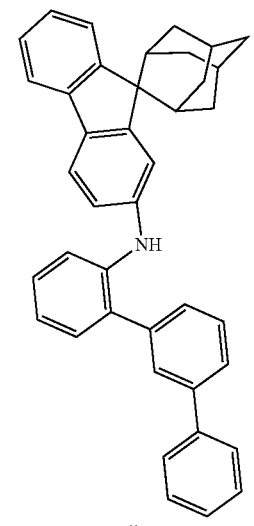
Intermediate-Z-37
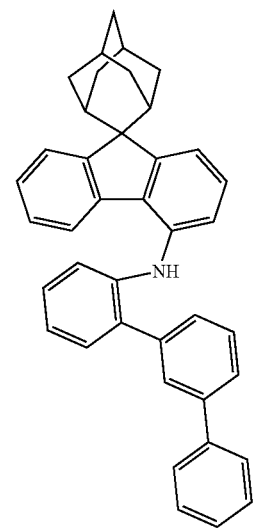 [SMILES: c1ccc(-c2cccc(-c3ccccc3Nc3cccc4c3-c3ccccc3C43C4CC5CC(C4)CC3C5)c2)cc1]
Intermediate-Z-36

TABLE 11-continued
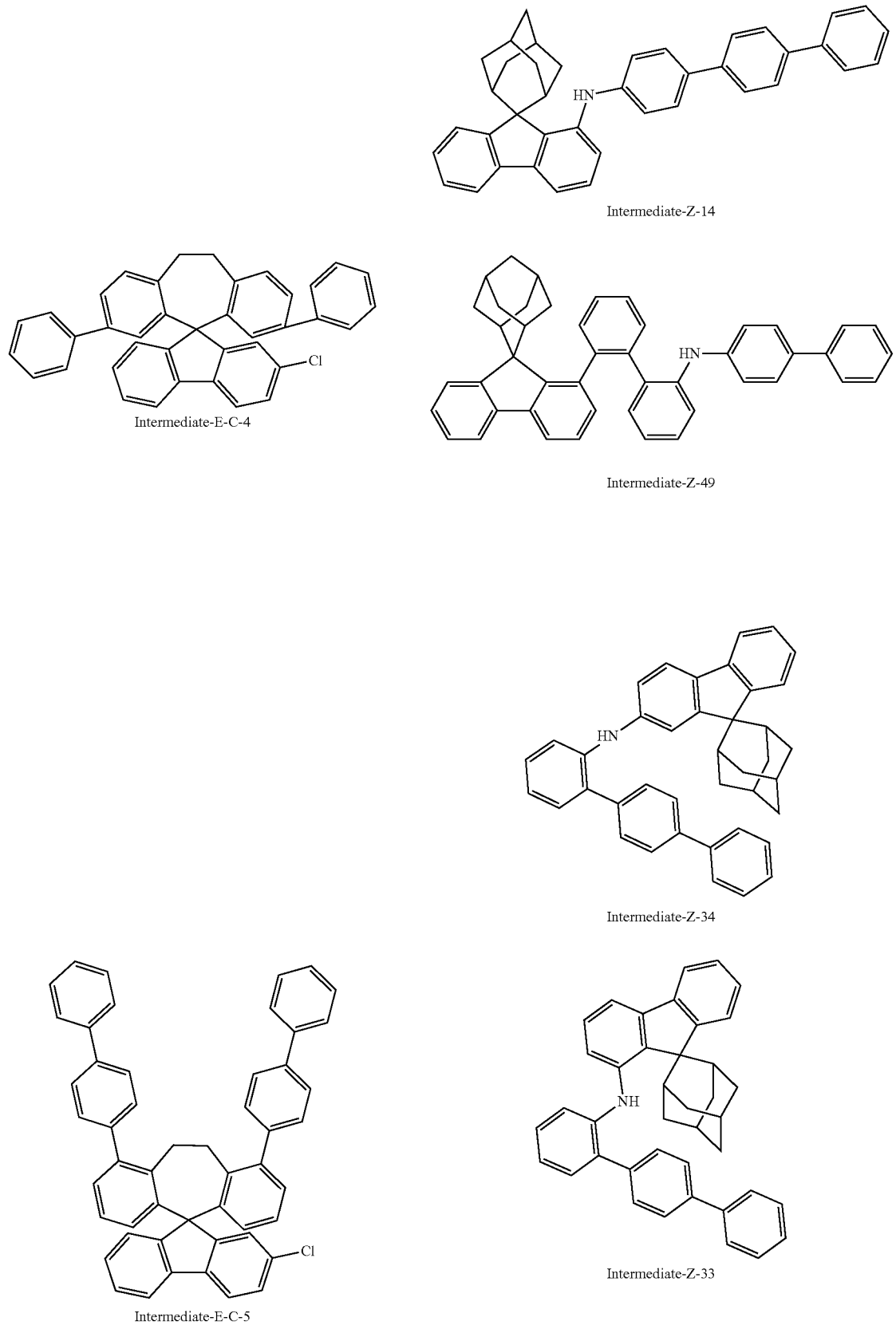

TABLE 11-continued
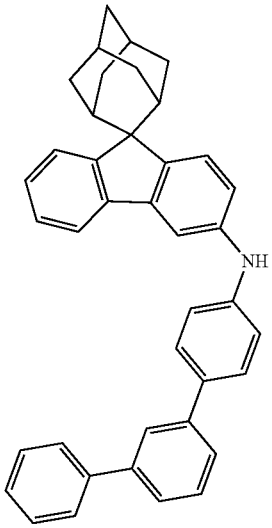 [SMILES: c1ccc(-c2cccc(-c3ccc(Nc4ccc5c(c4)-c4ccccc4C54C5CC6CC(C5)CC4C6)cc3)c2)cc1]
Intermediate-Z-17
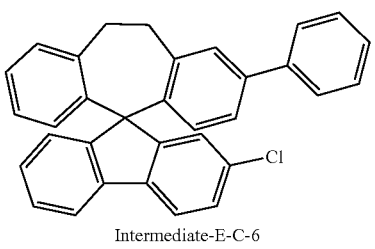
Intermediate-E-C-6
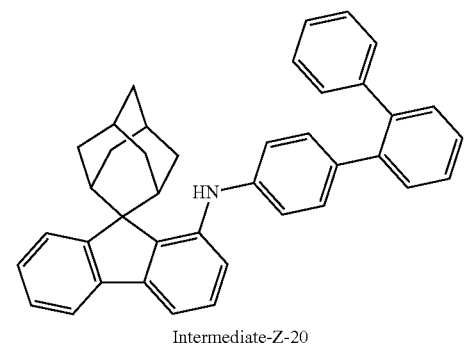
Intermediate-Z-20
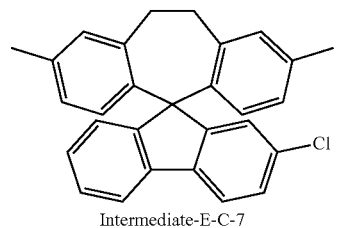
Intermediate-E-C-7
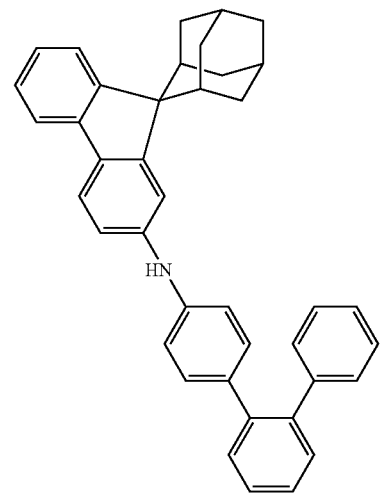 [SMILES: c1ccc(-c2ccccc2-c2ccc(Nc3ccc4c(c3)C3(c5ccccc5-4)C4CC5CC(C4)CC3C5)cc2)cc1]
Intermediate-Z-22

TABLE 11-continued
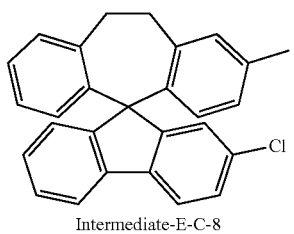
Intermediate-E-C-8
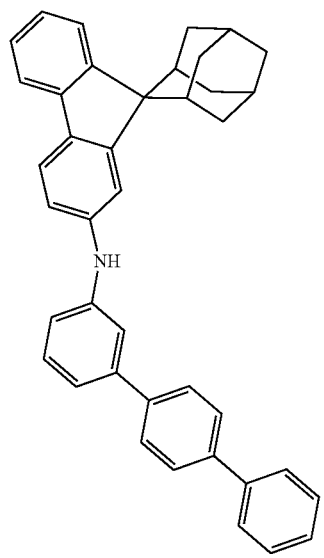 [SMILES: c1ccc(-c2ccc(-c3cccc(Nc4ccc5c(c4)C4(c6ccccc6-5)C5CC6CC(C5)CC4C6)c3)cc2)cc1]
Intermediate-Z-25
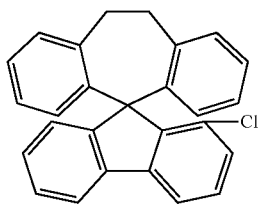 [SMILES: Clc1cccc2c1C1(c3ccccc3CCc3ccccc31)c1ccccc1-2]
Intermediate-E-C-10
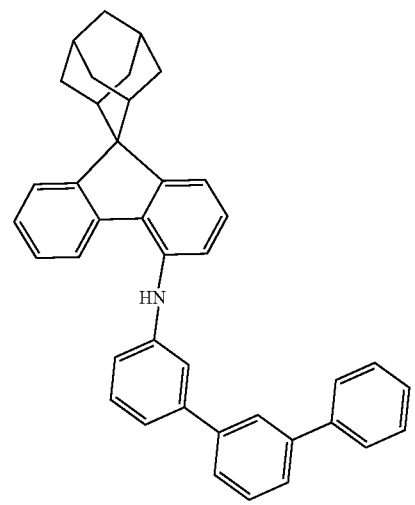 [SMILES: c1ccc(-c2cccc(-c3cccc(Nc4cccc5c4-c4ccccc4C54C5CC6CC(C5)CC4C6)c3)c2)cc1]
Intermediate-Z-27
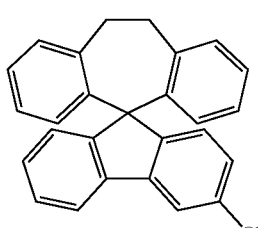
Intermediate-E-C-10-0
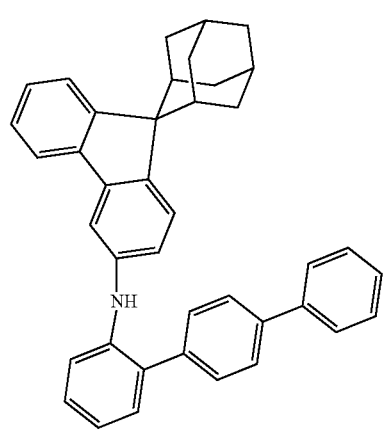 [SMILES: c1ccc(-c2ccc(-c3ccccc3Nc3ccc4c(c3)-c3ccccc3C43C4CC5CC(C4)CC3C5)cc2)cc1]
Intermediate-Z-32

TABLE 11-continued
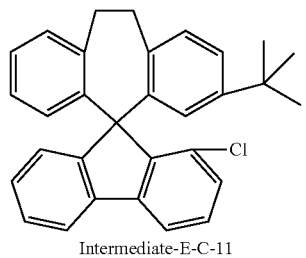
Intermediate-E-C-11
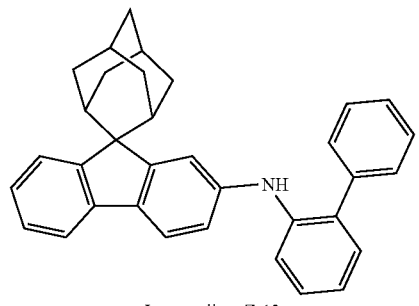
Intermediate-Z-13
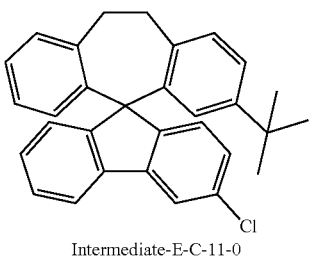
Intermediate-E-C-11-0
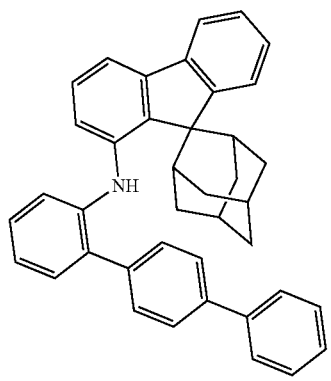 [SMILES: c1ccc(-c2ccc(-c3ccccc3Nc3cccc4c3C3(c5ccccc5-4)C4CC5CC(C4)CC3C5)cc2)cc1]
Intermediate-Z-33
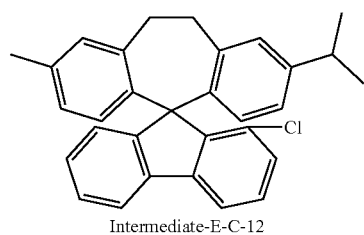
Intermediate-E-C-12
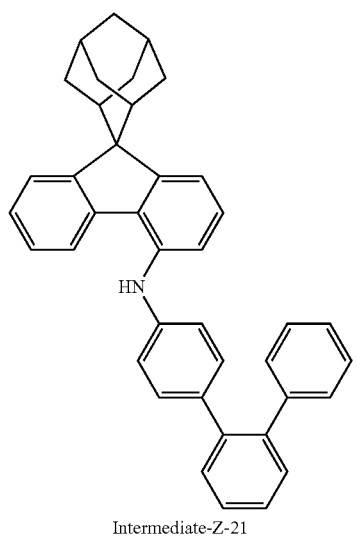
Intermediate-Z-21

TABLE 11-continued
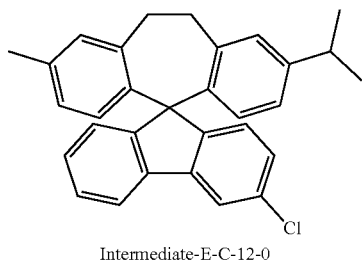
Intermediate-E-C-12-0
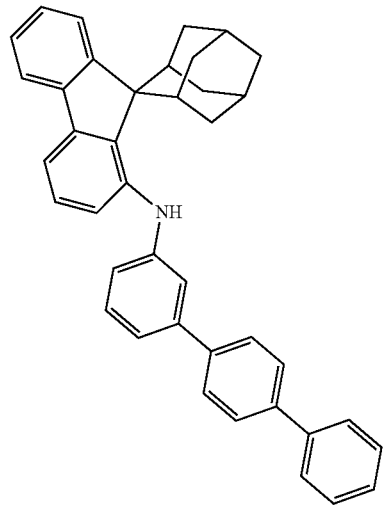 [SMILES: c1ccc(-c2ccc(-c3cccc(Nc4cccc5c4C4(c6ccccc6-5)C5CC6CC(C5)CC4C6)c3)cc2)cc1]
Intermediate-Z-24
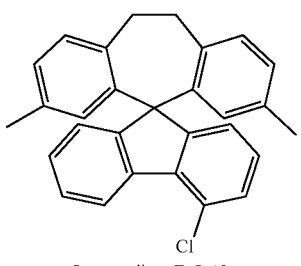
Intermediate-E-C-13
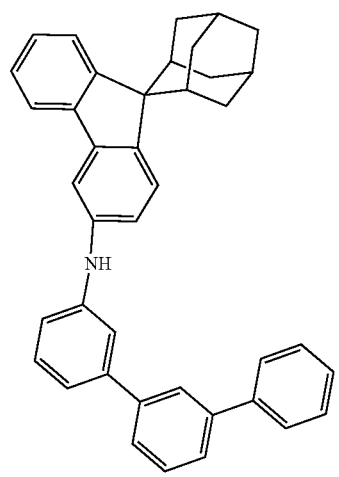 [SMILES: c1ccc(-c2cccc(-c3cccc(Nc4ccc5c(c4)-c4ccccc4C54C5CC6CC(C5)CC4C6)c3)c2)cc1]
Intermediate-Z-26
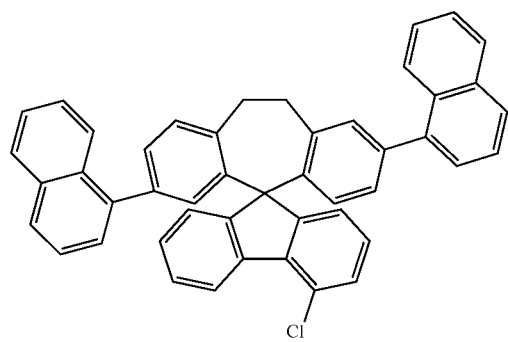 [SMILES: Clc1cccc2c1-c1ccccc1C21c2ccc(-c3cccc4ccccc34)cc2CCc2ccc(-c3cccc4ccccc34)cc21]
Intermediate-E-C-14
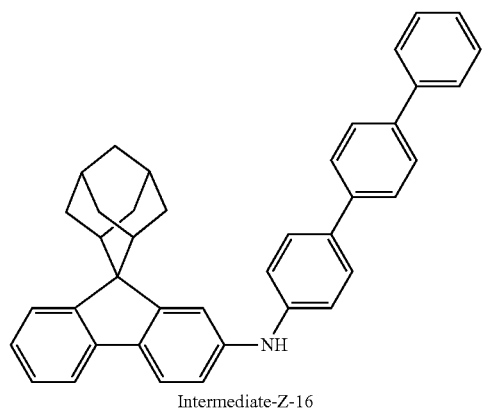
Intermediate-Z-16

TABLE 11-continued
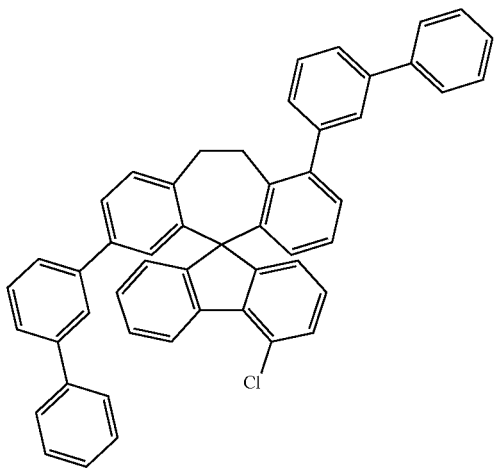 [SMILES: Clc1cccc2c1-c1ccccc1C21c2cc(-c3cccc(-c4ccccc4)c3)ccc2CCc2c(-c3cccc(-c4ccccc4)c3)cccc21]
Intermediate-E-C-15
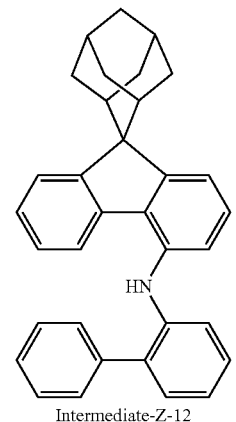
Intermediate-Z-12
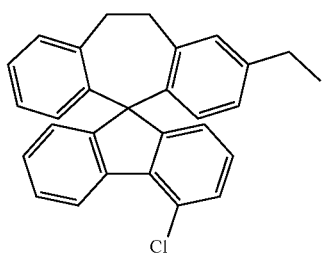 [SMILES: CCc1ccc2c(c1)CCc1ccccc1C21c2ccccc2-c2c(Cl)cccc21]
Intermediate-E-C-16
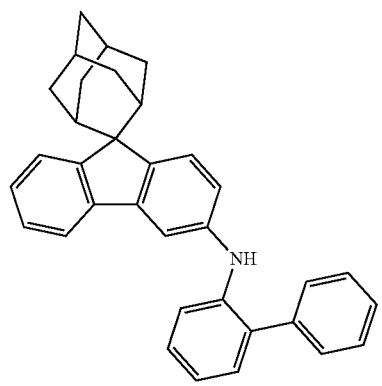 [SMILES: c1ccc(-c2ccccc2Nc2ccc3c(c2)-c2ccccc2C32C3CC4CC(C3)CC2C4)cc1]
Intermediate-Z-10
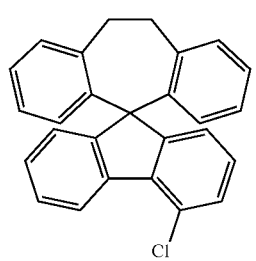 [SMILES: Clc1cccc2c1-c1ccccc1C21c2ccccc2CCc2ccccc21]
Intermediate-E-C-17
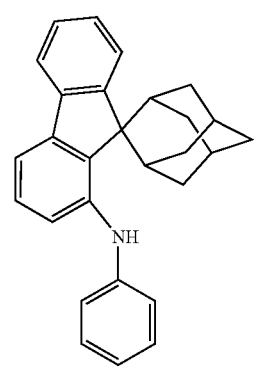 [SMILES: c1ccc(Nc2cccc3c2C2(c4ccccc4-3)C3CC4CC(C3)CC2C4)cc1]
Intermediate-Z-3

TABLE 11-continued
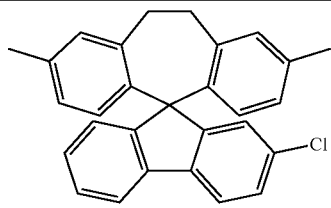
Intermediate-E-C-7
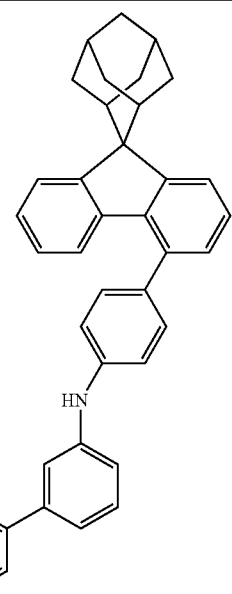
Intermediate-Z-50
| Compound M-X | Mass (g)/ Yield (%) | Mass spectrum/ (M + H) |
|---|---|---|
| 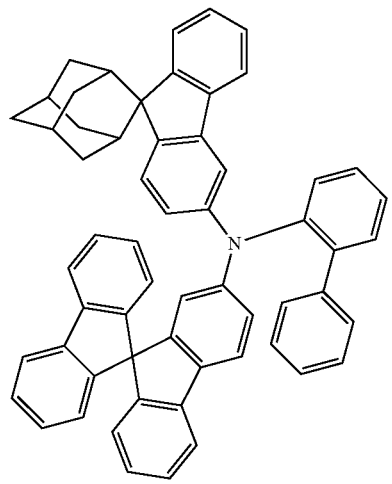 [SMILES: c1ccc(-c2ccccc2N(c2ccc3c(c2)-c2ccccc2C32C3CC4CC(C3)CC2C4)c2ccc3c(c2)C2(c4ccccc4-c4ccccc42)c2ccccc2-3)cc1] Compound A-2 | 2.8/74 | 768.4 |
| 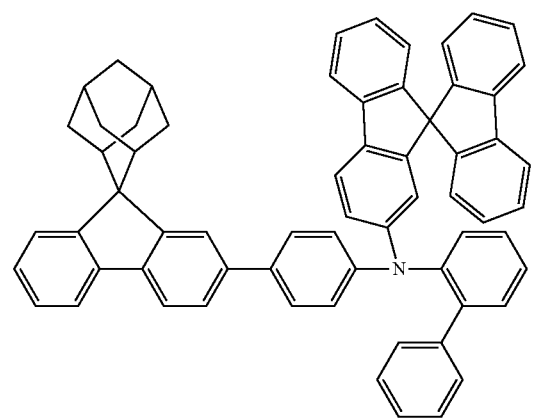 [SMILES: c1ccc(-c2ccccc2N(c2ccc(-c3ccc4c(c3)C3(c5ccccc5-4)C4CC5CC(C4)CC3C5)cc2)c2ccc3c(c2)C2(c4ccccc4-c4ccccc42)c2ccccc2-3)cc1] Compound A-3 | 2.9/70 | 844.3 |

TABLE 11-continued
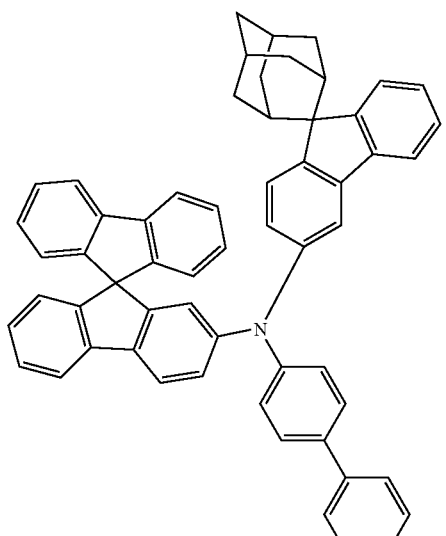
Compound A-4
2.9/75  768.4
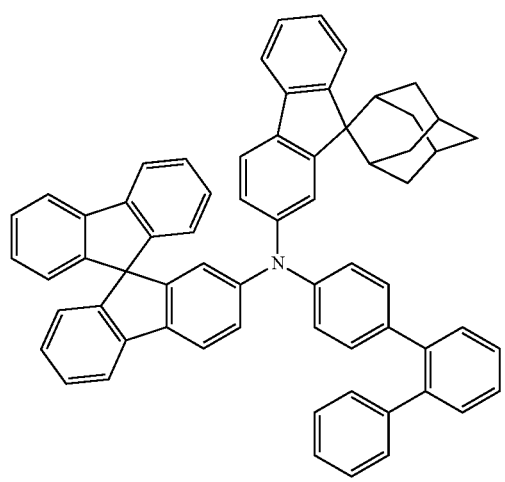 [SMILES: c1ccc(-c2ccccc2-c2ccc(N(c3ccc4c(c3)C3(c5ccccc5-c5ccccc53)c3ccccc3-4)c3ccc4c(c3)C3(c5ccccc5-4)C4CC5CC(C4)CC3C5)cc2)cc1]
Compound A-5
3.1/74  844.4
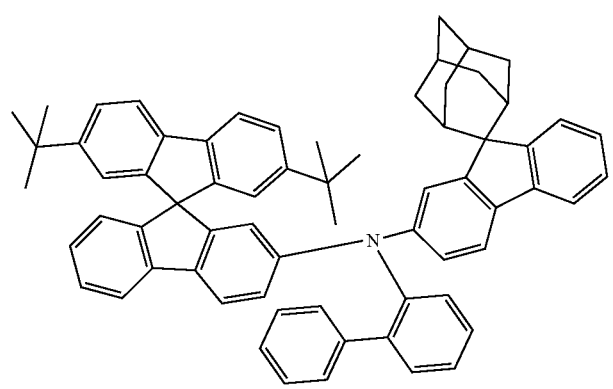 [SMILES: CC(C)(C)c1ccc2c(c1)C1(c3ccccc3-c3ccc(N(c4ccc5c(c4)C4(c6ccccc6-5)C5CC6CC(C5)CC4C6)c4ccccc4-c4ccccc4)cc31)c1cc(C(C)(C)C)ccc1-2]
Compound A-6
3.2/73  880.5

TABLE 11-continued
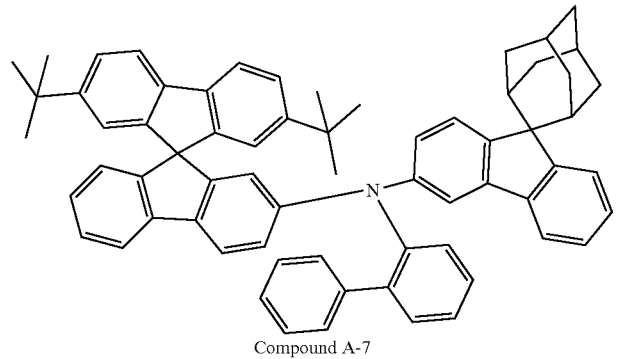
Compound A-7
3.3/74  880.5
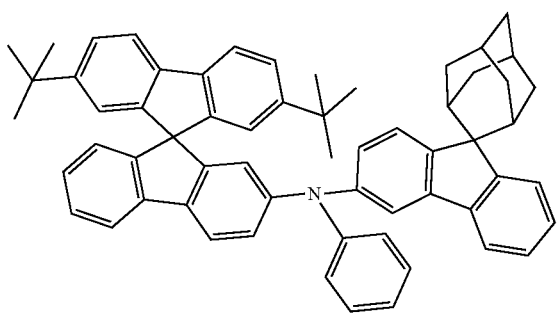 [SMILES: CC(C)(C)c1ccc2c(c1)C1(c3ccccc3-c3ccc(N(c4ccccc4)c4ccc5c(c4)-c4ccccc4C54C5CC6CC(C5)CC4C6)cc31)c1cc(C(C)(C)C)ccc1-2]
Compound A-8
2.9/73  804.5
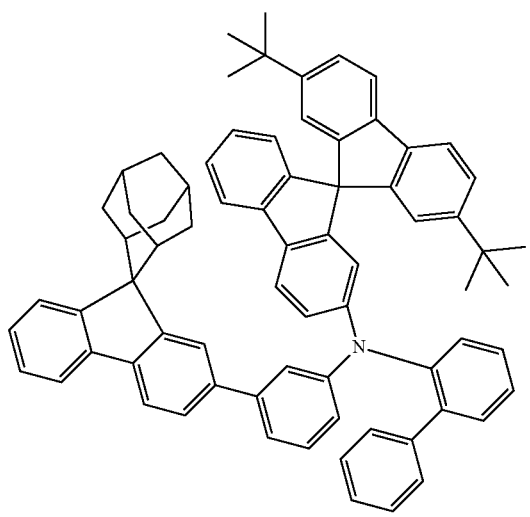 [SMILES: CC(C)(C)c1ccc2c(c1)C1(c3ccccc3-c3ccc(N(c4cccc(-c5ccc6c(c5)C5(c7ccccc7-6)C6CC7CC(C6)CC5C7)c4)c4ccccc4-c4ccccc4)cc31)c1cc(C(C)(C)C)ccc1-2]
Compound A-9
2.6/70  956.5
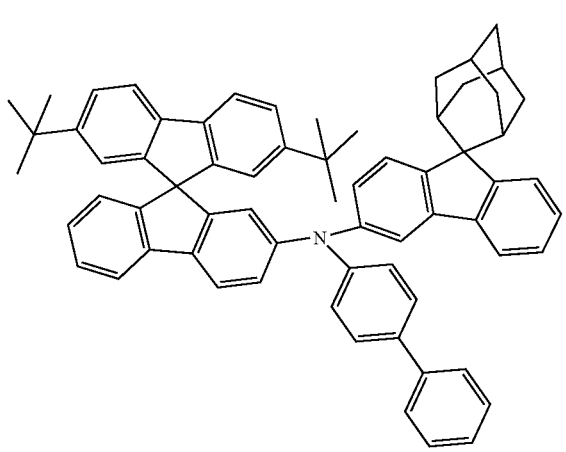 [SMILES: CC(C)(C)c1ccc2c(c1)C1(c3ccccc3-c3ccc(N(c4ccc(-c5ccccc5)cc4)c4ccc5c(c4)-c4ccccc4C54C5CC6CC(C5)CC4C6)cc31)c1cc(C(C)(C)C)ccc1-2]
3.0/72  880.5

TABLE 11-continued
Compound A-10
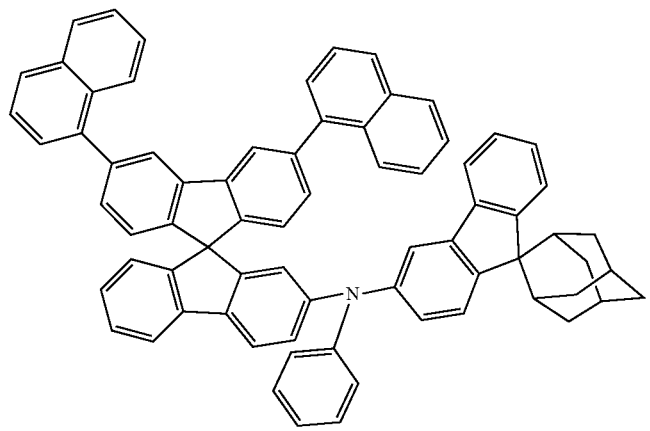 [SMILES: c1ccc(N(c2ccc3c(c2)-c2ccccc2C32C3CC4CC(C3)CC2C4)c2ccc3c(c2)C2(c4ccccc4-3)c3ccc(-c4cccc5ccccc45)cc3-c3cc(-c4cccc5ccccc45)ccc32)cc1]
3.3/70  944.4
Compound A-11
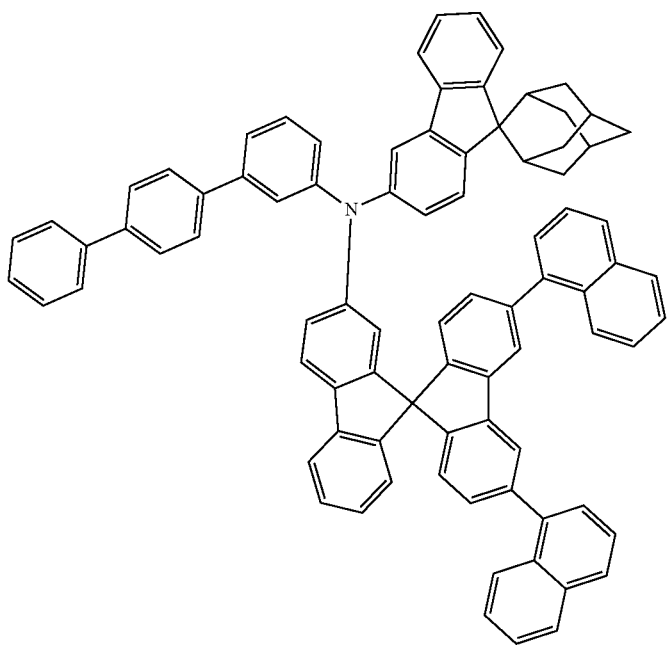 [SMILES: c1ccc(-c2ccc(-c3cccc(N(c4ccc5c(c4)-c4ccccc4C54C5CC6CC(C5)CC4C6)c4ccc5c(c4)C4(c6ccccc6-5)c5ccc(-c6cccc7ccccc67)cc5-c5cc(-c6cccc7ccccc67)ccc54)c3)cc2)cc1]
3.8/70  1096.5
Compound A-12
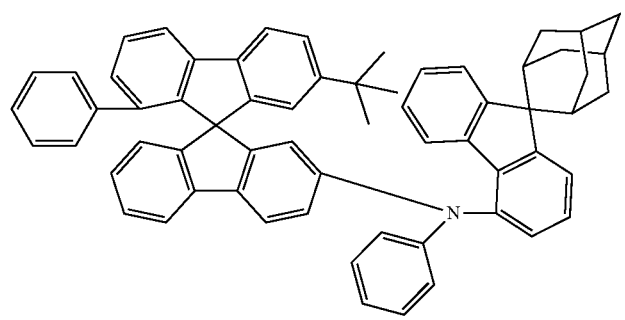 [SMILES: CC(C)(C)c1ccc2c(c1)C1(c3ccccc3-c3ccc(N(c4ccccc4)c4cccc5c4-c4ccccc4C54C5CC6CC(C5)CC4C6)cc31)c1c(-c3ccccc3)cccc1-2]
2.9/71  824.4
Compound A-13

TABLE 11-continued
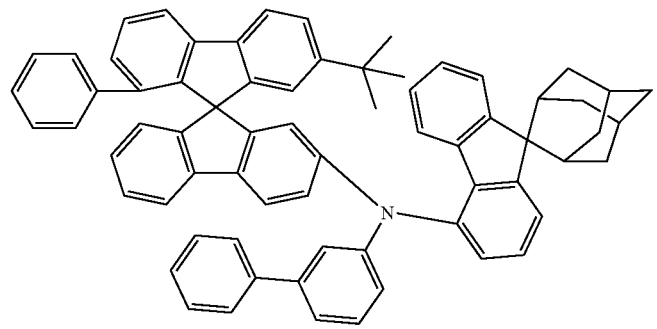 [SMILES: CC(C)(C)c1ccc2c(c1)C1(c3ccccc3-c3ccc(N(c4cccc(-c5ccccc5)c4)c4cccc5c4-c4ccccc4C54C5CC6CC(C5)CC4C6)cc31)c1c(-c3ccccc3)cccc1-2]
Compound A-14
3.3/72  900.4
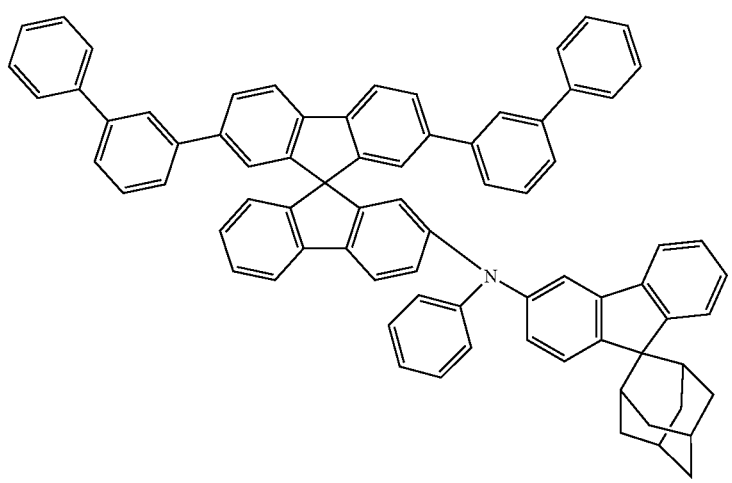 [SMILES: c1ccc(-c2cccc(-c3ccc4c(c3)C3(c5ccccc5-c5ccc(N(c6ccccc6)c6ccc7c(c6)-c6ccccc6C76C7CC8CC(C7)CC6C8)cc53)c3cc(-c5cccc(-c6ccccc6)c5)ccc3-4)c2)cc1]
Compound A-15
3.6/72  996.5
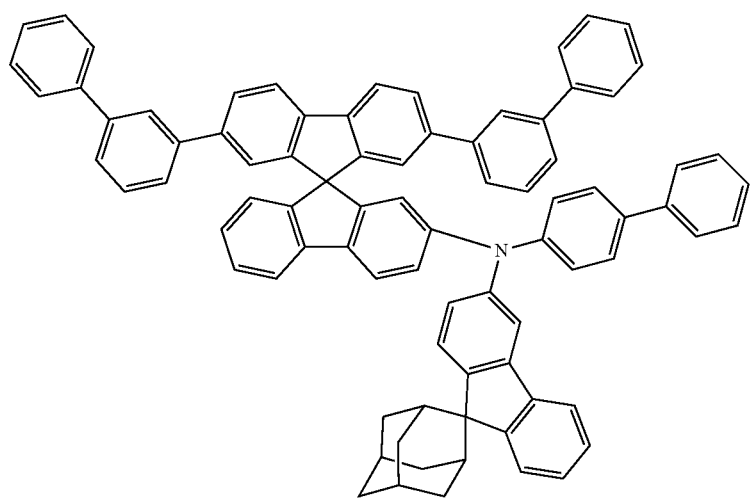 [SMILES: c1ccc(-c2ccc(N(c3ccc4c(c3)-c3ccccc3C43C4CC5CC(C4)CC3C5)c3ccc4c(c3)C3(c5ccccc5-4)c4cc(-c5cccc(-c6ccccc6)c5)ccc4-c4ccc(-c5cccc(-c6ccccc6)c5)cc43)cc2)cc1]
Compound A-16
3.8/70  1072.5

TABLE 11-continued
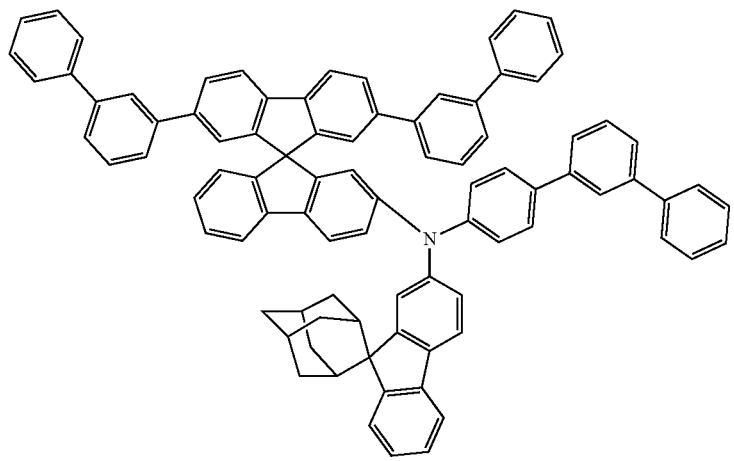 [SMILES: c1ccc(-c2cccc(-c3ccc(N(c4ccc5c(c4)C4(c6ccccc6-5)c5cc(-c6cccc(-c7ccccc7)c6)ccc5-c5ccc(-c6cccc(-c7ccccc7)c6)cc54)c4ccc5c(c4)C4(c6ccccc6-5)C5CC6CC(C5)CC4C6)cc3)c2)cc1]
Compound A-17
4.1/71  1148.5
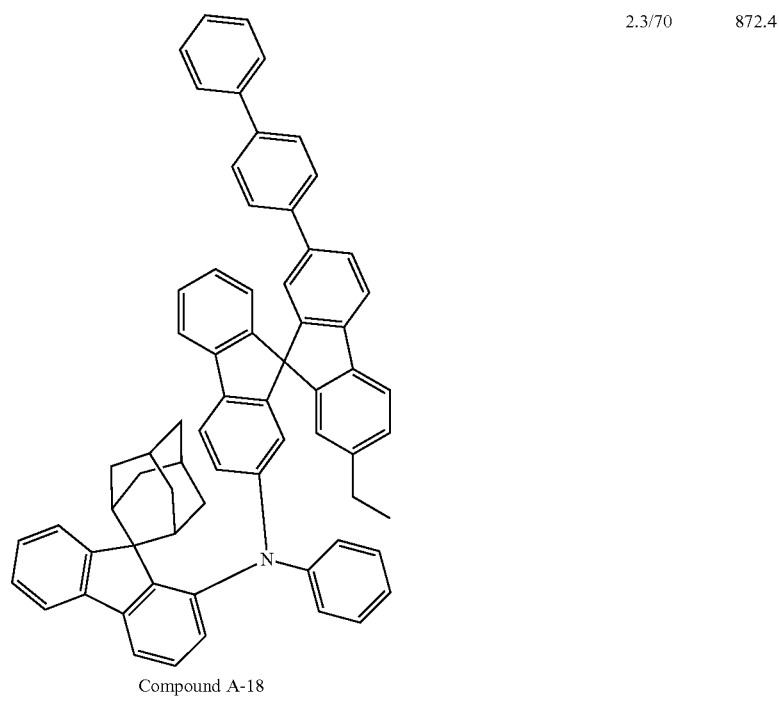
Compound A-18
2.3/70  872.4

TABLE 11-continued
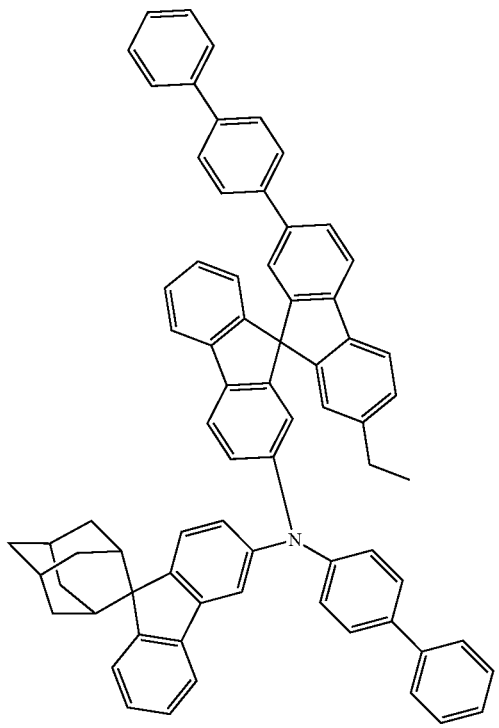
Compound A-19
2.5/70  948.5
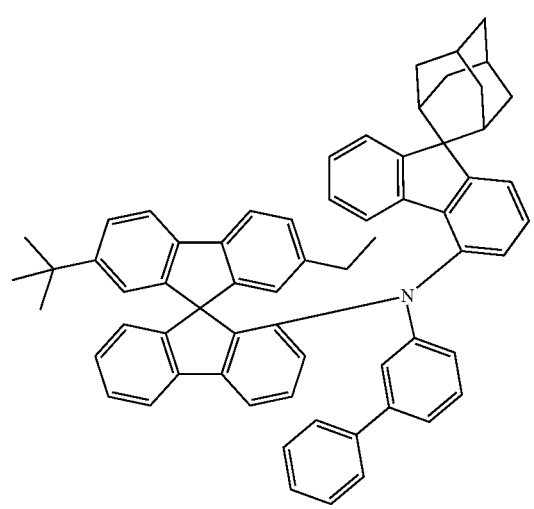 [SMILES: CCc1ccc2c(c1)C1(c3cc(C(C)(C)C)ccc3-2)c2ccccc2-c2cccc(N(c3cccc(-c4ccccc4)c3)c3cccc4c3-c3ccccc3C43C4CC5CC(C4)CC3C5)c21]
Compound A-20
2.8/72  852.5

TABLE 11-continued
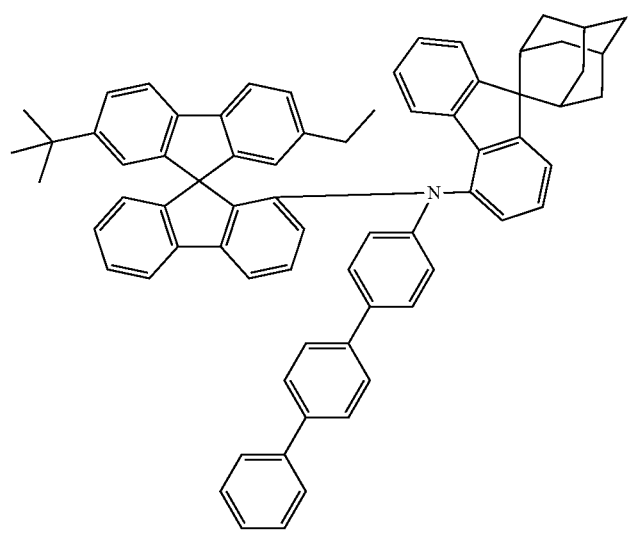 [SMILES: CCc1ccc2c(c1)C1(c3cc(C(C)(C)C)ccc3-2)c2ccccc2-c2cccc(N(c3ccc(-c4ccc(-c5ccccc5)cc4)cc3)c3cccc4c3-c3ccccc3C43C4CC5CC(C4)CC3C5)c21]
Compound A-21
3.0/71 928.5
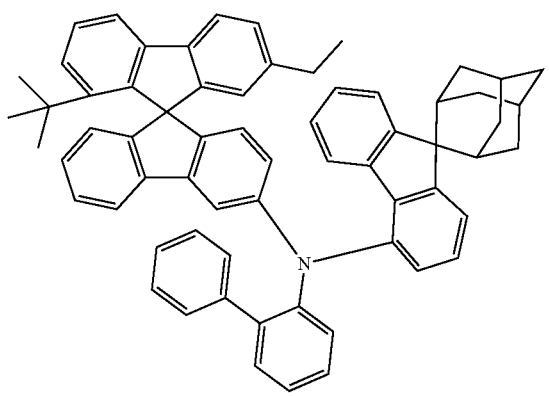 [SMILES: CCc1ccc2c(c1)C1(c3ccccc3-c3cc(N(c4ccccc4-c4ccccc4)c4cccc5c4-c4ccccc4C54C5CC6CC(C5)CC4C6)ccc31)c1c-2cccc1C(C)(C)C]
Compound A-22
2.8/72 852.5
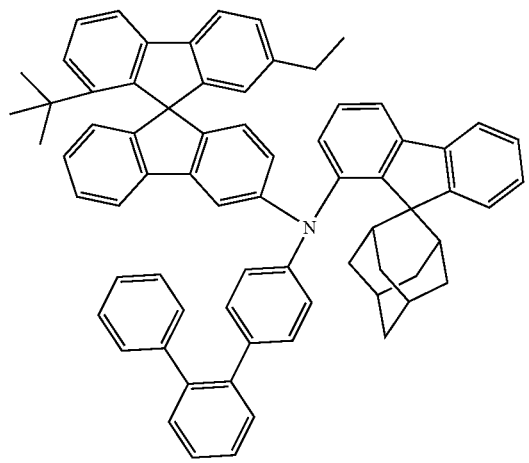 [SMILES: CCc1ccc2c(c1)C1(c3ccccc3-c3cc(N(c4ccc(-c5ccccc5-c5ccccc5)cc4)c4cccc5c4C4(c6ccccc6-5)C5CC6CC(C5)CC4C6)ccc31)c1c-2cccc1C(C)(C)C]
Compound A-23
3.0/71 928.5

TABLE 11-continued
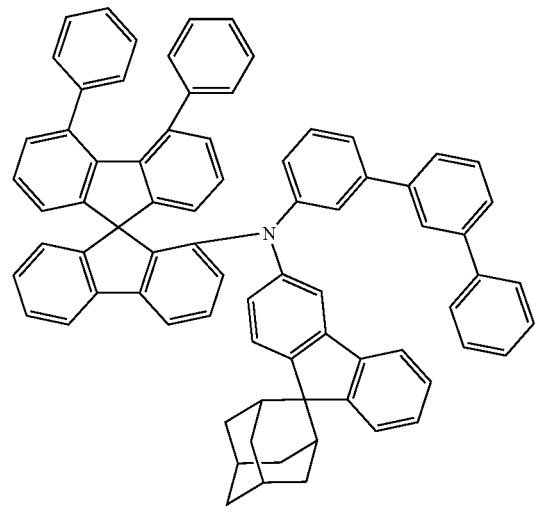 [SMILES: c1ccc(-c2cccc(-c3cccc(N(c4ccc5c(c4)-c4ccccc4C54C5CC6CC(C5)CC4C6)c4cccc5c4C4(c6ccccc6-5)c5cccc(-c6ccccc6)c5-c5c(-c6ccccc6)cccc54)c3)c2)cc1]
Compound A-24
2.7/70    996.4
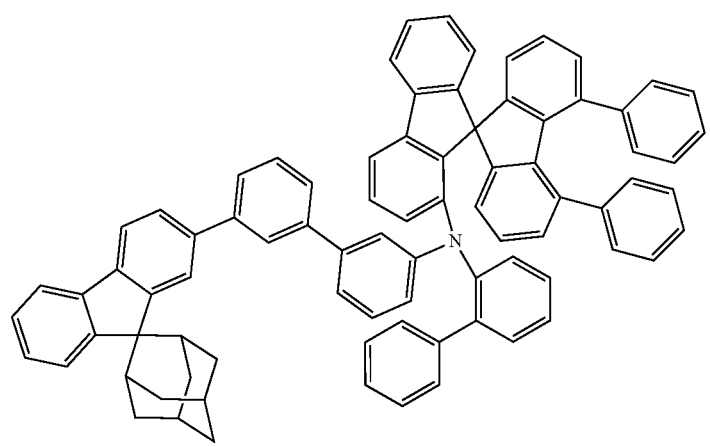 [SMILES: c1ccc(-c2ccccc2N(c2cccc(-c3cccc(-c4ccc5c(c4)C4(c6ccccc6-5)C5CC6CC(C5)CC4C6)c3)c2)c2cccc3c2C2(c4ccccc4-3)c3cccc(-c4ccccc4)c3-c3c(-c4ccccc4)cccc32)cc1]
Compound A-25
2.9/70    1072.5
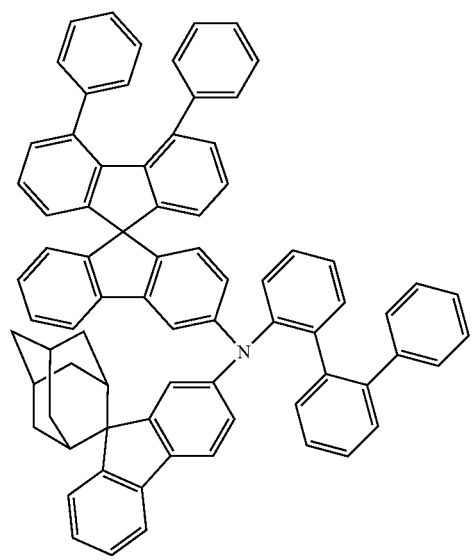 [SMILES: c1ccc(-c2ccccc2-c2ccccc2N(c2ccc3c(c2)-c2ccccc2C32c3cccc(-c4ccccc4)c3-c3c(-c4ccccc4)cccc32)c2ccc3c(c2)C2(c4ccccc4-3)C3CC4CC(C3)CC2C4)cc1]
Compound A-26
2.8/71    996.4

TABLE 11-continued
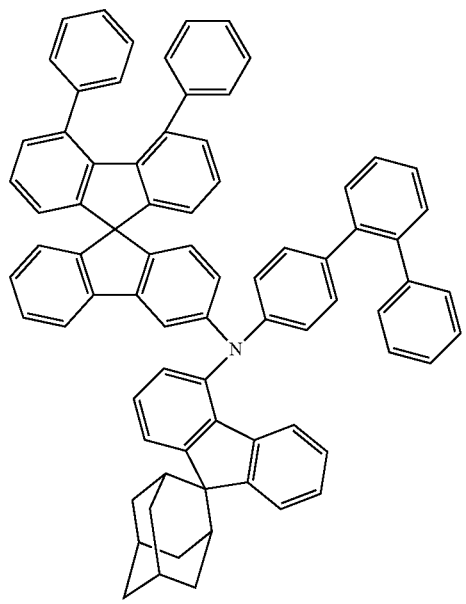 [SMILES: c1ccc(-c2ccccc2-c2ccc(N(c3ccc4c(c3)-c3ccccc3C43c4cccc(-c5ccccc5)c4-c4c(-c5ccccc5)cccc43)c3cccc4c3-c3ccccc3C43C4CC5CC(C4)CC3C5)cc2)cc1]
Compound A-27
2.8/71  996.4
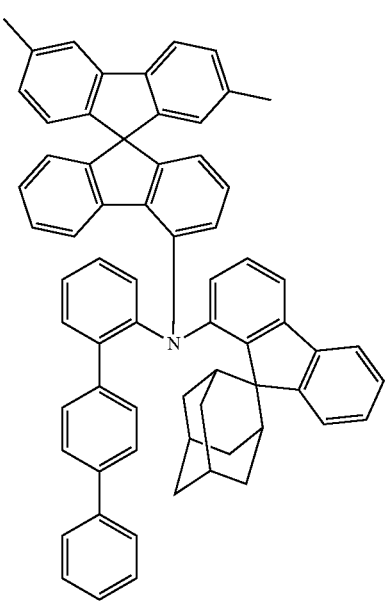 [SMILES: Cc1ccc2c(c1)-c1ccc(C)cc1C21c2ccccc2-c2c(N(c3ccccc3-c3ccc(-c4ccccc4)cc3)c3cccc4c3C3(c5ccccc5-4)C4CC5CC(C4)CC3C5)cccc21]
Compound A-28
3.2/70  872.4

TABLE 11-continued
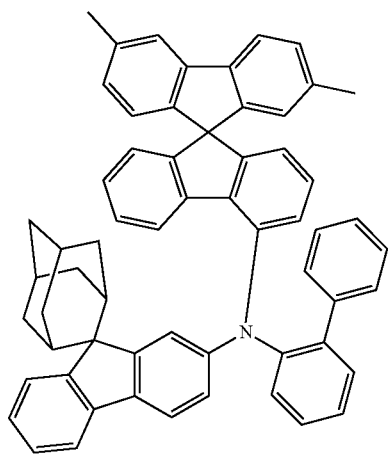 [SMILES: Cc1ccc2c(c1)-c1ccc(C)cc1C21c2ccccc2-c2c(N(c3ccc4c(c3)C3(c5ccccc5-4)C4CC5CC(C4)CC3C5)c3ccccc3-c3ccccc3)cccc21]
Compound A-29
2.9/71  796.4
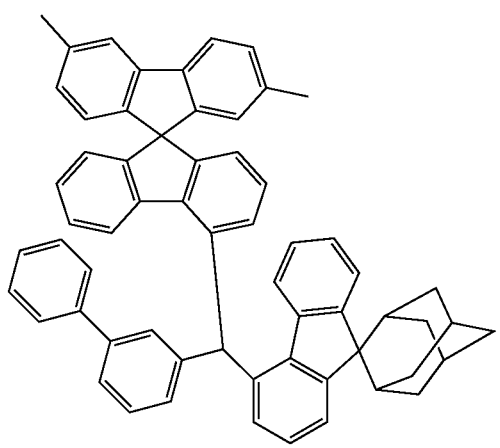 [SMILES: Cc1ccc2c(c1)-c1ccc(C)cc1C21c2ccccc2-c2c(C(c3cccc(-c4ccccc4)c3)c3cccc4c3-c3ccccc3C43C4CC5CC(C4)CC3C5)cccc21]
Compound A-30
2.9/71  769.4
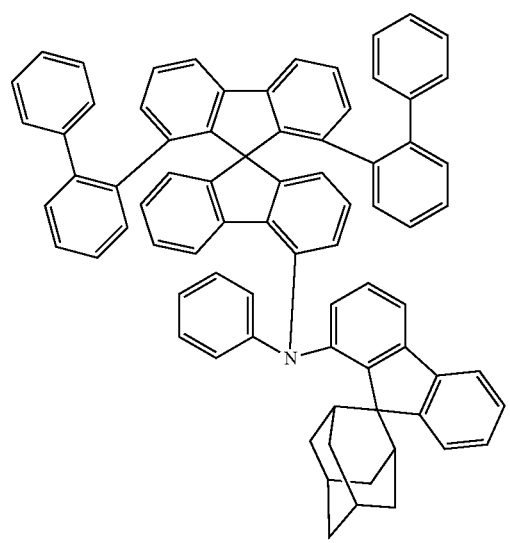 [SMILES: c1ccc(-c2ccccc2-c2cccc3c2C2(c4ccccc4-c4c(N(c5ccccc5)c5cccc6c5C5(c7ccccc7-6)C6CC7CC(C6)CC5C7)cccc42)c2c(-c4ccccc4-c4ccccc4)cccc2-3)cc1]
Compound A-31
2.1/71  996.5

TABLE 11-continued
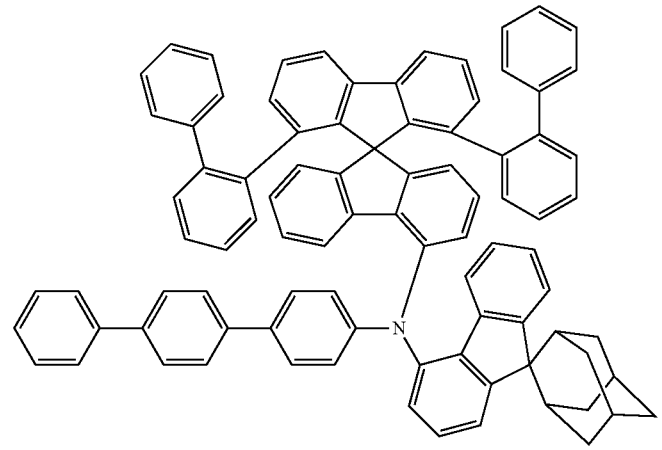 [SMILES: c1ccc(-c2ccc(-c3ccc(N(c4cccc5c4-c4ccccc4C54c5c(-c6ccccc6-c6ccccc6)cccc5-c5cccc(-c6ccccc6-c6ccccc6)c54)c4cccc5c4-c4ccccc4C54C5CC6CC(C5)CC4C6)cc3)cc2)cc1]
Compound A-32
2.4/70   1148.5
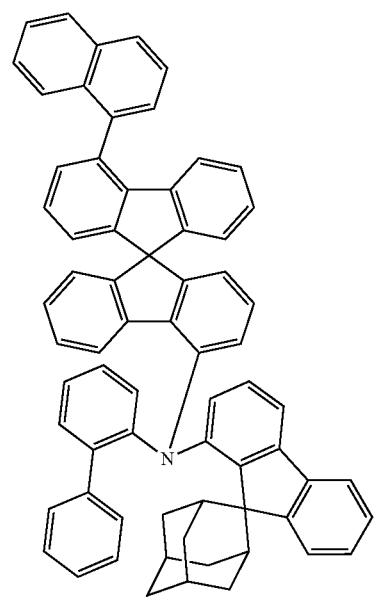 [SMILES: c1ccc(-c2ccccc2N(c2cccc3c2-c2ccccc2C32c3ccccc3-c3c(-c4cccc5ccccc45)cccc32)c2cccc3c2C2(c4ccccc4-3)C3CC4CC(C3)CC2C4)cc1]
Compound A-33
2.4/70   895.1

TABLE 11-continued
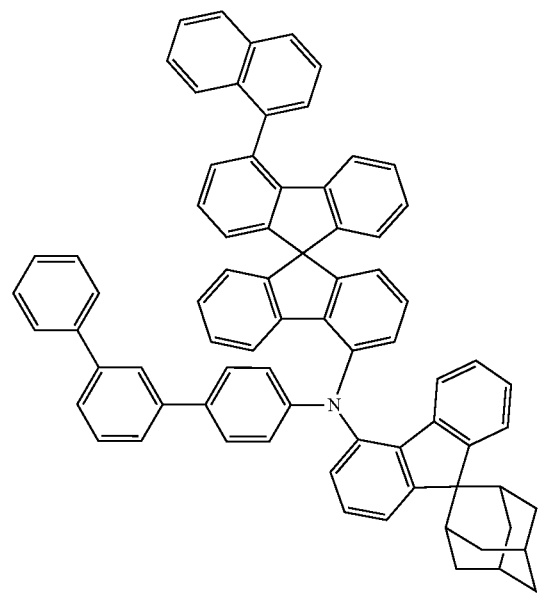 [SMILES: c1ccc(-c2cccc(-c3ccc(N(c4cccc5c4-c4ccccc4C54c5ccccc5-c5c(-c6cccc7ccccc67)cccc54)c4cccc5c4-c4ccccc4C54C5CC6CC(C5)CC4C6)cc3)c2)cc1]
Compound A-34
2.6/71 970.4
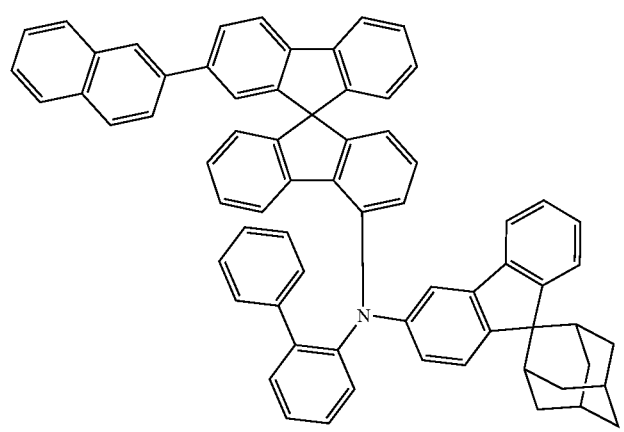 [SMILES: c1ccc(-c2ccccc2N(c2ccc3c(c2)-c2ccccc2C32C3CC4CC(C3)CC2C4)c2cccc3c2-c2ccccc2C32c3ccccc3-c3ccc(-c4ccc5ccccc5c4)cc32)cc1]
Compound A-35
2.4/72 894.4
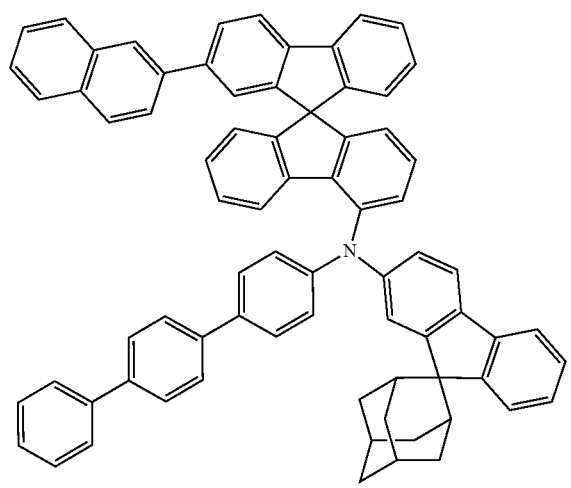 [SMILES: c1ccc(-c2ccc(-c3ccc(N(c4ccc5c(c4)C4(c6ccccc6-5)C5CC6CC(C5)CC4C6)c4cccc5c4-c4ccccc4C54c5ccccc5-c5ccc(-c6ccc7ccccc7c6)cc54)cc3)cc2)cc1]
Compound A-36
2.6/70 970.4

TABLE 11-continued
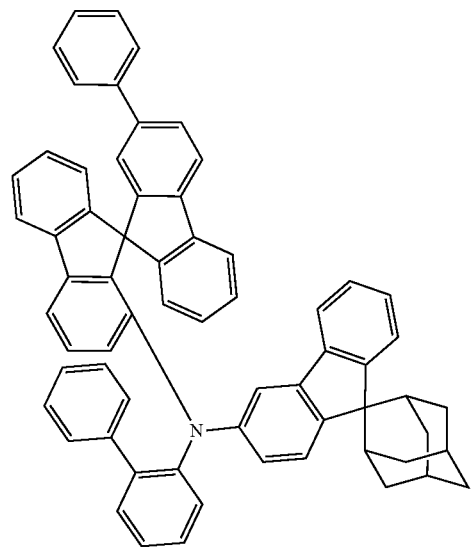 [SMILES: c1ccc(-c2ccc3c(c2)C2(c4ccccc4-3)c3ccccc3-c3cccc(N(c4ccc5c(c4)-c4ccccc4C54C5CC6CC(C5)CC4C6)c4ccccc4-c4ccccc4)c32)cc1]
Compound A-37
2.5/71  844.4
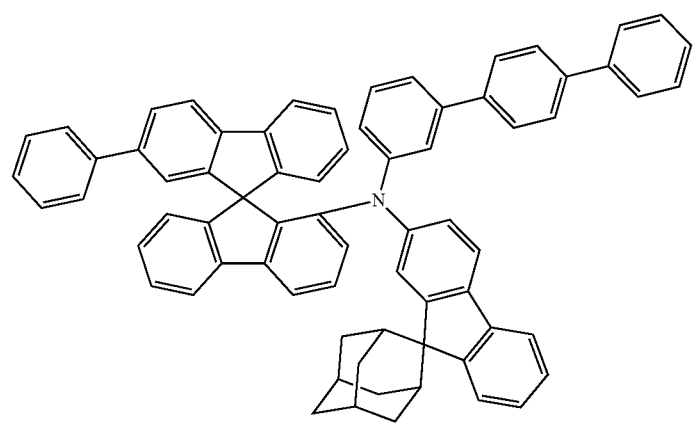 [SMILES: c1ccc(-c2ccc(-c3cccc(N(c4ccc5c(c4)C4(c6ccccc6-5)C5CC6CC(C5)CC4C6)c4cccc5c4C4(c6ccccc6-c6ccc(-c7ccccc7)cc64)c4ccccc4-5)c3)cc2)cc1]
Compound A-38
2.7/70  920.4
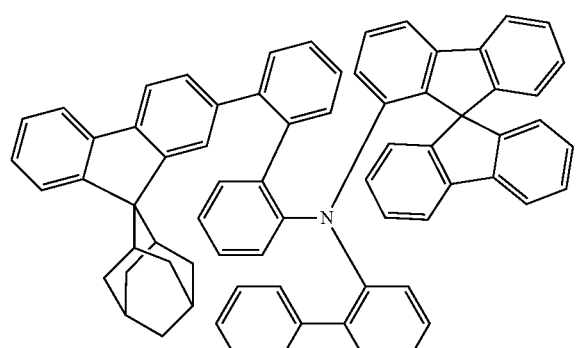
Compound A-39
3.2/70  920.4

TABLE 11-continued
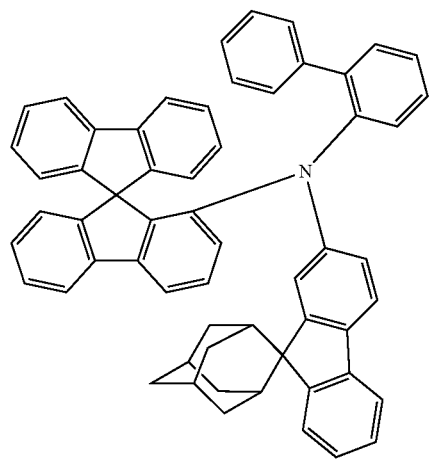 [SMILES: c1ccc(-c2ccccc2N(c2ccc3c(c2)C2(c4ccccc4-3)C3CC4CC(C3)CC2C4)c2cccc3c2C2(c4ccccc4-c4ccccc42)c2ccccc2-3)cc1]
Compound A-40
2.7/70  768.3
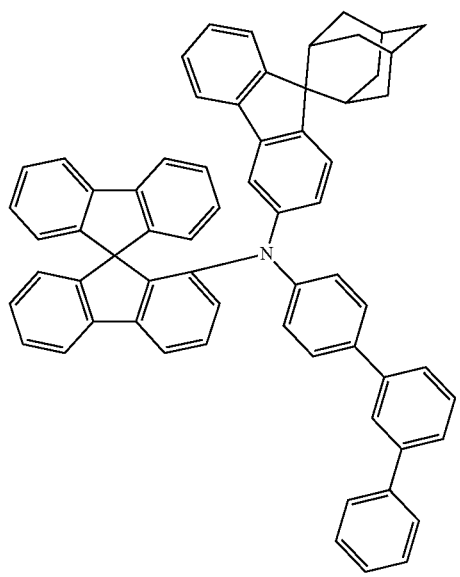 [SMILES: c1ccc(-c2cccc(-c3ccc(N(c4ccc5c(c4)-c4ccccc4C54C5CC6CC(C5)CC4C6)c4cccc5c4C4(c6ccccc6-c6ccccc64)c4ccccc4-5)cc3)c2)cc1]
Compound A-41
2.9/70  844.3
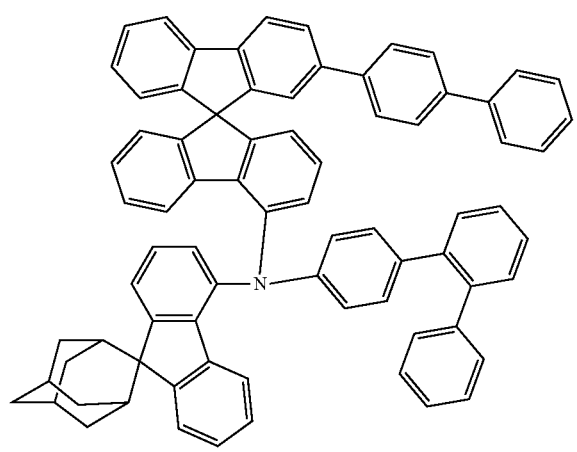 [SMILES: c1ccc(-c2ccc(-c3ccc4c(c3)C3(c5ccccc5-4)c4ccccc4-c4c(N(c5ccc(-c6ccccc6-c6ccccc6)cc5)c5cccc6c5-c5ccccc5C65C6CC7CC(C6)CC5C7)cccc43)cc2)cc1]
Compound A-42
2.5/70  996.5

TABLE 11-continued
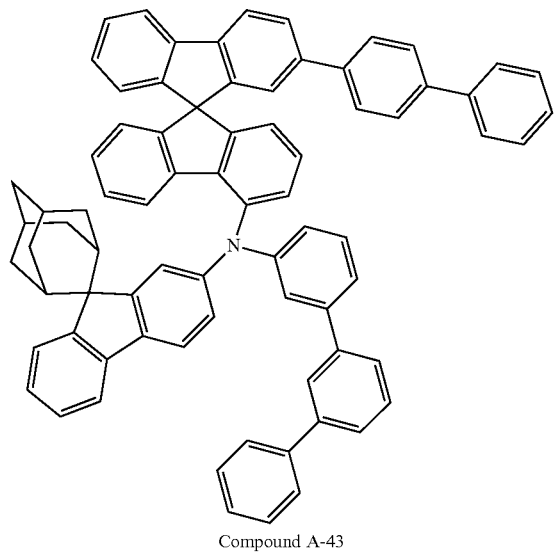
Compound A-43
2.6/71 996.5
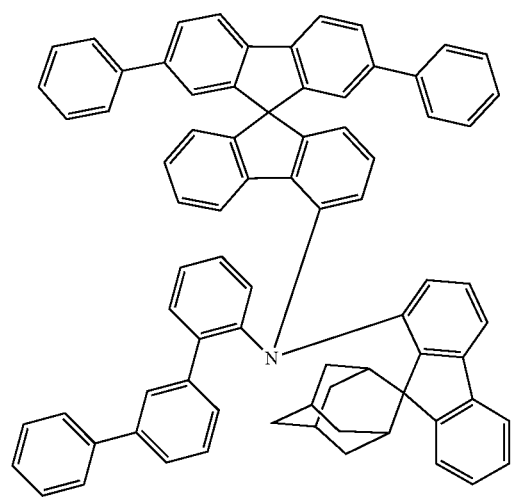 [SMILES: c1ccc(-c2cccc(-c3ccccc3N(c3cccc4c3-c3ccccc3C43c4cc(-c5ccccc5)ccc4-c4ccc(-c5ccccc5)cc43)c3cccc4c3C3(c5ccccc5-4)C4CC5CC(C4)CC3C5)c2)cc1]
Compound A-44
2.6/71 996.5
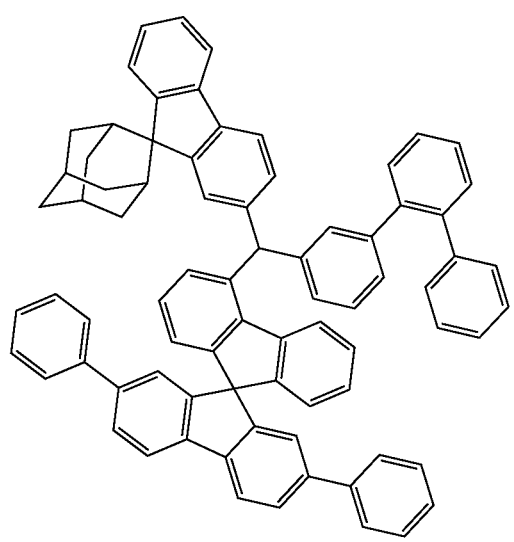 [SMILES: c1ccc(-c2ccc3c(c2)C2(c4cc(-c5ccccc5)ccc4-3)c3ccccc3-c3c(C(c4cccc(-c5ccccc5-c5ccccc5)c4)c4ccc5c(c4)C4(c6ccccc6-5)C5CC6CC(C5)CC4C6)cccc32)cc1]
Compound A-45
2.5/70 996.5

TABLE 11-continued
| | | |
|---|---|---|
| 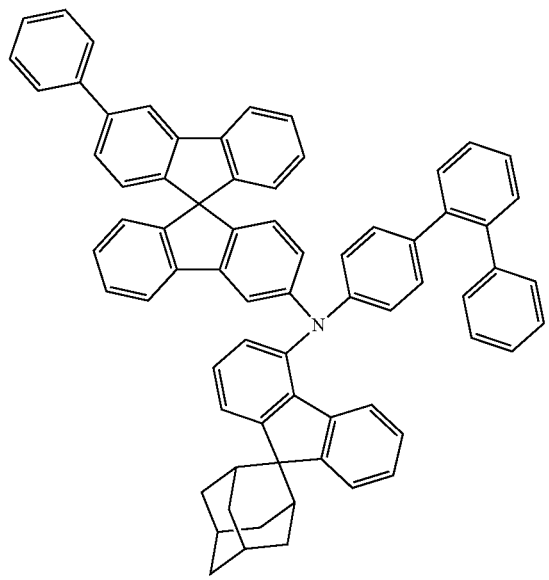 [SMILES: c1ccc(-c2ccc3c(c2)-c2ccccc2C32c3ccccc3-c3cc(N(c4ccc(-c5ccccc5-c5ccccc5)cc4)c4cccc5c4-c4ccccc4C54C5CC6CC(C5)CC4C6)ccc32)cc1]
Compound A-46 | 2.7/70 | 920.4 |
| 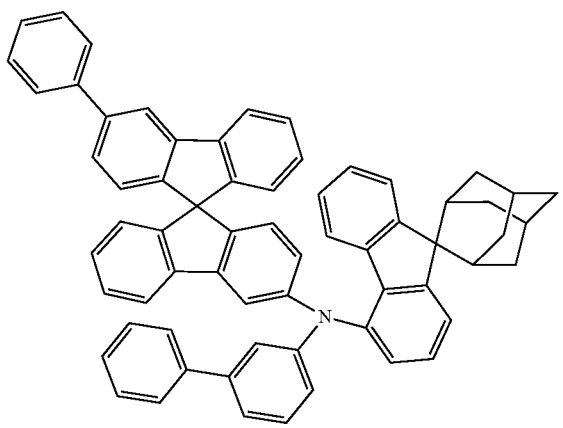 [SMILES: c1ccc(-c2cccc(N(c3ccc4c(c3)-c3ccccc3C43c4ccccc4-c4cc(-c5ccccc5)ccc43)c3cccc4c3-c3ccccc3C43C4CC5CC(C4)CC3C5)c2)cc1]
Compound A-47 | 2.5/70 | 844.4 |
| 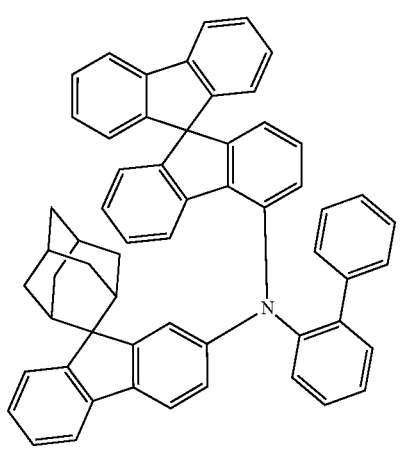 [SMILES: c1ccc(-c2ccccc2N(c2ccc3c(c2)C2(c4ccccc4-3)C3CC4CC(C3)CC2C4)c2cccc3c2-c2ccccc2C32c3ccccc3-c3ccccc32)cc1]
Compound A-48 | 2.7/70 | 768.3 |

TABLE 11-continued
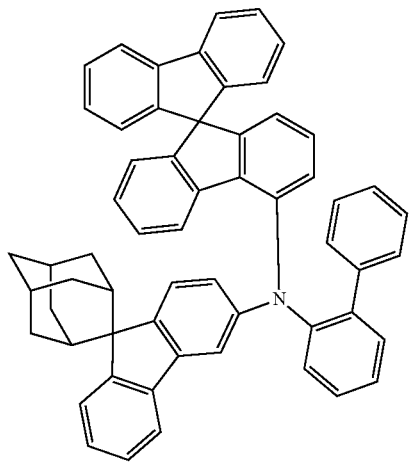 [SMILES: c1ccc(-c2ccccc2N(c2ccc3c(c2)-c2ccccc2C32C3CC4CC(C3)CC2C4)c2cccc3c2-c2ccccc2C32c3ccccc3-c3ccccc32)cc1]
Compound A-49
2.9/75 768.3
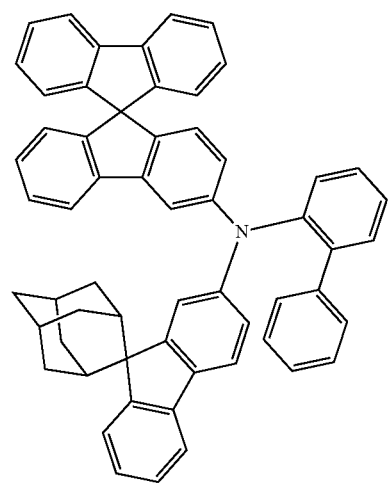 [SMILES: c1ccc(-c2ccccc2N(c2ccc3c(c2)-c2ccccc2C32c3ccccc3-c3ccccc32)c2ccc3c(c2)C2(c4ccccc4-3)C3CC4CC(C3)CC2C4)cc1]
Compound A-50
2.8/73 768.3
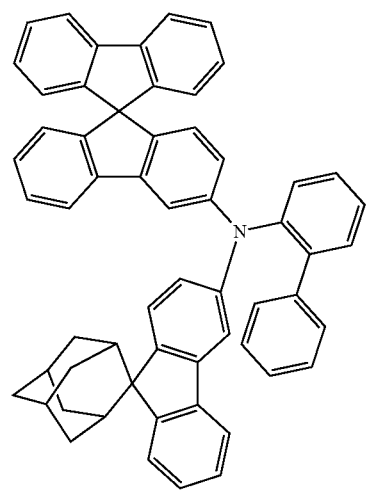 [SMILES: c1ccc(-c2ccccc2N(c2ccc3c(c2)-c2ccccc2C32c3ccccc3-c3ccccc32)c2ccc3c(c2)-c2ccccc2C32C3CC4CC(C3)CC2C4)cc1]
Compound A-51
2.7/74 768.3

TABLE 11-continued
| | |
|---|---|
| 2.1/70 | 922.4 |
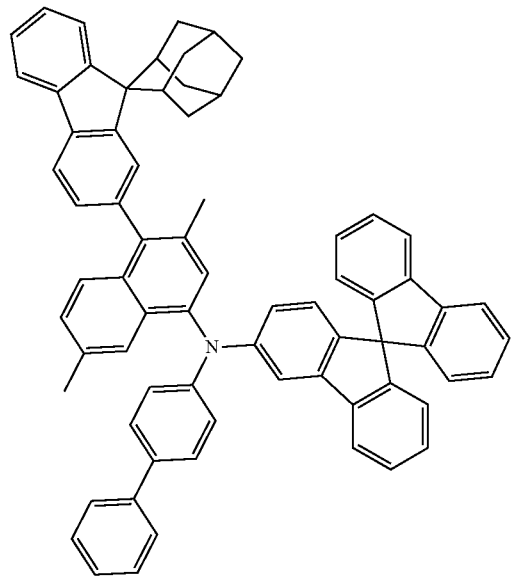 [SMILES: Cc1ccc2c(-c3ccc4c(c3)C3(c5ccccc5-4)C4CC5CC(C4)CC3C5)c(C)cc(N(c3ccc(-c4ccccc4)cc3)c3ccc4c(c3)-c3ccccc3C43c4ccccc4-c4ccccc43)c2c1]
Compound 127
| | |
|---|---|
| 3.2/71 | 880.5 |
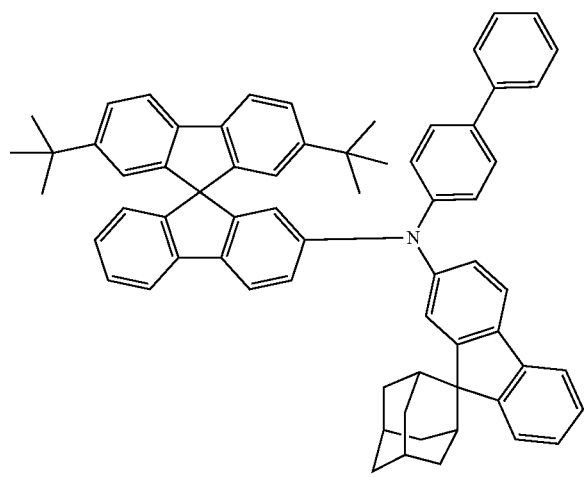 [SMILES: CC(C)(C)c1ccc2c(c1)C1(c3ccccc3-c3ccc(N(c4ccc(-c5ccccc5)cc4)c4ccc5c(c4)C4(c6ccccc6-5)C5CC6CC(C5)CC4C6)cc31)c1cc(C(C)(C)C)ccc1-2]
Compound A-52
| | |
|---|---|
| 2.8/73 | 768.4 |
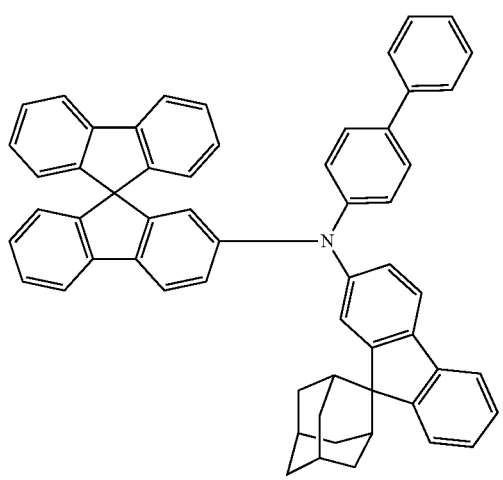 [SMILES: c1ccc(-c2ccc(N(c3ccc4c(c3)C3(c5ccccc5-c5ccccc53)c3ccccc3-4)c3ccc4c(c3)C3(c5ccccc5-4)C4CC5CC(C4)CC3C5)cc2)cc1]
Compound A-53

TABLE 11-continued
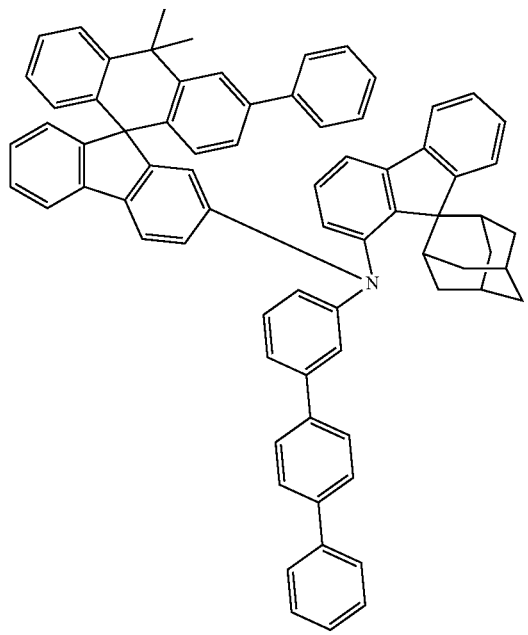 [SMILES: CC1(C)c2ccccc2C2(c3ccccc3-c3ccc(N(c4cccc(-c5ccc(-c6ccccc6)cc5)c4)c4cccc5c4C4(c6ccccc6-5)C5CC6CC(C5)CC4C6)cc32)c2ccc(-c3ccccc3)cc21]
Compound B-1
2.9/70   962.5
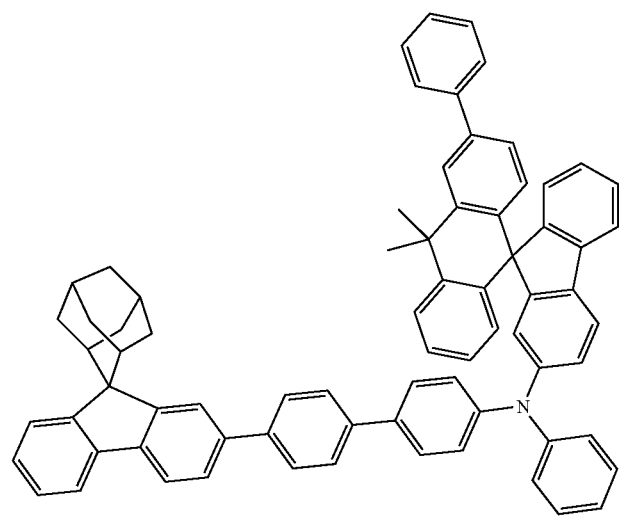 [SMILES: CC1(C)c2ccccc2C2(c3ccccc3-c3ccc(N(c4ccccc4)c4ccc(-c5ccc(-c6ccc7c(c6)C6(c8ccccc8-7)C7CC8CC(C7)CC6C8)cc5)cc4)cc32)c2ccc(-c3ccccc3)cc21]
Compound B-2
2.9/70   962.4
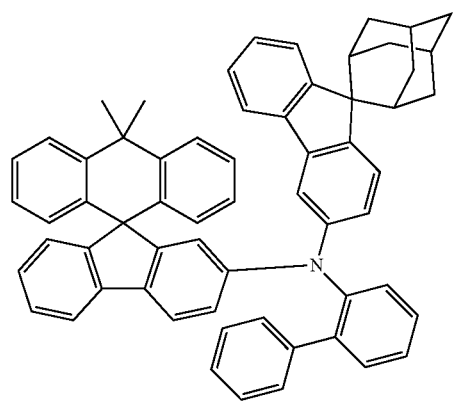 [SMILES: CC1(C)c2ccccc2C2(c3ccccc3-c3ccc(N(c4ccc5c(c4)-c4ccccc4C54C5CC6CC(C5)CC4C6)c4ccccc4-c4ccccc4)cc32)c2ccccc21]
Compound B-3
2.8/70   810.4

TABLE 11-continued
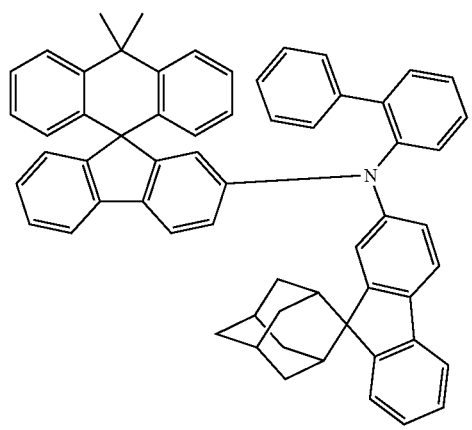 [SMILES: CC1(C)c2ccccc2C2(c3ccccc3-c3ccc(N(c4ccc5c(c4)C4(c6ccccc6-5)C5CC6CC(C5)CC4C6)c4ccccc4-c4ccccc4)cc32)c2ccccc21]
Compound B-4
2.9/71   810.4
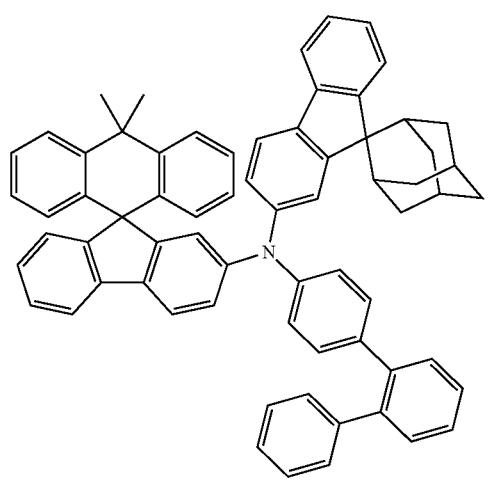 [SMILES: CC1(C)c2ccccc2C2(c3ccccc3-c3ccc(N(c4ccc(-c5ccccc5-c5ccccc5)cc4)c4ccc5c(c4)C4(c6ccccc6-5)C5CC6CC(C5)CC4C6)cc32)c2ccccc21]
Compound B-5
3.2/70   886.4
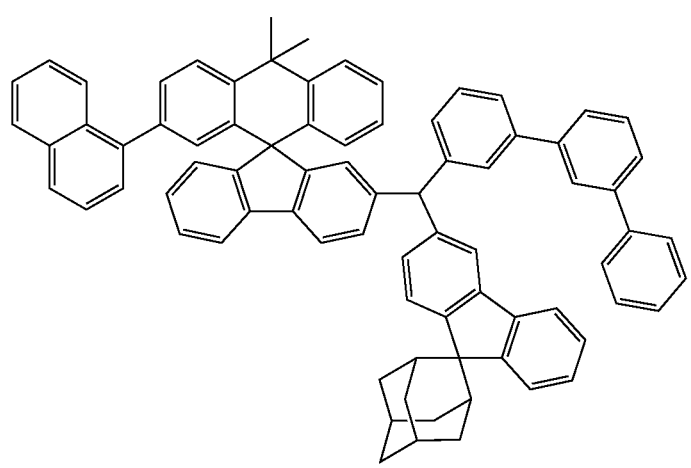 [SMILES: CC1(C)c2ccccc2C2(c3ccccc3-c3ccc(C(c4cccc(-c5cccc(-c6ccccc6)c5)c4)c4ccc5c(c4)-c4ccccc4C54C5CC6CC(C5)CC4C6)cc32)c2cc(-c3cccc4ccccc34)ccc21]
Compound B-6
2.7/70   1012.5

TABLE 11-continued
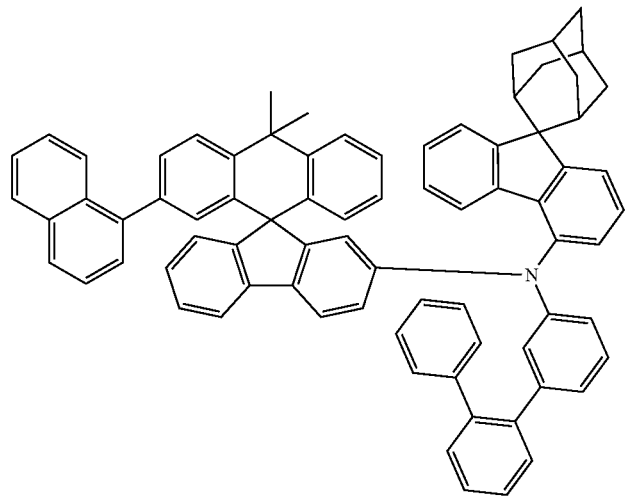 [SMILES: CC1(C)c2ccccc2C2(c3ccccc3-c3ccc(N(c4cccc(-c5ccccc5-c5ccccc5)c4)c4cccc5c4-c4ccccc4C54C5CC6CC(C5)CC4C6)cc32)c2cc(-c3cccc4ccccc34)ccc21]
Compound B-7
2.8/71  1012.5
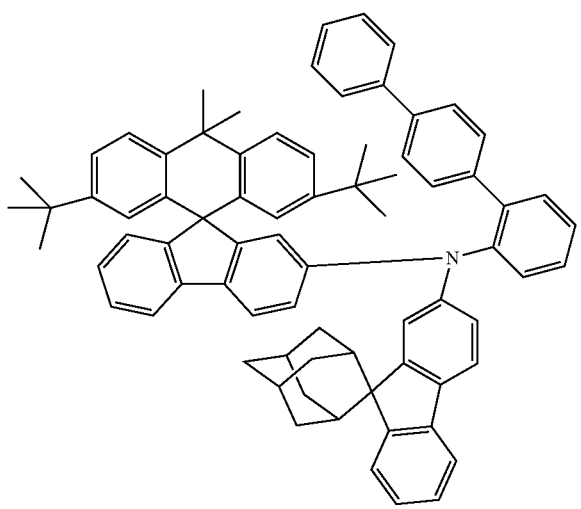 [SMILES: CC(C)(C)c1ccc2c(c1)C1(c3ccccc3-c3ccc(N(c4ccc5c(c4)C4(c6ccccc6-5)C5CC6CC(C5)CC4C6)c4ccccc4-c4ccc(-c5ccccc5)cc4)cc31)c1cc(C(C)(C)C)ccc1C2(C)C]
Compound B-8
2.7/70  998.6
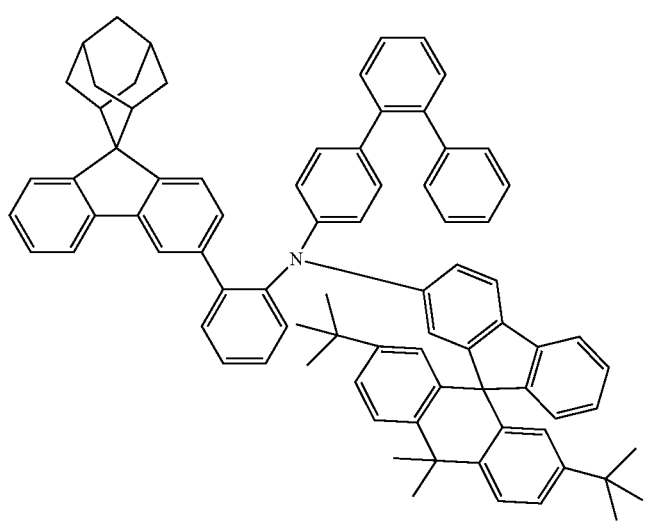 [SMILES: CC(C)(C)c1ccc2c(c1)C1(c3ccccc3-c3ccc(N(c4ccc(-c5ccccc5-c5ccccc5)cc4)c4ccccc4-c4ccc5c(c4)-c4ccccc4C54C5CC6CC(C5)CC4C6)cc31)c1cc(C(C)(C)C)ccc1C2(C)C]
Compound B-9
2.8/71  1074.6

TABLE 11-continued
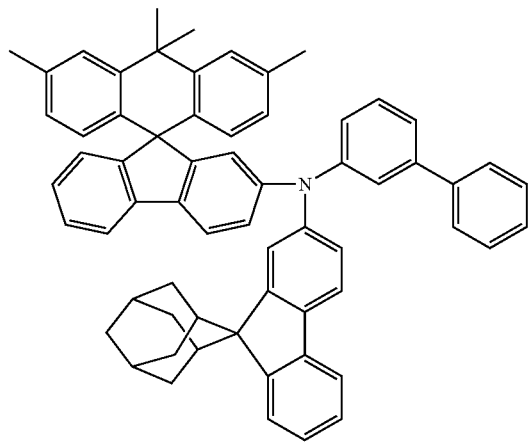 [SMILES: Cc1ccc2c(c1)C(C)(C)c1cc(C)ccc1C21c2ccccc2-c2ccc(N(c3cccc(-c4ccccc4)c3)c3ccc4c(c3)C3(c5ccccc5-4)C4CC5CC(C4)CC3C5)cc21]
Compound B-10
2.3/70  838.4
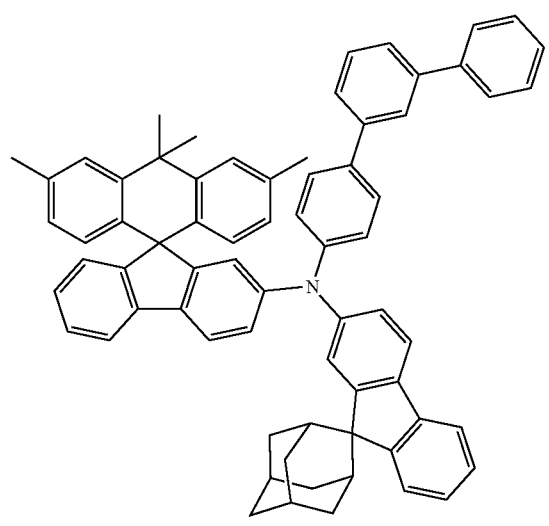 [SMILES: Cc1ccc2c(c1)C(C)(C)c1cc(C)ccc1C21c2ccccc2-c2ccc(N(c3ccc(-c4cccc(-c5ccccc5)c4)cc3)c3ccc4c(c3)C3(c5ccccc5-4)C4CC5CC(C4)CC3C5)cc21]
Compound B-11
2.5/70  914.5
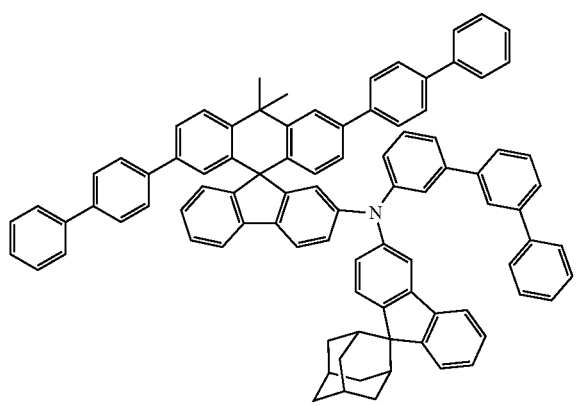 [SMILES: CC1(C)c2cc(-c3ccc(-c4ccccc4)cc3)ccc2C2(c3ccccc3-c3ccc(N(c4cccc(-c5cccc(-c6ccccc6)c5)c4)c4ccc5c(c4)-c4ccccc4C54C5CC6CC(C5)CC4C6)cc32)c2cc(-c3ccc(-c4ccccc4)cc3)ccc21]
Compound B-12
2.4/70  1190.5

TABLE 11-continued
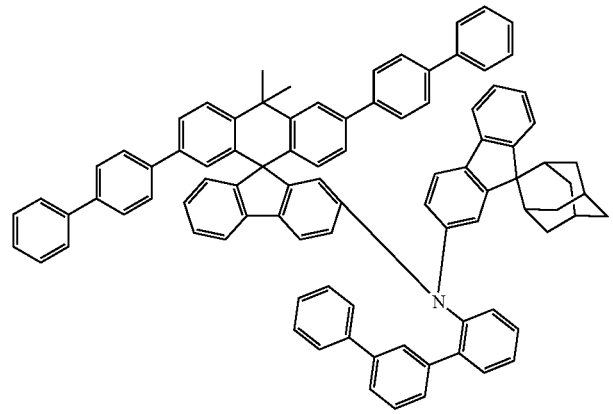 [SMILES: CC1(C)c2cc(-c3ccc(-c4ccccc4)cc3)ccc2C2(c3ccccc3-c3ccc(N(c4ccc5c(c4)C4(c6ccccc6-5)C5CC6CC(C5)CC4C6)c4ccccc4-c4cccc(-c5ccccc5)c4)cc32)c2cc(-c3ccc(-c4ccccc4)cc3)ccc21]
Compound B-13
2.4/70  1190.5
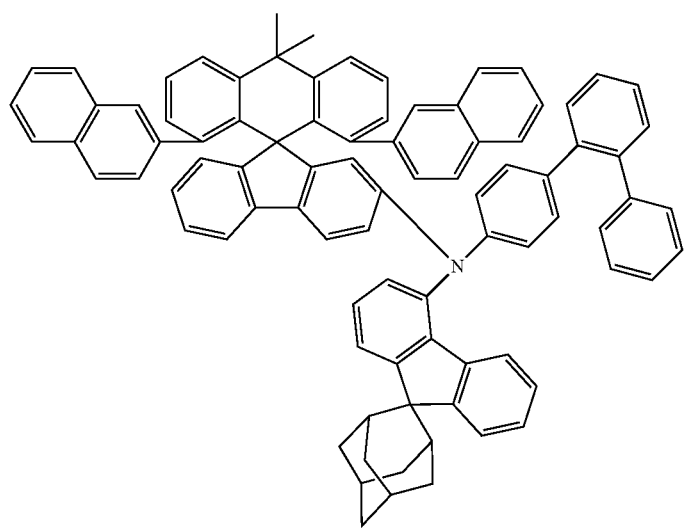 [SMILES: CC1(C)c2cccc(-c3ccc4ccccc4c3)c2C2(c3ccccc3-c3ccc(N(c4ccc(-c5ccccc5-c5ccccc5)cc4)c4cccc5c4-c4ccccc4C54C5CC6CC(C5)CC4C6)cc32)c2c(-c3ccc4ccccc4c3)cccc21]
Compound B-14
2.5/70  1138.5
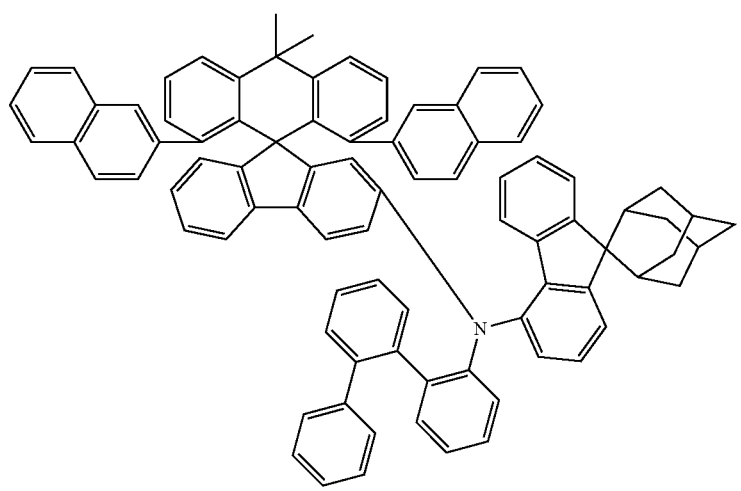 [SMILES: CC1(C)c2cccc(-c3ccc4ccccc4c3)c2C2(c3ccccc3-c3ccc(N(c4ccccc4-c4ccccc4-c4ccccc4)c4cccc5c4-c4ccccc4C54C5CC6CC(C5)CC4C6)cc32)c2c(-c3ccc4ccccc4c3)cccc21]
Compound B-15
2.4/69  1138.5

TABLE 11-continued
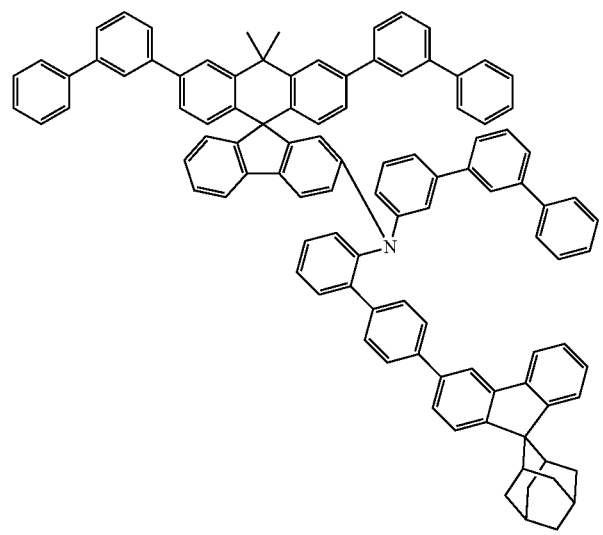 [SMILES: CC1(C)c2cc(-c3cccc(-c4ccccc4)c3)ccc2C2(c3ccccc3-c3ccc(N(c4cccc(-c5cccc(-c6ccccc6)c5)c4)c4ccccc4-c4ccc(-c5ccc6c(c5)-c5ccccc5C65C6CC7CC(C6)CC5C7)cc4)cc32)c2ccc(-c3cccc(-c4ccccc4)c3)cc21]
Compound B-16
2.6/70 1343.3
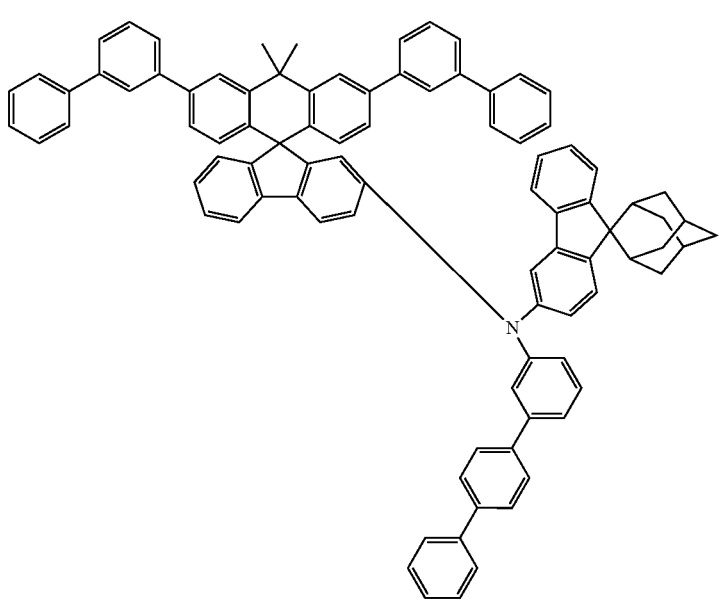 [SMILES: CC1(C)c2cc(-c3cccc(-c4ccccc4)c3)ccc2C2(c3ccccc3-c3ccc(N(c4cccc(-c5ccc(-c6ccccc6)cc5)c4)c4ccc5c(c4)-c4ccccc4C54C5CC6CC(C5)CC4C6)cc32)c2ccc(-c3cccc(-c4ccccc4)c3)cc21]
Compound B-17
2.5/74 1189.5
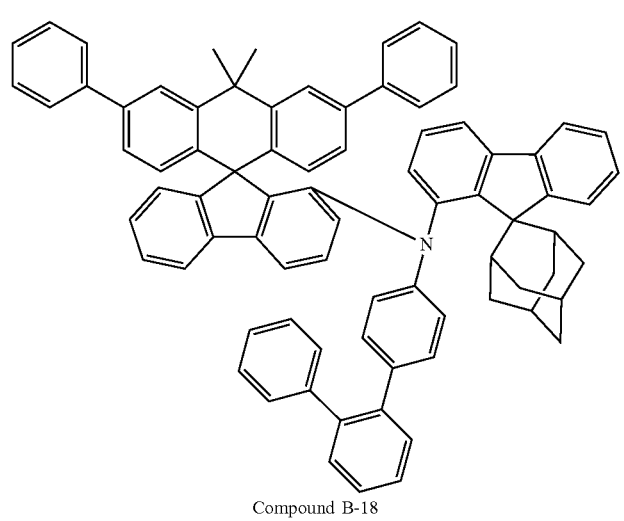
Compound B-18
2.6/70 1038.5

TABLE 11-continued
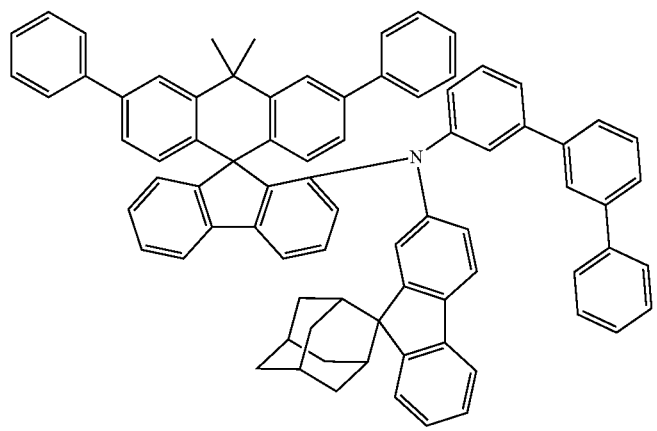 [SMILES: CC1(C)c2cc(-c3ccccc3)ccc2C2(c3ccccc3-c3cccc(N(c4cccc(-c5cccc(-c6ccccc6)c5)c4)c4ccc5c(c4)C4(c6ccccc6-5)C5CC6CC(C5)CC4C6)c32)c2ccc(-c3ccccc3)cc21]
Compound B-19
2.7/72  1038.5
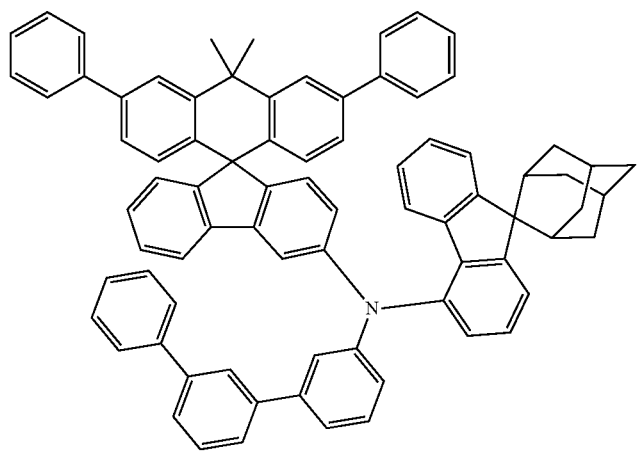 [SMILES: CC1(C)c2cc(-c3ccccc3)ccc2C2(c3ccccc3-c3cc(N(c4cccc(-c5cccc(-c6ccccc6)c5)c4)c4cccc5c4-c4ccccc4C54C5CC6CC(C5)CC4C6)ccc32)c2ccc(-c3ccccc3)cc21]
Compound B-20
2.6/70  1038.5
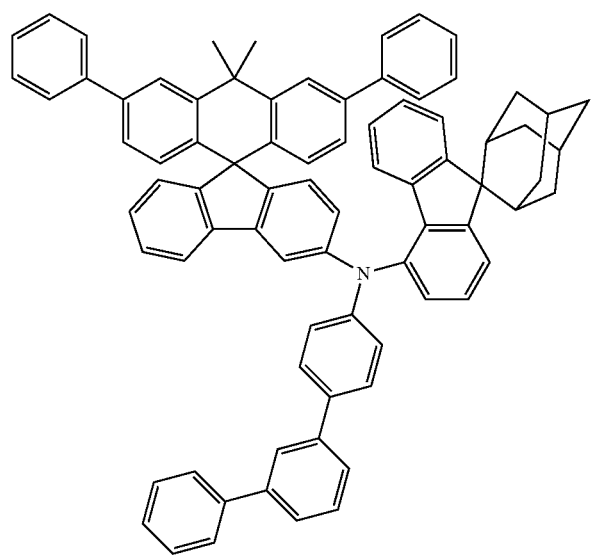 [SMILES: CC1(C)c2cc(-c3ccccc3)ccc2C2(c3ccccc3-c3cc(N(c4ccc(-c5cccc(-c6ccccc6)c5)cc4)c4cccc5c4-c4ccccc4C54C5CC6CC(C5)CC4C6)ccc32)c2ccc(-c3ccccc3)cc21]
Compound B-21
2.7/72  1038.5

TABLE 11-continued
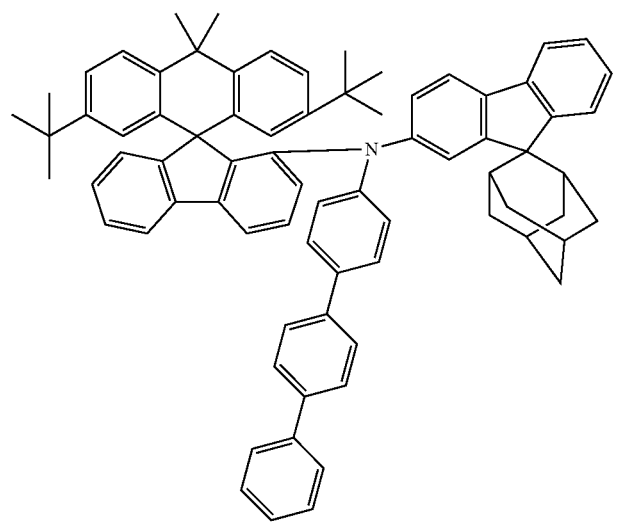 [SMILES: CC(C)(C)c1ccc2c(c1)C1(c3ccccc3-c3cccc(N(c4ccc(-c5ccc(-c6ccccc6)cc5)cc4)c4ccc5c(c4)C4(c6ccccc6-5)C5CC6CC(C5)CC4C6)c31)c1cc(C(C)(C)C)ccc1C2(C)C]
Compound B-22
2.7/70  998.6
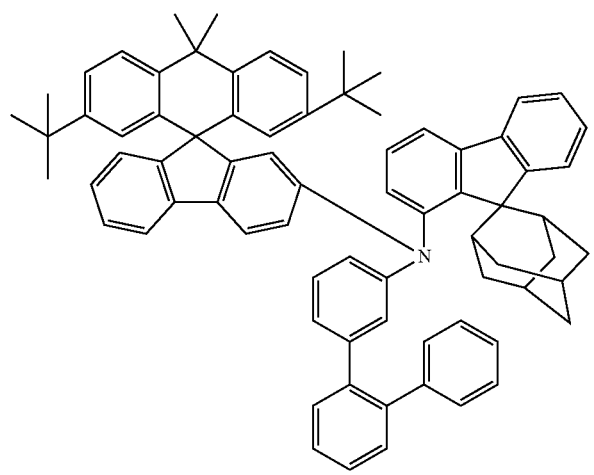 [SMILES: CC(C)(C)c1ccc2c(c1)C1(c3ccccc3-c3ccc(N(c4cccc(-c5ccccc5-c5ccccc5)c4)c4cccc5c4C4(c6ccccc6-5)C5CC6CC(C5)CC4C6)cc31)c1cc(C(C)(C)C)ccc1C2(C)C]
Compound B-23
2.8/71  998.6
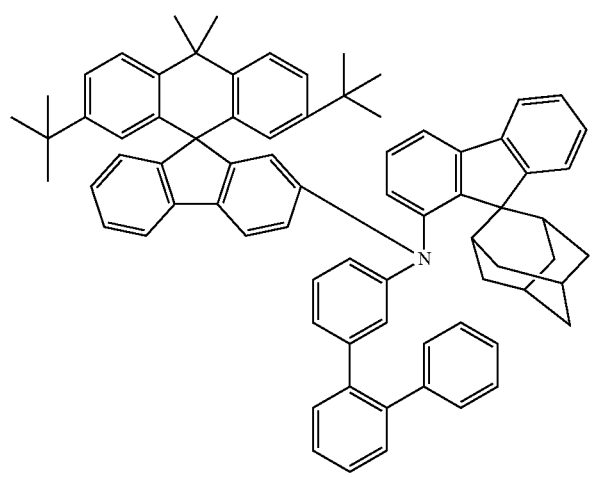 [SMILES: CC(C)(C)c1ccc2c(c1)C1(c3ccccc3-c3ccc(N(c4cccc(-c5ccccc5-c5ccccc5)c4)c4cccc5c4C4(c6ccccc6-5)C5CC6CC(C5)CC4C6)cc31)c1cc(C(C)(C)C)ccc1C2(C)C]
Compound B-24
2.7/70  998.6

TABLE 11-continued
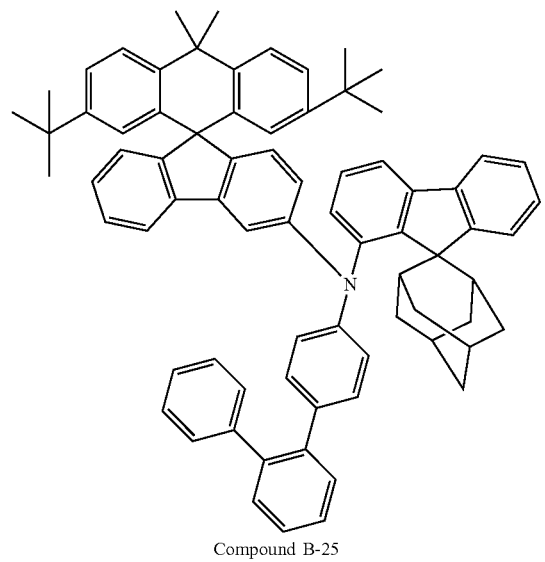
Compound B-25
2.8/71   998.6
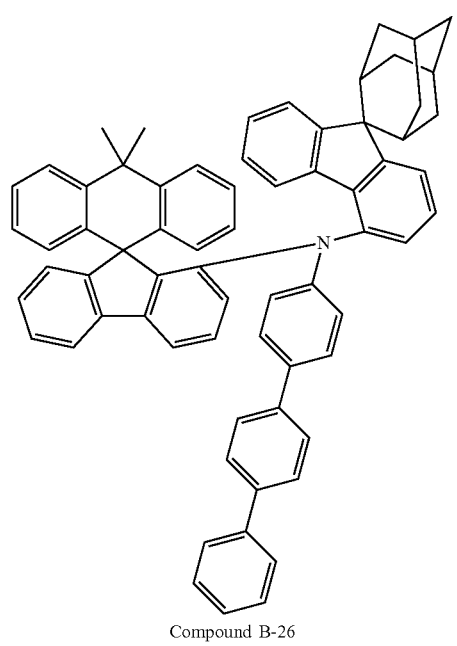
Compound B-26
3.1/70   886.4
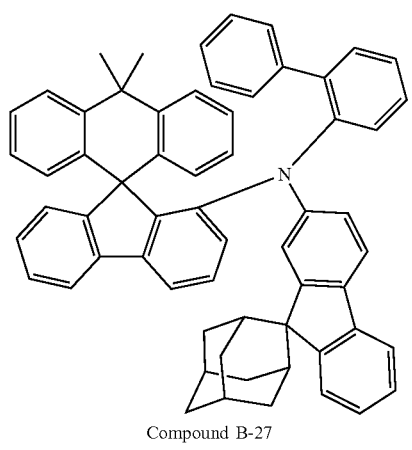
Compound B-27
2.9/71   810.4

TABLE 11-continued
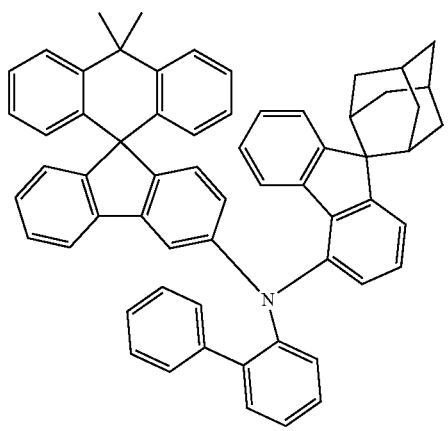 [SMILES: CC1(C)c2ccccc2C2(c3ccccc3-c3cc(N(c4ccccc4-c4ccccc4)c4cccc5c4-c4ccccc4C54C5CC6CC(C5)CC4C6)ccc32)c2ccccc21]
Compound B-28
2.8/70  810.4
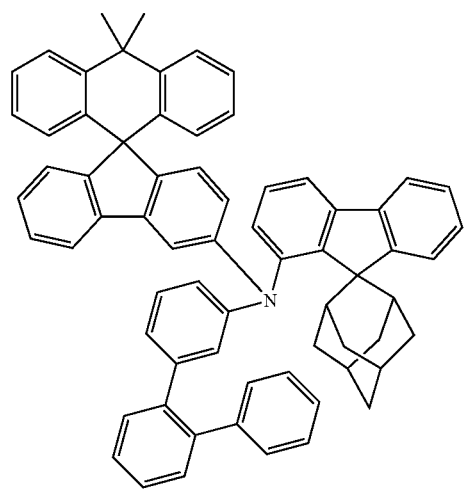 [SMILES: CC1(C)c2ccccc2C2(c3ccccc3-c3cc(N(c4cccc(-c5ccccc5-c5ccccc5)c4)c4cccc5c4C4(c6ccccc6-5)C5CC6CC(C5)CC4C6)ccc32)c2ccccc21]
Compound B-29
3.1/70  886.4
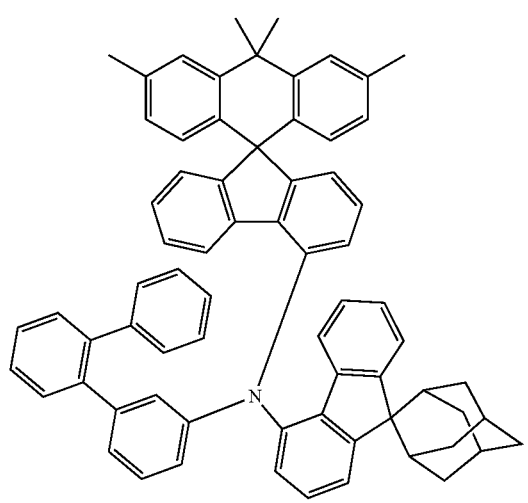 [SMILES: Cc1ccc2c(c1)C(C)(C)c1cc(C)ccc1C21c2ccccc2-c2c(N(c3cccc(-c4ccccc4-c4ccccc4)c3)c3cccc4c3-c3ccccc3C43C4CC5CC(C4)CC3C5)cccc21]
Compound B-30
3.0/70  914.5

TABLE 11-continued
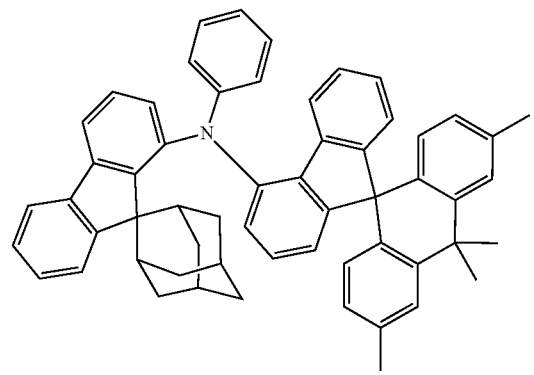 [SMILES: Cc1ccc2c(c1)C(C)(C)c1cc(C)ccc1C21c2ccccc2-c2c(N(c3ccccc3)c3cccc4c3C3(c5ccccc5-4)C4CC5CC(C4)CC3C5)cccc21]
Compound B-31
2.6/72  762.4
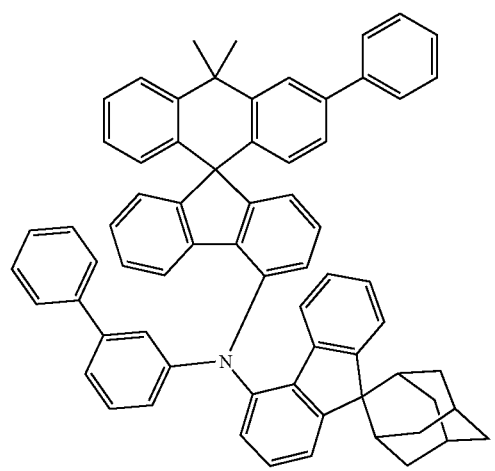 [SMILES: CC1(C)c2ccccc2C2(c3ccccc3-c3c(N(c4cccc(-c5ccccc5)c4)c4cccc5c4-c4ccccc4C54C5CC6CC(C5)CC4C6)cccc32)c2ccc(-c3ccccc3)cc21]
Compound B-32
2.6/71  886.4
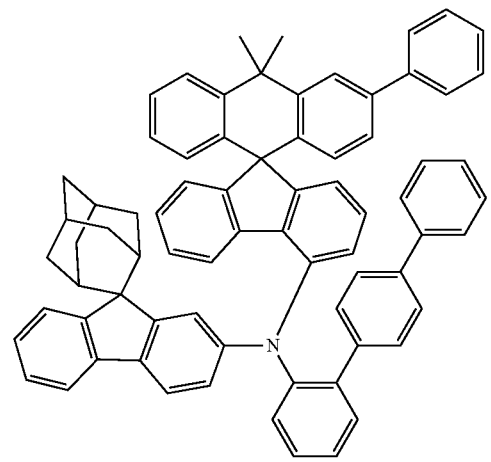 [SMILES: CC1(C)c2ccccc2C2(c3ccccc3-c3c(N(c4ccc5c(c4)C4(c6ccccc6-5)C5CC6CC(C5)CC4C6)c4ccccc4-c4ccc(-c5ccccc5)cc4)cccc32)c2ccc(-c3ccccc3)cc21]
Compound B-33
2.8/70  962.4

TABLE 11-continued
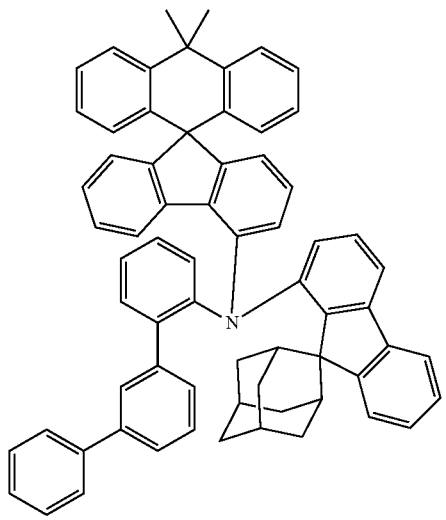 [SMILES: CC1(C)c2ccccc2C2(c3ccccc3-c3c(N(c4ccccc4-c4cccc(-c5ccccc5)c4)c4cccc5c4C4(c6ccccc6-5)C5CC6CC(C5)CC4C6)cccc32)c2ccccc21]
Compound B-34
3.1/70　886.4
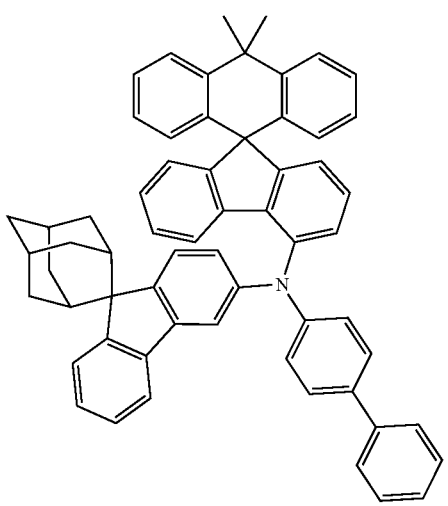 [SMILES: CC1(C)c2ccccc2C2(c3ccccc3-c3c(N(c4ccc(-c5ccccc5)cc4)c4ccc5c(c4)-c4ccccc4C54C5CC6CC(C5)CC4C6)cccc32)c2ccccc21]
Compound B-35
2.8/70　810.4
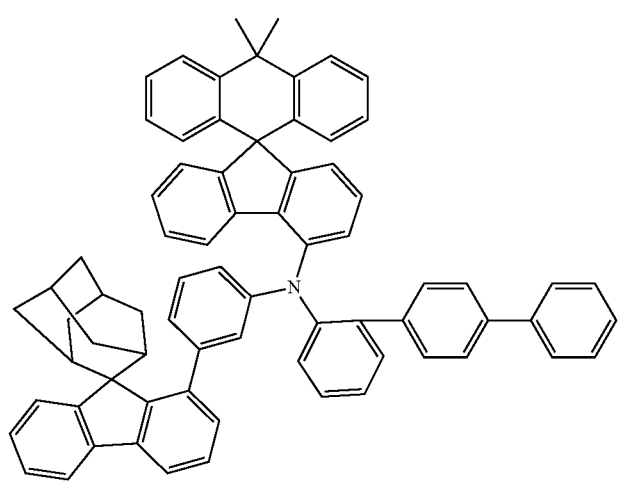 [SMILES: CC1(C)c2ccccc2C2(c3ccccc3-c3c(N(c4cccc(-c5cccc6c5C5(c7ccccc7-6)C6CC7CC(C6)CC5C7)c4)c4ccccc4-c4ccc(-c5ccccc5)cc4)cccc32)c2ccccc21]
Compound B-36
3.4/70　962.4

TABLE 11-continued
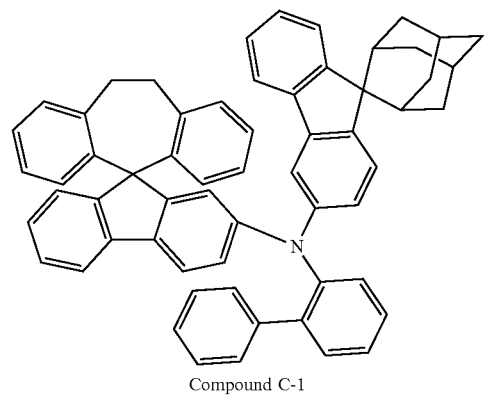
Compound C-1
2.9/70  796.4
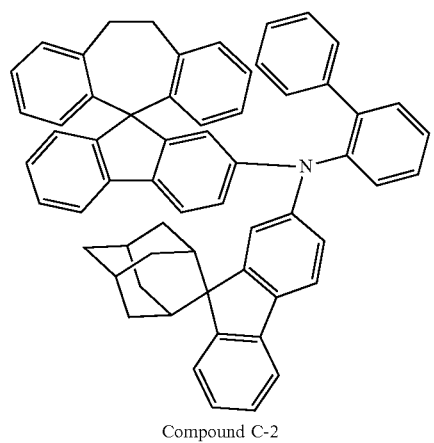
Compound C-2
2.9/70  796.4
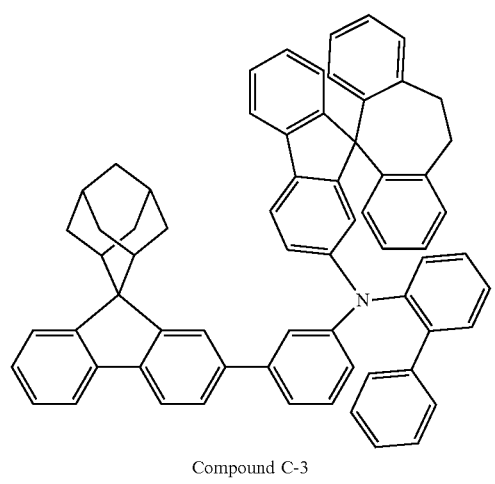
Compound C-3
3.2/70  872.4

TABLE 11-continued
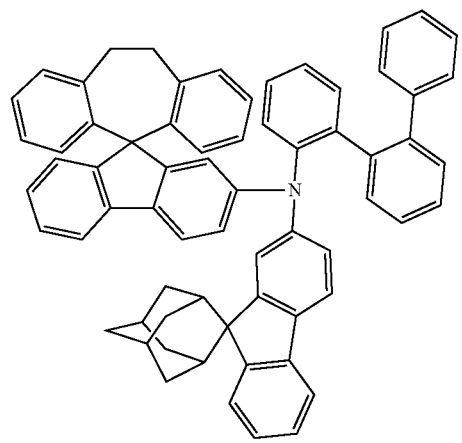 [SMILES: c1ccc(-c2ccccc2-c2ccccc2N(c2ccc3c(c2)C2(c4ccccc4CCc4ccccc42)c2ccccc2-3)c2ccc3c(c2)C2(c4ccccc4-3)C3CC4CC(C3)CC2C4)cc1]
Compound C-4
3.2/70  872.4
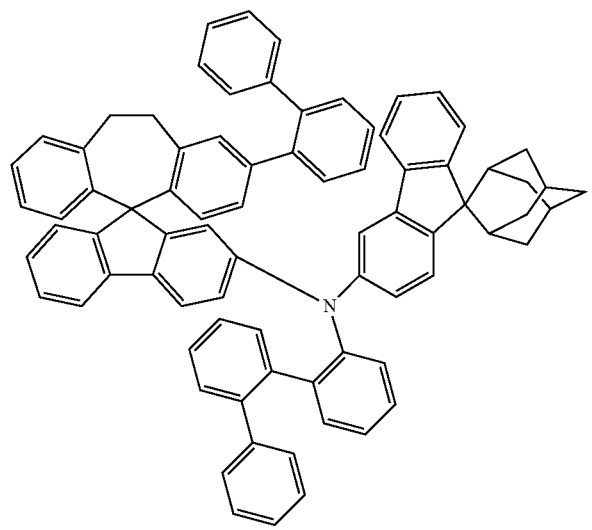 [SMILES: c1ccc(-c2ccccc2-c2ccc3c(c2)CCc2ccccc2C32c3ccccc3-c3ccc(N(c4ccc5c(c4)-c4ccccc4C54C5CC6CC(C5)CC4C6)c4ccccc4-c4ccccc4-c4ccccc4)cc32)cc1]
Compound C-5
2.7/70  1024.4
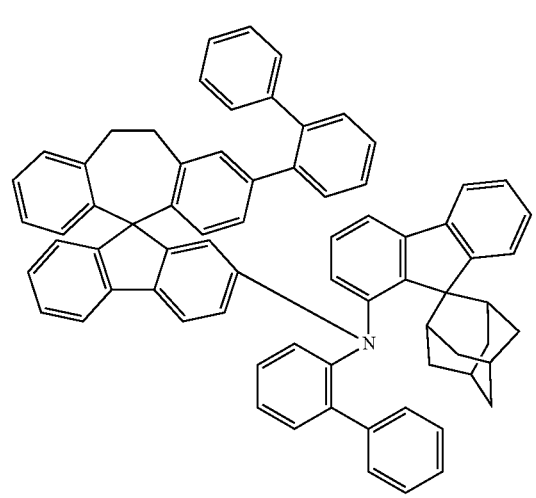 [SMILES: c1ccc(-c2ccccc2-c2ccc3c(c2)CCc2ccccc2C32c3ccccc3-c3ccc(N(c4ccccc4-c4ccccc4)c4cccc5c4C4(c6ccccc6-5)C5CC6CC(C5)CC4C6)cc32)cc1]
Compound C-6
2.4/70  948.4

TABLE 11-continued
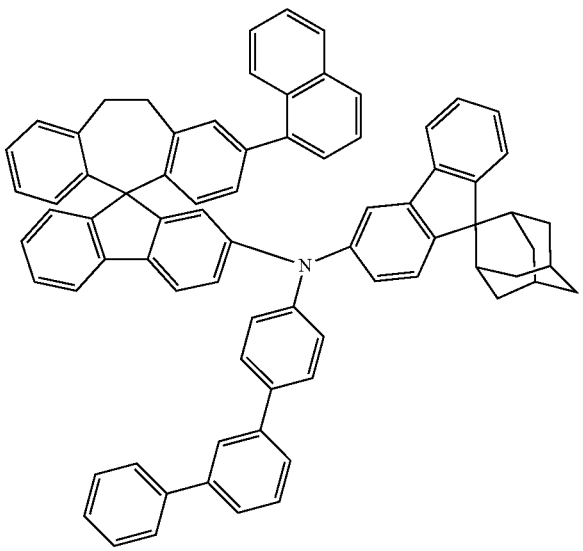 [SMILES: c1ccc(-c2cccc(-c3ccc(N(c4ccc5c(c4)-c4ccccc4C54C5CC6CC(C5)CC4C6)c4ccc5c(c4)C4(c6ccccc6CCc6cc(-c7cccc8ccccc78)ccc64)c4ccccc4-5)cc3)c2)cc1]
Compound C-7
2.8/71 998.4
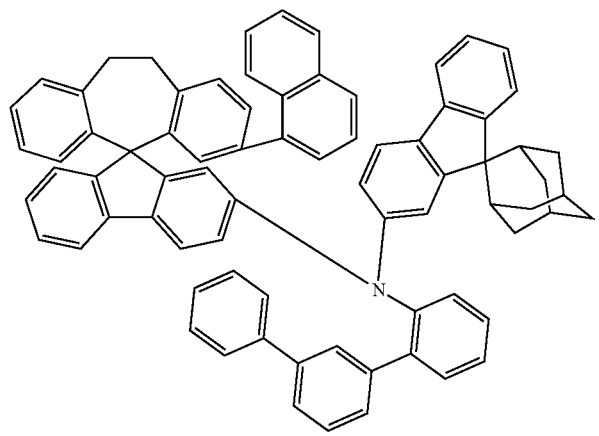 [SMILES: c1ccc(-c2cccc(-c3ccccc3N(c3ccc4c(c3)C3(c5ccccc5CCc5ccc(-c6cccc7ccccc67)cc53)c3ccccc3-4)c3ccc4c(c3)C3(c5ccccc5-4)C4CC5CC(C4)CC3C5)c2)cc1]
Compound C-8
2.7/70 998.4
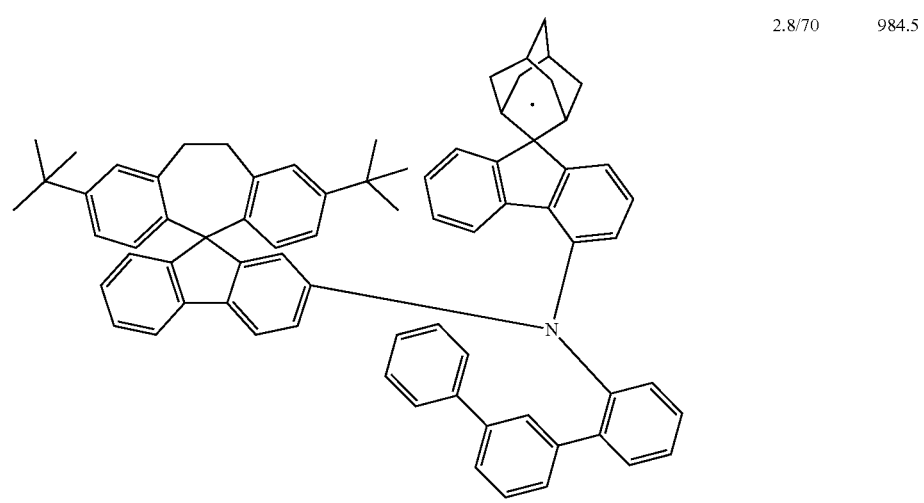
Compound C-9
2.8/70 984.5

TABLE 11-continued
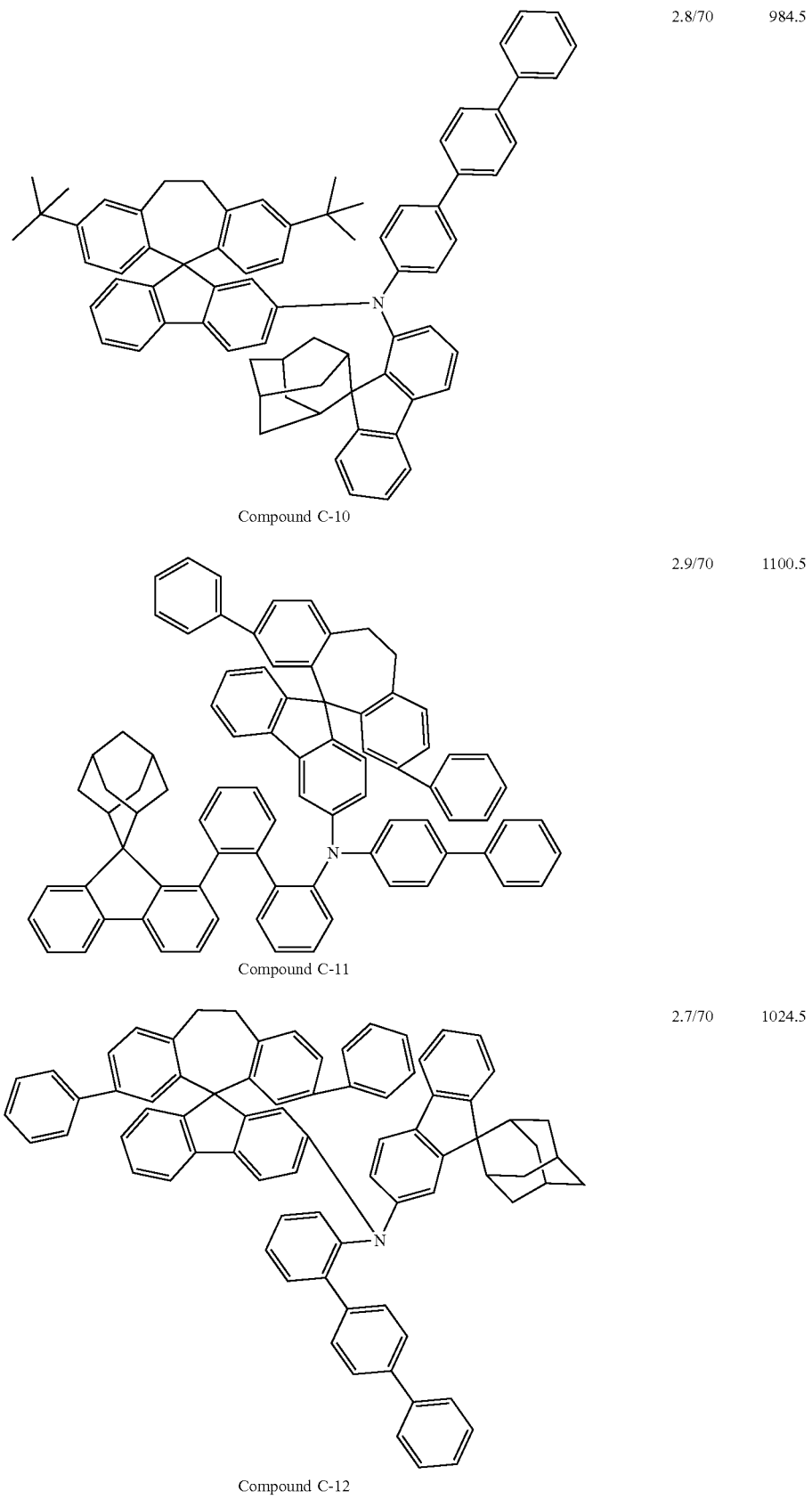
Compound C-10    2.8/70    984.5
Compound C-11    2.9/70    1100.5
Compound C-12    2.7/70    1024.5

TABLE 11-continued
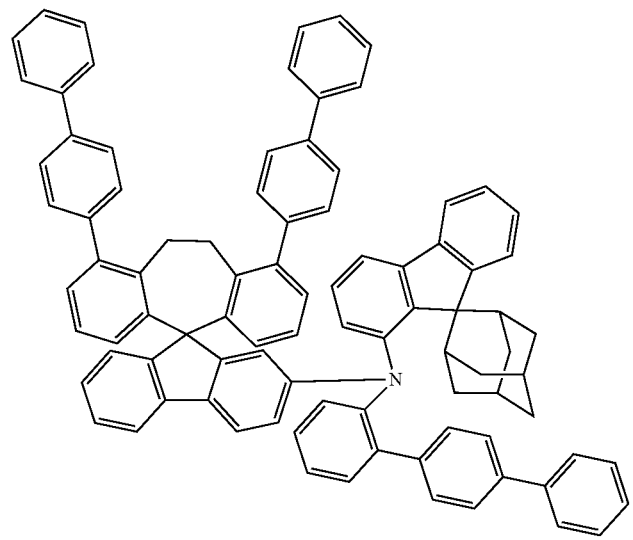 [SMILES: c1ccc(-c2ccc(-c3ccccc3N(c3ccc4c(c3)C3(c5ccccc5-4)c4cccc(-c5ccc(-c6ccccc6)cc5)c4CCc4c(-c5ccc(-c6ccccc6)cc5)cccc43)c3cccc4c3C3(c5ccccc5-4)C4CC5CC(C4)CC3C5)cc2)cc1]
Compound C-13
2.4/70  1176.5
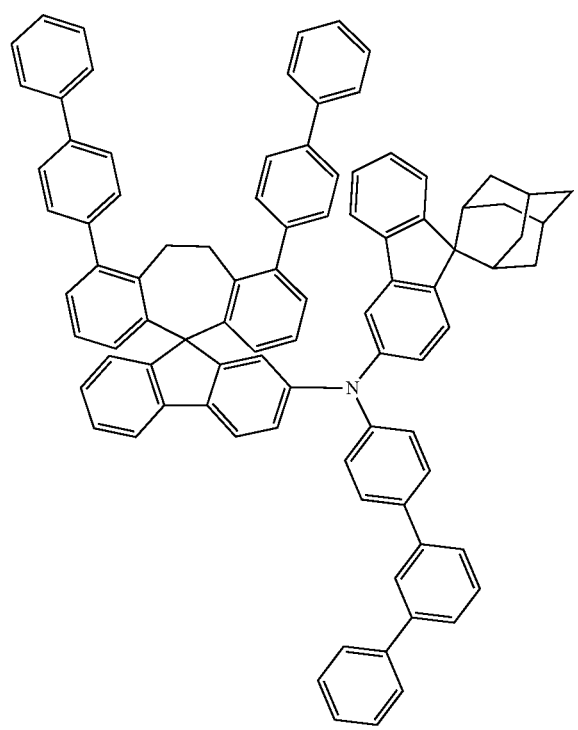 [SMILES: c1ccc(-c2ccc(-c3cccc4c3CCc3c(-c5ccc(-c6ccccc6)cc5)cccc3C43c4ccccc4-c4ccc(N(c5ccc(-c6cccc(-c7ccccc7)c6)cc5)c5ccc6c(c5)-c5ccccc5C65C6CC7CC(C6)CC5C7)cc43)cc2)cc1]
Compound C-14
2.5/73  1176.5

TABLE 11-continued
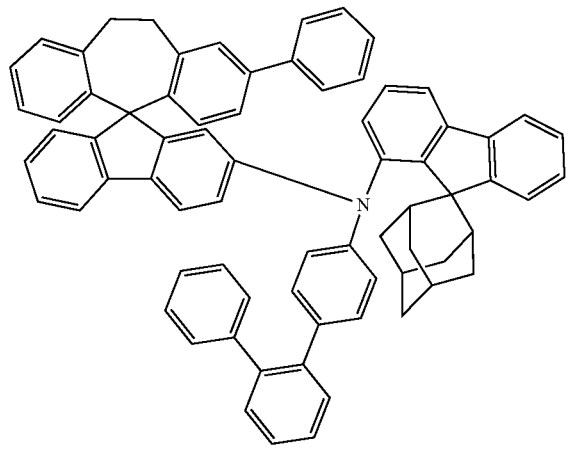 [SMILES: c1ccc(-c2ccc3c(c2)CCc2ccccc2C32c3ccccc3-c3ccc(N(c4ccc(-c5ccccc5-c5ccccc5)cc4)c4cccc5c4C4(c6ccccc6-5)C5CC6CC(C5)CC4C6)cc32)cc1]
Compound C-15
2.9/70　　948.5
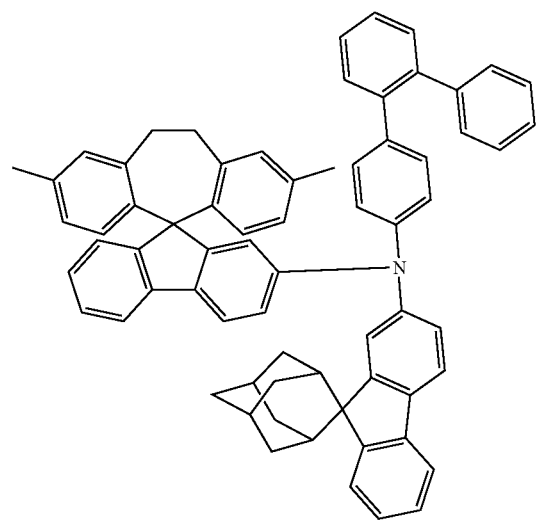 [SMILES: Cc1ccc2c(c1)CCc1cc(C)ccc1C21c2ccccc2-c2ccc(N(c3ccc(-c4ccccc4-c4ccccc4)cc3)c3ccc4c(c3)C3(c5ccccc5-4)C4CC5CC(C4)CC3C5)cc21]
Compound C-16
3.2/73　　900.4
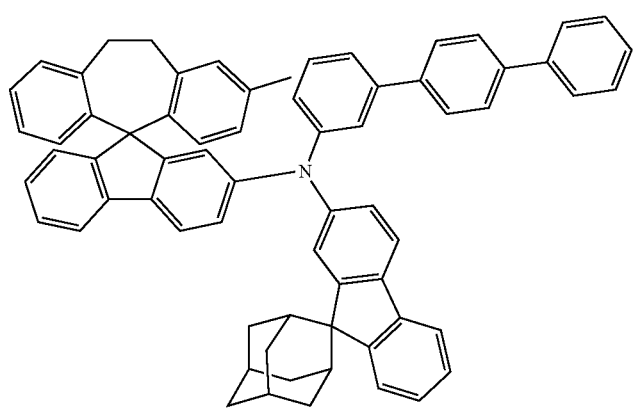 [SMILES: Cc1ccc2c(c1)CCc1ccccc1C21c2ccccc2-c2ccc(N(c3cccc(-c4ccc(-c5ccccc5)cc4)c3)c3ccc4c(c3)C3(c5ccccc5-4)C4CC5CC(C4)CC3C5)cc21]
Compound C-17
3.1/70　　886.4

TABLE 11-continued
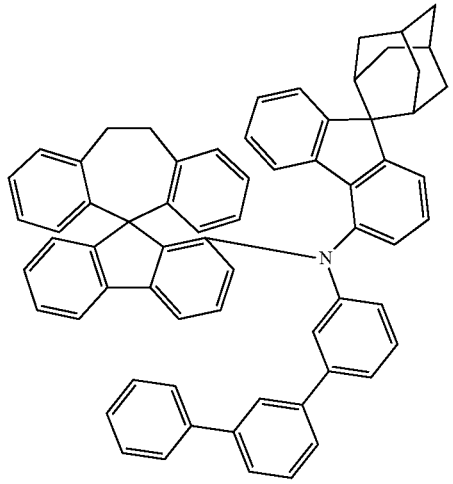 [SMILES: c1ccc(-c2cccc(-c3cccc(N(c4cccc5c4-c4ccccc4C54C5CC6CC(C5)CC4C6)c4cccc5c4C4(c6ccccc6CCc6ccccc64)c4ccccc4-5)c3)c2)cc1]
Compound C-18
3.2/71   872.4
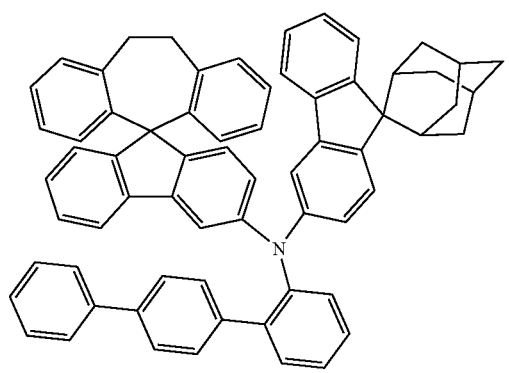 [SMILES: c1ccc(-c2ccc(-c3ccccc3N(c3ccc4c(c3)-c3ccccc3C43c4ccccc4CCc4ccccc43)c3ccc4c(c3)-c3ccccc3C43C4CC5CC(C4)CC3C5)cc2)cc1]
Compound C-19
3.2/71   872.4
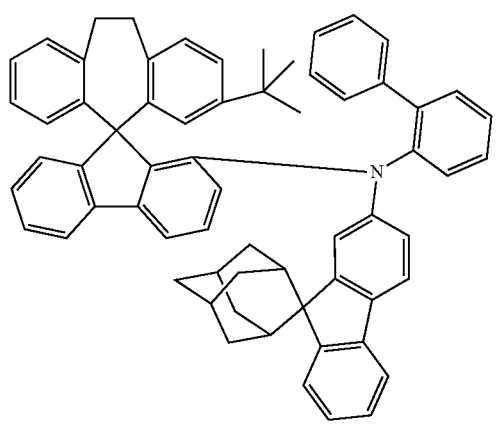 [SMILES: CC(C)(C)c1ccc2c(c1)C1(c3ccccc3CC2)c2ccccc2-c2cccc(N(c3ccc4c(c3)C3(c5ccccc5-4)C4CC5CC(C4)CC3C5)c3ccccc3-c3ccccc3)c21]
Compound C-20
2.7/70   852.5

TABLE 11-continued
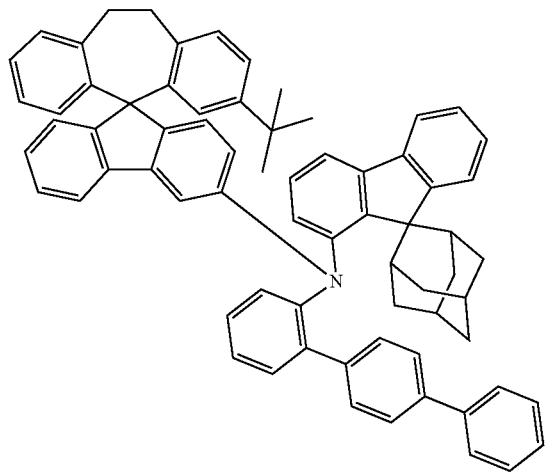 [SMILES: CC(C)(C)c1ccc2c(c1)C1(c3ccccc3CC2)c2ccccc2-c2cc(N(c3ccccc3-c3ccc(-c4ccccc4)cc3)c3cccc4c3C3(c5ccccc5-4)C4CC5CC(C4)CC3C5)ccc21]
Compound C-21
3.0/71  928.5
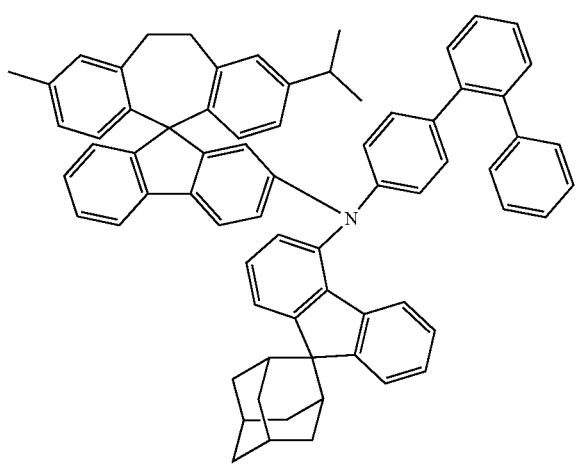 [SMILES: Cc1ccc2c(c1)CCc1cc(C(C)C)ccc1C21c2ccccc2-c2ccc(N(c3ccc(-c4ccccc4-c4ccccc4)cc3)c3cccc4c3-c3ccccc3C43C4CC5CC(C4)CC3C5)cc21]
Compound C-22
2.9/70  928.5
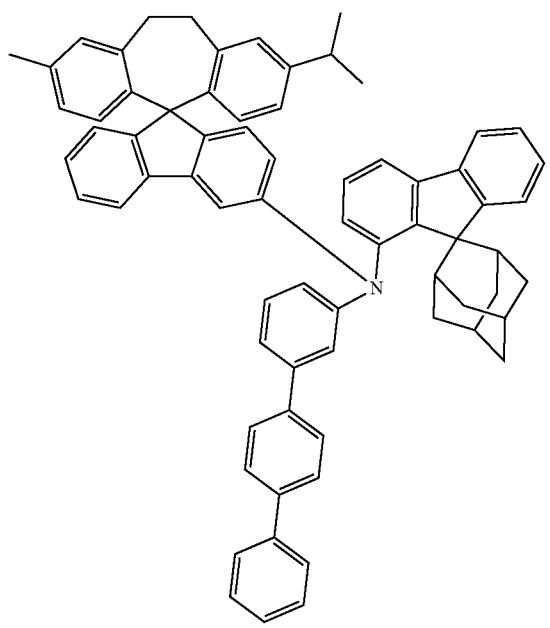 [SMILES: Cc1ccc2c(c1)CCc1cc(C(C)C)ccc1C21c2ccccc2-c2cc(N(c3cccc(-c4ccc(-c5ccccc5)cc4)c3)c3cccc4c3C3(c5ccccc5-4)C4CC5CC(C4)CC3C5)ccc21]
Compound C-23
3.0/71  928.5

TABLE 11-continued
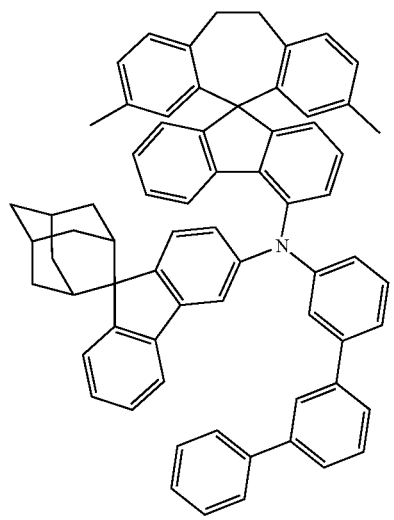 [SMILES: Cc1ccc2c(c1)C1(c3cc(C)ccc3CC2)c2ccccc2-c2c(N(c3cccc(-c4cccc(-c5ccccc5)c4)c3)c3ccc4c(c3)-c3ccccc3C43C4CC5CC(C4)CC3C5)cccc21]
Compound C-24
3.0/70  900.5
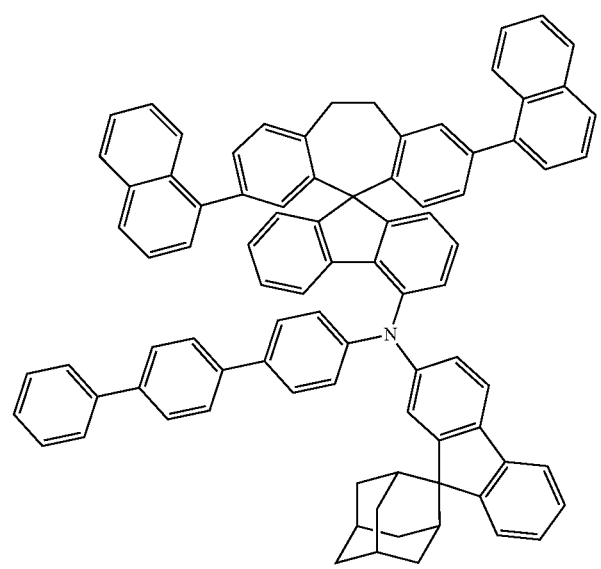 [SMILES: c1ccc(-c2ccc(-c3ccc(N(c4ccc5c(c4)C4(c6ccccc6-5)C5CC6CC(C5)CC4C6)c4cccc5c4-c4ccccc4C54c5ccc(-c6cccc7ccccc67)cc5CCc5ccc(-c6cccc7ccccc67)cc54)cc3)cc2)cc1]
Compound C-25
2.5/70  1124.5

TABLE 11-continued
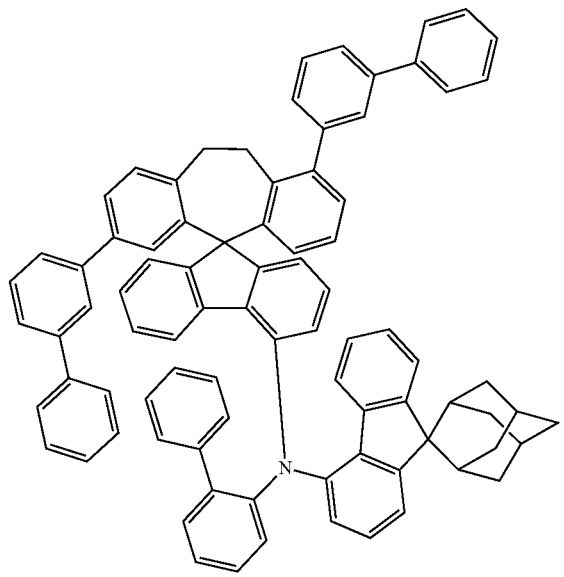 [SMILES: c1ccc(-c2cccc(-c3ccc4c(c3)C3(c5ccccc5-c5c(N(c6ccccc6-c6ccccc6)c6cccc7c6-c6ccccc6C76C7CC8CC(C7)CC6C8)cccc53)c3cccc(-c5cccc(-c6ccccc6)c5)c3CC4)c2)cc1]
Compound C-26
2.3/70　　1100.5
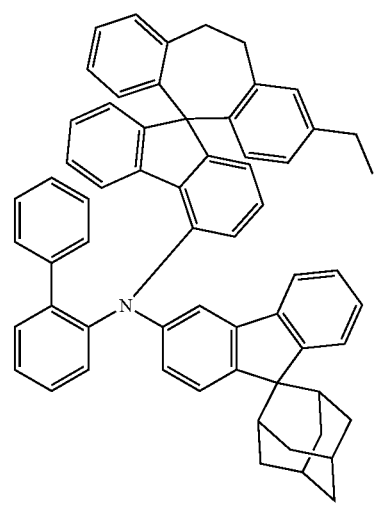 [SMILES: CCc1ccc2c(c1)CCc1ccccc1C21c2ccccc2-c2c(N(c3ccc4c(c3)-c3ccccc3C43C4CC5CC(C4)CC3C5)c3ccccc3-c3ccccc3)cccc21]
Compound C-27
2.8/70　　824.4
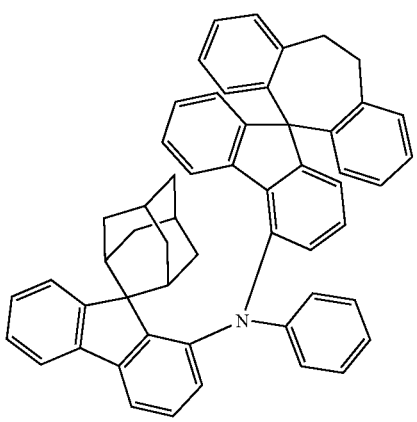 [SMILES: c1ccc(N(c2cccc3c2-c2ccccc2C32c3ccccc3CCc3ccccc32)c2cccc3c2C2(c4ccccc4-3)C3CC4CC(C3)CC2C4)cc1]
Compound C-28
2.6/70　　720.4

TABLE 11-continued

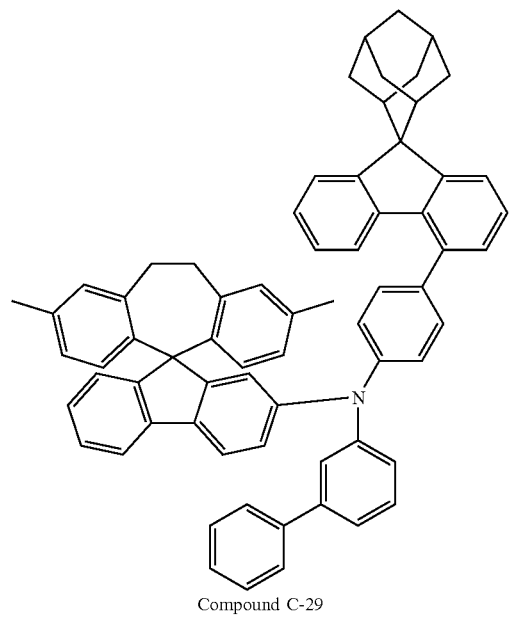

Compound C-29

3.0/70    900.4

The NMR data of some compounds are shown in Table 12 below

TABLE 12

| Compound | NMR data |
|---|---|
| Compound A-2 | $^1$H NMR (400 Hz, CD$_2$Cl$_2$): 8.02 (d, 1H), 7.73-7.71 (m, 3H), 7.67 (d, 1H), 7.51 (d, 1H), 7.33-7.18 (m, 13H), 7.08 (d, 2H), 7.00-6.95 (m, 4H), 6.75 (br, 1H), 6.67-6.66 (m, 3H), 6.54 (d, 1H), 6.28 (s, 1H), 2.85 (d, 2H), 2.75 (d, 2H), 2.15 (s, 1H), 2.11 (s, 1H), 1.95 (s, 2H), 1.74 (t, 4H), 1.47 (s, 2H). |
| Compound A-7 | $^1$H NMR (CD$_2$Cl$_2$, 400 MHz): 8.01 (d, 1H), 7.72 (d, 1H), 7.63 (d, 2H), 7.57 (d, 1H), 7.52 (d, 1H), 7.37 (d, 2H), 7.31 (t, 1H), 7.28-7.18 (m, 7H), 7.08-7.07 (m, 2H), 7.02-7.00 (m, 2H), 6.97-6.96 (m, 3H), 6.83 (d, 1H), 6.71 (s, 2H), 6.58 (d, 1H), 6.49 (d, 1H), 6.35 (s, 1H), 2.84 (d, 2H), 2.68 (d, 2H), 2.15 (s, 1H), 2.09 (s, 1H), 1.95 (s, 2H), 1.76-1.70 (m, 4H), 1.42 (s, 2H), 1.22 (s, 18H). |
| Compound A-6 | $^1$H NMR (400 Hz, CD$_2$Cl$_2$): 7.97 (d, 1H), 7.74 (d, 1H), 7.65-7.62 (m, 3H), 7.52 (d, 1H), 7.37 (d, 2H), 7.31 (t, 2H), 7.27-7.15 (m, 7H), 7.05-6.97 (m, 7H), 6.73 (s, 2H), 6.62-6.57 (m, 2H), 6.37 (s, 1H), 2.81 (d, 2H), 2.28 (d, 2H), 2.09 (s, 1H), 1.84(s, 2H), 1.74 (s, 1H), 1.67 (d, 2H), 1.50 (d, 2H), 1.35 (s, 2H), 1.22 (s, 18H). |
| Compound A-50 | $^1$H NMR (CD$_2$Cl$_2$, 400 MHz):8.03 (d, 1H), 7.85 (d, 2H), 7.65-7.62 (m, 2H), 7.59 (d, 1H), 7.50 (d, 1H), 7.45-7.44 (m, 2H), 7.41-7.36 (m, 4H), 7.32-7.26 (m, 3H), 7.23-7.15 (m, 5H), 7.10-7.01 (m, 4H), 6.95 (d, 1H), 6.70-6.67 (m, 3H), 6.61 (d, 1H), 6.41 (d, 1H), 2.87 (d, 2H), 2.45 (d, 2H), 2.12 (s, 1H), 1.87 (s, 2H), 1.79 (s, 1H), 1.72 (d, 2H), 1.59 (d, 2H), 1.48 (s, 2H). |
| Compound C-1 | $^1$H NMR (400 MHz, CD$_2$Cl$_2$): 7.88(d, 1H), 7.85(d, 1H), 7.80-7.75(m, 7H), 7.66-7.55(m, 7H), 7.42-7.38(m, 3H), 7.22(d, 1H), 7.16(s, 1H), 6.93(d, 2H), 6.86-6.70(m, 8H), , 3.43(d, 4H), , 2.89 (d, 2H), 2.72 (d, 2H), 2.17 (s, 1H), 2.13 (s, 1H), 1.97 (s, 2H), 1.72 (t, 4H), 1.49 (s, 2H). |
| Compound B-3 | $^1$H NMR (400 MHz, CD$_2$Cl$_2$): 7.77-7.73(m, 4H), 7.69(d, 1H), 7.63-7.59(m, 2H), 7.52-7.46(m, 3H), 7.42-7.18(m, 9H), 7.00-7.02(m, 4H), 6.98(d, 1H), 6.93(d, 2H), 6.89-6.71(m, 5H), 2.85 (d, 2H), 2.31 (d, 2H), 2.12 (s, 1H), , 1.85(s, 2H), 1.76 (s, 1H), 1.65 (d, 2H), 1.56(s, 6H), 1.51 (d, 2H), 1.33(s, 2H). |

Preparation and Evaluation of Organic Electroluminescent Device

Example 1: Red Organic Electroluminescent Device

Prepare the anode by the following process: Cut ITO substrates (made by Corning) with a thickness of 1500 Å to a size of 40 mm×40 mm×0.7 mm, prepare experimental substrates with cathode, anode and insulating layer patterns through lithography, and perform surface treatment using UV ozone and O$_2$:N$_2$ plasma to increase the work function of the anode (experimental substrate) and to remove scum.

The experimental substrate (anode) was vacuum vaporized with F4-TCNQ to form a hole injection layer (HIL) with a thickness of 100 Å, and NPB was vaporized on the hole injection layer to form a hole transport layer with a thickness of 950 Å.

The compound A-1 was vacuum-evaporated on the hole transport layer to form a hole adjustment layer with a thickness of 850 Å.

CBP: Ir(piq)$_2$(acac) were co-evaporated on the hole adjustment layer with a film thickness ratio of 100:3 to form a red light emitting layer (R-EML) with a thickness of 450 Å.

ET-06 and LiQ were vaporized at a film thickness ratio of 1:1 to form a 280 Å thick electron transport layer (ETL), Yb was vaporized on the ETL to form an electron injection layer (EIL) with a thickness of 15 Å, and then magnesium (Mg) and silver (Ag) were vacuum vaporized on the EIL at a film thickness ratio of 1:9 to form a cathode with a thickness of 110 Å.

In addition, the CP-05 was vapor-deposited on the cathode, with a thickness of 630 Å to form an organic covering layer (CPL), thereby completing the manufacture of the organic light-emitting device.

Examples 2-60

Except that the compound shown in Table 13 below was used to replace Compound A-1 when forming the hole adjustment layer, the method same with Example 1 was used to produce the organic electroluminescent device.

Comparative Example 1

Except that Compound 1 was used to replace Compound A-1 when forming the hole adjustment layer, the method same with Example 1 was used to produce the organic electroluminescent device.

Comparative Example 2

Except that Compound 2 was used to replace Compound A-1 when forming the hole adjustment layer, the method same with Example 1 was used to produce the organic electroluminescent device.

Comparative Example 3

Except that Compound 3 was used to replace Compound A-1 when forming the hole adjustment layer, the method same with Example 1 was used to produce the organic electroluminescent device.

Comparative Example 4

Except that Compound 7 was used to replace Compound A-1 when forming the hole adjustment layer, the method same with Example 1 was used to produce the organic electroluminescent device.

Comparative Example 5

Except that compound 8 was used to replace compound A-1 when forming the hole adjustment layer, the method same with Example 1 was used to produce the organic electroluminescent device.

The material structures used in the examples and comparative examples above were shown below:

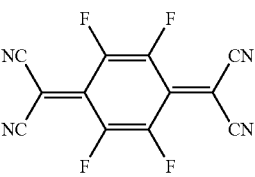

F4-TCNQ

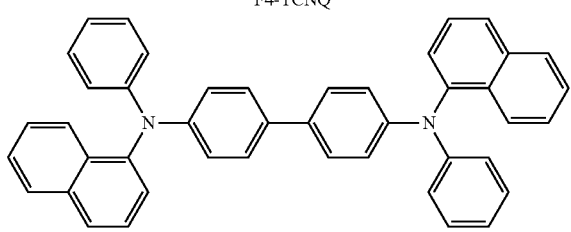

NPB

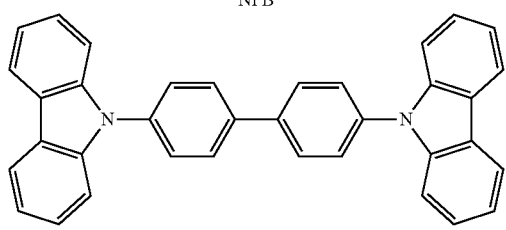

CBP

-continued

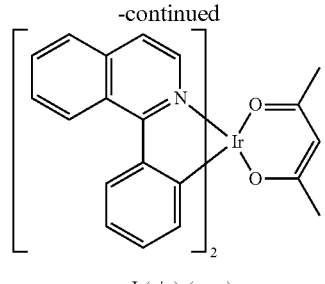

Ir(piq)$_2$(acac)

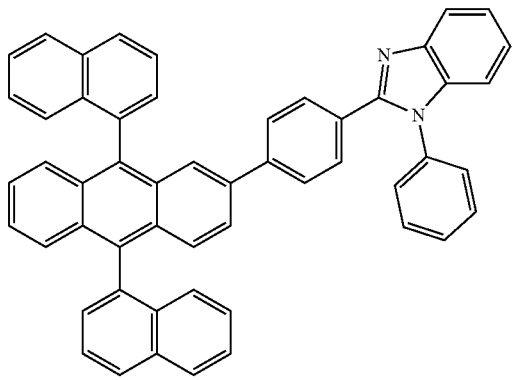

ET-06

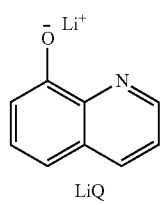

LiQ

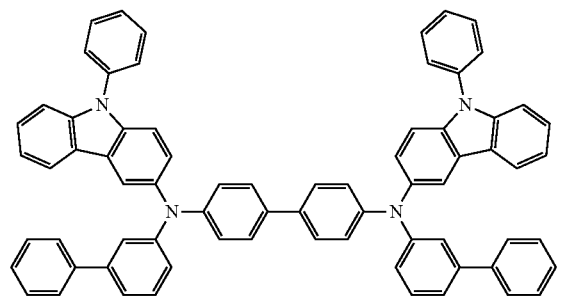

CP-05

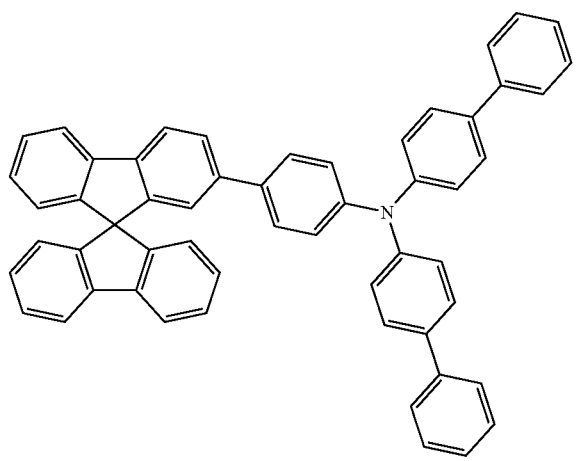

Compound 1

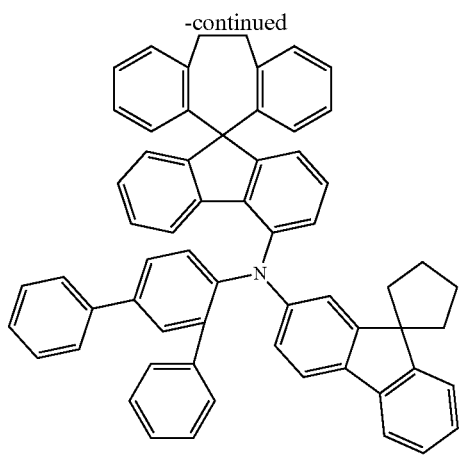

Compound 2

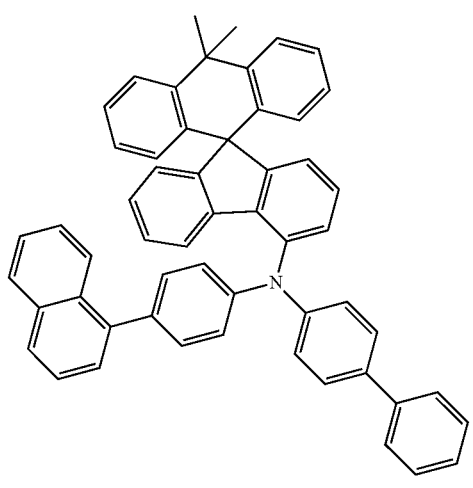

Compound 3

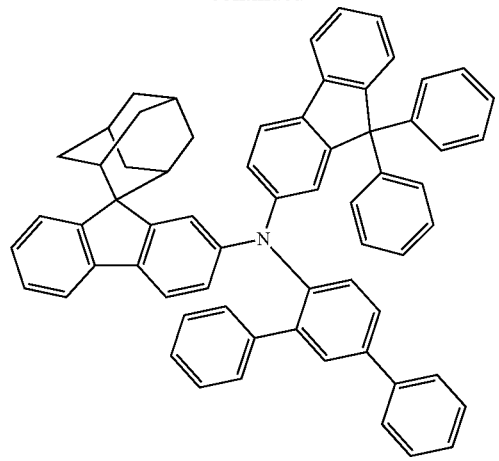

Compound 7

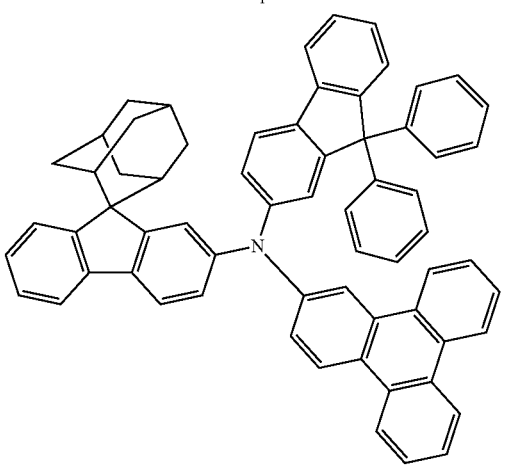

Compound 8

As for the organic electroluminescent device produced as above, the performance of the device is analyzed under the condition of 20 mA/cm$^2$, and the results are shown in Table 13 below:

TABLE 13

| Example | Hole adjustment layer | Driving voltage (V) | Current efficiency (Cd/A) | Power efficiency (lm/W) | Chromaticity coordinate CIEx | Chromaticity coordinate CIEy | External quantum efficiency (%) | T95 life (h)20 mA/cm$^2$ |
|---|---|---|---|---|---|---|---|---|
| Example 1 | Compound A-1 | 4.18 | 34.94 | 26.26 | 0.68 | 0.32 | 27.95 | 461 |
| Example 2 | Compound A-2 | 4.13 | 36.55 | 26.52 | 0.68 | 0.32 | 29.24 | 536 |
| Example 3 | Compound A-3 | 4.12 | 36.18 | 27.59 | 0.68 | 0.32 | 28.94 | 473 |
| Example 4 | Compound A-4 | 4.07 | 34.52 | 26.64 | 0.68 | 0.32 | 27.62 | 491 |
| Example 5 | Compound A-5 | 4.42 | 32.02 | 25.41 | 0.68 | 0.32 | 25.22 | 442 |
| Example 6 | Compound A-6 | 3.98 | 34.64 | 27.34 | 0.68 | 0.32 | 27.71 | 454 |
| Example 7 | Compound A-7 | 4.01 | 35.89 | 28.12 | 0.68 | 0.32 | 28.71 | 495 |
| Example 8 | Compound A-8 | 4.19 | 34.45 | 25.83 | 0.68 | 0.32 | 27.56 | 499 |
| Example 9 | Compound A-9 | 4.18 | 34.06 | 25.62 | 0.68 | 0.32 | 27.25 | 513 |

TABLE 13-continued

| Example | Hole adjustment layer | Driving voltage (V) | Current efficiency (Cd/A) | Power efficiency (lm/W) | Chromaticity coordinate CIEx | Chromaticity coordinate CIEy | External quantum efficiency (%) | T95 life (h)20 mA/cm$^2$ |
|---|---|---|---|---|---|---|---|---|
| Example 10 | Compound A-10 | 3.94 | 34.81 | 27.75 | 0.68 | 0.32 | 27.84 | 539 |
| Example 11 | Compound A-11 | 4.11 | 35.78 | 26.72 | 0.68 | 0.32 | 28.62 | 520 |
| Example 12 | Compound A-12 | 4.41 | 31.85 | 23.12 | 0.68 | 0.32 | 23.88 | 447 |
| Example 13 | Compound A-13 | 4.39 | 34.96 | 25.02 | 0.68 | 0.32 | 27.97 | 476 |
| Example 14 | Compound A-14 | 4.18 | 36.15 | 27.17 | 0.68 | 0.32 | 28.92 | 492 |
| Example 15 | Compound A-15 | 4.11 | 36.84 | 28.23 | 0.68 | 0.32 | 29.47 | 539 |
| Example 16 | Compound A-16 | 3.98 | 34.88 | 27.53 | 0.68 | 0.32 | 27.95 | 499 |
| Example 17 | Compound A-17 | 4.42 | 32.45 | 23.92 | 0.68 | 0.32 | 23.56 | 450 |
| Example 18 | Compound A-18 | 4.02 | 34.85 | 27.24 | 0.68 | 0.32 | 27.84 | 454 |
| Example 19 | Compound A-19 | 4.07 | 35.96 | 27.76 | 0.68 | 0.32 | 28.77 | 482 |
| Example 20 | Compound A-20 | 3.94 | 36.16 | 28.83 | 0.68 | 0.32 | 28.93 | 510 |
| Example 21 | Compound A-21 | 4.41 | 32.59 | 23.04 | 0.68 | 0.32 | 23.27 | 435 |
| Example 22 | Compound A-22 | 4.13 | 36.83 | 27.99 | 0.68 | 0.32 | 29.44 | 522 |
| Example 23 | Compound A-23 | 4.43 | 32.04 | 23.09 | 0.68 | 0.32 | 23.83 | 444 |
| Example 24 | Compound A-24 | 4.45 | 32.29 | 23.21 | 0.68 | 0.32 | 24.03 | 440 |
| Example 25 | Compound B-1 | 4.43 | 32.15 | 23.30 | 0.68 | 0.32 | 23.32 | 445 |
| Example 26 | Compound B-2 | 4.04 | 34.95 | 25.34 | 0.68 | 0.32 | 27.96 | 457 |
| Example 27 | Compound B-3 | 4.11 | 35.16 | 25.63 | 0.68 | 0.32 | 28.13 | 522 |
| Example 28 | Compound B-4 | 4.06 | 35.14 | 27.19 | 0.68 | 0.32 | 28.11 | 499 |
| Example 29 | Compound B-5 | 4.47 | 32.47 | 23.61 | 0.68 | 0.32 | 23.58 | 448 |
| Example 30 | Compound B-6 | 4.48 | 32.65 | 23.68 | 0.68 | 0.32 | 23.72 | 448 |
| Example 31 | Compound B-7 | 4.44 | 33.04 | 24.36 | 0.68 | 0.32 | 24.03 | 442 |
| Example 32 | Compound B-8 | 4.46 | 32.46 | 23.02 | 0.68 | 0.32 | 23.57 | 451 |
| Example 33 | Compound B-9 | 4.39 | 32.89 | 23.16 | 0.68 | 0.32 | 23.91 | 446 |
| Example 34 | Compound B-10 | 4.03 | 34.58 | 25.09 | 0.68 | 0.32 | 27.66 | 504 |
| Example 35 | Compound B-11 | 4.45 | 32.48 | 24.91 | 0.68 | 0.32 | 24.58 | 447 |
| Example 36 | Compound B-12 | 4.39 | 32.83 | 24.42 | 0.68 | 0.32 | 23.84 | 447 |
| Example 37 | Compound B-13 | 4.43 | 32.39 | 24.49 | 0.68 | 0.32 | 23.51 | 443 |
| Example 38 | Compound B-14 | 4.48 | 32.41 | 24.26 | 0.68 | 0.32 | 24.33 | 451 |
| Example 39 | Compound B-15 | 4.39 | 32.49 | 23.86 | 0.68 | 0.32 | 23.59 | 455 |
| Example 40 | Compound B-16 | 4.43 | 33.01 | 23.99 | 0.68 | 0.32 | 24.01 | 442 |
| Example 41 | Compound B-17 | 4.43 | 32.44 | 23.93 | 0.68 | 0.32 | 23.32 | 444 |
| Example 42 | Compound B-18 | 4.48 | 33.88 | 23.73 | 0.68 | 0.32 | 23.73 | 449 |
| Example 43 | Compound C-1 | 4.14 | 35.47 | 26.92 | 0.68 | 0.32 | 28.38 | 510 |
| Example 44 | Compound C-2 | 4.05 | 35.54 | 27.57 | 0.68 | 0.32 | 28.43 | 476 |
| Example 45 | Compound C-3 | 4.11 | 34.94 | 25.47 | 0.68 | 0.32 | 27.95 | 466 |
| Example 46 | Compound C-4 | 4.43 | 33.89 | 24.89 | 0.68 | 0.32 | 23.91 | 441 |

TABLE 13-continued

| Example | Hole adjustment layer | Driving voltage (V) | Current efficiency (Cd/A) | Power efficiency (lm/W) | Chromaticity coordinate CIEx | Chromaticity coordinate CIEy | External quantum efficiency (%) | T95 life (h)20 mA/cm² |
|---|---|---|---|---|---|---|---|---|
| Example 47 | Compound C-5 | 4.48 | 33.09 | 24.17 | 0.68 | 0.32 | 24.07 | 440 |
| Example 48 | Compound C-6 | 4.19 | 35.44 | 25.36 | 0.68 | 0.32 | 28.35 | 501 |
| Example 49 | Compound C-7 | 4.47 | 33.92 | 24.06 | 0.68 | 0.32 | 23.74 | 440 |
| Example 50 | Compound C-8 | 4.46 | 32.97 | 23.41 | 0.68 | 0.32 | 23.98 | 443 |
| Example 51 | Compound C-9 | 4.46 | 32.95 | 23.77 | 0.68 | 0.32 | 23.96 | 448 |
| Example 52 | Compound C-10 | 4.44 | 33.80 | 24.52 | 0.68 | 0.32 | 23.64 | 446 |
| Example 53 | Compound C-11 | 3.95 | 35.56 | 27.28 | 0.68 | 0.32 | 28.45 | 495 |
| Example 54 | Compound C-12 | 4.47 | 32.29 | 24.24 | 0.68 | 0.32 | 24.23 | 445 |
| Example 55 | Compound C-13 | 4.18 | 35.87 | 26.73 | 0.68 | 0.32 | 28.70 | 504 |
| Example 56 | Compound C-14 | 4.40 | 32.86 | 25.47 | 0.68 | 0.32 | 23.89 | 445 |
| Example 57 | Compound C-15 | 4.41 | 31.84 | 24.92 | 0.68 | 0.32 | 23.67 | 447 |
| Example 58 | Compound A-48 | 3.98 | 36.31 | 28.25 | 0.68 | 0.32 | 27.94 | 529 |
| Example 59 | Compound A-50 | 4.02 | 35.98 | 28.22 | 0.68 | 0.32 | 27.81 | 498 |
| Example 60 | Compound A-51 | 4.05 | 36.45 | 28.13 | 0.68 | 0.32 | 27.86 | 501 |
| Comparative example 1 | Compound 1 | 4.73 | 27.72 | 18.41 | 0.68 | 0.32 | 18.85 | 372 |
| Comparative example 2 | Compound 2 | 4.74 | 28.13 | 18.64 | 0.68 | 0.32 | 19.13 | 386 |
| Comparative example 3 | Compound 3 | 4.76 | 28.21 | 18.62 | 0.68 | 0.32 | 19.58 | 383 |
| Comparative example 4 | Compound 7 | 4.14 | 27.98 | 18.54 | 0.68 | 0.32 | 19.03 | 376 |
| Comparative example 5 | Compound 8 | 4.06 | 27.83 | 18.42 | 0.68 | 0.32 | 18.95 | 373 |

According to the results in Table 13, it can be seen that the compounds used in this application were prepared as the hole-adjusting layer in comparison with the comparative examples 1-5 corresponding to the devices corresponding to the well-known compounds in Examples 1-60 as the compound for the hole-adjusting layer. the luminescence efficiency (Cd/A) of the organic electroluminescent devices prepared with the compounds used as the hole adjustment layer in the present application was improved by at least 12.87%, the external quantum efficiency was improved by at least 18.85%, the lifetime was at least improved to 13.99%, and the highest lifetime was improved to 167 h.

Example 61: Green Organic Electroluminescent Device

Prepare the anode by the following process: Cut ITO substrates (made by Corning) with a thickness of 1500 Å to a size of 40 mm×40 mm×0.7 mm, prepare experimental substrates with cathode, anode and insulating layer patterns through lithography, and perform surface treatment using UV ozone and $O_2:N_2$ plasma to increase the work function of the anode (experimental substrate) and to remove scum.

The experimental substrate (anode) was vacuum vaporized with F4-TCNQ to form a hole injection layer (HIL) with a thickness of 100 Å, and NPB was vaporized on the hole injection layer to form a hole transport layer with a thickness of 880 Å.

The compound A-25 was vacuum-evaporated on the hole transport layer to form a hole adjustment layer with a thickness of 400 Å.

CBP: Ir(ppy)$_3$ was co-evaporated on the hole adjustment layer with a film thickness ratio of 90%:10% to form a green light emitting layer (G-EML) with a thickness of 400 Å.

ET-06 and LiQ were vaporized at a film thickness ratio of 1:1 to form a 280 Å thick electron transport layer (ETL), Yb was vaporized on the ETL to form an electron injection layer (EIL) with a thickness of 15 Å, and then magnesium (Mg) and silver (Ag) were vacuum vaporized on the EIL at a film thickness ratio of 1:9 to form a cathode with a thickness of 110 Å.

In addition, the CP-05 was vapor-deposited on the cathode, with a thickness of 630 Å to form an organic covering layer (CPL), thereby completing the manufacture of the organic light-emitting device.

Examples 62-119

Except that the compound shown in Table 14 below was used to replace Compound A-25 when forming the hole adjustment layer, the method same with Example 61 was used to produce the organic electroluminescent device.

Comparative Example 6

Except that Compound 4 was used to replace Compound A-25 when forming the hole adjustment layer, the method same with Example 61 was used to produce the organic electroluminescent device.

Comparative Example 7

Except that Compound 5 was used to replace Compound A-25 when forming the hole adjustment layer, the method same with Example 61 was used to produce the organic electroluminescent device.

Comparative Example 8

Except that Compound 6 was used to replace Compound A-25 when forming the hole adjustment layer, the method same with Example 61 was used to produce the organic electroluminescent device.

Comparative Example 9

Except that Compound 7 was used to replace Compound A-25 when forming the hole adjustment layer, the method same with Example 61 was used to produce the organic electroluminescent device.

Comparative Example 10

Except that Compound 8 was used to replace Compound A-25 when forming the hole adjustment layer, the method same with Example 61 was used to produce the organic electroluminescent device.

The material structures used in the examples and comparative examples above were shown below:

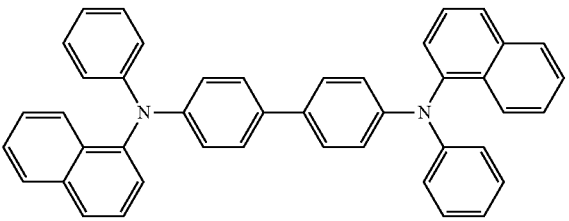

NPB

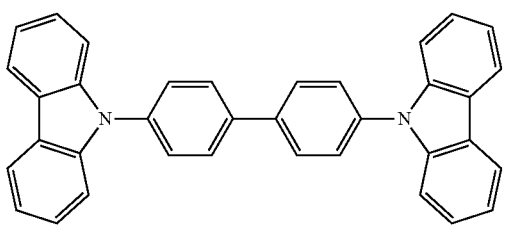

CBP

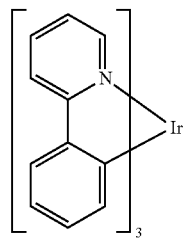

Ir(ppy)$_3$

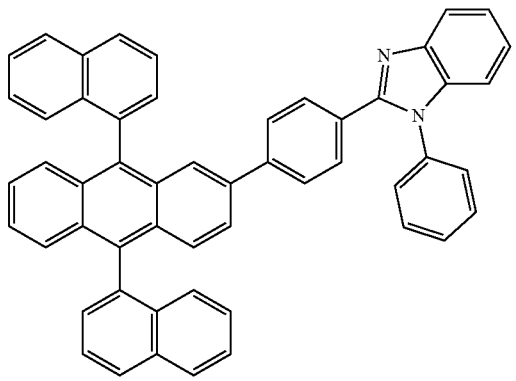

Et-06

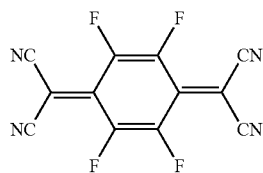

F4-TCNQ

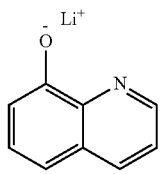

LiQ

CP-05
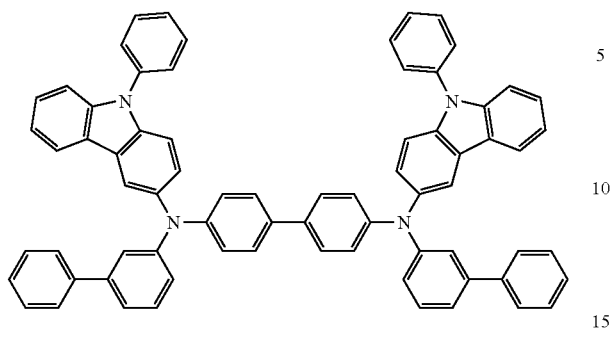
Compound 4
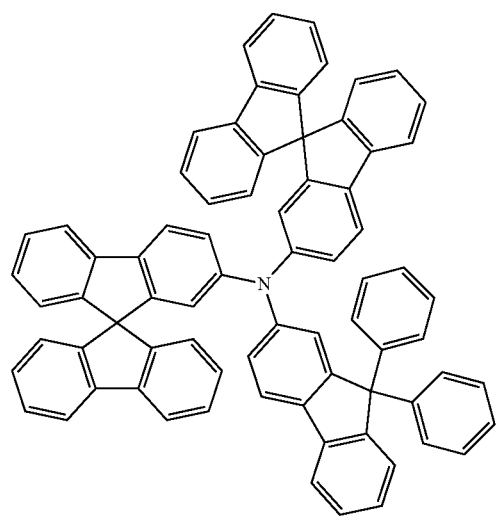
Compound 5
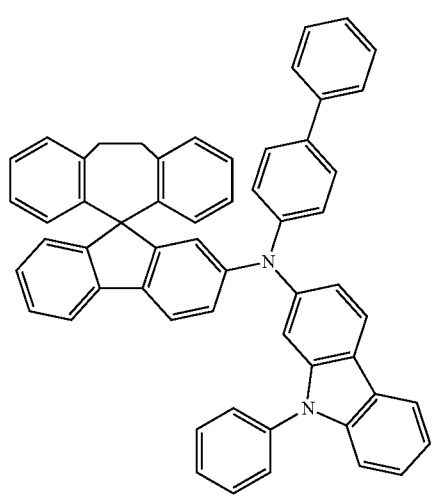
Compound 6
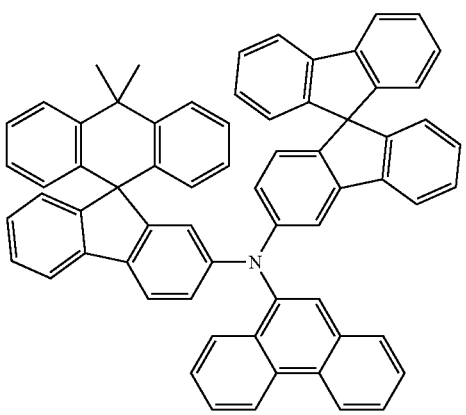
Compound 7
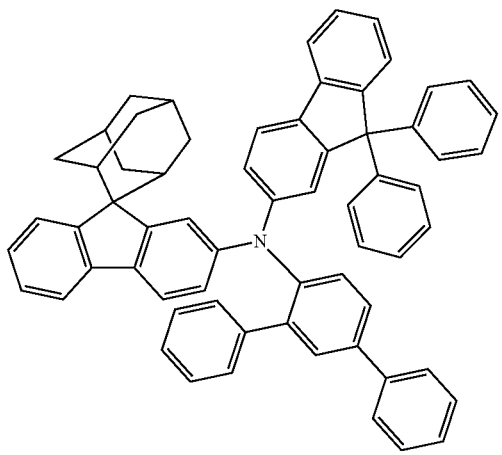
Compound 8
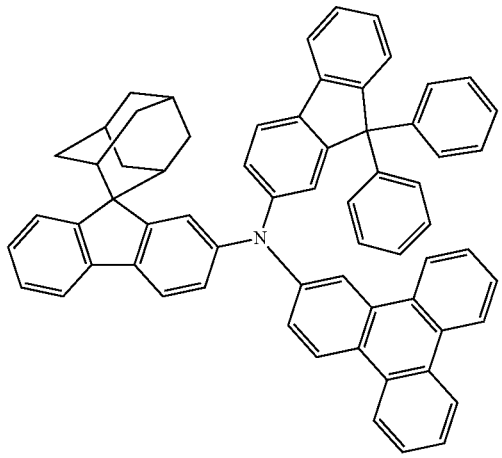
As for the organic electroluminescent device produced as above, the performance of the device is analyzed under the condition of 20 mA/cm², and the results are shown in Table 14 below:

TABLE 14

| Example | Hole adjustment layer | Driving voltage (V) | Current efficiency (Cd/A) | Power efficiency (lm/W) | Chromaticity coordinate CIEx | Chromaticity coordinate CIEy | External quantum efficiency EQE (%) | T96 life (h) 20 mA/cm² |
|---|---|---|---|---|---|---|---|---|
| Example 61 | Compound A-25 | 4.33 | 80.49 | 56.23 | 0.22 | 0.73 | 19.24 | 253 |
| Example 62 | Compound A-26 | 4.09 | 77.47 | 64.17 | 0.22 | 0.73 | 18.17 | 305 |
| Example 63 | Compound A-27 | 4.38 | 75.77 | 56.31 | 0.22 | 0.73 | 19.52 | 310 |
| Example 64 | Compound A-28 | 4.09 | 78.95 | 59.05 | 0.22 | 0.73 | 19.22 | 261 |
| Example 65 | Compound A-29 | 4.10 | 82.37 | 53.97 | 0.22 | 0.73 | 19.65 | 277 |
| Example 66 | Compound A-30 | 4.44 | 78.33 | 57.44 | 0.22 | 0.73 | 19.06 | 295 |
| Example 67 | Compound A-31 | 4.11 | 79.95 | 60.58 | 0.22 | 0.73 | 18.56 | 283 |
| Example 68 | Compound A-32 | 4.18 | 81.27 | 57.07 | 0.22 | 0.73 | 18.19 | 246 |
| Example 69 | Compound A-33 | 4.14 | 81.26 | 56.62 | 0.22 | 0.73 | 19.62 | 251 |
| Example 70 | Compound A-34 | 4.30 | 81.62 | 60.63 | 0.22 | 0.73 | 18.43 | 308 |
| Example 71 | Compound A-35 | 4.00 | 81.01 | 59.48 | 0.22 | 0.73 | 18.61 | 288 |
| Example 72 | Compound A-36 | 4.22 | 80.96 | 53.67 | 0.22 | 0.73 | 18.28 | 271 |
| Example 73 | Compound A-37 | 4.20 | 78.66 | 58.45 | 0.22 | 0.73 | 19.73 | 240 |
| Example 74 | Compound A-38 | 4.21 | 76.11 | 56.91 | 0.22 | 0.73 | 18.18 | 243 |
| Example 75 | Compound A-39 | 4.35 | 82.80 | 59.36 | 0.22 | 0.73 | 19.42 | 306 |
| Example 76 | Compound A-40 | 4.21 | 82.51 | 62.67 | 0.22 | 0.73 | 18.71 | 241 |
| Example 77 | Compound A-41 | 4.33 | 79.17 | 61.51 | 0.22 | 0.73 | 18.47 | 274 |
| Example 78 | Compound A-42 | 4.24 | 76.13 | 59.06 | 0.22 | 0.73 | 19.68 | 253 |
| Example 79 | Compound A-43 | 4.16 | 83.09 | 56.71 | 0.22 | 0.73 | 18.16 | 277 |
| Example 80 | Compound A-44 | 4.30 | 78.23 | 55.27 | 0.22 | 0.73 | 18.82 | 247 |
| Example 81 | Compound A-45 | 4.02 | 78.13 | 56.32 | 0.22 | 0.73 | 18.33 | 267 |
| Example 82 | Compound A-46 | 4.13 | 81.02 | 57.99 | 0.22 | 0.73 | 19.88 | 285 |
| Example 83 | Compound A-47 | 4.37 | 82.71 | 58.51 | 0.22 | 0.73 | 18.28 | 270 |
| Example 84 | Compound ndB-19 | 4.12 | 75.86 | 57.84 | 0.22 | 0.73 | 18.21 | 278 |
| Example 85 | Compound B-20 | 4.22 | 77.12 | 57.41 | 0.22 | 0.73 | 18.51 | 261 |
| Example 86 | Compound B-21 | 4.24 | 76.72 | 56.84 | 0.22 | 0.73 | 18.41 | 256 |
| Example 87 | Compound B-22 | 4.19 | 73.39 | 55.02 | 0.22 | 0.73 | 17.61 | 242 |
| Example 88 | Compound B-23 | 4.14 | 72.48 | 55.21 | 0.22 | 0.73 | 17.4 | 254 |
| Example 89 | Compound B-24 | 4.17 | 80.06 | 60.31 | 0.22 | 0.73 | 19.21 | 263 |
| Example 90 | Compound B-25 | 4.12 | 73.53 | 56.07 | 0.22 | 0.73 | 17.65 | 258 |
| Example 91 | Compound B-26 | 4.13 | 76.99 | 58.56 | 0.22 | 0.73 | 18.48 | 270 |
| Example 92 | Compound B-27 | 4.50 | 75.05 | 52.39 | 0.22 | 0.73 | 18.01 | 280 |
| Example 93 | Compound B-28 | 4.22 | 72.59 | 54.34 | 0.22 | 0.73 | 17.42 | 260 |
| Example 94 | Compound B-29 | 4.35 | 77.23 | 55.77 | 0.22 | 0.73 | 18.54 | 262 |
| Example 95 | Compound ndB-30 | 4.18 | 75.44 | 56.75 | 0.22 | 0.73 | 18.11 | 259 |
| Example 96 | Compound ndB-31 | 4.31 | 74.73 | 54.47 | 0.22 | 0.73 | 17.94 | 254 |
| Example 97 | Compound B-32 | 4.21 | 78.79 | 58.79 | 0.22 | 0.73 | 18.91 | 288 |

TABLE 14-continued

| Example | Hole adjustment layer | Driving voltage (V) | Current efficiency (Cd/A) | Power efficiency (lm/W) | Chromaticity coordinate CIEx | Chromaticity coordinate CIEy | External quantum efficiency EQE (%) | T96 life (h) 20 mA/cm$^2$ |
|---|---|---|---|---|---|---|---|---|
| Example 98 | Compound B-33 | 4.48 | 72.88 | 51.11 | 0.22 | 0.73 | 17.49 | 279 |
| Example 99 | Compound B-34 | 4.23 | 77.50 | 57.56 | 0.22 | 0.73 | 18.61 | 275 |
| Example 100 | Compound ndB-35 | 4.16 | 74.60 | 56.34 | 0.22 | 0.73 | 17.92 | 259 |
| Example 101 | Compound ndB-36 | 4.17 | 76.11 | 57.34 | 0.22 | 0.73 | 18.27 | 247 |
| Example 102 | Compound C-16 | 4.14 | 73.89 | 56.07 | 0.22 | 0.73 | 17.73 | 276 |
| Example 103 | Compound C-17 | 4.14 | 75.36 | 57.18 | 0.22 | 0.73 | 18.09 | 271 |
| Example 104 | Compound C-18 | 4.31 | 76.02 | 55.41 | 0.22 | 0.73 | 18.24 | 288 |
| Example 105 | Compound C-19 | 4.43 | 76.34 | 54.14 | 0.22 | 0.73 | 18.32 | 286 |
| Example 106 | Compound C-20 | 4.42 | 77.03 | 54.75 | 0.22 | 0.73 | 18.49 | 274 |
| Example 107 | Compound C-21 | 4.28 | 72.71 | 53.37 | 0.22 | 0.73 | 17.45 | 282 |
| Example 108 | Compound C-22 | 4.32 | 74.24 | 53.99 | 0.22 | 0.73 | 17.82 | 286 |
| Example 109 | Compound C-23 | 4.38 | 74.01 | 53.08 | 0.22 | 0.73 | 17.76 | 278 |
| Example 110 | Compound C-24 | 4.39 | 72.44 | 51.84 | 0.22 | 0.73 | 17.39 | 257 |
| Example 111 | Compound C-25 | 4.43 | 72.94 | 51.72 | 0.22 | 0.73 | 17.51 | 253 |
| Example 112 | Compound C-26 | 4.17 | 76.05 | 57.29 | 0.22 | 0.73 | 18.25 | 290 |
| Example 113 | Compound C-27 | 4.42 | 75.27 | 53.74 | 0.22 | 0.73 | 18.06 | 282 |
| Example 114 | Compound C-28 | 4.50 | 76.49 | 53.42 | 0.22 | 0.73 | 18.36 | 257 |
| Example 115 | Compound C-29 | 4.45 | 74.24 | 52.41 | 0.22 | 0.73 | 17.82 | 279 |
| Example 116 | Compound C-30 | 4.15 | 79.80 | 60.41 | 0.22 | 0.73 | 19.15 | 266 |
| Example 117 | Compound A-49 | 4.09 | 78.84 | 60.62 | 0.22 | 0.73 | 18.93 | 282 |
| Example 118 | Compound A-52 | 4.19 | 79.69 | 59.81 | 0.22 | 0.73 | 19.14 | 275 |
| Example 119 | Compound A-53 | 4.31 | 80.92 | 59.02 | 0.22 | 0.73 | 19.42 | 297 |
| Comparative example 6 | Compound 4 | 4.58 | 63.98 | 45.68 | 0.22 | 0.73 | 15.36 | 192 |
| Comparative example 7 | Compound 5 | 4.65 | 60.51 | 45.05 | 0.22 | 0.73 | 14.52 | 187 |
| Comparative example 8 | Compound 6 | 4.80 | 59.13 | 47.03 | 0.22 | 0.73 | 14.19 | 196 |
| Comparative example 9 | Compound 7 | 4.21 | 62.68 | 47.33 | 0.22 | 0.73 | 15.04 | 209 |
| Comparative example 10 | Compound 8 | 4.06 | 64.05 | 46.69 | 0.22 | 0.73 | 15.37 | 187 |

According to the results in Table 14, it can be seen that the compounds used in this application were prepared as the hole-adjusting layer in comparison with the comparative examples 6-10 to the devices corresponding to the well-known compounds in Examples 61-119 as the compound for the hole-adjusting layer, the luminescence efficiency (Cd/A) of the organic electroluminescent devices prepared with the compounds used as the hole adjustment layer in the present application was improved by at least 13.10%, the external quantum efficiency was improved by at least 13.14%, the lifetime was at least improved to 14.83%, and the highest lifetime was improved to 123 h.

Example 120: Blue Organic Electroluminescent Device

Prepare the anode by the following process: Cut ITO substrates (made by Corning) with a thickness of 1500 Å to a size of 40 mm×40 mm×0.7 mm, prepare experimental substrates with cathode, anode and insulating layer patterns through lithography, and perform surface treatment using UV ozone and O$_2$:N$_2$ plasma to increase the work function of the anode (experimental substrate) and to remove scum.

The experimental substrate (anode) was vacuum vaporized with F4-TCNQ to form a hole injection layer (HIL) with a thickness of 100 Å, and Compound A-1 was vaporized on the hole injection layer to form a hole transport layer with a thickness of 950 Å.

The compound EB-01 was was vacuum-evaporated on the hole transport layer to form a hole adjustment layer with a thickness of 100 Å.

BH-01 and BD-01 were co-evaporated on the hole adjustment layer with a film thickness ratio of 98%:2% to form a blue light emitting layer (EML) with a thickness of 220 Å.

ET-06 and LiQ were vaporized at a film thickness ratio of 1:1 to form a 280 Å thick electron transport layer (ETL), Yb was vaporized on the ETL to form an electron injection layer (EIL) with a thickness of 15 Å, and then magnesium (Mg) and silver (Ag) were vacuum vaporized on the EIL at a film thickness ratio of 1:9 to form a cathode with a thickness of 110 Å.

In addition, the CP-05 was vapor-deposited on the cathode, with a thickness of 630 Å to form an organic covering layer (CPL), thereby completing the manufacture of the organic light-emitting device.

Examples 121-136

Except that the compound shown in Table 15 below was used to replace Compound A-1 when forming the hole transport layer, the method same with Example 120 was used to produce the organic electroluminescent device.

Comparative Example 11

Except that Compound 9 was used to replace Compound A-1 when forming the hole transport layer, the method same with Example 120 was used to produce the organic electroluminescent device.

Comparative Example 12

Except that Compound 7 was used to replace Compound A-1 when forming the hole transport layer, the method same with Example 120 was used to produce the organic electroluminescent device.

Comparative Example 13

Except that Compound 8 was used to replace Compound A-1 when forming the hole transport layer, the method same with Example 120 was used to produce the organic electroluminescent device.

The structure of materials used in the examples and comparative examples above were shown below:

F4-TCNQ

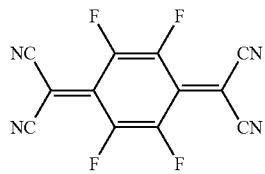

-continued

EB-01

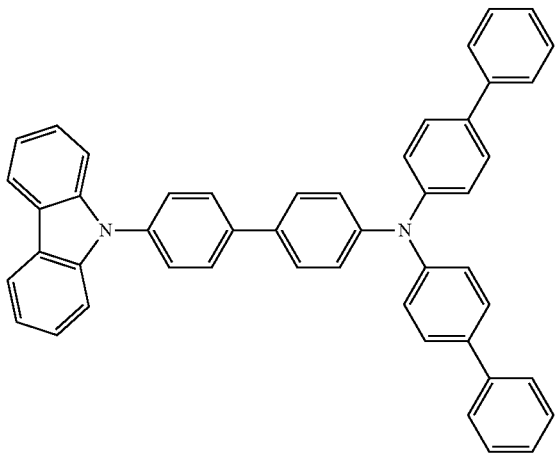

BH-01

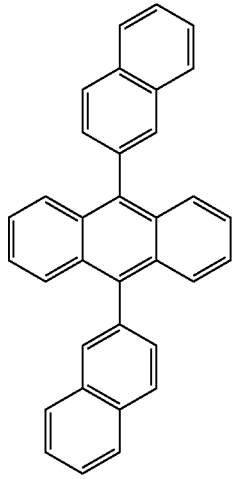

BD-01

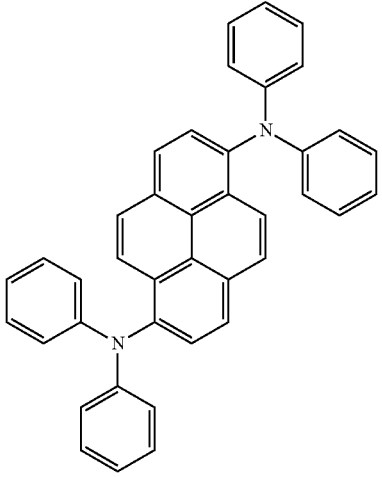

ET-06

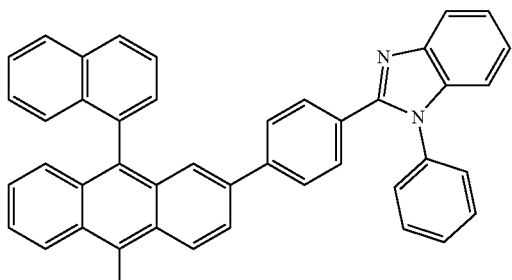

LiQ

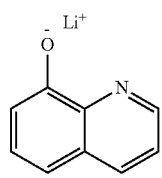

CP-05

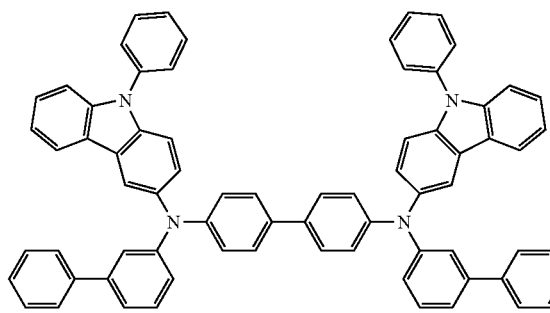

Compound 9

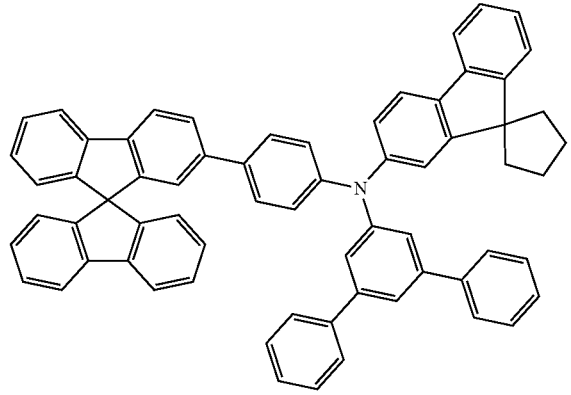

Compound 7

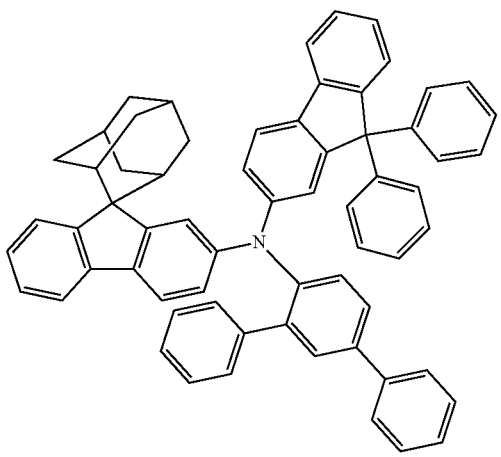

Compound 8

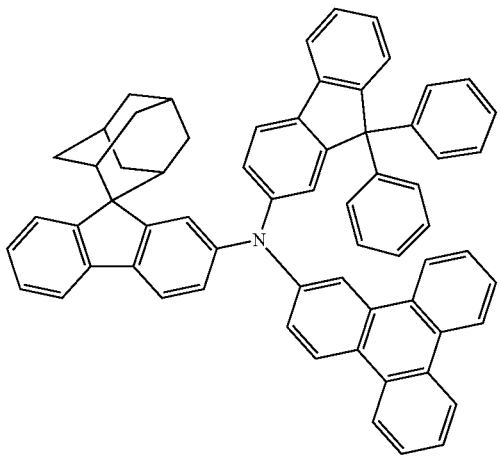

As for the organic electroluminescent device produced as above, the performance of the device is analyzed under the condition of 20 mA/cm$^2$, and the results are shown in Table 15 below:

TABLE 15

| Example | Hole transport layer | Driving voltage (V) | Current efficiency (Cd/A) | Chromaticity coordinate CIEx | Chromaticity coordinate CIEy | T95 life (h)20 mA/cm$^2$ |
|---|---|---|---|---|---|---|
| Example 120 | Compound A-1 | 3.98 | 9.91 | 0.14 | 0.09 | 203 |
| Example 121 | Compound A-2 | 3.99 | 9.81 | 0.14 | 0.09 | 201 |
| Example 122 | Compound A-3 | 3.95 | 9.78 | 0.14 | 0.09 | 202 |

TABLE 15-continued

| Example | Hole transport layer | Driving voltage (V) | Current efficiency (Cd/A) | Chromaticity coordinate CIEx | Chromaticity coordinate CIEy | T95 life (h)20 mA/cm$^2$ |
|---|---|---|---|---|---|---|
| Example 123 | Compound A-4 | 3.94 | 9.92 | 0.14 | 0.09 | 213 |
| Example 124 | Compound A-6 | 4.02 | 9.84 | 0.14 | 0.09 | 210 |
| Example 125 | Compound A-7 | 3.92 | 9.84 | 0.14 | 0.09 | 198 |
| Example 126 | Compound A-48 | 4.00 | 9.89 | 0.14 | 0.09 | 200 |
| Example 127 | Compound A-49 | 3.92 | 9.77 | 0.14 | 0.09 | 202 |
| Example 128 | Compound A-50 | 3.94 | 9.98 | 0.14 | 0.09 | 213 |
| Example 129 | Compound A-51 | 3.92 | 9.86 | 0.14 | 0.09 | 215 |
| Example 130 | Compound A-52 | 3.91 | 9.84 | 0.14 | 0.09 | 213 |
| Example 131 | Compound A-25 | 4.01 | 9.66 | 0.14 | 0.09 | 188 |
| Example 132 | Compound A-127 | 4.03 | 9.61 | 0.14 | 0.09 | 183 |
| Example 133 | Compound B-3 | 4.00 | 9.49 | 0.14 | 0.09 | 181 |
| Example 134 | Compound B-36 | 4.02 | 9.43 | 0.14 | 0.09 | 189 |
| Example 135 | Compound C-1 | 4.01 | 9.36 | 0.14 | 0.09 | 188 |
| Example 136 | Compound C-2 | 4.04 | 9.34 | 0.14 | 0.09 | 180 |
| Comparative example 11 | Compound 9 | 4.05 | 7.84 | 0.14 | 0.09 | 158 |
| Comparative example 12 | Compound 7 | 4.08 | 7.69 | 0.14 | 0.09 | 160 |
| Comparative example 13 | Compound 8 | 4.13 | 7.67 | 0.14 | 0.09 | 157 |

According to the results in Table 15, it can be seen that the compounds used in this application were prepared as the hole-adjusting layer in comparison with the comparative examples 11-13 corresponding to the devices corresponding to the well-known compounds in Examples 120-136 as the compound for the hole-adjusting layer, the luminescence efficiency (Cd/A) of the organic electroluminescent devices prepared with the compounds used as the hole transport layer in the present application was improved by at least 19.13%, and the lifetime was at least improved to 12.5%.

The heat stability data of some materials were shown in Table 16 below:

TABLE 16

| Example | Compound | Tg (° C.) | Te (° C.) |
|---|---|---|---|
| Example 120 | Compound A-1 | 145 | 230 |
| Example 121 | Compound A-2 | 147 | 235 |
| Example 122 | Compound A-4 | 145 | 232 |
| Example 123 | Compound A-3 | 148 | 240 |
| Example 124 | Compound A-6 | 143 | 230 |
| Example 125 | Compound A-7 | 144 | 238 |
| Example 126 | Compound A-48 | 145 | 235 |
| Example 127 | Compound A-49 | 142 | 236 |
| Example 128 | Compound A-50 | 146 | 240 |
| Example 129 | Compound A-25 | 141 | 243 |
| Example 130 | Compound A-127 | 140 | 247 |
| Example 131 | Compound B-3 | 140 | 262 |
| Example 132 | Compound B-36 | 139 | 264 |
| Example 133 | Compound C-1 | 140 | 265 |
| Example 134 | Compound C-2 | 138 | 258 |
| Comparative example 11 | Compound 9 | 121 | 278 |
| Comparative example 12 | Compound 7 | 125 | 289 |
| Comparative example 13 | Compound 8 | 126 | 285 |

Based on the results in Table 16, it can be seen that the compounds of the present application have a lower decomposition potential during the evaporation film formation process of high temperature devices and have a higher crystallization resistance in the electro Joule heat environment during device operation.

Compared with the compound of the comparative example, the compounds of the present application have a higher glass transition temperature (Tg) under the condition that the molecular weight was not much different. Due to the higher steric hindrance, the vapor deposition temperature of the compound of the present application is (Te) decreases. Therefore, the compounds of the present application have better thermal stability.

It can be seen that when the nitrogen-containing compound of the present application was used as the material of hole adjustment layer or hole transport layer, it was possible to produce organic electroluminescent devices with high efficiency, high heat resistance, and long life with excellent characteristics such as driving voltage, luminescence efficiency, external quantum efficiency, and heat stability.

It should be understood that the present application does not limit its application to the detailed structure and arrangement of the components presented in this specification. The present application can have other embodiments and can be implemented and performed in a variety of ways. The said transformed forms and modified forms fall within the scope of the present application. It should be understood that this specification discloses and limits the present application to all alternative combinations of two or more individual properties mentioned or apparent in the text and/or attached figures. All these different combinations constitute multiple alternative aspects of the present application. The embodiments of this specification provides the known best mode used to realize the present application, and allow the technicians in this field to use the present application.

The invention claimed is:

1. A nitrogen-containing compound, characterized in that its structure is represented by Formula 1:

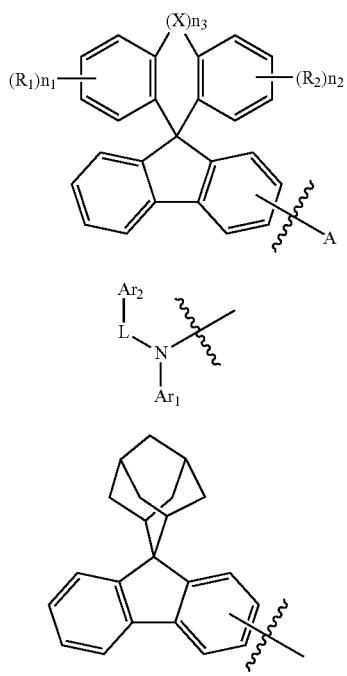

Formula 1

Formula 2

Formula 3 wherein ⁃ represents a chemical bond;
A is a group represented by Formula 2;
X is C (R$_3$R$_4$), and R$_3$ and R$_4$ are each independently selected from hydrogen, methyl
R$_1$ and R$_2$ are identical or different, and are each independently selected from hydrogen, alkyl with 1-6 carbon atoms, and the aryl with 6-12 carbon atoms;
n$_1$ is selected from 1, 2, 3, or 4, and when n$_1$ is greater than or equal to 2, any two R$_1$ are identical or different;
n$_2$ is selected from 1, 2, 3, or 4, and when n$_2$ is greater than or equal to 2, any two R$_2$ are identical or different;
n$_3$ is selected from 0, 1, or 2, and when n$_3$ is greater than or equal to 2, any two R$_3$ are identical or different and any two R$_4$ are identical or different;
L is selected from single bond or the following groups:

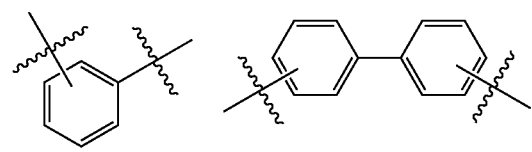

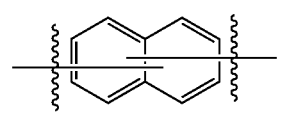

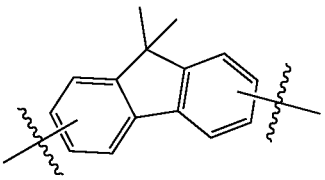

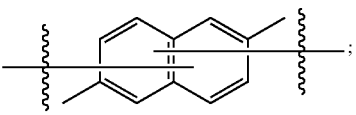

Ar$_1$ is selected from a group consisting of the following groups:

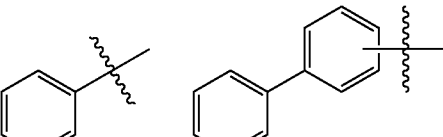

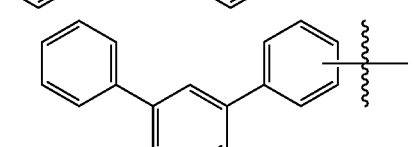

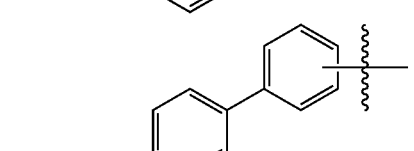

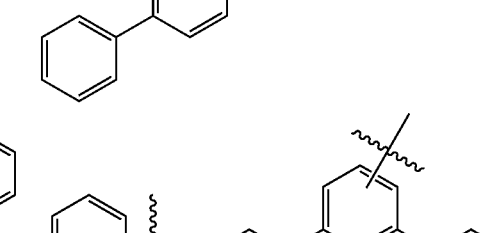

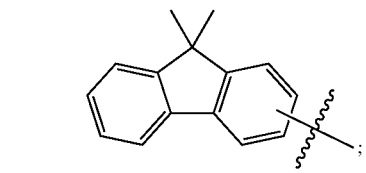

and

Ar$_2$ is a group represented by Formula 3.

2. The nitrogen-containing compound according to claim 1, characterized in that the nitrogen-containing compound is selected from a group consisting of the following formulae:

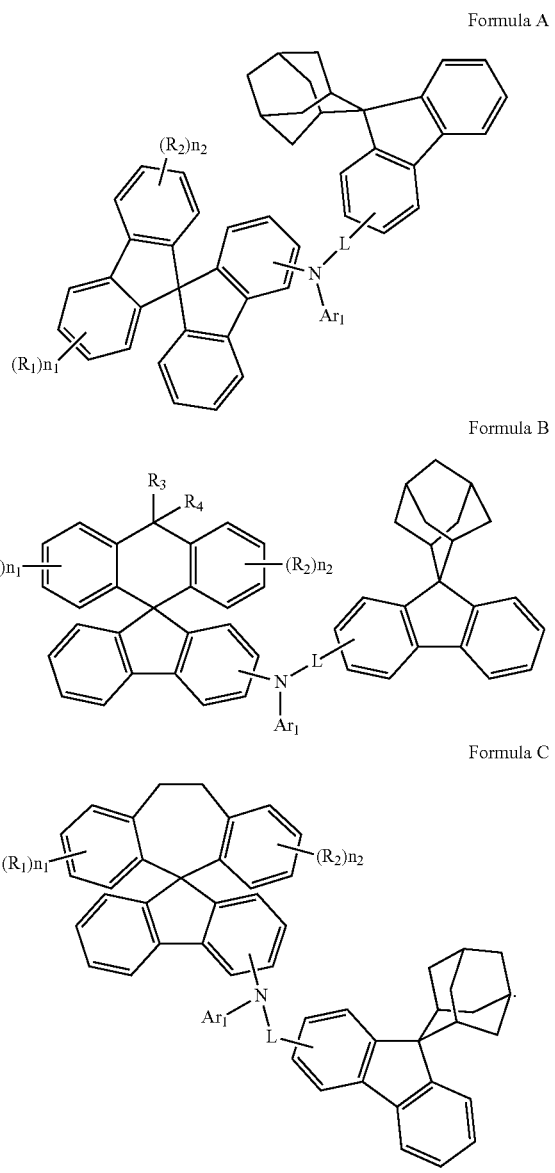

Formula A

Formula B

Formula C

3. The nitrogen-containing compound according to claim 1, wherein $R_1$ and $R_2$ are identical or different, and are each independently selected from hydrogen, methyl, ethyl, n-propyl, tert-butyl, phenyl, biphenyl, and naphthyl, respectively.

4. The nitrogen-containing compound according to claim 1, wherein the nitrogen-containing compound is selected from the group consisting of compounds represented by the following formulae:

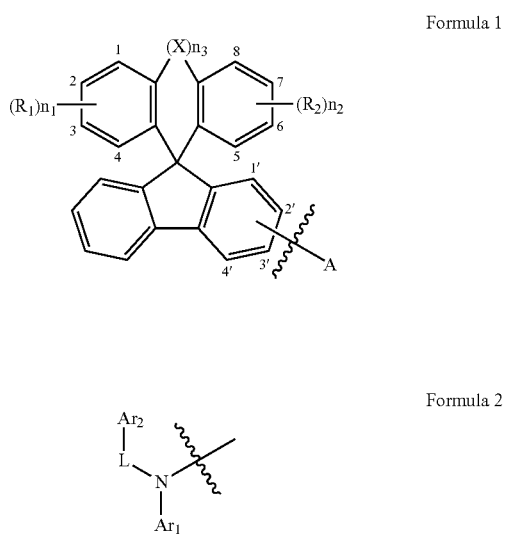

Formula 1

Formula 2

Formula 3

| Compound No. | n₃ | Connection position between Formulae 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| A-1 | 0 | 2' | b | 4 | H | | 4 | H | | I-D | Single bond |
| A-2 | 0 | 2' | c | 4 | H | | 4 | H | | I-D | Single bond |
| A-3 | 0 | 2' | b | 4 | H | | 4 | H | | I-D | L-A |
| A-4 | 0 | 2' | b | 4 | H | | 4 | H | | I-B | Single bond |
| A-5 | 0 | 2' | b | 4 | H | | 4 | H | | I-K | Single bond |
| A-39 | 0 | 1' | b | 4 | H | | 4 | H | | I-D | L-G |
| A-40 | 0 | 1' | b | 4 | H | | 4 | H | | I-D | Single bond |
| A-41 | 0 | 1' | c | 4 | H | | 4 | H | | I-E | Single bond |
| A-48 | 0 | 4' | b | 4 | H | | 4 | H | | I-D | Single bond |

-continued

| Compound No. | $n_3$ | Connection position between Formulae 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| A-49 | 0 | 4' | c | 4 | H | | 4 | H | | I-D | Single bond |
| B-3 | 1 | 2' | c | 4 | H | | 4 | H | | I-D | Single bond |
| B-4 | 1 | 2' | b | 4 | H | | 4 | H | | I-D | Single bond |
| B-5 | 1 | 2' | b | 4 | H | | 4 | H | | I-K | Single bond |
| B-26 | 1 | 1' | d | 4 | H | | 4 | H | | I-J | Single bond |
| B-27 | 1 | 1' | b | 4 | H | | 4 | H | | I-D | Single bond |
| B-28 | 1 | 3' | d | 4 | H | | 4 | H | | I-D | Single bond |
| B-29 | 1 | 3' | a | 4 | H | | 4 | H | | I-L | Single bond |
| B-34 | 1 | 4' | a | 4 | H | | 4 | H | | I-G | Single bond |
| B-35 | 1 | 4' | c | 4 | H | | 4 | H | | I-B | Single bond |
| B-36 | 1 | 4' | a | 4 | H | | 4 | H | | I-H | L-C |
| C-1 | 2 | 2' | c | 4 | H | | 4 | H | | I-D | Single bond |
| C-2 | 2 | 2' | b | 4 | H | | 4 | H | | I-D | Single bond |
| C-3 | 2 | 2' | b | 4 | H | | 4 | H | | I-D | L-C |
| C-4 | 2 | 2' | b | 4 | H | | 4 | H | | I-M | Single bond |
| C-18 | 2 | 1' | d | 4 | H | | 4 | H | | I-F | Single bond |
| C-19 | 2 | 3' | c | 4 | H | | 4 | H | | I-G | Single bond |
| C-28 | 2 | 4' | a | 4 | H | | 4 | H | | I-A | Single bond |
| A-50 | 0 | 3' | b | 4 | H | | 4 | H | | I-D | Single bond |
| A-51 | 0 | 3' | c | 4 | H | | 4 | H | | I-D | Single bond |
| A-53 | 0 | 2' | b | 4 | H | | 4 | H | | I-B | Single bond |
| A-52 | 0 | 2' | b | 1 | tert-butyl | 3 | 1 | tert-butyl | 6 | I-B | Single bond |
| A-6 | 0 | 2' | b | 1 | tert-butyl | 3 | 1 | tert-butyl | 6 | I-D | Single bond |
| A-7 | 0 | 2' | c | 1 | tert-butyl | 3 | 1 | tert-butyl | 6 | I-D | Single bond |
| A-8 | 0 | 2' | c | 1 | tert-butyl | 3 | 1 | tert-butyl | 6 | I-A | Single bond |
| A-9 | 0 | 2' | b | 1 | tert-butyl | 3 | 1 | tert-butyl | 6 | I-D | L-C |
| A-10 | 0 | 2' | c | 1 | tert-butyl | 3 | 1 | tert-butyl | 6 | I-B | Single bond |
| A-11 | 0 | 2' | c | 1 | R-E | 2 | 1 | R-E | 7 | I-A | Single bond |
| A-12 | 0 | 2' | c | 1 | R-E | 2 | 1 | R-E | 7 | I-I | Single bond |
| A-13 | 0 | 2' | d | 1 | R-A | 4 | 1 | tert-butyl | 6 | I-A | Single bond |
| A-14 | 0 | 2' | d | 1 | R-A | 4 | 1 | tert-butyl | 6 | I-C | Single bond |
| A-15 | 0 | 2' | c | 1 | R-B | 3 | 1 | R-B | 6 | I-A | Single bond |
| A-16 | 0 | 2' | c | 1 | R-B | 3 | 1 | R-B | 6 | I-B | Single bond |
| A-17 | 0 | 2' | b | 1 | R-B | 3 | 1 | R-B | 6 | I-E | Single bond |
| A-18 | 0 | 2' | a | 1 | R-C | 3 | 1 | Ethyl | 6 | I-A | Single bond |
| A-19 | 0 | 2' | c | 1 | R-C | 3 | 1 | Ethyl | 6 | I-B | Single bond |
| A-20 | 0 | 1' | d | 1 | tert-butyl | 4 | 1 | Ethyl | 6 | I-C | Single bond |

-continued

| Compound No. | $n_3$ | Connection position between Formulae 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| A-21 | 0 | 1' | d | 1 | tert-butyl | 4 | 1 | Ethyl | 6 | I-J | Single bond |
| A-22 | 0 | 3' | d | 1 | tert-butyl | 4 | 1 | Ethyl | 6 | I-D | Single bond |
| A-23 | 0 | 3' | a | 1 | tert-butyl | 4 | 1 | Ethyl | 6 | I-K | Single bond |
| A-24 | 0 | 1' | c | 1 | R-A | 1 | 1 | R-A | 8 | I-F | Single bond |
| A-25 | 0 | 1' | b | 1 | R-A | 1 | 1 | R-A | 8 | I-D | L-I |
| A-26 | 0 | 3' | b | 1 | R-A | 1 | 1 | R-A | 8 | I-M | Single bond |
| A-27 | 0 | 3' | d | 1 | R-A | 1 | 1 | R-A | 8 | I-K | Single bond |
| A-28 | 0 | 4' | a | 1 | Methyl | 2 | 1 | Methyl | 6 | I-H | Single bond |
| A-29 | 0 | 4' | b | 1 | Methyl | 2 | 1 | Methyl | 6 | I-D | Single bond |
| A-30 | 0 | 4' | d | 1 | Methyl | 2 | 1 | Methyl | 6 | I-C | Single bond |
| A-31 | 0 | 4' | a | 1 | R-D | 4 | 1 | R-D | 5 | I-A | Single bond |
| A-32 | 0 | 4' | d | 1 | R-D | 4 | 1 | R-D | 5 | I-J | Single bond |
| A-44 | 0 | 4' | a | 1 | R-A | 3 | 1 | R-A | 6 | I-G | Single bond |
| A-45 | 0 | 4' | b | 1 | R-A | 3 | 1 | R-A | 6 | I-L | Single bond |
| B-8 | 1 | 2' | b | 1 | tert-butyl | 3 | 1 | tert-butyl | 6 | I-H | Single bond |
| B-9 | 1 | 2' | c | 1 | tert-butyl | 3 | 1 | tert-butyl | 6 | I-K | L-B |
| B-10 | 1 | 2' | b | 1 | Methyl | 2 | 1 | Methyl | 7 | I-C | Single bond |
| B-11 | 1 | 2' | b | 1 | Methyl | 2 | 1 | Methyl | 7 | I-E | Single bond |
| B-12 | 1 | 2' | b | 1 | R-C | 3 | 1 | R-C | 7 | I-F | Single bond |
| B-13 | 1 | 2' | b | 1 | R-C | 3 | 1 | R-C | 7 | I-G | Single bond |
| B-14 | 1 | 2' | d | 1 | R-F | 4 | 1 | R-F | 5 | I-K | Single bond |
| B-15 | 1 | 2' | d | 1 | R-F | 4 | 1 | R-F | 5 | I-M | Single bond |
| B-16 | 1 | 2' | c | 1 | R-B | 2 | 1 | R-B | 7 | I-F | L-E |
| B-17 | 1 | 2' | b | 1 | R-B | 2 | 1 | R-B | 7 | I-G | Single bond |
| B-18 | 1 | 1' | a | 1 | R-A | 2 | 1 | R-A | 7 | I-K | Single bond |
| B-19 | 1 | 1' | b | 1 | R-A | 2 | 1 | R-A | 7 | I-F | Single bond |
| B-20 | 1 | 3' | d | 1 | R-A | 2 | 1 | R-A | 7 | I-F | Single bond |
| B-21 | 1 | 3' | d | 1 | R-A | 2 | 1 | R-A | 7 | I-E | Single bond |
| B-22 | 1 | 1' | b | 1 | tert-butyl | 3 | 1 | tert-butyl | 6 | I-J | Single bond |
| B-23 | 1 | 1' | a | 1 | tert-butyl | 3 | 1 | tert-butyl | 6 | I-L | Single bond |
| B-24 | 1 | 3' | c | 1 | tert-butyl | 3 | 1 | tert-butyl | 6 | I-H | Single bond |
| B-25 | 1 | 3' | a | 1 | tert-butyl | 3 | 1 | tert-butyl | 6 | I-K | Single bond |
| B-30 | 1 | 4' | d | 1 | Methyl | 2 | 1 | Methyl | 7 | I-L | Single bond |
| B-31 | 1 | 4' | d | 1 | Methyl | 2 | 1 | Methyl | 7 | I-A | Single bond |
| C-9 | 2 | 2' | d | 1 | tert-butyl | 2 | 1 | tert-butyl | 7 | I-H | Single bond |
| C-10 | 2 | 2' | a | 1 | tert-butyl | 2 | 1 | tert-butyl | 7 | I-J | Single bond |
| C-11 | 2 | 3' | a | 1 | R-A | 3 | 1 | R-A | 6 | I-B | L-G |
| C-12 | 2 | 2' | b | 1 | R-A | 3 | 1 | R-A | 6 | I-H | Single bond |

-continued

| Compound No. | n₃ | Connection position between Formulae 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| C-13 | 2 | 2' | a | 1 | R-C | 1 | 1 | R-C | 8 | I-H | Single bond |
| C-14 | 2 | 2' | b | 1 | R-C | 1 | 1 | R-C | 8 | I-E | Single bond |
| C-16 | 2 | 2' | b | 1 | Methyl | 2 | 1 | Methyl | 7 | I-K | Single bond |
| C-22 | 2 | 1' | a | 1 | Methyl | 2 | 1 | Isopropyl | 7 | I-K | Single bond |
| C-23 | 2 | 3' | a | 1 | Methyl | 2 | 1 | Isopropyl | 7 | I-I | Single bond |
| C-24 | 2 | 4' | c | 1 | Methyl | 3 | 1 | Methyl | 6 | I-F | Single bond |
| C-25 | 2 | 4' | b | 1 | R-E | 3 | 1 | R-E | 6 | I-J | Single bond |
| C-26 | 2 | 4' | d | 1 | R-B | 3 | 1 | R-B | 8 | I-D | Single bond |
| C-29 | 2 | 2' | d | 1 | Methyl | 2 | 1 | Methyl | 7 | I-C | L-A |
| C-30 | 2 | 2' | d | 1 | tert-butyl | 2 | 1 | tert-butyl | 7 | I-G | L-F |
| A-42 | 0 | 4' | d | 4 | H | | 1 | R-C | 6 | I-K | Single bond |
| A-43 | 0 | 4' | b | 4 | H | | 1 | R-C | 6 | I-F | Single bond |
| B-1 | 1 | 2' | a | 4 | H | | 1 | R-A | 7 | I-I | Single bond |
| B-32 | 1 | 4' | d | 4 | H | | 1 | R-A | 7 | I-C | Single bond |
| B-33 | 1 | 4' | b | 4 | H | | 1 | R-A | 7 | I-H | Single bond |
| C-5 | 2 | 2' | b | 4 | H | | 1 | R-D | 7 | I-M | Single bond |
| C-6 | 2 | 2' | a | 4 | H | | 1 | R-D | 7 | I-D | Single bond |
| C-7 | 2 | 2' | c | 4 | H | | 1 | R-E | 6 | I-E | Single bond |
| C-8 | 2 | 2' | b | 4 | H | | 1 | R-E | 6 | I-G | Single bond |
| C-15 | 2 | 2' | a | 4 | H | | 1 | R-A | 7 | I-K | Single bond |
| C-17 | 2 | 2' | b | 4 | H | | 1 | Methyl | 7 | I-I | Single bond |
| C-20 | 2 | 2' | b | 4 | H | | 1 | tert-butyl | 6 | I-F | Single bond |
| C-21 | 2 | 3' | a | 4 | H | | 1 | tert-butyl | 6 | I-H | Single bond |
| C-27 | 2 | 4' | c | 4 | H | | 1 | Ethyl | 7 | I-D | Single bond |
| A-33 | 0 | 4' | a | 1 | R-E | 1 | 4 | H | | I-D | Single bond |
| A-34 | 0 | 4' | d | 1 | R-E | 1 | 4 | H | | I-E | Single bond |
| A-35 | 0 | 4' | c | 1 | R-F | 3 | 4 | H | | I-D | Single bond |
| A-36 | 0 | 4' | b | 1 | R-F | 3 | 4 | H | | I-J | Single bond |
| A-37 | 0 | 1' | c | 1 | R-A | 3 | 4 | H | | I-D | Single bond |
| A-38 | 0 | 1' | b | 1 | R-A | 2 | 4 | H | | I-I | Single bond |
| A-46 | 0 | 3' | d | 1 | R-A | 2 | 4 | H | | I-K | Single bond |
| A-47 | 0 | 3' | d | 1 | R-A | 2 | 4 | H | | I-C | Single bond |
| B-2 | 1 | 2' | b | 1 | R-A | 2 | 4 | H | | I-A | L-D |
| B-6 | 1 | 2' | c | 1 | R-E | 3 | 4 | H | | I-K | Single bond |
| B-7 | 1 | 2' | d | 1 | R-E | 3 | 4 | H | | I-L | Single bond |
| A-54 | 0 | 2' | b | 4 | H | | 4 | H | | I-C | Single bond |
| A-55 | 0 | 1' | b | 4 | H | | 4 | H | | I-C | Single bond |

-continued

| Compound No. | n₃ | Connection position between Formulae 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| A-56 | 0 | 1' | b | 4 | H | | 4 | H | | I-K | Single bond |
| A-57 | 0 | 1' | b | 4 | H | | 4 | H | | I-B | Single bond |
| A-58 | 0 | 1' | a | 4 | H | | 4 | H | | I-C | Single bond |
| A-59 | 0 | 1' | a | 4 | H | | 4 | H | | I-D | Single bond |
| A-60 | 0 | 1' | a | 4 | H | | 4 | H | | I-B | Single bond |
| A-61 | 0 | 1' | c | 4 | H | | 4 | H | | I-C | Single bond |
| A-62 | 0 | 1' | c | 4 | H | | 4 | H | | I-D | Single bond |
| A-63 | 0 | 1' | c | 4 | H | | 4 | H | | I-B | Single bond |
| A-64 | 0 | 1' | d | 4 | H | | 4 | H | | I-C | Single bond |
| A-65 | 0 | 1' | d | 4 | H | | 4 | H | | I-D | Single bond |
| A-66 | 0 | 1' | d | 4 | H | | 4 | H | | I-B | Single bond |
| A-67 | 0 | 2' | c | 4 | H | | 4 | H | | I-B | Single bond |
| A-68 | 0 | 2' | c | 4 | H | | 4 | H | | I-C | Single bond |
| A-69 | 0 | 3' | b | 4 | H | | 4 | H | | I-B | Single bond |
| A-70 | 0 | 3' | b | 4 | H | | 4 | H | | I-C | Single bond |
| A-71 | 0 | 3' | c | 4 | H | | 4 | H | | I-B | Single bond |
| A-72 | 0 | 3' | c | 4 | H | | 4 | H | | I-C | Single bond |
| A-73 | 0 | 3' | d | 4 | H | | 4 | H | | I-C | Single bond |
| A-74 | 0 | 3' | d | 4 | H | | 4 | H | | I-D | Single bond |
| A-75 | 0 | 3' | d | 4 | H | | 4 | H | | I-B | Single bond |
| A-76 | 0 | 3' | a | 4 | H | | 4 | H | | I-C | Single bond |
| A-77 | 0 | 3' | a | 4 | H | | 4 | H | | I-D | Single bond |
| A-78 | 0 | 3' | a | 4 | H | | 4 | H | | I-B | Single bond |
| A-79 | 0 | 4' | a | 4 | H | | 4 | H | | I-C | Single bond |
| A-80 | 0 | 4' | a | 4 | H | | 4 | H | | I-D | Single bond |
| A-81 | 0 | 4' | a | 4 | H | | 4 | H | | I-B | Single bond |
| A-82 | 0 | 4' | b | 4 | H | | 4 | H | | I-B | Single bond |
| A-83 | 0 | 4' | b | 4 | H | | 4 | H | | I-C | Single bond |
| A-84 | 0 | 4' | c | 4 | H | | 4 | H | | I-B | Single bond |
| A-85 | 0 | 4' | c | 4 | H | | 4 | H | | I-C | Single bond |
| A-86 | 0 | 4' | d | 4 | H | | 4 | H | | I-C | Single bond |
| A-87 | 0 | 4' | d | 4 | H | | 4 | H | | I-D | Single bond |
| A-88 | 0 | 4' | d | 4 | H | | 4 | H | | I-B | Single bond |
| A-89 | 0 | 2' | b | 1 | tert-butyl | 3 | 1 | tert-butyl | 6 | I-C | Single bond |
| A-90 | 0 | 1' | b | 1 | tert-butyl | 3 | 1 | tert-butyl | 6 | I-C | Single bond |
| A-91 | 0 | 1' | b | 1 | tert-butyl | 3 | 1 | tert-butyl | 6 | I-E | Single bond |

-continued

| Compound No. | $n_3$ | Connection position between Formulae 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| A-92 | 0 | 1' | b | 1 | tert-butyl | 3 | 1 | tert-butyl | 6 | I-B | Single bond |
| A-93 | 0 | 1' | a | 1 | tert-butyl | 3 | 1 | tert-butyl | 6 | I-C | Single bond |
| A-94 | 0 | 1' | a | 1 | tert-butyl | 3 | 1 | tert-butyl | 6 | I-D | Single bond |
| A-95 | 0 | 1' | a | 1 | tert-butyl | 3 | 1 | tert-butyl | 6 | I-B | Single bond |
| A-96 | 0 | 1' | c | 1 | tert-butyl | 3 | 1 | tert-butyl | 6 | I-C | Single bond |
| A-97 | 0 | 1' | c | 1 | tert-butyl | 3 | 1 | tert-butyl | 6 | I-D | Single bond |
| A-98 | 0 | 1' | c | 1 | tert-butyl | 3 | 1 | tert-butyl | 6 | I-B | Single bond |
| A-99 | 0 | 1' | d | 1 | tert-butyl | 3 | 1 | tert-butyl | 6 | I-C | Single bond |
| A-100 | 0 | 1' | d | 1 | tert-butyl | 3 | 1 | tert-butyl | 6 | I-D | Single bond |
| A-101 | 0 | 1' | d | 1 | tert-butyl | 3 | 1 | tert-butyl | 6 | I-B | Single bond |
| A-102 | 0 | 2' | c | 1 | tert-butyl | 3 | 1 | tert-butyl | 6 | I-C | Single bond |
| A-103 | 0 | 3' | b | 1 | tert-butyl | 3 | 1 | tert-butyl | 6 | I-B | Single bond |
| A-104 | 0 | 3' | b | 1 | tert-butyl | 3 | 1 | tert-butyl | 6 | I-C | Single bond |
| A-105 | 0 | 3' | c | 1 | tert-butyl | 3 | 1 | tert-butyl | 6 | I-B | Single bond |
| A-106 | 0 | 3' | c | 1 | tert-butyl | 3 | 1 | tert-butyl | 6 | I-C | Single bond |
| A-107 | 0 | 3' | d | 1 | tert-butyl | 3 | 1 | tert-butyl | 6 | I-C | Single bond |
| A-108 | 0 | 3' | d | 1 | tert-butyl | 3 | 1 | tert-butyl | 6 | I-D | Single bond |
| A-109 | 0 | 3' | d | 1 | tert-butyl | 3 | 1 | tert-butyl | 6 | I-B | Single bond |
| A-110 | 0 | 3' | a | 1 | tert-butyl | 3 | 1 | tert-butyl | 6 | I-C | Single bond |
| A-111 | 0 | 3' | a | 1 | tert-butyl | 3 | 1 | tert-butyl | 6 | I-D | Single bond |
| A-112 | 0 | 3' | a | 1 | tert-butyl | 3 | 1 | tert-butyl | 6 | I-B | Single bond |
| A-113 | 0 | 4' | a | 1 | tert-butyl | 3 | 1 | tert-butyl | 6 | I-C | Single bond |
| A-114 | 0 | 4' | a | 1 | tert-butyl | 3 | 1 | tert-butyl | 6 | I-D | Single bond |
| A-115 | 0 | 4' | a | 1 | tert-butyl | 3 | 1 | tert-butyl | 6 | I-B | Single bond |
| A-116 | 0 | 4' | b | 1 | tert-butyl | 3 | 1 | tert-butyl | 6 | I-C | Single bond |
| A-117 | 0 | 4' | b | 1 | tert-butyl | 3 | 1 | tert-butyl | 6 | I-D | Single bond |
| A-118 | 0 | 4' | b | 1 | tert-butyl | 3 | 1 | tert-butyl | 6 | I-B | Single bond |
| A-119 | 0 | 4' | c | 1 | tert-butyl | 3 | 1 | tert-butyl | 6 | I-C | Single bond |
| A-120 | 0 | 4' | c | 1 | tert-butyl | 3 | 1 | tert-butyl | 6 | I-D | Single bond |
| A-121 | 0 | 4' | c | 1 | tert-butyl | 3 | 1 | tert-butyl | 6 | I-B | Single bond |
| A-122 | 0 | 4' | d | 1 | tert-butyl | 3 | 1 | tert-butyl | 6 | I-C | Single bond |
| A-123 | 0 | 4' | d | 1 | tert-butyl | 3 | 1 | tert-butyl | 6 | I-D | Single bond |
| A-124 | 0 | 4' | d | 1 | tert-butyl | 3 | 1 | tert-butyl | 6 | I-B | Single bond |
| A-125 | 0 | 3' | b | 1 | tert-butyl | 3 | 1 | tert-butyl | 6 | I-D | Single bond |
| A-126 | 0 | 3' | c | 1 | tert-butyl | 3 | 1 | tert-butyl | 6 | I-D | Single bond |
| B-37 | 1 | 2' | b | 4 | H | | 4 | H | | I-C | Single bond |

-continued

| Compound No. | n₃ | Connection position between Formulae 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| B-38 | 1 | 1' | b | 4 | H | | 4 | H | | I-C | Single bond |
| B-39 | 1 | 1' | b | 4 | H | | 4 | H | | I-K | Single bond |
| B-40 | 1 | 1' | b | 4 | H | | 4 | H | | I-B | Single bond |
| B-41 | 1 | 1' | a | 4 | H | | 4 | H | | I-C | Single bond |
| B-42 | 1 | 1' | a | 4 | H | | 4 | H | | I-D | Single bond |
| B-43 | 1 | 1' | a | 4 | H | | 4 | H | | I-B | Single bond |
| B-44 | 1 | 1' | c | 4 | H | | 4 | H | | I-C | Single bond |
| B-45 | 1 | 1' | c | 4 | H | | 4 | H | | I-D | Single bond |
| B-46 | 1 | 1' | c | 4 | H | | 4 | H | | I-B | Single bond |
| B-47 | 1 | 1' | d | 4 | H | | 4 | H | | I-C | Single bond |
| B-48 | 1 | 1' | d | 4 | H | | 4 | H | | I-D | Single bond |
| B-49 | 1 | 1' | d | 4 | H | | 4 | H | | I-B | Single bond |
| B-50 | 1 | 2' | c | 4 | H | | 4 | H | | I-B | Single bond |
| B-51 | 1 | 2' | c | 4 | H | | 4 | H | | I-C | Single bond |
| B-52 | 1 | 3' | b | 4 | H | | 4 | H | | I-B | Single bond |
| B-53 | 1 | 3' | b | 4 | H | | 4 | H | | I-C | Single bond |
| B-54 | 1 | 3' | c | 4 | H | | 4 | H | | I-B | Single bond |
| B-55 | 1 | 3' | c | 4 | H | | 4 | H | | I-C | Single bond |
| B-56 | 1 | 3' | d | 4 | H | | 4 | H | | I-C | Single bond |
| B-57 | 1 | 3' | d | 4 | H | | 4 | H | | I-D | Single bond |
| B-58 | 1 | 3' | d | 4 | H | | 4 | H | | I-B | Single bond |
| B-59 | 1 | 3' | a | 4 | H | | 4 | H | | I-C | Single bond |
| B-60 | 1 | 3' | a | 4 | H | | 4 | H | | I-D | Single bond |
| B-61 | 1 | 3' | a | 4 | H | | 4 | H | | I-B | Single bond |
| B-62 | 1 | 4' | a | 4 | H | | 4 | H | | I-C | Single bond |
| B-63 | 1 | 4' | a | 4 | H | | 4 | H | | I-D | Single bond |
| B-64 | 1 | 4' | a | 4 | H | | 4 | H | | I-B | Single bond |
| B-65 | 1 | 4' | b | 4 | H | | 4 | H | | I-B | Single bond |
| B-66 | 1 | 4' | b | 4 | H | | 4 | H | | I-C | Single bond |
| B-67 | 1 | 4' | c | 4 | H | | 4 | H | | I-B | Single bond |
| B-68 | 1 | 4' | c | 4 | H | | 4 | H | | I-C | Single bond |
| B-69 | 1 | 4' | d | 4 | H | | 4 | H | | I-C | Single bond |
| B-70 | 1 | 4' | d | 4 | H | | 4 | H | | I-D | Single bond |
| B-71 | 1 | 4' | d | 4 | H | | 4 | H | | I-B | Single bond |
| B-72 | 1 | 2' | b | 1 | tert-butyl | 3 | 1 | tert-butyl | 6 | I-C | Single bond |
| B-73 | 1 | 1' | b | 1 | tert-butyl | 3 | 1 | tert-butyl | 6 | I-C | Single bond |

-continued

| Compound No. | $n_3$ | Connection position between Formulae 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| B-74 | 1 | 1' | b | 1 | tert-butyl | 3 | 1 | tert-butyl | 6 | I-E | Single bond |
| B-75 | 1 | 1' | b | 1 | tert-butyl | 3 | 1 | tert-butyl | 6 | I-B | Single bond |
| B-76 | 1 | 1' | a | 1 | tert-butyl | 3 | 1 | tert-butyl | 6 | I-C | Single bond |
| B-77 | 1 | 1' | a | 1 | tert-butyl | 3 | 1 | tert-butyl | 6 | I-D | Single bond |
| B-78 | 1 | 1' | a | 1 | tert-butyl | 3 | 1 | tert-butyl | 6 | I-B | Single bond |
| B-79 | 1 | 1' | c | 1 | tert-butyl | 3 | 1 | tert-butyl | 6 | I-C | Single bond |
| B-80 | 1 | 1' | c | 1 | tert-butyl | 3 | 1 | tert-butyl | 6 | I-D | Single bond |
| B-81 | 1 | 1' | c | 1 | tert-butyl | 3 | 1 | tert-butyl | 6 | I-B | Single bond |
| B-82 | 1 | 1' | d | 1 | tert-butyl | 3 | 1 | tert-butyl | 6 | I-C | Single bond |
| B-83 | 1 | 1' | d | 1 | tert-butyl | 3 | 1 | tert-butyl | 6 | I-D | Single bond |
| B-84 | 1 | 1' | d | 1 | tert-butyl | 3 | 1 | tert-butyl | 6 | I-B | Single bond |
| B-85 | 1 | 2' | c | 1 | tert-butyl | 3 | 1 | tert-butyl | 6 | I-C | Single bond |
| B-86 | 1 | 3' | b | 1 | tert-butyl | 3 | 1 | tert-butyl | 6 | I-B | Single bond |
| B-87 | 1 | 3' | b | 1 | tert-butyl | 3 | 1 | tert-butyl | 6 | I-C | Single bond |
| B-88 | 1 | 3' | c | 1 | tert-butyl | 3 | 1 | tert-butyl | 6 | I-B | Single bond |
| B-89 | 1 | 3' | c | 1 | tert-butyl | 3 | 1 | tert-butyl | 6 | I-C | Single bond |
| B-90 | 1 | 3' | d | 1 | tert-butyl | 3 | 1 | tert-butyl | 6 | I-C | Single bond |
| B-91 | 1 | 3' | d | 1 | tert-butyl | 3 | 1 | tert-butyl | 6 | I-D | Single bond |
| B-92 | 1 | 3' | d | 1 | tert-butyl | 3 | 1 | tert-butyl | 6 | I-B | Single bond |
| B-93 | 1 | 3' | a | 1 | tert-butyl | 3 | 1 | tert-butyl | 6 | I-C | Single bond |
| B-94 | 1 | 3' | a | 1 | tert-butyl | 3 | 1 | tert-butyl | 6 | I-D | Single bond |
| B-95 | 1 | 3' | a | 1 | tert-butyl | 3 | 1 | tert-butyl | 6 | I-B | Single bond |
| B-96 | 1 | 4' | a | 1 | tert-butyl | 3 | 1 | tert-butyl | 6 | I-C | Single bond |
| B-97 | 1 | 4' | a | 1 | tert-butyl | 3 | 1 | tert-butyl | 6 | I-D | Single bond |
| B-98 | 1 | 4' | a | 1 | tert-butyl | 3 | 1 | tert-butyl | 6 | I-B | Single bond |
| B-99 | 1 | 4' | b | 1 | tert-butyl | 3 | 1 | tert-butyl | 6 | I-C | Single bond |
| B-101 | 1 | 4' | b | 1 | tert-butyl | 3 | 1 | tert-butyl | 6 | I-D | Single bond |
| B-102 | 1 | 4' | b | 1 | tert-butyl | 3 | 1 | tert-butyl | 6 | I-B | Single bond |
| B-103 | 1 | 4' | c | 1 | tert-butyl | 3 | 1 | tert-butyl | 6 | I-C | Single bond |
| B-104 | 1 | 4' | c | 1 | tert-butyl | 3 | 1 | tert-butyl | 6 | I-D | Single bond |
| B-105 | 1 | 4' | c | 1 | tert-butyl | 3 | 1 | tert-butyl | 6 | I-B | Single bond |
| B-106 | 1 | 4' | d | 1 | tert-butyl | 3 | 1 | tert-butyl | 6 | I-C | Single bond |
| B-107 | 1 | 4' | d | 1 | tert-butyl | 3 | 1 | tert-butyl | 6 | I-D | Single bond |
| B-108 | 1 | 4' | d | 1 | tert-butyl | 3 | 1 | tert-butyl | 6 | I-B | Single bond |
| B-109 | 1 | 3' | b | 1 | tert-butyl | 3 | 1 | tert-butyl | 6 | I-D | Single bond |
| B-110 | 1 | 3' | c | 1 | tert-butyl | 3 | 1 | tert-butyl | 6 | I-D | Single bond |

-continued

| Compound No. | n₃ | Connection position between Formulae 1 and 2 | Connection position of Ar₂ | n₁ | R₁ | Position of R₁ | n₂ | R₂ | Position of R₂ | Ar₁ | L |
|---|---|---|---|---|---|---|---|---|---|---|---|
| C-31 | 2 | 2' | b | 4 | H | | 4 | H | | I-C | Single bond |
| C-32 | 2 | 1' | b | 4 | H | | 4 | H | | I-C | Single bond |
| C-33 | 2 | 1' | b | 4 | H | | 4 | H | | I-K | Single bond |
| C-34 | 2 | 1' | b | 4 | H | | 4 | H | | I-B | Single bond |
| C-35 | 2 | 1' | a | 4 | H | | 4 | H | | I-C | Single bond |
| C-36 | 2 | 1' | a | 4 | H | | 4 | H | | I-D | Single bond |
| C-37 | 2 | 1' | a | 4 | H | | 4 | H | | I-B | Single bond |
| C-38 | 2 | 1' | c | 4 | H | | 4 | H | | I-C | Single bond |
| C-39 | 2 | 1' | c | 4 | H | | 4 | H | | I-D | Single bond |
| C-40 | 2 | 1' | c | 4 | H | | 4 | H | | I-B | Single bond |
| C-41 | 2 | 1' | d | 4 | H | | 4 | H | | I-C | Single bond |
| C-42 | 2 | 1' | d | 4 | H | | 4 | H | | I-D | Single bond |
| C-43 | 2 | 1' | d | 4 | H | | 4 | H | | I-B | Single bond |
| C-44 | 2 | 2' | c | 4 | H | | 4 | H | | I-B | Single bond |
| C-45 | 2 | 2' | c | 4 | H | | 4 | H | | I-C | Single bond |
| C-46 | 2 | 3' | b | 4 | H | | 4 | H | | I-B | Single bond |
| C-47 | 2 | 3' | b | 4 | H | | 4 | H | | I-C | Single bond |
| C-48 | 2 | 3' | c | 4 | H | | 4 | H | | I-B | Single bond |
| C-49 | 2 | 3' | c | 4 | H | | 4 | H | | I-C | Single bond |
| C-50 | 2 | 3' | d | 4 | H | | 4 | H | | I-C | Single bond |
| C-51 | 2 | 3' | d | 4 | H | | 4 | H | | I-D | Single bond |
| C-52 | 2 | 3' | d | 4 | H | | 4 | H | | I-B | Single bond |
| C-53 | 2 | 3' | a | 4 | H | | 4 | H | | I-C | Single bond |
| C-54 | 2 | 3' | a | 4 | H | | 4 | H | | I-D | Single bond |
| C-55 | 2 | 3' | a | 4 | H | | 4 | H | | I-B | Single bond |
| C-56 | 2 | 4' | a | 4 | H | | 4 | H | | I-C | Single bond |
| C-57 | 2 | 4' | a | 4 | H | | 4 | H | | I-D | Single bond |
| C-58 | 2 | 4' | a | 4 | H | | 4 | H | | I-B | Single bond |
| C-59 | 2 | 4' | b | 4 | H | | 4 | H | | I-B | Single bond |
| C-60 | 2 | 4' | b | 4 | H | | 4 | H | | I-C | Single bond |
| C-61 | 2 | 4' | c | 4 | H | | 4 | H | | I-B | Single bond |
| C-62 | 2 | 4' | c | 4 | H | | 4 | H | | I-C | Single bond |
| C-63 | 2 | 4' | d | 4 | H | | 4 | H | | I-C | Single bond |
| C-64 | 2 | 4' | d | 4 | H | | 4 | H | | I-D | Single bond |
| C-65 | 2 | 4' | d | 4 | H | | 4 | H | | I-B | Single bond |
| C-66 | 2 | 2' | b | 1 | tert-butyl | 3 | 1 | tert-butyl | 6 | I-C | Single bond |

-continued

| Compound No. | $n_3$ | Connection position between Formulae 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| C-67 | 2 | 1' | b | 1 | tert-butyl | 3 | 1 | tert-butyl | 6 | I-C | Single bond |
| C-68 | 2 | 1' | b | 1 | tert-butyl | 3 | 1 | tert-butyl | 6 | I-E | Single bond |
| C-69 | 2 | 1' | b | 1 | tert-butyl | 3 | 1 | tert-butyl | 6 | I-B | Single bond |
| C-70 | 2 | 1' | a | 1 | tert-butyl | 3 | 1 | tert-butyl | 6 | I-C | Single bond |
| C-71 | 2 | 1' | a | 1 | tert-butyl | 3 | 1 | tert-butyl | 6 | I-D | Single bond |
| C-72 | 2 | 1' | a | 1 | tert-butyl | 3 | 1 | tert-butyl | 6 | I-B | Single bond |
| C-73 | 2 | 1' | c | 1 | tert-butyl | 3 | 1 | tert-butyl | 6 | I-C | Single bond |
| C-74 | 2 | 1' | c | 1 | tert-butyl | 3 | 1 | tert-butyl | 6 | I-D | Single bond |
| C-75 | 2 | 1' | c | 1 | tert-butyl | 3 | 1 | tert-butyl | 6 | I-B | Single bond |
| C-76 | 2 | 1' | d | 1 | tert-butyl | 3 | 1 | tert-butyl | 6 | I-C | Single bond |
| C-77 | 2 | 1' | d | 1 | tert-butyl | 3 | 1 | tert-butyl | 6 | I-D | Single bond |
| C-78 | 2 | 1' | d | 1 | tert-butyl | 3 | 1 | tert-butyl | 6 | I-B | Single bond |
| C-79 | 2 | 2' | c | 1 | tert-butyl | 3 | 1 | tert-butyl | 6 | I-C | Single bond |
| C-80 | 2 | 3' | b | 1 | tert-butyl | 3 | 1 | tert-butyl | 6 | I-B | Single bond |
| C-81 | 2 | 3' | b | 1 | tert-butyl | 3 | 1 | tert-butyl | 6 | I-C | Single bond |
| C-82 | 2 | 3' | c | 1 | tert-butyl | 3 | 1 | tert-butyl | 6 | I-B | Single bond |
| C-83 | 2 | 3' | c | 1 | tert-butyl | 3 | 1 | tert-butyl | 6 | I-C | Single bond |
| C-84 | 2 | 3' | d | 1 | tert-butyl | 3 | 1 | tert-butyl | 6 | I-C | Single bond |
| C-85 | 2 | 3' | d | 1 | tert-butyl | 3 | 1 | tert-butyl | 6 | I-D | Single bond |
| C-86 | 2 | 3' | d | 1 | tert-butyl | 3 | 1 | tert-butyl | 6 | I-B | Single bond |
| C-87 | 2 | 3' | a | 1 | tert-butyl | 3 | 1 | tert-butyl | 6 | I-C | Single bond |
| C-88 | 2 | 3' | a | 1 | tert-butyl | 3 | 1 | tert-butyl | 6 | I-D | Single bond |
| C-89 | 2 | 3' | a | 1 | tert-butyl | 3 | 1 | tert-butyl | 6 | I-B | Single bond |
| C-90 | 2 | 4' | a | 1 | tert-butyl | 3 | 1 | tert-butyl | 6 | I-C | Single bond |
| C-91 | 2 | 4' | a | 1 | tert-butyl | 3 | 1 | tert-butyl | 6 | I-D | Single bond |
| C-92 | 2 | 4' | a | 1 | tert-butyl | 3 | 1 | tert-butyl | 6 | I-B | Single bond |
| C-93 | 2 | 4' | b | 1 | tert-butyl | 3 | 1 | tert-butyl | 6 | I-C | Single bond |
| C-94 | 2 | 4' | b | 1 | tert-butyl | 3 | 1 | tert-butyl | 6 | I-D | Single bond |
| C-95 | 2 | 4' | b | 1 | tert-butyl | 3 | 1 | tert-butyl | 6 | I-B | Single bond |
| C-96 | 2 | 4' | c | 1 | tert-butyl | 3 | 1 | tert-butyl | 6 | I-C | Single bond |
| C-97 | 2 | 4' | c | 1 | tert-butyl | 3 | 1 | tert-butyl | 6 | I-D | Single bond |
| C-98 | 2 | 4' | c | 1 | tert-butyl | 3 | 1 | tert-butyl | 6 | I-B | Single bond |
| C-99 | 2 | 4' | d | 1 | tert-butyl | 3 | 1 | tert-butyl | 6 | I-C | Single bond |
| C-100 | 2 | 4' | d | 1 | tert-butyl | 3 | 1 | tert-butyl | 6 | I-D | Single bond |
| C-101 | 2 | 4' | d | 1 | tert-butyl | 3 | 1 | tert-butyl | 6 | I-B | Single bond |

-continued

| Compound No. | $n_3$ | Connection position between Formulae 1 and 2 | Connection position of $Ar_2$ | $n_1$ | $R_1$ | Position of $R_1$ | $n_2$ | $R_2$ | Position of $R_2$ | $Ar_1$ | L |
|---|---|---|---|---|---|---|---|---|---|---|---|
| C-102 | 2 | 3' | b | 1 | tert-butyl | 3 | 1 | tert-butyl | 6 | I-D | Single bond |
| C-103 | 2 | 3' | c | 1 | tert-butyl | 3 | 1 | tert-butyl | 6 | I-D | Single bond | wherein when $n_3=0$, the structural formula of Formula 1 is

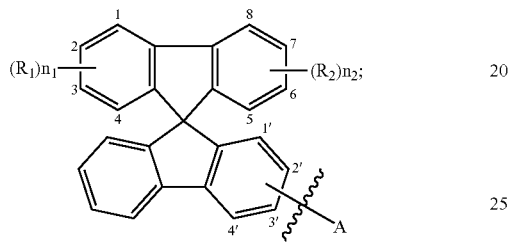

when $n_3=1$, both $R_3$ and $R_4$ are methyl, and the structural formula of Formula 1 is

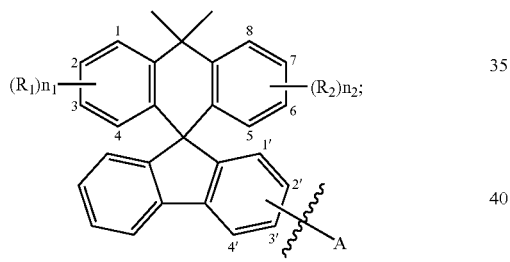

when $n_3=2$, both $R_3$ and $R_4$ are H, and the structural formula of Formula 1 is

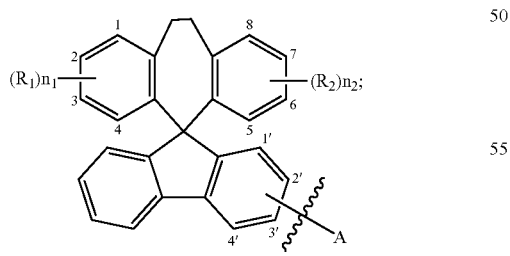

"-" means that $R_1$ is connected at the 1, 2, 3, and 4 position of the Formula 1, and "--" means that $R_2$ is connected at the 5, 6, 7, and 8 position of the Formula 1;

R-A, R-B, R-C, R-D, R-E, and R-f refer to $R_1$ or $R_2$ with different structures and respectively correspond to the groups shown below:

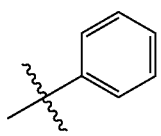

R-A

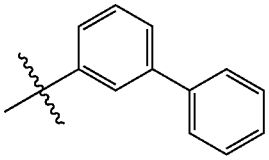

R-B

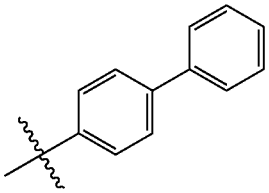

R-C

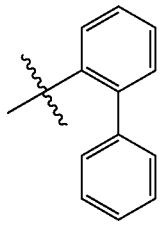

R-D

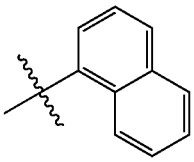

R-E

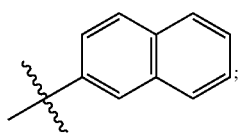

R-F

L-A, L-B, L-C, L-D, L-E, L-F, L-G, L-H, and L-I refer to L with different structures and respectively correspond to the groups shown below:

L-A 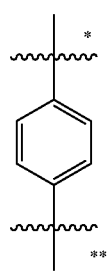
L-B
L-C
L-D
L-E
L-F
L-G 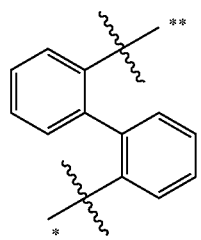
L-H
L-I 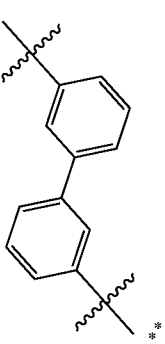
** means the connection to
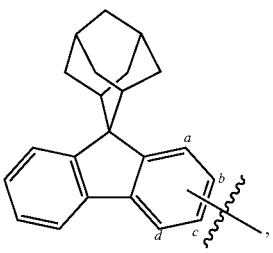
and * means the connection to
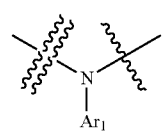
$-\xi\xi-$ ;
I-A, I-B, I-C, I-D, I-E, I-F, I-G, I-H, I-I, I-J, I-K, I-L, and I-M mean Ar₁ with different structures and respectively correspond to the groups shown below:

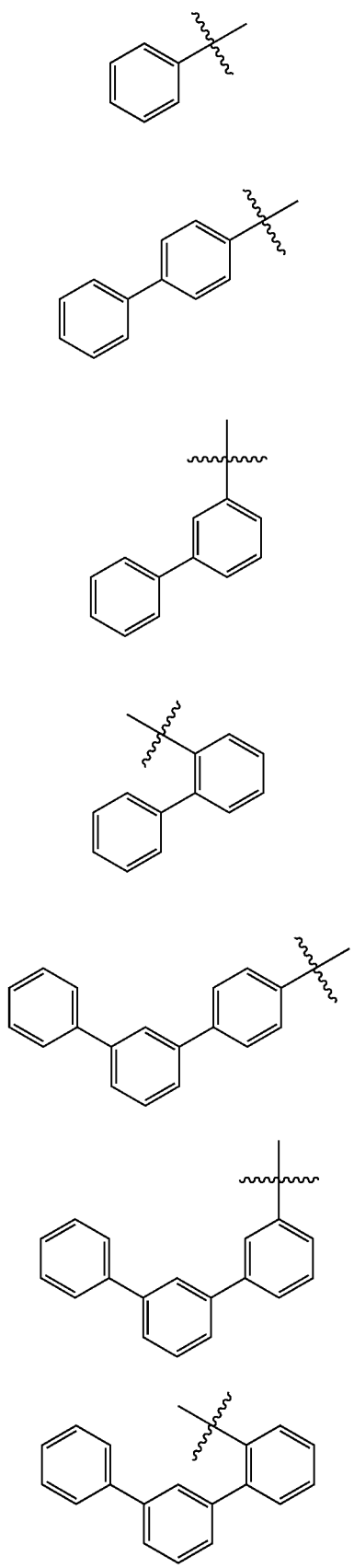
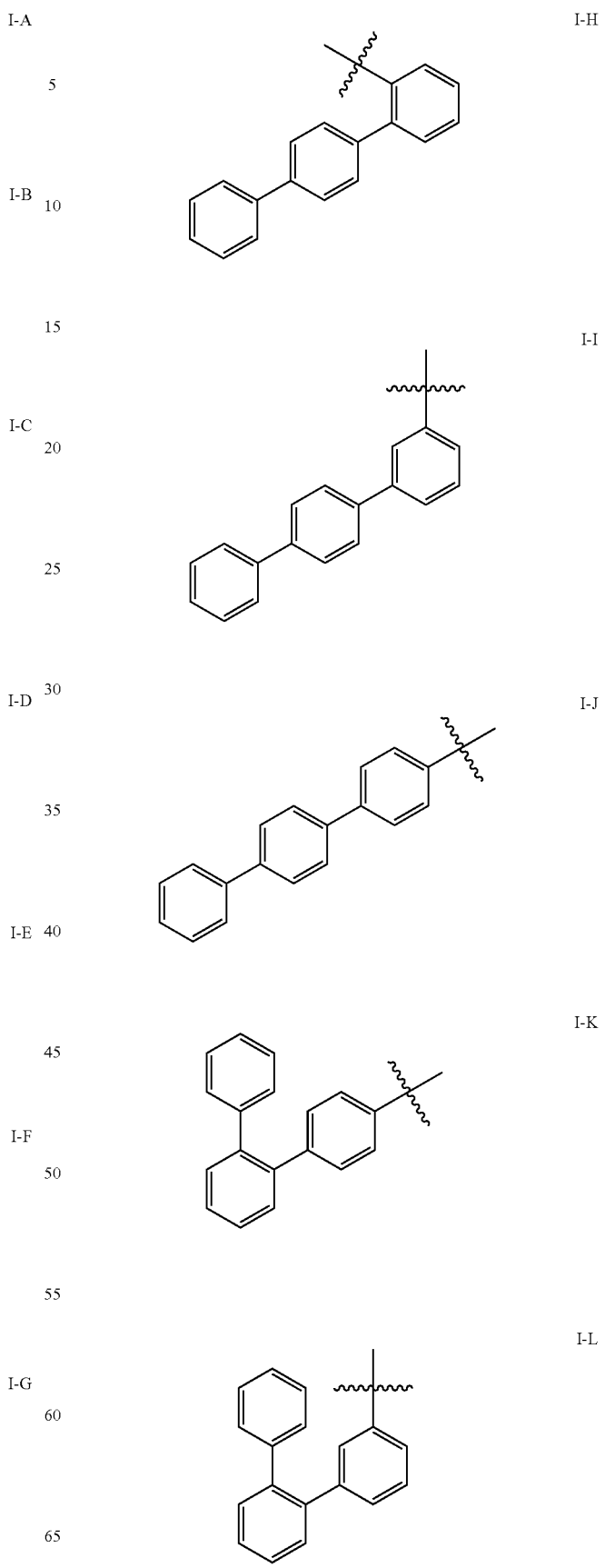

-continued

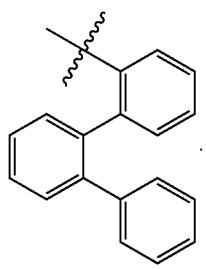
I-M

5. An electronic component, characterized in that it comprises an anode and a cathode arranged oppositely and a functional layer arranged there between, wherein the functional layer comprises the nitrogen-containing compound according to claim 1.

6. The electronic component according to claim 5, characterized in that the functional layer comprises a hole adjustment layer comprising the nitrogen-containing compound.

7. The electronic component according to claim 5, characterized in that the electronic component is an organic electroluminescent device or a photoelectric conversion device.

8. The electronic component according to claim 5, characterized in that the functional layer comprises a hole transport layer comprising the nitrogen-containing compound.

9. An electronic device, characterized in that it comprises the electronic component according to claim 5.

10. The nitrogen-containing compound according to claim 1, wherein $R_1$ and $R_2$ are identical, and are each independently selected from isopropyl.

11. The nitrogen-containing compound according to claim 1, wherein the nitrogen-containing compound is selected from the following compounds:

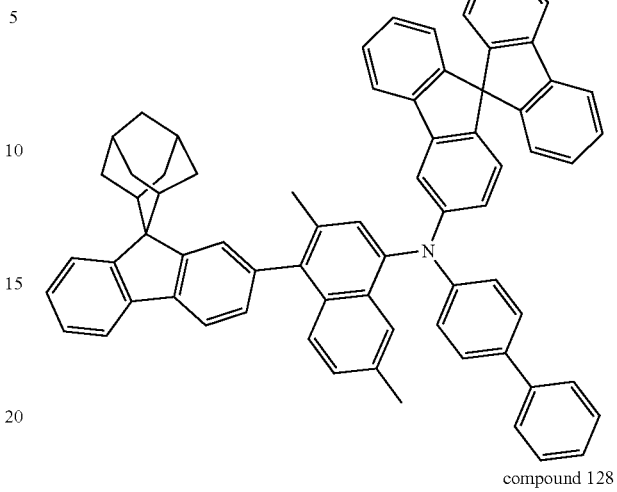
compound 127

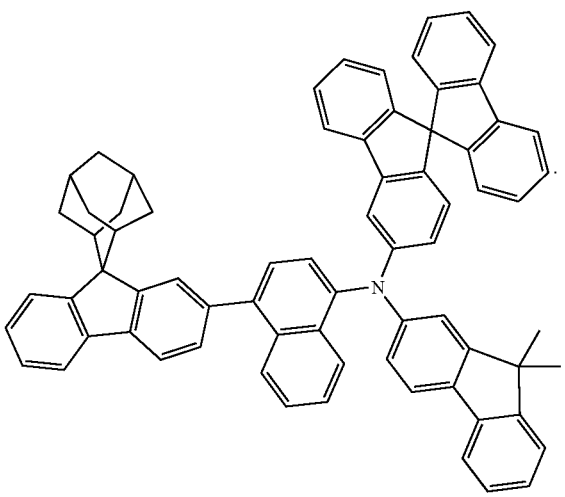
compound 128

12. The electronic component according to claim 7, wherein the organic electroluminescent device is a red organic electroluminescent device or a green organic electroluminescent device.

13. The electronic component according to claim 7, characterized in that the organic electroluminescent device is a blue organic electroluminescent device.

* * * * *